US012350267B2

(12) United States Patent
Gedulin et al.

(10) Patent No.: US 12,350,267 B2
(45) Date of Patent: *Jul. 8, 2025

(54) BILE ACID RECYCLING INHIBITORS FOR TREATMENT OF PEDIATRIC CHOLESTATIC LIVER DISEASES

(71) Applicant: SHIRE HUMAN GENETIC THERAPIES, INC., Lexington, MA (US)

(72) Inventors: Bronislava Gedulin, Del Mar, CA (US); Michael Grey, Rancho Sante Fe, CA (US); Niall O'Donnell, Encintas, CA (US)

(73) Assignee: SHIRE HUMAN GENETIC THERAPIES, INC., Lexington, MA (US)

( * ) Notice: Subject to any disclaimer, the term of this patent is extended or adjusted under 35 U.S.C. 154(b) by 602 days.

This patent is subject to a terminal disclaimer.

(21) Appl. No.: 17/730,737

(22) Filed: Apr. 27, 2022

(65) Prior Publication Data

US 2022/0265649 A1 Aug. 25, 2022

Related U.S. Application Data

(63) Continuation of application No. 17/498,586, filed on Oct. 11, 2021, now Pat. No. 11,376,251, which is a
(Continued)

(51) Int. Cl.
| | |
|---|---|
| *A61K 31/4995* | (2006.01) |
| *A61K 9/00* | (2006.01) |
| *A61K 9/16* | (2006.01) |
| *A61K 9/20* | (2006.01) |
| *A61K 31/155* | (2006.01) |
| *A61K 31/38* | (2006.01) |
| *A61K 31/41* | (2006.01) |
| *A61K 31/495* | (2006.01) |
| *A61K 31/4965* | (2006.01) |
| *A61K 31/4985* | (2006.01) |
| *A61K 31/5377* | (2006.01) |
| *A61K 31/554* | (2006.01) |
| *A61K 45/06* | (2006.01) |
| *A61P 1/16* | (2006.01) |
| *C07D 281/10* | (2006.01) |
| *C07D 337/08* | (2006.01) |
| *C07D 409/10* | (2006.01) |
| *C07D 487/08* | (2006.01) |

(Continued)

(52) U.S. Cl.
CPC ........ *A61K 31/4995* (2013.01); *A61K 9/0053* (2013.01); *A61K 9/0056* (2013.01); *A61K 9/1611* (2013.01); *A61K 9/1617* (2013.01); *A61K 9/1623* (2013.01); *A61K 9/1635* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2081* (2013.01); *A61K 31/155* (2013.01); *A61K 31/38* (2013.01); *A61K 31/41* (2013.01); *A61K 31/495* (2013.01); *A61K 31/4965* (2013.01); *A61K 31/4985* (2013.01); *A61K 31/5377* (2013.01); *A61K 31/554* (2013.01); *A61K 45/06* (2013.01); *A61P 1/16* (2018.01); *C07D 281/10* (2013.01); *C07D 337/08* (2013.01); *C07D 409/10* (2013.01); *C07D 487/08* (2013.01); *C07H 15/26* (2013.01); *A61K 31/4436* (2013.01); *A61K 31/7042* (2013.01)

(58) Field of Classification Search
CPC ...... A61P 1/16; A61K 31/138; A61K 31/4995
See application file for complete search history.

(56) References Cited

U.S. PATENT DOCUMENTS

| | | |
|---|---|---|
| 3,287,370 A | 11/1966 | Mohrbacher et al. |
| 3,308,020 A | 3/1967 | Wolf et al. |

(Continued)

FOREIGN PATENT DOCUMENTS

| | | |
|---|---|---|
| CA | 2123050 A1 | 11/1994 |
| CN | 1284953 A | 2/2001 |

(Continued)

OTHER PUBLICATIONS

Office Action issued Jun. 21, 2022 in connection with Korean Patent Application No. 10-2021-7033783.
Anna Glantz, et al., Intrahepatic cholestasis of pregnancy: Relationships between bile acid levels and fetal complication rates, Hepatology, 2004, 40(2), 467-474. (Aug. 31, 2004).
(Continued)

*Primary Examiner* — Theodore R. Howell
(74) *Attorney, Agent, or Firm* — Troutman Pepper Locke LLP

(57) ABSTRACT

Provided herein are methods of treating or ameliorating a pediatric cholestatic liver disease by non-systemically administering to an individual in need thereof a therapeutically effective amount of a pediatric formulation comprising an Apical Sodium-dependent Bile Acid Transporter Inhibitor (ASBTI) or a pharmaceutically acceptable salt thereof. Also provided are methods for treating or ameliorating a pediatric liver disease, decreasing the levels of serum bile acids or hepatic bile acids, treating or ameliorating pruritis, reducing liver enzymes, or reducing bilirubin comprising non-systemically administering to an individual in need thereof a therapeutically effective amount of a pediatric formulation comprising an ASBTI or a pharmaceutically acceptable salt thereof.

20 Claims, 5 Drawing Sheets

Related U.S. Application Data continuation of application No. 16/679,864, filed on Nov. 11, 2019, now Pat. No. 11,229,661, which is a continuation of application No. 15/137,323, filed on Apr. 25, 2016, now Pat. No. 10,512,657, which is a continuation of application No. 13/866,906, filed on Apr. 19, 2013, now abandoned, which is a continuation of application No. 13/662,387, filed on Oct. 26, 2012, now abandoned.

(60) Provisional application No. 61/607,487, filed on Mar. 6, 2012, provisional application No. 61/607,503, filed on Mar. 6, 2012, provisional application No. 61/553,094, filed on Oct. 28, 2011.

(51) Int. Cl.
*C07H 15/26* (2006.01)
*A61K 31/4436* (2006.01)
*A61K 31/7042* (2006.01)

(56) References Cited

U.S. PATENT DOCUMENTS

| | | |
|---|---|---|
| 3,383,281 A | 5/1968 | Wolf et al. |
| 3,389,144 A | 6/1968 | Mohrbacher et al. |
| 3,520,891 A | 7/1970 | Mohrbacher et al. |
| 3,694,446 A | 9/1972 | Houlihan et al. |
| 3,758,528 A | 9/1973 | Malen et al. |
| 3,769,399 A | 10/1973 | Hagerman et al. |
| 3,770,728 A | 11/1973 | Bourquin et al. |
| 3,821,249 A | 6/1974 | Malen et al. |
| 3,846,541 A | 11/1974 | Howard |
| 3,853,915 A | 12/1974 | Bourquin et al. |
| 3,928,383 A | 12/1975 | Kaplan et al. |
| 3,954,764 A | 5/1976 | Gerecke et al. |
| 3,974,272 A | 8/1976 | Poli et al. |
| 4,044,010 A | 8/1977 | Gerecke et al. |
| 4,045,570 A | 8/1977 | Dorhofer et al. |
| 4,153,612 A | 5/1979 | McCall |
| 4,172,120 A | 10/1979 | Todd et al. |
| 4,185,109 A | 1/1980 | Rosen |
| 4,207,239 A | 6/1980 | McCall |
| 4,237,296 A | 12/1980 | Gadient |
| 4,247,533 A | 1/1981 | McCall |
| 4,251,526 A | 2/1981 | McCall |
| 4,252,790 A | 2/1981 | Higuchi |
| 4,340,585 A | 7/1982 | Borzatta et al. |
| 4,436,749 A | 3/1984 | Hatinguais et al. |
| 4,647,459 A | 3/1987 | Peters et al. |
| 4,814,354 A | 3/1989 | Ghebre-Sellassie et al. |
| 4,874,744 A | 10/1989 | Nordlund et al. |
| 4,895,723 A | 1/1990 | Amer et al. |
| 4,997,665 A | 3/1991 | Grethlein |
| 5,037,825 A | 8/1991 | Klaus et al. |
| 5,070,103 A | 12/1991 | Iwasaki et al. |
| 5,158,943 A | 10/1992 | Sohda et al. |
| 5,164,387 A | 11/1992 | Klaus et al. |
| 5,169,857 A | 12/1992 | Angerbauer et al. |
| 5,275,823 A | 1/1994 | France et al. |
| 5,300,522 A | 4/1994 | Klaus et al. |
| 5,415,872 A | 5/1995 | Sipos |
| 5,420,273 A | 5/1995 | Klaus et al. |
| 5,430,116 A | 7/1995 | Kramer et al. |
| 5,491,152 A | 2/1996 | Wilde et al. |
| 5,512,558 A | 4/1996 | Enhsen et al. |
| 5,534,505 A | 7/1996 | Widauer |
| 5,547,975 A | 8/1996 | Talley et al. |
| 5,589,358 A | 12/1996 | Dawson |
| 5,594,001 A | 1/1997 | Teleha et al. |
| 5,602,152 A | 2/1997 | Berthelon et al. |
| 5,607,669 A | 3/1997 | Mandeville, III et al. |
| 5,652,252 A | 7/1997 | Berthelon et al. |
| 5,663,165 A | 9/1997 | Brieaddy |
| 5,670,532 A | 9/1997 | Talley et al. |
| 5,693,675 A | 12/1997 | Mandeville, III et al. |
| 5,695,749 A | 12/1997 | Friess et al. |
| 5,723,458 A | 3/1998 | Brieaddy et al. |
| 5,817,652 A | 10/1998 | Brieaddy et al. |
| 5,874,451 A | 2/1999 | Giombik et al. |
| 5,886,016 A | 3/1999 | Talley et al. |
| 5,900,233 A | 5/1999 | Day |
| 5,908,830 A | 6/1999 | Smith et al. |
| 5,910,494 A | 6/1999 | Brieaddy |
| 5,994,391 A | 11/1999 | Lee et al. |
| 5,998,400 A | 12/1999 | Brieaddy et al. |
| 6,013,809 A | 1/2000 | Zimmer et al. |
| 6,020,330 A | 2/2000 | Enhsen et al. |
| 6,034,118 A | 3/2000 | Bischofberger et al. |
| 6,066,336 A | 5/2000 | Ullah et al. |
| 6,069,167 A | 5/2000 | Sokol |
| 6,083,977 A | 7/2000 | Boehm et al. |
| 6,096,780 A | 8/2000 | Shiraishi et al. |
| 6,107,494 A | 8/2000 | Lee et al. |
| 6,114,322 A | 9/2000 | Enhsen et al. |
| 6,143,765 A | 11/2000 | Bocan |
| 6,180,660 B1 | 1/2001 | Whitney et al. |
| 6,221,897 B1 | 4/2001 | Frick et al. |
| 6,235,771 B1 | 5/2001 | Shiraishi et al. |
| 6,245,797 B1 | 6/2001 | Winokur |
| 6,251,852 B1 | 6/2001 | Gould et al. |
| 6,262,277 B1 | 7/2001 | Lee et al. |
| 6,264,938 B1 | 7/2001 | Huval et al. |
| 6,268,392 B1 | 7/2001 | Keller et al. |
| 6,277,831 B1 | 8/2001 | Frick et al. |
| 6,303,661 B1 | 10/2001 | Demuth et al. |
| 6,309,663 B1 | 10/2001 | Patel et al. |
| 6,329,404 B1 | 12/2001 | Ikeda et al. |
| 6,329,405 B1 | 12/2001 | Kurata et al. |
| 6,337,327 B1 | 1/2002 | Tuffin et al. |
| 6,355,672 B1 | 3/2002 | Yasuma et al. |
| 6,369,220 B1 | 4/2002 | Li et al. |
| 6,387,924 B2 | 5/2002 | Lee et al. |
| 6,387,944 B1 | 5/2002 | Frick et al. |
| 6,420,417 B1 | 7/2002 | Keller et al. |
| 6,441,022 B1 | 8/2002 | Frick et al. |
| 6,458,851 B1 | 10/2002 | Keller et al. |
| 6,465,451 B1 | 10/2002 | Handion |
| 6,586,434 B2 | 7/2003 | Babiak et al. |
| 6,642,268 B2 | 11/2003 | Keller et al. |
| 6,740,663 B2 | 5/2004 | Tremont et al. |
| 6,784,201 B2 | 8/2004 | Lee et al. |
| 6,852,763 B2 | 2/2005 | Koeller et al. |
| 6,861,053 B1 | 3/2005 | Lin et al. |
| 6,875,877 B2 | 4/2005 | Li et al. |
| 6,890,898 B2 | 5/2005 | Bachovchin et al. |
| 6,906,058 B2 | 6/2005 | Starke et al. |
| 6,943,189 B2 | 9/2005 | Keller et al. |
| 7,125,864 B2 | 10/2006 | Starke et al. |
| 7,132,416 B2 | 11/2006 | Starke et al. |
| 7,179,792 B2 | 2/2007 | Glombik et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,312,208 B2 | 12/2007 | Sasahara et al. |
| 7,413,536 B1 | 8/2008 | Dowor et al. |
| 7,514,421 B2 | 4/2009 | Abrahamsson et al. |
| 7,803,792 B2 | 9/2010 | Sasahara et al. |
| 7,956,085 B2 | 6/2011 | Frick et al. |
| 7,973,030 B2 | 7/2011 | Sasahara et al. |
| 8,067,584 B2 | 11/2011 | Starke et al. |
| 8,106,026 B2 | 1/2012 | Nabel et al. |
| 10,512,657 B2 | 12/2019 | Gedulin ............ A61K 31/4436 |
| 11,229,661 B2 * | 1/2022 | Gedulin ............... A61P 17/04 |
| 2002/0004065 A1 | 1/2002 | Kanios |
| 2002/0032329 A1 | 3/2002 | Babiak et al. |
| 2002/0061888 A1 | 5/2002 | Keller et al. |
| 2002/0147184 A1 | 10/2002 | Kosoglou et al. |
| 2003/0017996 A1 | 1/2003 | Frick et al. |
| 2003/0119809 A1 | 6/2003 | Davis |
| 2003/0139434 A1 | 7/2003 | Balkan et al. |
| 2003/0149010 A1 | 8/2003 | Keller et al. |

(56) References Cited

U.S. PATENT DOCUMENTS

| | | |
|---|---|---|
| 2003/0203939 A1 | 10/2003 | Kliewer et al. |
| 2003/0219472 A1 | 11/2003 | Pauletti et al. |
| 2004/0014803 A1 | 1/2004 | Lee ................ C07D 495/10 514/431 |
| 2004/0014806 A1 | 1/2004 | Bhat et al. |
| 2004/0029845 A1 | 2/2004 | Keller et al. |
| 2004/0067872 A1 | 4/2004 | Tremont et al. |
| 2004/0087648 A1 | 5/2004 | Frick et al. |
| 2004/0092500 A1 | 5/2004 | Fine et al. |
| 2004/0097424 A1 | 6/2004 | Giombik et al. |
| 2004/0122033 A1 | 6/2004 | Nargund et al. |
| 2004/0138145 A1 | 7/2004 | Canton et al. |
| 2004/0147774 A1 | 7/2004 | Crocq-Stuerga et al. |
| 2004/0176438 A1 | 9/2004 | Tremont et al. |
| 2004/0180860 A1 | 9/2004 | Burnett et al. |
| 2004/0180861 A1 | 9/2004 | Burnett et al. |
| 2004/0186154 A1 | 9/2004 | Seibert et al. |
| 2005/0009805 A1 | 1/2005 | Sasahara et al. |
| 2005/0012455 A1 | 1/2005 | Lee et al. |
| 2005/0031651 A1 | 2/2005 | Gervais et al. |
| 2005/0101611 A1 | 5/2005 | Starke et al. |
| 2005/0124557 A1 | 6/2005 | Lundqvist |
| 2006/0069080 A1 | 3/2006 | Veltri |
| 2006/0083790 A1 | 4/2006 | Anderberg et al. |
| 2006/0094884 A1 | 5/2006 | Starke et al. |
| 2006/0193895 A1 | 8/2006 | Miura |
| 2006/0199797 A1 | 9/2006 | Abrahamsson et al. |
| 2006/0241121 A1 | 10/2006 | Greenlee et al. |
| 2006/0269510 A1 | 11/2006 | Barbier et al. |
| 2007/0025953 A1 | 2/2007 | Jones |
| 2007/0032420 A1 | 2/2007 | Polidori et al. |
| 2007/0065428 A1 | 3/2007 | Arkesteijn et al. |
| 2007/0066844 A1 | 3/2007 | de Lera Ruiz et al. |
| 2007/0161578 A1 | 7/2007 | Hwa et al. |
| 2007/0190041 A1 | 8/2007 | Sasahara et al. |
| 2007/0197628 A1 | 8/2007 | Chackalamannil et al. |
| 2007/0203115 A1 | 8/2007 | Sasahara et al. |
| 2007/0203183 A1 | 8/2007 | Scott et al. |
| 2007/0254952 A1 | 11/2007 | Wang et al. |
| 2008/0031968 A1 | 2/2008 | Bianco et al. |
| 2008/0065136 A1 | 3/2008 | Young |
| 2008/0070888 A1 | 3/2008 | McKittrick et al. |
| 2008/0070889 A1 | 3/2008 | Burnett et al. |
| 2008/0070892 A1 | 3/2008 | Harris et al. |
| 2008/0070984 A1 | 3/2008 | Tran |
| 2008/0089858 A1 | 4/2008 | MicKittrick et al. |
| 2008/0096921 A1 | 4/2008 | Navas et al. |
| 2008/0145453 A1 | 6/2008 | Lopez et al. |
| 2008/0161400 A1 | 7/2008 | Virsik et al. |
| 2008/0167356 A1 | 7/2008 | Calciwell et al. |
| 2008/0194598 A1 | 8/2008 | Woltering et al. |
| 2008/0214633 A1 | 9/2008 | Rohrig et al. |
| 2008/0221161 A1 | 9/2008 | Pinkerton et al. |
| 2008/0255202 A1 | 10/2008 | Bischoff et al. |
| 2008/0261990 A1 | 10/2008 | Dittrich-Wengenroth et al. |
| 2009/0118201 A1 | 6/2009 | Chen et al. |
| 2009/0253153 A1 | 10/2009 | Chu et al. |
| 2010/0035834 A1 | 2/2010 | Glombik et al. |
| 2010/0035961 A1 | 2/2010 | Frick et al. |
| 2010/0055066 A1 | 3/2010 | Suzuki et al. |
| 2010/0062991 A1 | 3/2010 | Glombik et al. |
| 2010/0130426 A1 | 6/2010 | Young et al. |
| 2010/0130472 A1 | 6/2010 | Young et al. |
| 2011/0065876 A1 | 3/2011 | Perelman et al. |
| 2011/0152204 A1 | 6/2011 | Gedulin et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0059807 A1 | 3/2013 | Gedulin et al. |
| 2013/0108573 A1 | 5/2013 | Gedulin et al. |
| 2013/0109871 A1 | 5/2013 | Gedulin et al. |
| 2013/0225511 A1 | 8/2013 | Gilberg et al. |
| 2013/0338093 A1 | 12/2013 | Gedulin et al. |
| 2014/0024328 A1 | 8/2014 | Gedulin et al. |
| 2014/0275090 A1 | 9/2014 | Gedulin |
| 2017/0368085 A1 | 12/2017 | Gedulin |

FOREIGN PATENT DOCUMENTS

| | | |
|---|---|---|
| CN | 1439638 A | 9/2003 |
| CN | 1726016 | 1/2006 |
| DE | 2011806 A1 | 10/1970 |
| DE | 19825804 A1 | 12/1999 |
| EP | 0067086 A1 | 12/1982 |
| EP | 0250265 A1 | 12/1987 |
| EP | 251315 A2 | 1/1988 |
| EP | 0263493 A2 | 4/1988 |
| EP | 0350846 A2 | 1/1990 |
| EP | 417725 A2 | 3/1991 |
| EP | 489423 A1 | 6/1992 |
| EP | 0508425 A1 | 10/1992 |
| EP | 0509335 A1 | 10/1992 |
| EP | 549967 A1 | 7/1993 |
| EP | 573848 A2 | 12/1993 |
| EP | 597107 A4 | 2/1994 |
| EP | 624593 A2 | 11/1994 |
| EP | 624594 A2 | 11/1994 |
| EP | 624595 A2 | 11/1994 |
| EP | 0781278 A1 | 7/1997 |
| EP | 0791592 A2 | 8/1997 |
| EP | 0864582 A2 | 9/1998 |
| EP | 869121 A1 | 10/1998 |
| EP | 0922703 A1 | 6/1999 |
| EP | 1070703 A1 | 1/2001 |
| EP | 1173205 A1 | 1/2002 |
| EP | 1273659 A1 | 1/2003 |
| EP | 1347052 A1 | 9/2003 |
| EP | 1535913 A1 | 6/2005 |
| EP | 1719768 A1 | 11/2006 |
| EP | 1810689 A1 | 7/2007 |
| FR | 2661676 A1 | 11/1991 |
| FR | 2698873 A1 | 6/1994 |
| GB | 929391 A | 6/1963 |
| GB | 1211258 A | 11/1970 |
| GB | 1286949 A | 8/1972 |
| GB | 1428110 A | 3/1976 |
| GB | 2465677 A | 6/2010 |
| JP | S63-96138 A | 4/1968 |
| JP | 10-072371 | 3/1998 |
| JP | 2000-026300 A | 1/2000 |
| JP | 2002-542208 | 12/2002 |
| JP | 2002-542208 A | 12/2002 |
| JP | 2005-507854 | 3/2005 |
| JP | 2005-097216 A | 4/2005 |
| JP | 2008-517921 A | 5/2008 |
| JP | 2008-534523 A | 8/2008 |
| JP | 4497472 B2 | 7/2010 |
| JP | 4711953 | 6/2011 |
| JP | 4711953 B2 | 6/2011 |
| JP | 2013-541584 | 11/2013 |
| JP | 2014532663 | 12/2014 |
| KR | 970005178 Y1 | 5/1997 |
| KR | 1020090082396 | 7/2009 |
| SU | 506297 A3 | 3/1976 |
| SU | 550982 A3 | 3/1977 |
| SU | 591146 A3 | 1/1978 |
| WO | 93/008155 A1 | 4/1993 |
| WO | 93/016055 A1 | 8/1993 |
| WO | 94/018183 A1 | 8/1994 |
| WO | 94/018184 A1 | 8/1994 |
| WO | 94/024087 A1 | 10/1994 |
| WO | 96/005188 A1 | 2/1996 |
| WO | 96/08484 A1 | 3/1996 |
| WO | 96/16051 A1 | 5/1996 |
| WO | 97/33882 A1 | 9/1997 |
| WO | 98/07749 A1 | 2/1998 |
| WO | 98/40375 A2 | 8/1998 |
| WO | 98/038182 A1 | 9/1998 |
| WO | 98/55118 A2 | 12/1998 |
| WO | 98/56757 A1 | 12/1998 |
| WO | 99/32478 A1 | 7/1999 |
| WO | 99/35135 A1 | 7/1999 |

(56) References Cited

FOREIGN PATENT DOCUMENTS

| | | |
|---|---|---|
| WO | 2000/01687 A1 | 1/2000 |
| WO | 2000/20392 A1 | 4/2000 |
| WO | 2000/20393 A1 | 4/2000 |
| WO | 2000/20410 A1 | 4/2000 |
| WO | 2000/20437 A1 | 4/2000 |
| WO | 2000/35889 A1 | 6/2000 |
| WO | 2000/38725 A1 | 7/2000 |
| WO | 2000/38726 A1 | 7/2000 |
| WO | 2000/38727 A1 | 7/2000 |
| WO | 2000/38728 A1 | 7/2000 |
| WO | 2000/47568 A2 | 8/2000 |
| WO | 2000/61568 A2 | 10/2000 |
| WO | 2000/062810 A1 | 10/2000 |
| WO | 200062810 | 10/2000 |
| WO | 2001/34570 A1 | 6/2001 |
| WO | 2001/66533 A1 | 9/2001 |
| WO | 2001/68096 A2 | 9/2001 |
| WO | 2001/68637 A2 | 9/2001 |
| WO | 2002/08211 A2 | 1/2002 |
| WO | 2002/032428 A1 | 4/2002 |
| WO | 2002/50027 A1 | 6/2002 |
| WO | 2002/50051 A1 | 6/2002 |
| WO | 2002/078626 A2 | 10/2002 |
| WO | 2003/018024 A1 | 3/2003 |
| WO | 2003/020710 A1 | 3/2003 |
| WO | 2003/022286 A1 | 3/2003 |
| WO | 2003/022825 A1 | 3/2003 |
| WO | 2003/022830 A1 | 3/2003 |
| WO | 2003/040127 A1 | 5/2003 |
| WO | 2003/061663 A1 | 7/2003 |
| WO | 2003/091232 A2 | 11/2003 |
| WO | 2003/106482 A1 | 12/2003 |
| WO | 2004/005247 A1 | 1/2004 |
| WO | 2004/006899 A1 | 1/2004 |
| WO | 2004/020421 A1 | 3/2004 |
| WO | 2004062662 | 7/2004 |
| WO | 2018193006 | 7/2004 |
| WO | 2004/076430 A1 | 9/2004 |
| WO | 2004/089350 A1 | 10/2004 |
| WO | 2005/046797 A2 | 5/2005 |
| WO | 2006/017257 A2 | 2/2006 |
| WO | 2006/031501 A2 | 3/2006 |
| WO | 2006/031931 A2 | 3/2006 |
| WO | 2006/039829 A2 | 4/2006 |
| WO | 2006/57637 A1 | 6/2006 |
| WO | 2006/105912 A2 | 10/2006 |
| WO | 2006/105913 A1 | 10/2006 |
| WO | 2006/116499 A1 | 11/2006 |
| WO | 2006/116814 A1 | 11/2006 |
| WO | 2006/117076 A1 | 11/2006 |
| WO | 2006/121861 A2 | 11/2006 |
| WO | 2006/122186 A2 | 11/2006 |
| WO | 2006/124713 A2 | 11/2006 |
| WO | 2007/009655 A1 | 1/2007 |
| WO | 2007/041368 A2 | 4/2007 |
| WO | 2007/050628 A2 | 5/2007 |
| WO | 2007/095174 A2 | 8/2007 |
| WO | 2007/101531 A1 | 9/2007 |
| WO | 2007/127505 A2 | 11/2007 |
| WO | 2007/134862 A1 | 11/2007 |
| WO | 2007/140894 A1 | 12/2007 |
| WO | 2007/140934 A1 | 12/2007 |
| WO | 2008/002573 A2 | 1/2008 |
| WO | 2008/028590 A1 | 3/2008 |
| WO | 2008/031500 A1 | 3/2008 |
| WO | 2008/033431 A1 | 3/2008 |
| WO | 2008/033464 A2 | 3/2008 |
| WO | 2008/033465 A1 | 3/2008 |
| WO | 2008/034534 A1 | 3/2008 |
| WO | 2008/058628 A1 | 5/2008 |
| WO | 2008/058630 A1 | 5/2008 |
| WO | 2008/058631 A1 | 5/2008 |
| WO | 2008058628 | 5/2008 |
| WO | 2008/064788 A1 | 6/2008 |
| WO | 2008/064789 A1 | 6/2008 |
| WO | 2008/067219 A2 | 6/2008 |
| WO | 2008/088836 A2 | 7/2008 |
| WO | 2008/091540 A2 | 7/2008 |
| WO | 2008/104306 A2 | 8/2008 |
| WO | 2008/124505 A2 | 10/2008 |
| WO | 2008/130616 A2 | 10/2008 |
| WO | 2009115398 | 9/2009 |
| WO | 2010/014836 A2 | 2/2010 |
| WO | 2010/059853 A1 | 5/2010 |
| WO | 2010/062861 A2 | 6/2010 |
| WO | 2010062861 | 6/2010 |
| WO | 2011/022838 A1 | 3/2011 |
| WO | 2012/064266 A1 | 5/2012 |
| WO | 2012/064267 A1 | 5/2012 |
| WO | 2012/064268 A1 | 5/2012 |
| WO | 2012064266 | 5/2012 |
| WO | 2013/063512 A1 | 5/2013 |
| WO | 2013063526 | 5/2013 |
| WO | 2017167935 | 10/2017 |

OTHER PUBLICATIONS

Office Action issued Jul. 11, 2022 in connection with Japanese Patent Application No. 2018-218627.
Gyo-Medical, Jun. 2011, vol. 43, No. 6,pp. 971-975.
Wang et al., Cell & Bioscience, vol. 13, pp. 1-10 (published in 2023).
Japanese Journal of Pediatric Medicine, vol. 43, No. 6, Jun. 6, 2011, pp. 965-966.
Japanese Journal of Pediatric Medicine, vol. 43, No. 6, Jun. 6, 2011, pp. 1034-1037.
Minagawa N. et al., "Partial External Biliary Diversion Prevents Progression of Liver Fibrosis in Progressive Familial Intrahepatic Cholestasis", JSPS, 2006, pp. 236-242.
Minagawa N. et al., "A case in which partial extracholecystia was effective in preventing the progression of liver fibrosis in progressive familial intrahepatic cholestasis," Japan Journal of Pediatric Surgery, vol. 42, No. 2, 2006, pp. 236-242.
Jacquemin E., "Progressive familiar intrahepatic cholestasis," Clinics and Research in Hepatology and Gastroenterology, (2012) vol. 36, pp. S26-S35.
Jacquemin E., "Progressive familial intrahepatic cholestasis," Clinics and Research in Hepatology and Gastroenterology, vol. 36, Supplement 1, Sep. 2012, pp. S26-235.
Morotti R. A. et al., "Progressive Familial Intrahepatic Cholestasis (PFIC) Type 1, 2, and 3: A Review of the Liver Pathology Findings," Seminars in Liver Disease, vol. 31, No. 1, 2011, pp. 3-10.
Japanese Journal of Pediatric Medicine, vol. 43, No. 6, Jun. 6, 2011, pp. 1077-1081.
Japanese Journal of Pediatric Medicine, vol. 43, No. 6, Jun. 6, 2011, pp. 1046-1049.
Tazawa Y., "Liver disease in children (III)," Sendai Medical Center Medical Journal, vol. 2, Apr. 2012. pp. 4-15.
Mannion M. et al., "Sarcoidosis in a young child with Alagille syndrome: a case report," Pediatric Rheumatology, 2012, 10:32, pp. 1-6.
Mannion M. et al., "Sarcoidosis in a young child with Alagille syndrome: a case report", Pediatric Rheumatology, 2012, 10:32.
Poupon R. et al., "Chronic cholestatic disease," Journal of Hepatology, 2000, 32 (suppl. 1), pp. 129-140.
Japanese Journal of Pediatric Medicine, vol. 43, No. 6, Jun. 6, 2011, pp. 1073-1076.
Aranha, M.M. et al., "Bile acid levels are increased in the liver of patients with steatohepatitis" Eur. J. Gastroenterol Hepatol. Jun. 2008; vol. 20, No. 6, pp. 519-525.
Torres, D.M. et al., "Features, diagnosis, and treatment of nonalcoholic fatty liver disease" Clin. Gastroenterol Hepatol 2012, vol. 10, pp. 837-858.
Bahar et al., "Bile acid transport," Gastroenterol. Clin. North Am. Mar. 1999;28(1):27-58. PMID: 10198777. (Year: 1999).
Extended European Search Report issued Dec. 11. 2017 in connection with EPO No. 1/168880.0.
Sun et al., "Sorting of rat liver and ileal sodium-dependent bile acid transporters in polarized epithelial cells.", Am. J. Physiol. Nov. 1998; 275 (S Pt 1): G1046-66.

(56) References Cited

OTHER PUBLICATIONS

Morotti et al. Progressive Familial Intraheptic Cholestasis (PFIC) Type 1, 2 and 3: A Review of the Liver Pathology Findings. Seminars in Liver Disease, vol. 31, No. 1, 2011.
Lefebvre et al. Role of bile acids and bile acid receptors in metabolic regulation. Physiol. Rev. 89: 147-191, 2009.
Horng-Chih Huang et al. "Discovery of Potent, Nonsystemic Apical Sodium-Codependent Bile Acid Transporter Inhibitors (Part 2)" Journal of Medical Chemistry. vol. 48. No 18. pp. 5853-5868.
Israel Official Notification dated Jan. 16, 2017 issued in corresponding Israeli Application No. 232149.
Israel Official Notification dated Jan. 15, 2017 issued in corresponding Israeli Application No. 232150.
Japan Office Action dated Jul. 6, 2016 issued in corresponding Japanese Application No. 2014-539087.
Japan Office Action dated Jul. 4, 2016 issued in corresponding Japanese Application No. 2014-539093.
Mexico Office Action dated Nov. 16, 2016 issued in corresponding Mexican Application No. MX/a/2014/005122 with Enghsh translation.
"Cholestasis" retrieved from the Internet: URL: http://emedicine com/ped/topic383.htm.
Diabolologica 53(1): S294, Abstract No. 735, 2010.
U.S. Appl. No. 61/410,957, Specification, abstract and claims. filed Nov. 8, 2010.
Seerden et al, Neurogatroenterol. Motil. 19: 856-864. (2007).
Dominguez-Munoz et al., Aliment Pharmacol Ther. 21 993-1000. (2005).
Hoogerwerf et al., Pharmacological Management of Pancreatitis, Current Opinion in Pharmacology 5(6): 578-582 (2005).
Annaba et al., "Green tea catechin EGCG inhibits ilea apical sodium bile acid transporter ASBT" Am J Physiol Gastrointest Liver Physiol 298 G467-G473 (2010).
Kremer et al. Pathophysiology and current management of pruntis in liver disease. Clinics and Research in Hepatology and Gastroenterology, 2011, 35, 89-97.
Marzioni et al. "Glucagon-like peptide-1 and its receptor agonist exendin-4 modulate cholangiocyte adaptive response to cholestasis" Gastroenterology 133:244-255 (2007).
Mazelin et al "Protective role of vagal afferents in experimentally-induced colitis in rats" J Auton Nerv SYst 73:38-45 (1998).
Mennella et al. "Optimizing Oral Medications for Children", Clinical Therapeutics, 30(11).2120-2132 (2008).
Morris et al. "Hapten-induced model of chronic inflammation and ulceration in the rat colon" Gastroenterology 96:798-803 (1989).
Moss et al "Necrotizing enterocolitis and total parenteral nutrition-associated cholestasis" Nutrition 12(5):340-3 (1996).
Niwa et al. "Lack of effect of incretin hormones on insulin release from pancreatic islets in the bile duct-ligsted rats", Am J Physiol Endocrinol Metab 280:E59-64 (2001).
Nunn et al., "Formulation of Medicines for Children," British Journal of Clinical Pharmacology, 2005, 59(6):674-676.
Pappas et al "Enterogastrone like effect of peptide YY is vagally mediated in the dog" J Clin Invest. 77:49-53 (1986).
Pappas et al. "Peptide YY inhibits meal-stimulated pancreatic and gastric secretion" Am J Physiol 248:G118-G123 (1985).
Pappas et al "Peptide YY release by fatty acids is sufficient to inhibit gastnc emptying in dogs" Gastroenterology 91(6):1386-9 (1986).
Rink et al., "Clinical and Molecular Characteristics of Gastrointestinal Stromal Tumar in the Pediatric and Young Adult Population", Curr Oncol Rep., 11(4):314 (Jul. 2009).
Root et al., "Ileal bile acid transporter inhibition, CYP7A1 induction, and antilipemic action of 264W94," J Lipid Res 43 (8):1320-30 (2002).
Savage et al. "Effects of peptide YY (PYY) on mouth to caecum intestinal transit time and on the rate of gastric emptying in healthy volunteers" Gut 28:166-70 (1987).
Schlosser et al., "Multiple Cerebral Aneurysms and Subarachnoid Hemorrhage in a Patient with Alagille Syndrome" AJNR, 25.1366-1367 (2004).

Shneider et al. "Cloning and molecular characterization of the ontogeny of a rat ileal sodium-dependent bile acid transporter" J Clin Invest. 95(2):745-754 (1995).
Shneider, "A New Era in Bile Acid Transport Pathophysiology" Journal of Pediatric Gastroenterology & Nutrition 26:236-237 (1998).
Sobala et al. "Bile reflux and intestinal metaplasia in gastric mucosa" J Clin Pathol 46:235-40 (1993).
Steinbrook, "Testing Medications in Children", Engl J Med. 347(18):1462-1470 (2002).
Tremont et al., J Med. Chem 2005, 48:5837-5852.
Tsai el al., Am J Physiol Mar. 1997; 272(3 Pt 1):G662-8.
Tumpenny, "Alagille syndrome: pathogenesis, diagnosis and management", EP Journal of Human Genetics. 20:251-257 (2012).
U.S. Office Action dated Sep. 18, 2014, which issued during prosecution of U.S. Appl. No. 13/866,906, which corresponds to the present application.
U.S. Appl. No. 13/566,898 Office Action dated Nov. 27, 2013.
U.S. Appl. No. 13/881,447 Response to Restriction Requirement dated Feb. 14, 2014, including Exhibits A-G.
Walters et al. "Expression, transport properties, and chromosomal localization of organic anion transporter subtype 3" Am J Physiol 279:G1188-1200 (2000).
Wettergen et al. "Glucagon-Like Peplidet 7-36 Amide and Peptide YY Have Additive Inhibitory Effect on Gastric Acid Secretion in Man" Scand J. Gastroenterol 32:552-5 (1997).
Worthington et al., "Primary sclerosing cholangitis", Orphanet Journal of Rare Diseases 2006, 7 pgs.
Adrian, T.E. et al "Deoxycholate is an important releaser of peptide YY and enteroglucagon from the human colon." Gut 1993, 34:1219-1224.
Ali, M. et al. "Reactions with 2,3,4,5-Tetrahydro-benzo (B) Thiepin-6-One and Its Derivatives." J. Prakt Chem 316 (2):259-266 (1974).
Almena J. et al. "Reductive Opening of Thiophthalan a New Route to Functionalised Sulfur-Containing Compounds", J. Org. Chem., 61:1859-1862 (1996).
Balas et al "The Dipeptidyl Peptidase IV Inhibitor Vicagliptin Sopresses Endogenous Glucose Production and Enhances Istet Function after Single-Dose Administration in Type 2 Diabetic Patients." The Journal of Clinical Endocrinology & Metabolism, 2007, vol. 92(4):1249-1255.
Baumgarth M. et al., "Bicyclic Acylguanadine Na+/H+ Antiporte Inhibitors". J. Med Chem., 41.3736-3747 (1998).
Bentley, K W et al. "Pharmaceutical Antihypertensive and Vasodilator Compositions", Chemical Abstracts, 85-516 (1976).
Bohme, H. and Haack, B. "[Derivatives of 1,3,4,5-tetrahydro-2-benzothiepin with a basic side chain in the 1-position]." Arch. Pharm. Ber. Dtsch. Pharm. Ges. 302(1):72-74 (1969).
Braun et al. "2,3,4,5,6-Penta-O-Acetyl-D-Gluconic Acid and 2,3,4,5,6-Penta-O-Acetyl-D-Gluconyl Chloride," Organic Synthesis, 5:887-891 (1973).
Brinton, "Novel pathways for glycaemic control in type 2 diabetes: focus on bile acid modulation" Diabetes, Obesity and Metabolism, 2008, 10(11):1004-1011 (2008).
Chatterjee, A. et al. "Ring contraction of some 1-benzothiepin derivatives to 1-benzothiephens." J. Chem. Soc. Perkin Trans. 1:1707-1711 (1981).
Chen, F. et al., "Liver Receptor Homologue-1 Mediates Species-and Cell Line-specific Bile Acid-dependent Negative Feedback Regulation of the Apical Sodium-dependent Bile Acid Transporter," J. Biol Chem 2003, 278. 19909-19916.
Corelli F. et al , "Diltiazem-like Calcium Entry Blockers: A Hypothesis of the Receptor-Binding Site Based on a Comparative Molecular Field Analysis Model", J. Med. Chem., 40:125-131 (1997).
Crosignani et al., "Clinical pharmacokinetics of therapeutic bile acids," Clin Pharmacokinet 30:333-358 (1996).
Definition of 'conceivable,' from the Free Dictionary, [online] 2009 [Retrieved on Jul. 30, 2012] Retrieved from the Internet: http://www.thefreedictionary.com/conceivable.
Derwent Abstract of DE 2011806.
Derwent Abstract of EP 350846.
Derwent Abstract of EP 67086.
Derwent Abstract of EP 922703.
Derwent Abstract of FR 2,661,676.

(56) References Cited

OTHER PUBLICATIONS

Derwent Abstract of FR 2,698,873.
Derwent Abstract of SU 506297.
Derwent Abstract of SU 550982.
Derwent Abstract of SU 591146.
Macchiarulo et al., "Molecular field analysis and 3D quantitative structure activity relationship study (MF-A 3D-QSAR) unveil novel features of bile acid recognition at TGR5," J Chem Inf Model 48(9): 1792-801 (2008).
Menozzi G. et al., "Reaction of Ketenes with N, N-Disubstituted ?—Aminomethyleneketones. XVII. Synthesis of 2H-[1] Benzothiepino[5,4-b]pyran Derivatives", J. Heterocyclic Chem. 23:449-454 (1986).
Menozzi G. et al., "Reaction of Sulfenes with Heterocyclic N,N-Disubstituted?—Aminoethyleneketones XII. Synthesis of [1]Benzothiepino[5,4-e] [1,2]oxathiin Derivatives", J Heterocyclic Chem 23:455-458 (1986).
Murata, I , "Some new aspects of thiepine and thiazepine chemistry," Phosphorus, SUlfur Silicon Relat. ELam. 43 (3-4) 243-260 (1989).
Nagamatsu T. et al. "Polycyclic N-Hetero Compounds XXXVII. A Convenient Synthesis and Evaluation of ANti-platelet Aggregation Activity of 1,2,4,5-Tetrahydro[ 1]-benzothiepino[S,4-e]imidazo[ 1,2-c]pyrimidine and its Related Compounds.", Journal of Heterocyclic Chemistry, 28:513-515 (1991).
Nakao S et al. Studies on the Synthesis of Condensed Pyrdazine Derivatives, IV. Synthesis and Anxiolytic Activity of 2-Aryl-5,6 dihydro(1)Benzothiepino[5,4-c]pyridazin-3(2H)-ones and Related Compound. Chem Pharm. Bull. 39 (10):2556-2563 (1991).
Nakao S. et al., "4-(Aminomethyl)-2,3-dihydri-1-benzothiepins as Cardiovascular Agents", Chemical Abstracts, 114:825 (1991).
Namba et al., "GLP-1 derivatives, for the prevention and treatment of type 2 diabetes mellitus," Magazine of Japanese Society of Gastroenterology, 2005, vol. 102, No 11, p. 1398-1404.
Oda T et al., "Synthesis of Novel 2-Benzothiopyran and 3-Benzothiepin Derivatives and Their Stimulatory Effect on Bone Formation", J. Med. Chem., 42:751-760 (1999).
Onaga et al., "Multiple regulation of peptide YY secretion in the digestive tract," Peptides 17(5):279-290 (2002).
Patra R et al., "Conformational and Steric Requirements of the Side Chain for Sulphur Participation in Benzothiepin Derivatives", Tetrahedron Letters, 30 4279-4282 (1969).
Pellicciari et al., "Nongenomic actions of bile acids, Synthesis and preliminary characterization of 23- and 6-23-alkyl-substituted bile acid derivatives as selective modulators for the G-protein coupled receptor TGR5," J Med Chem 50 (18):4265-8 (2007).
Pozsgay, V. et al., Synthesis of Kojidextrins and Their Protein Conjugates, Incidence of Stenc Mismaich in Oligosaccharide Synthesis, J. Org. Chem., (1997), vol. 62, pp. 2832-2846.
Profiva, M., "Neurotropic and psychotropic drugs," Pharm. Ind 32(10A):923-935 (1970).
Pye C. et al., "Examination of the Valence Tautomers Benzene Oxide and Oxepin and Two Derivative Systems by ab Intro Methods", J Phys Chem A, pp. 3371-3376 (1997).
Raun K. et al., "Liraglutide, a Long-Action Glucagon-Like Peptide-1 Analog, Reduces Body Weight and Food Intake in Obese Candy-Fed Rats, Whereas a Dipeptidyl Peptidase-IV Inhibitor, Vildagliptin, Does No," Diabetes, vol. 56, Jan. 2007, p. 8-15.
Rohse K. and Bienfait R. "Anticoagulante eigenschaften heterocyelischer 1,3-dikelone [Anticoagulant activities of heterocyclic 1,3 diones]," Archiv. der Pharmazie (Weinheim) 317(5):385-393 (1964).
Reimann et al., "Signaling mechanisms underlying the release of glucagon-like peptide 1," Diabetes 55(Supp 2): S78-85 (2006).
Ricci A. et al., "New heterocyclic systems, IV. Derivatives of (1) Benzothiepine," Gazz Chim. Ital. 107(1-2):19-26 (1977).
Saito S et al., Synthesis of Glycymhetic Acid Diglycosides and Their Cytoprotective Activities Against CC14-Induced Hepatic Injury in Vitro, Eur J Med. Chem. (1996), vol. 31, pp. 557-574.

Salo et al , "Anti-hyperglycomic activity of a TGR5 agonist isolated from Olea europaea," Biochem Biophys Res Commun 362(4):793-8 (2007).
Sato et al , "Novel potent and selective bile acid derivatives as TORS agonists, biological screening, structure-activity relationships, and molecular modeling studies," J Med Chem 51(6):1831-41 (2008).
Shafiee A. et al., "Chemistry of 1,2,3,-Thiadiazole, IV. Synthesis of [1]Benzoxepino-[3,4-d] [1,2,3]thiadiazole, [1]Benzothiepino-[3,4-d] [1,2,3]thiadiazole, [1]Benzoxepino(4,3-dloxazole and [1]Benzoxepino[3,4-d]oxazole Four Novel Heterocycles", J. Heterocyclic Chem. 18:899-903 (1981).
Sindelar K. et al., "Benzocycloheptenes and Heterocyclic Analogues as Potential Drugs III. Further Synthetic Experiments in the Series of 1-Benzothiepin Derivatives.", Collection Czechoslov Chem Comm., 37:1195-1206 (1972).
Sindelar K. et al., "Dibenzo[b,f] Thiepin-10-Carbonitrile, ITS 10,11-Hydro Denvate Some Transformation Products and Related Compounds", Neurotropic and Psychotropic Agents, Part CLXXX, Journal 48, 1173, pp. 1187-1211 (1983).
Sindelar K. et al., "Neurotropic and Psychotropic Compounds. XXIX. Derivatives of 2,3,4,5-Tetrahydro-1-Benzothiepin ", Collection Czechoslov Chem Common., 33:4315-4327 (1968).
Solladie G. et al., "A New Family of Enantiomerically Pure Smectic C' Liquid Crystals with a Bridged Chiral Biphenyl Core.", J. Org. Chem., 63:3895-3898 (1998).
Spangeus and El-Salhy, "Large intestinal endocrine cells in non-obese diabetic mice." J Diabetes Complications 12 (6):321-7 (1998).
Takada T., "Oxidatie Biaryl Coupling Reaction of Phenol Ether Derivatives Using a Hypervalent Iodine (III) Reagent.". J. Org. Chem., 63:7698-7706 (1998).
Talley J.J., "Discovery of the COX-2 inhibitor Celebrex", Nippon Yakugakkai Nenka I Koen Yoshishu, 120(1) 80 (2000).
Tamura Y et al., "Rearrangement of 4-Oxothiochroman-1-io(bismethoxycarbonyl)methanides to Tetrahydro-1-Benzothiepin-5-ones", J.C S. Perkin I, pp. 2978-2981 (1981).
Tenjarla et al., "Release of 5-Aminosalicylafe from and MMX mesalamine tablet during transit through a simulated gastrointestinal tract system," Advances in Therapy 23:826-940 (2007).
Thomas et al., "Decreased developmental of experimental necrotizing entercolitis in apical sodium-dependent bile acid transporter knockout mice" Gastroenterology, (May 2009) vol. 136, No. 5 Suppl. 1, p. A41.
Tozaki et al., "Chitosan capsules for colon-specific drug delivery improvement of insulin absorption from the rat colon." J Pharm Sci 86: 1016-1021 (1997).
Traynelis V et al., "Seven-membered heterocycles, viii. 1-benzothiepin sulfoxides and a convenient synthesis of sulfoxides." J. Org. Chem. 38(23):3986-3990 (1973).
Traynelis V. et al., "Seven-membered heterocycles, ix. Synthesis and properties of some 5-alkyl and -aryl derivatives of 1-benzothiepin." J. Org. Chem. 43(17):3379-3384 (1978).
Traynelis V. et al . "Seven-membered heterocycles, vii. The synthesis and properties of 1-benzothlepin and its chlorinated derivatives," J. Org. Chem. 38(23):3978-3986 (1973).
Traynelis V et al., Seven-membered heterocycles, vi. 4-alkylidene-1-benzothiepin-(2H)-ones and the reaction of halogenated 3,4-dihydro-1-benzothiepin-5(2H)-ones with base 1_3, J. Org. Chem., 38(15):2629-2637 (1973).
Traynelis V. et al , "Seven-membered heterocycles, iii Homoallylic resonance and a unique sulfur extrusion reaction in seven membered sulfur heterocycles", 29 1092-1097 (1964).
U.S. Appl. No. 12/623,977 Office Action mailed Apr. 26, 2013.
U.S. Appl. No. 12/623,977 Office Action mailed Sep. 25, 2012.
U.S. Appl. No. 12/623,977 Office Action mailed Jan. 31, 2012.
U.S. Appl. No. 12/624,345 Notice of Allowance mailed Sep. 21, 2012.
U.S. Appl. No. 12/624,345 Office Action mailed Feb. 15, 2012.
U.S. Appl. No. 12/624,345 Office Action mailed May 26, 2011.
U.S. Appl. No. 12/624,345 Office Action mailed Nov. 18, 2011.
U.S. Appl. No. 13/116,988 Office Action mailed Jul. 30, 2014.
U.S. Appl. No. 13/116,988 Office Action mailed Nov. 15, 2013.
U.S. Appl. No. 13/402,819 Office Action mailed Aug. 1, 2014.

(56) References Cited

OTHER PUBLICATIONS

U.S. Appl. No. 13/402,819 Office Action dated Jan. 14, 2014.
Deshayes C. et al. "Synthesis of some 4-Acetyl-3,5-dioxo-2,3,4-tetrahydro[1]benzoxepine or Benzothiepine and 6-Acetyl-5,7-dioxo-6,7,8,9-tetrahydor-5H-benzocycloheptene Derivatives", J Heterocyclic Chem., 22(6):1659-1662 (1985).
Dominguez-Munoz et al. "Effect of the administration schedule on the therapeutic efficacy of oral pancreatic enzyme supplements in patients with exocrine pancreatic insufficiency: a randomized, three-way crossover study" Aliment. Pharmacol Ther. 21 993-1000 (2005).
Dumoulin V et al., "Peptide YY, Glucagon-Like Peptide-1, and Neurotensin Responses to Luminal Factors in the Isolated Vascularty Perfused Rat Ileum," Endocrinology, 1998, vol. 139, No. 9, p. 3780-3786.
Edney et al., "Cholesterol Drugs Have 'Small' Increased Diabetes Risk, U.S. FDA Says." Bloomberg [online] Feb. 28, 2012 [Retrieved on Jul. 30, 2012] Retrieved from the Internet: http://bloomberg.com/news/2012-02-28/cholesterol-drugs-have small-increased-diabetes-risk-u-s-tda-says html.
El-Shattawy et al., "Effectiveness of rectal insulin suppositories containing sodium cholate in normal and insulin dependent diabetic subjects," Pharmaceutical Res 8:S157 (1991).
Enhsen et al., "Bile acids in drug discovery," Drug Discover Today 3(9) 409-418 (1998).
European Search Report dated Nov. 13, 2013, which issued during prosecution of European Application No. 11787464.4.
European Serach Report dated Nov. 28, 2012, which issued during prosecution of European Application No. 09829741.9.
Ferrari R et al., "How do calcium antagonists differ in clinical practice?." Cardiovascular drugs and therapy 8:565-575 (1994).
GB 0920703.6 Search Report dated Mar. 10, 2010.
GB 1021390.8 Search Report dated Mar. 24, 2011.
GB 0920704.4 Examination Report dated Jul. 1, 2011.
Genet C et al., "Structure-Actrivity Relationship Study of Betulinic Acid. A Novel and Selective TGR6 Agonist. and its Synthetic Derivatives: Potential Impact in Diabetes," J Med. Chem. 2010, 53, 178-90.
Geyer et al., "The solute carrier family SLC 10: More than a family of bile acid transporters regarding function and phylogenetic relationships," Naunyn-Schmiedeberg's Archives of Pharmacology, 372(6):413-431 (2006).
Hofmann H and Dickert F, "The dynamic behaviour of the 1-methyl-1-benzothiepinium ring system." Z Naturforsch. B Anorg. Chem. Org Chem. 36(8):974-977 (1981).
Hofmann H and Djafari H, "Heterocyclic seven membered ring compounds, xxviii . on 5-acetoxy-and-5-methoxy-1-benzothiepine and analogous 1-benzoxepines," Liebigs Ann. Chem. 3:599-604 (1985).
Hofmann H and Djafari H. "Heterocyclic seven-membered ring compounds, xxxiv. A simple synthesis of 1-benzoxepine and 1-benzothiepine," Z. Natuforsch. B 44(2):220-224 (1989).
Hofmann H and Heidrich R, "Heterocyclic seven-membered ring compounds, xxiIl. Synthesis and thermolytic behavior of 2-methyl-4-phenyl-1-benzothiepins" Z. Naturforsch. B 34(8): 1145-1148 (1979).
Hofmann H and Heidrich R, "Heterocyclic seven-membered ring compounds, xxiv Photochemical reaction of 2-methyl-4-phenyl-1-benzothiepins," Z. Naturforsch. B. Anorg. Chem. Org Chem 37(10) 1344-1345 (1982).
Hofmann H and Loew G., "Heterocyclic seven membered ring compounds, xxvii. Synthesis and thermal reactivity of 1,2 -dimethyl-4-phenyl-1-benzothiopinium salts," Z. Naturforsch. B Anorg Chem Org. Chem. 39(7):985-989 (1984).
Hofmann H et al , "Heterocyclic seven-membered ring compounds, xxv—synthesis and thermolysis of substituted 1-methyl-4-phenyl-1-benzolhiepinium salts," Liebigs Ann. Chem. 3:425-432 (1983).
Hofmann H et al., "Synthesis of stable 1-benzothiepins," Angew Chem Int Ed. Engl. 11(5) 423-424 (1972).
Hofmann H and Djafari H. "Heterocyclic seven-membered ring compounds. xxxi. the photochemical behaviour of monosubstituted 1-benzothiopines," Liebigs Ann. Chem 505-508 (1987).

Holquist et al., "FDA safety page: Delayed-release vs. extended release Rxs." Drug Topics [online] Jul. 23, 2007 [Retrieved on Jul. 30, 2012| Retrieved from the Internet: https://www.drugtopics.com/pharmacy/fda-safety-page-delayed-release-vs-extended-release-rxs.
Hosny E.A. et al., "Evaluation of efficiency of insulin suppository formulations containing sodium salicylate or sodium cholate in insulin dependent diabetic" Chiico Farmceutico 142:361-366 (2003).
Hosny E.A. et al., "Effect of Different Bile Salts on the Relative Hypoglycemia of Witepsol W35 Suppositories Containing Insulin in Diabetic Beagle Dogs," Drug Dev Ind Pharm. 2001, 27, 837-845.
Hosny E.A., "Relative Hypoglycemia of Rectal Insulin Suppositories Containing Deoxycholic Acid, Sodium Taurocholate, Polycarbophil, and Their Combinations in Diabetic Rabbits," Drug Dev Ind. Pharm. 1999, 25, 745-752.
Huckle et al., "4-amino-2,3,4,5-terlahydro-1-benzoxepin-5-ois. 4-amino-2,3,4,6-tetrahydro-1-benzothiepin-5-ols and related compounds." J. Chem. Soc. C 12.2252-2260 (1971).
International Search Report dated Jan. 19, 2012, which issued during prosecution of International Application No. PCT/US2011/038251.
International Search Report dated Jul. 27, 2010, which issued during prosecution of International Application No. PCT/US09/065687.
International Search Report dated Mar. 2, 2010, which issued during prosecution of International Application No. PCT/EP2009/003102.
Ishino Y et al., "Novel Synthesis of 4,5-Bis(arylthio)-2,3,4,6-tetrahydro-1-benzathiepinis Noteworthy Cyclization by the Reaction of 2-Butynedion with Arenthiols in the Presence of Zinc Iodide.", Communications, pp. 827-829, 1987.
Ito et al., "Benzoxepinopyridine derivatives," Chemical Abstracts, 121:1161 (1994).
J.G. Cannon, Chapter Nineteen in Burger's Medicinal Chemistry and Drug Discovery, Fifth Edition, vol. I: Principles and Practice, Wiley-Interscience 1995, pp. 783-802.
Jilek J et al., "8-Chloro and 8-Methylthio Derivatives of 10-Piperazino-10,11-DiHydrodisenzo[b,f]Thiepins: New Compounds and New Procedures", Neurotropic and Psychotropic Agents: Part CLXXXVII. Journal 48, pp. 906-927 (1983).
Journal Bioorganicheskaya khimiya. (Bioorganic chemistry), Publisher Nauka, Academy of Sciences of the USSR, v. 9, No. 10, 1983, pp. 1357-1358 and partial translation.
Journal of organic chemistry, Publisher Nauka, Russian Academy of Sciences. v. 34. Issue 3. p 324, 1998 and partial translation.
Katsuma et al., "Bile acids promote glucagon-like peptide-1 secretion through TGR6 in a murine enteroendocrine cellline STC-1," Biochem Biophys Res Commun 329(1) 386-390 (2005).
Kawamata Y et al., "A G Protein-coupled Receplor Responsive to Bile Acid." J. Biol. Chem. 2003, 278, 9435-9440.
Khailova et al., "Inhibition of the apical sodium-dependent bile acid transporter in experimental necrotizing enterocolitis" DatabaseBIOSIS Apr. 2007 XP002715581. Database accession No. PREV200700602750 *abstract* & Gastroenterology, vol. 132, No. 4 Suppl. Apr. 2, 2007 (Apr. 2007), p. A57.
Khimiko-farmatsevticheskij zhurnal, (Chemical and pharmaceutical journal), Moscow, Meditsina, Ministry of medical and microbiological industry of the USSR, 1998, No. 8, and partial translation.
Khimiko-farmatsevticheskij zhurnal, (Chemical -and -pharmaceutical journal), Moscow, Meditsina, Ministry of medical industry of the USSR. monthly science-engineering and production journal, 1982. v XVI. No. 2, pp. 173-176 and partial translation.
Khimiko-farmatsevticheskij zhurnal. (Chemical -and -pharmaceutical journal), Moscow, Meditsina, Ministry of medical industry of the USSR, monthly science-engineering and production journal. 1985. v. XIX. No 9, pp. 1057-1060 and partial translation.
Khimiko farmatsevticheskij zhumal, (Chemical and pharmaceutical journal), Moscow, Meditsina, Ministry of medical industry of the USSR, monthly science-engineering and production journal, 1965, v. XIX, No. 9, pp. 1080-1086 and partial translation.
Khimiko farmatsevticheskij zhumal, (Chemical and -pharmaceutical journal), 1984, V XVII, No. 9. pp. 1105-1110, and partial translation.
Kramer W et al., "Bile Acid Denved HMG-CoA reductase inhibitors", Biochimica et Biophysica Acta 1227, pp. 137-154 (1994).

(56) References Cited

OTHER PUBLICATIONS

Kvis F et al., "Benzocycloheptenes and Heterocyclic Analogues as Potential Drugs VII. 4-Phenyl-2,3,4,5-Tetrahydro-1-Benzothiepins and some related compounds", Collection Czechoslov. Chem Comm . 37:3808-3816 (1972).
Lee et al . "Metforming Decreases Food Consumption and Induces Weight Loss in Subjects with Obesity with Type II Non-Insulin-Dependent Diabetes," Obesity Research, 6(1) 47-53 (1998).
Lenz G.R., "The Synthesis of the Isoquinoline Alkaloid Calycotomine via Functionalization of Enamide Double Bonds" Department of Medicinal Chemistry, G.D. Searle & Company, Heterocycles, 26(3) 721-730 (1987).
Lim and Brubaker, "Glucagon-like peptide 1 secretion by the t-cell," Diabetes 55(Supp 2):S70-77 (2006).
Huang (Tremont) et al., "Discovery of potent, nonsystemic apical sodium-codependent bile acid transporter inhibitors (Part 1)," J. Med Chem 48(18):5837-52 (2005).
Huang et al., "Discovery of potent nonsystemic apical sodium-codependent bile acid transporter inhibitors (Part 2)," J. Med. Chem. 48(18):5853-68 (2005).
Lykaviris et al , "Outcome of liver disease in children with Alagile Syndrome: a study of 163 patients" Gut, 49:431-435 (2001).
Sun et al., "Sorting of rat liver and ileal sodium-dependent bile acid transporters in polarized epithelial cells", Am. J. Physiol., Nov. ; 275 (5Pt 1) G1 045-55 (1998).
Supplementary European Search Report dated Sep. 2, 2014, which issued during prosecution of European Application No. 12801442.0, which corresponds to the present application.
Adrian et al., "Effect of peptide YY on Gastric, Pancreatic, and Binary Function in humans," Gastroenterology 89 (3):494-499 (1985).
Adrian et al., "Peptide YY abnormalities in gastrointestinal diseases" Gastroenterology 90(2):379-84 (1986).
Al-Saffar et al., "Correlation between Peptide YY-Induced Mycelectric Activity and Transit of Small-Intestinal Contents in Rats" Scand. J. Gatroenterol 20(5):577-82 (1986).
Amelsberg et al., Evidence for an anion exchange mechanism for uptake of conjugated bile acid from the rat jejunum Am. J. Physiol. Gastrointest. Liver Physiol. 276(3 Pt 1):G737-42 (1999).
Annunziato et al., "Orthotopic liver transplantation for adults with Alagille syndrome", Clin. Transplant. 26:E94-E100 (2012).
Bhat et al., "Inhibition of ileal bile acid transport and reduced atherosclerosis in apoE-/-mice by SC-435." J Lipid Res. 44(9) 1614-21 (2003).
Bogdanos et al., "What is New in Primary Biliary Cirrhosis", Dig Dis. 30 (suppl-1) (2012).
Chance et al , "Preservation of intestine protein by peptide YY during total parenteral nutrition" Life Sci 58 (21): 1785-1794 (1996).
Chen et al , "PYY and NPY: control of gastric motilily via action on Y1 and Y2 receptors in the DVC" Neurogastroenterol Motil. 9(2):109-16 (1997).
Claudel et al., "Role of nuclear receptors for bile acid metabolism, bile secretion,cholestasis, and gallstone disease" Biochim Biophys Acta 1812(8):867-78 (2011).
Davit-Spraul etal., "Progressive familial intrahepatic cholestasis", Orphanet Journal of Rare Diseases 2009, 12 pgs.
Dawson et al., "Bile Acid Transporters," Journal of Lipid Research, 50:2340-2357 (2009).
Derig et al., "Novel ATP881 mulation in an adult male with progressive familial intrahepatic cholestasis", WJG. 18 (44):6504-6509 (2012).
Dixon et al., "Bile reflux gastritis and Barrett's oesophagus, further evidence of a role for duodengastro-oesophageal reflux?" Gut 49(3):359-363 (2001).
Dixon et al., "Bile reflux gastritis and intestinal metaplasia at the cardia" Gut 51:351-355 (2002).
Emerick et al., "Features of Alagille Syndrome in 92 Patients: Frequency and Relation to Prognosis", Hepatology 29 (3):822-829 (1999).
European Associatian for the Study of the Liver, EASL Clinical Practice Guidelines: Management of cholestatic liver diseases, Journal of Hepatology, 51:237-267 (2009).
Fischler et al., "Cholestatic liver disease in adults may be due to an inherited defect in bile acid biosynthesis" Journal of International Medicine, 262:254-262 (2007).
Fu Cheng et al., "Antisceretory effect of peptide YY through neural receptors in the rat jejunum in vitro" Peptides 20:987-93 (1999).
Gomez et al , "Intestinal peptide YY: onfogeny of gene expression in rat bowel and trophic actions on rat and mouse bowel" Am. J. Physiol. 268(1 Pt 1):G71-81 (1995).
Goodlad et al. Is peptide YY trophic to the intestinal epithelium of parenterally fed rats? Digestion 46:Suppl 2:177-81 (1990).
Gully et al., "Peripheral biological activity of SR 27897: a new potent non-peptide antagonist of CCKA receptors" Eur. J Pharmacol 232:13-19 (1993).
Hagenbuch et al.. "Functional expression cloning and characterization of the hepatocyte Na +/bile acid cotransport system" PNAS (USA) 88:10629-33 (1991).
Hara, Drugs of the Future. 24 425-430 (1999).
Hartwig et al., Surgery 2007, 142:327-336.
Hines, "The ontogeny of drug metabolism enzymes and implications for adverse drug events", Pharmacology & Therapeutics, 118:250-267 (2008).
Hoentjen et al., "Effect of circulating peptide YY on gallbladder emptying in humans" Scand. J. Gastroenterol. 36:1086-1091 (2001).
International Preliminary Report on Patentability and Written Opinion of the International Searching Authority dated Feb. 13, 2013, which issued during prosecution of International Application No. PCT/US2012/049637.
International Search Report dated Feb. 28, 2013, which issued during prosecution of International Application No. PCT/US2012/049637.
International Search Report dated Mar. 14, 2013, which issued during prosecution of International Application No. PCT/US2012/062284.
International Search Report dated Mar. 29, 2013, which issued during prosecution of International Application No. PCT/US2012/062303.
Jacquet et al., "Alagille Syndrome in Adult Patients: It is Never Too Late", Amer. Journal of Kidney Disease, 49 (5): 705-709 (2007).
Jansen et al , "The molecular genetics of tamilial intraheptic cholestasis", Downloaded from gut bmj com on Mar. 7, 2014.
Johann-Liang et al., "Pediatric drug surveillance and the food and drug administration's adverse event reporting system, an overview of reports, 2003-2007", Pharmacoepidemiology and drug safety 18:24-27 (2009).
Kamath et al , "Conseqeunces of JAG1 mutations", J Med Genet, 40:891-895 (2003).
Kamath et al., "Medical Management of Alagille Syndrome", JPGN, 50(6) 580-586 (Jun. 2010).
Kawakubi et al., "Intracisternal PYY inhibits gastric lesions induced by ethanol in rats role of PYY-preferring receptors?" Brai Res 854:30 (2000).
Kearns et al., "Developmental Pharmacology—Drug Disposition, Action, and Therapy in Infants and Children", N Engl J Med, 349:1157-67 (2003).
Kramer and Glombik, "Bile acid reabsorption inhibitors (BARI) novel hypolipidemic drugs." Curr Med Chem (9):997 1016 (2006).
Krantz et al., "Alagille syndrome", J Med Genet, 34:152-157 (1997).
Kronsten et al., "Management of Cholestatic Pruritis in Paediatric Patients with Alagille Syndrome: The King's College Hospital Expenence", JPGN. 57(2):149-154 (Aug. 2013).
Lindor et al. "Primary Biliary Cirrhosis", Hepatology, pp. 291-308 (Jul. 2009).
Liu et al., "Intraluminal peptide YY induces colonic absorption in vivo" Dis Colon Rectum. 40:278-82 (1997).
Lynch et al., "Cell proliferation in the gastric corpus in Helicobacter pylori associated gastritis and after gastric resection" Gut 26:351-353 (1995).

(56) References Cited

OTHER PUBLICATIONS

Marzioni et al. "Exendin-4, a glucagon-like peptide 1 receptor agonist, protects cholanglocyles from apoptosis" Gut 58:990-7 (2009).
Vejdelek Z and Profiva M., Synthetic experiments aiming at 1,2,4,5-tetrahydro-3-benzothiepin derivatives,: Collect. Czech CHem. Commun. 55(9):2351-2356 (1990).
Viou, F, Thesis, Syntheses d'heterocycles derives do disubstitute-3,4-benzenethiol a potentialite anti allergique [Synthesis of heterocycles derived from 3,4-disubstituted benzenethiol, potent antiallergies,] Montpellier Univ. France (1986).
Watanabe, "Bile acids and diabetes" Functional Food. Apr. 2008, vol. 2, No. 1 p. 57-63.
Wess G et al., "Synthesis and Biological Activity of Bile Acid-Derived HMG-CoA Reductase Inhibitors. The Role of 21-Methyl in Recognition of HMG-CoA Reductase and the Ileal Bile Acid Transport System", J Med. Chem, pp. 3240-3246 (1994).
West et al, "SC-435, an ileal apical sodium-codependent bile acid transporter inhibitor alters mRNA levels and enzyme activities of selected genes involved in hepatic cholesterol and lipoprotein metabolism in guinea pigs" Journal of Nutritional Biochemistry, 16(12):722-728 (2005).
Wu S.V et al., "Expression of bitter taste receptors of the T2R family in the gastrointestinal tract and enteroendocrine STC-1 cells," Proc. Natl. Acad Sci 2002, 99:2392-2397.
Wynne et al, "Appetite control," J Endocrinol 184:291-318 (2006).
Yamamoto et al., "Colon-specific delivery of peptide drugs and anti-inflammatory drugs using chitosan capsules," Sciences Techniques et Pratiques 10:23-34 (2000).
Ziv E et al., "Bile Salts Promote the Absorption of Insulin from the Rat Colon," Life Sci 1981, 29, 803-909.
Emerick et al., "Partial External Biliary Diversion for Intractable Pruntis and Xanthomas in Alagille syndrome", Hepatology, 2002, 35:1501-1506.
Pinto et al. (Digestive Diseases and Sciences, vol. 41. No. Jan. 1, 1996).
Office Action mailed Apr. 6, 2020 in connection with Japanese Patent Application No. 2019-070187.
Hitoshi Kurata et al, A novel class of apical sodium-dependent bile acid transporter inhibitors the amphiphilic 4-oxo-1-phenyl-1,4-dihydroquinoline derivatives, Bioorganic & Medicinal Chemistry Letters 14. 1183-1186, (2004).
Office Action issued Mar. 17, 2020 in connection with Korean Patnt Application No. 10-2019-7034945.
Gyo-medical, Jun. 2011, vol. 43, No. 6,pp. 971-975 (documents showing common general technical knowledge [cited Jul. 7, 2020 by Examiner in office action application No. 2018-218627, 254409. 000108].
Office Action mailed Jul. 16, 2020 in connection with Japanese Patent Application No. 2018-218627.
Office Action mailed Jan. 28, 2021 in connection with Japanese Patent Application No. 2019-070187.
Tanaka Naomi, et al., an inventive step of the treatment of non obstructive banidioji for diagnosis of yasuhiis, gastroendoscope, and vol. 16, No. 1, pp. 97-101 (documents showing well-known arts, documents newly cited), published in 2004.
Office Action issued Feb. 17, 2021 in connection with Korean application No. 10-2019-7034945.
PubChem [Online]. "Maralixibat Chloride" (CID 9831642). [Retrieved Mar. 2, 2021]. Retrieved from the Internet: <URL: https://pubchem.ncbi.nlm nih .gov/compound/Maralixibat-chlonde> pp. 1-15. (Year 2021).
Quiros-Tejeira et al "Does Liver Transplantation Affect Growth Pattern in Allagille Syndrome?", Liver Transpl. 2000. 6:582-587. (Year: 2000).
Shneider et al. "Results of ITCH, A Multi-Center Randomized Double-Blind Placebo-Controlled Trial of Meralixibat, an iieal Apicalu Sodium-Dependent Bile Acid Transporter Inhibitor (ASBTi), for Pruntus in Alagille Syndrome (ALGS)", Hepatology, Oct. 2017, 66(S1):84A, Abstract 144, (Year: 2017).
Gonzales et al. "Phase 2 Open-Label Study with a Placebo-Controlled Drug Withdrawal Period of the Apical Sodium-Dependent V Bile Acid Transporter Inhibitor Maralixibat in Children with Alagille Syndrome 48 Week Interim Efficacy Analysis", Journal of Hepalology, Apr. 2019; 70:e119-120. Abstract PS-193. (Year: 2019).
Gonzales et al. "Durability of Treatment Effect with Long-Term Maralixibat in Children with Alagille Syndrome: 4-Year Safety and Efficacy Results from the ICONIC Study", Hepatology, Nov. 29, 2019, 70(6.Suppl.): Abstract L03, p. 1479A, (Year: 2019).
Shneider et al "Placebo-Controlled Randomized Trial of an Intestinal Bile Salt Transport Inhibitor for Pruritus in Alagille Syndrome", Hepatology Communications, 2018; 2(10):1184-1198. Published Online Sep. 24, 2018. (Year: 2018).
ISR mailed Jul. 29, 2020 in connection with PCT/US20/017941.
Watten Opinion mailed Jul. 29, 2020 in connection with PCT/US20/017941.
Al-Dury et al., "Ileal Bile Acid Transporter Inhibition for the Treatment of Chronic Constipation, Cholestatic Pruritus, and NASH", Frontiers In Pharmacology, 2018, vol. 9, Article 931. 8 pages, entire document, especially: abstract: p. 5, col. 2. para 4; p. 6, col. 1. para 2: p. 6, col. 1, para 3.
Lee et al., Primary Sclerosis Cholangitis (N. Engl. J. Med. 1995: 332; 924-933, Apr. 6, 1995).
Geenes et al., Intrahepatic cholestasis of pregnancy. World / Gastroenterol May 7, 2009, 15(17). 2049-2066.
Nov. 28, 2019 Office Action issued in connection with Chinese Patent Application No. 2017101531590.
Ali AH, Carey EJ, Lider KD. Current research on the treatment of primary sclerosing cholangitis. Intractable & rare diseases research. 2015;4(1): 1-6.
Chapman R, Fevery J. Kalloo A, Nagomey DM, Boberg KM, Shneider B, et al. Diagnosis and management of primary clerosing cholangitis. Hepatology (Baltimore, Md). 2010;51(2):660-78.
Chapman MH, Thorbum D, Hirschfield GM, Webster GGJ, Rushbrook SM, Alexander G, et al. British Society of astroenterology and UK-PSC guidelines for the diagnosis and management of primary sclerosing cholangitis Gut J019;68(8): 1356-78.
EASI European Association for the Study of the Liver Clinical Practice Guidelines: management of cholestatic liver diseases. Journal of hepatology_ 2009.51 (2):237-67.
Hegade VS, Kendrick SF, Dobbins RL, Miller SR, Thompson D, Richards D, et al Effect of ileal bile acid transporter nhibitor GSK2330672 on pruntus in primary biliary cholangitis a double blind, randomised, placebo-controlled, crossover, phase 2a study. Lancet (London, England). 2017.369(10074):1114-23. (Abstract Only).
Karlsen TH, Folseraas T, Thorburn D, Vesterhus M. Primary sclerosing cholangitis—a comprehensive review. Journal of hepatology . . . 2017.67(6):1298-323.
Lazaridis KN, LaRusso NF. Primary Sclerosing Cholangitis. The New England journal of medicine 2016;375 (12) 1161-70.
Lindor KD, Kowdley KV, Harrison ME. ACG Clinical Guideline: Primary Sclerosing Cholangitis. The American journal o Jastroenterology_2015;110(5):646-59; quiz 60. (Abstract Only).
Saffioti F, Gurusamy KS, Hawkins N, Toon CD, Tsochetzis E, Davidson BR, et al. Pharmacological interventions for primary sclerosing cholangitis: an attempted network meta-analysis. The Cochrane database of systematic reviews. 2017.3.Cd011343.
Davit-Spraul et al. Progressive familial intrahepatic cholestasis. Orphanet Journal of Rare Disease, 2009, 4:1.
Search Report issued May 23, 2023 in connection with Singapore Patent Application No. 10201903512S.
Written Opinion issued May 29, 2023 in connection with Singapore Patent Application No. 10201903512S.
Office Action issued Mar. 5, 2023 in connection with Japanese Patent Application No. 2022-14526.
Ko and Yoshiad, "Acute Fatty Liver of Pregnancy", (Can J. Gastroenterol., vol. 20, pp. 25-30, 2006).
Reagan-Shaw et al., "Dose Translation from Animal to Human Studies Revisited" (FASEBJ, vol. 22, pp. 659-661, published 2007). Year: 2007.

(56) References Cited

OTHER PUBLICATIONS

Search Report issued Oct. 24, 2023 in connection with Singapore Patent Application No. 10201909122Q.
Written Opinion issued Nov. 13, 2023 in connection with Singapore Patent Application No. 10201909122Q.
Office Action issued Dec. 20, 2023 in connection with U.S. Appl. No. 17/951,326.

* cited by examiner

LUM001 decreases serum bile acids AUC 0-15 hr in study NB4-02-06-003
(measured on day 14; * p<0.05, ** p<0.01 compared to placebo.)

LUM001 increases the mean daily total fecal bile acids in study NB4-02-06-003 (measured between day 23-28; * $p < 0.05$, ** $p < 0.01$ compared to placebo.)

BILE ACID RECYCLING INHIBITORS FOR TREATMENT OF PEDIATRIC CHOLESTATIC LIVER DISEASES

CROSS REFERENCE TO RELATED APPLICATIONS

This application is a continuation of U.S. application Ser. No. 17/498,586, filed Oct. 11, 2021, which is a continuation of U.S. application Ser. No. 16/679,864, filed Nov. 11, 2019, now U.S. Pat. No. 11,229,661, issued Jan. 15, 2022, which is a continuation of U.S. application Ser. No. 15/137,323, filed Apr. 25, 2016, now patented U.S. Pat. No. 10,512,657, issued Dec. 24, 2019, which is a continuation of U.S. application Ser. No. 13/866,906, filed Apr. 19, 2013, abandoned, which is a continuation of application Ser. No. 13/662,387, filed Oct. 26, 2012, abandoned, which claims the benefit under 35 U.S.C. § 119(e) of U.S. Provisional Application No. 61/607,487, filed Mar. 6, 2012, U.S. Provisional Application No. 61/607,503, filed Mar. 6, 2012, and U.S. Provisional Application No. 61/553,094, filed Oct. 28, 2011, which are incorporated herein by reference in their entirety.

BACKGROUND OF THE INVENTION

Pediatric cholestatic liver diseases affect a small percentage of children, but therapy results in significant healthcare costs each year. Currently, many of the pediatric cholestatic liver diseases require invasive and costly treatments such as liver transplantation and surgery. An effective and less invasive treatment that is suitable for the pediatric population is not available.

It is well understood and accepted that the therapeutic needs of children are sufficiently different than those of adults as to require specific studies of medications in children. For example, oral administration of a solid dosage form of medication is painless and simple for most adult patients, but for the pediatric patient population, swallowing an oral solid dosage form produced for adults can be problematic. In addition, the drugs used in solid dosages often have an unpleasant taste. More importantly, oral administration of adult medication targeting cholestatic liver diseases may result in side effects such as diarrhea and intestinal discomfort. Such problems pose a safety risk and affect compliance. Effective and acceptable forms of pediatric medication for pediatric cholestastatic liver diseases are needed.

SUMMARY OF THE INVENTION

Provided herein are therapeutic compositions and methods for treating or ameliorating a pediatric cholestatic liver disease or pediatric cholestasis. In certain embodiments, provided herein are methods for treating or ameliorating a pediatric cholestatic liver disease comprising non-systemically administering to a pediatric patient a therapeutically effective amount of a composition comprising an Apical Sodium-dependent Bile Transporter Inhibitor (ASBTI) or a pharmaceutically acceptable salt thereof. In certain embodiments, provided herein are methods for treating or ameliorating a pediatric cholestatic liver disease comprising administering to an individual in need thereof a therapeutically effective amount of a composition comprising a non-systemically absorbed ASBTI or a pharmaceutically acceptable salt thereof. In certain embodiments, provided herein are methods for treating or ameliorating a pediatric cholestatic liver disease comprising non-systemically administering to a pediatric patient a therapeutically effective amount of a pediatric dosage form comprising an Apical Sodium-dependent Bile Transporter Inhibitor (ASBTI) or a pharmaceutically acceptable salt thereof. In certain embodiments, provided herein are methods for treating or ameliorating a pediatric cholestatic liver disease comprising administering to an individual in need thereof a therapeutically effective amount of a pediatric dosage form comprising a non-systemically absorbed ASBTI or a pharmaceutically acceptable salt thereof.

In certain embodiments, provided herein are pediatric dosage forms comprising a pediatric dosage of a non-systemically absorbed Apical Sodium-dependent Bile Acid Transporter Inhibitor (ASBTI) or a pharmaceutically acceptable salt thereof. In some embodiments, provided herein are pediatric dosage forms comprising any non-systemically absorbed ASBTI or a pharmaceutically acceptable salt thereof described herein. In some embodiments, provided herein are pediatric dosage forms comprising any non-systemically absorbed ASBTI or a pharmaceutically acceptable salt thereof and a second agent described herein.

Provided herein are therapeutic compositions and methods for treating or ameliorating pruritis. In certain embodiments, provided herein are methods for treating or ameliorating pruritis comprising non-systemically administering to a pediatric patient suffering from a pediatric cholestatic liver disease a therapeutically effective amount of a composition comprising an ASBTI or a pharmaceutically acceptable salt thereof. In certain embodiments, provided herein are methods for treating or ameliorating pruritis comprising administering to an individual in need thereof a therapeutically effective amount of a composition comprising a non-systemically absorbed ASBTI or a pharmaceutically acceptable salt thereof. In certain embodiments, provided herein are methods for treating or ameliorating pruritis comprising non-systemically administering to a pediatric patient suffering from a pediatric cholestatic liver disease a therapeutically effective amount of a pediatric dosage form comprising an ASBTI or a pharmaceutically acceptable salt thereof. In certain embodiments, provided herein are methods for treating or ameliorating pruritis comprising administering to an individual in need thereof a therapeutically effective amount of a pediatric dosage form comprising a non-systemically absorbed ASBTI or a pharmaceutically acceptable salt thereof.

Provided herein are therapeutic compositions and methods for treating or ameliorating pediatric hypercholemia. In certain embodiments, provided herein are methods for treating or ameliorating pediatric hypercholemia comprising non-systemically administering to a pediatric patient a therapeutically effective amount of a composition comprising an ASBTI or a pharmaceutically acceptable salt thereof. In certain embodiments, provided herein are methods for treating or ameliorating pediatric hypercholemia comprising administering to an individual in need thereof a therapeutically effective amount of a composition comprising a non-systemically absorbed ASBTI or a pharmaceutically acceptable salt thereof. In certain embodiments, provided herein are methods for treating or ameliorating pediatric hypercholemia comprising non-systemically administering to a pediatric patient a therapeutically effective amount of a pediatric dosage form comprising an ASBTI or a pharmaceutically acceptable salt thereof. In certain embodiments, provided herein are methods for treating or ameliorating pediatric hypercholemia comprising administering to an individual in need thereof a therapeutically effective amount of a pediatric dosage form comprising a non-systemically absorbed ASBTI or a pharmaceutically acceptable salt thereof.

Provided herein are therapeutic compositions and methods for lowering serum bile acid concentrations or hepatic bile acid concentrations. In certain embodiments, provided herein are methods for decreasing serum bile acid levels or concentrations or hepatic bile acid levels or concentrations comprising non-systemically administering to a pediatric patient suffering from a pediatric cholestatic liver disease a therapeutically effective amount of a composition comprising an ASBTI or a pharmaceutically acceptable salt thereof. In certain embodiments, provided herein are methods for decreasing serum bile acids or hepatic bile acids comprising administering to an individual in need thereof a therapeutically effective amount of a composition comprising a non-systemically absorbed ASBTI or a pharmaceutically acceptable salt thereof. In certain embodiments, provided herein are methods for decreasing serum bile acid levels or concentrations or hepatic bile acid levels or concentrations comprising non-systemically administering to a pediatric patient suffering from a pediatric cholestatic liver disease a therapeutically effective amount of a pediatric dosage form comprising an ASBTI or a pharmaceutically acceptable salt thereof. In certain embodiments, provided herein are methods for decreasing serum bile acids or hepatic bile acids comprising administering to an individual in need thereof a therapeutically effective amount of a pediatric dosage form comprising a non-systemically absorbed ASBTI or a pharmaceutically acceptable salt thereof.

In some embodiments, compositions and methods provided herein decrease serum or hepatic bile acid levels by at least 50%, 45%, 40%, 35%, 30%, 25%, 20%, 15%, or 10%, as compared to the levels prior to administration of the compositions provided herein or as compared to control subjects. In some embodiments, methods provided herein decrease serum or hepatic bile acid levels by at least 30%. In some embodiments, methods provided herein decrease serum or hepatic bile acid levels by at least 25%. In some embodiments, methods provided herein decrease serum or hepatic bile acid levels by at least 20%. In some embodiments, methods provided herein decrease serum or hepatic bile acid levels by at least 15%.

Provided herein are therapeutic compositions and methods for treating or ameliorating xanthoma. In certain embodiments, provided herein are methods for treating or ameliorating xanthoma comprising non-systemically administering to a pediatric patient suffering from a pediatric cholestatic liver disease a therapeutically effective amount of a composition comprising an ASBTI or a pharmaceutically acceptable salt thereof. In certain embodiments, provided herein are methods for treating or ameliorating xanthoma comprising administering to an individual in need thereof a therapeutically effective amount of a composition comprising a non-systemically absorbed ASBTI or a pharmaceutically acceptable salt thereof. In certain embodiments, provided herein are methods for treating or ameliorating xanthoma comprising non-systemically administering to a pediatric patient suffering from a pediatric cholestatic liver disease a therapeutically effective amount of a pediatric dosage form comprising an ASBTI or a pharmaceutically acceptable salt thereof. In certain embodiments, provided herein are methods for treating or ameliorating xanthoma comprising administering in need thereof a therapeutically effective amount of a pediatric dosage form comprising a non-systemically absorbed ASBTI or a pharmaceutically acceptable salt thereof.

In some embodiments, provided herein are compositions and methods decreasing serum lipoprotein X levels or concentrations comprising non-systemically administering to a pediatric patient suffering from xanthoma a therapeutically effective amount of a composition comprising an ASBTI or a pharmaceutically acceptable salt thereof. In certain embodiments, provided herein are methods for decreasing serum lipoprotein X comprising administering to an individual in need thereof a therapeutically effective amount of a composition comprising a non-systemically absorbed ASBTI or a pharmaceutically acceptable salt thereof. In certain embodiments, provided herein are methods for decreasing serum lipoprotein X levels or concentrations comprising non-systemically administering to a pediatric patient suffering from xanthoma a therapeutically effective amount of a pediatric dosage form comprising an ASBTI or a pharmaceutically acceptable salt thereof. In certain embodiments, provided herein are methods for decreasing serum lipoprotein X comprising administering to an individual in need thereof a therapeutically effective amount of a pediatric dosage form comprising a non-systemically absorbed ASBTI or a pharmaceutically acceptable salt thereof.

In certain embodiments, described herein are compositions and methods for reducing serum levels of bilirubin, gamma-glutamyl transpeptidase or gamma-glutamyl transferase (GGT), or liver enzymes, such as alkaline phosphatase, ALT and AST, in an individual in need thereof comprising non-systemically administering a therapeutically effective amount of a composition of an ASBTI or a pharmaceutically acceptable salt thereof. In some embodiments, methods comprise administering a therapeutically effective amount of a composition comprising a non-systemically absorbed ASBTI or a pharmaceutically acceptable salt thereof. In certain embodiments, described herein are methods for reducing serum levels of bilirubin, gamma-glutamyl transpeptidase or gamma-glutamyl transferase (GGT), or liver enzymes, such as alkaline phosphatase, ALT and AST, in an individual in need thereof comprising non-systemically administering a therapeutically effective amount of a pediatric dosage form of an ASBTI or a pharmaceutically acceptable salt thereof. In some embodiments, methods comprise administering a therapeutically effective amount of a pediatric dosage form comprising a non-systemically absorbed ASBTI or a pharmaceutically acceptable salt thereof.

In certain embodiments, methods provided herein comprise administering compounds that inhibit the ASBT or any recuperative bile salt transporter. In certain embodiments, use of the compounds provided herein reduces or inhibits recycling of bile acid salts in the gastrointestinal tract. In some embodiments, the methods provided herein reduce intraenterocyte bile acids/salts or reduce necrosis and/or damage to intestinal or hepatocellular architecture.

In certain embodiments, the methods described herein treat or ameliorate a pediatric cholestatic liver disease by increasing intraluminal concentrations of bile acids/salts, which are then excreted in the feces, thereby reducing overall bile acid and serum bile acid or hepatic bile acid load in an individual in need thereof. In certain embodiments, increasing intraluminal bile acid concentrations according to methods described herein provide protection and/or control of the integrity of an individual's liver and/or intestine that has been injured by cholestasis and/or cholestatic liver disease.

In certain embodiments, the methods described herein treat or ameliorate pruritis by increasing intraluminal concentrations, and/or reducing serum concentrations, or hepatic concentrations of bile acids/salts in an individual in need thereof. In certain embodiments, increasing intraluminal bile acid concentrations according to methods described herein provide protection and/or control of the integrity of an individual's liver and/or intestine that has been injured by a cholestatic liver disease.

In certain embodiments, the methods described herein lower serum bile acid concentrations or hepatic bile acid concentrations by increasing intraluminal concentrations of bile acids/salts in an individual in need thereof. In certain embodiments, increasing intraluminal bile acid concentrations according to methods described herein provide protection and/or control of the integrity of an individual's liver and/or intestine that has been injured by a cholestatic liver disease.

In certain embodiments, provided herein is an ASBTI or a pharmaceutically acceptable salt thereof for use in the treatment of a pediatric cholestatic liver disease, wherein the ASBTI is non-systemically absorbed or is formulated to be non-systemically absorbed. In some embodiments, provided herein is a pharmaceutical composition for use in the treatment of a pediatric cholestatic liver disease, wherein the composition comprises a pediatric dosage form of an ASBTI and a pharmaceutically acceptable excipient, wherein the ASBTI is non-systemically absorbed or is formulated to be non-systemically absorbed. In some embodiments, a composition provided herein is suitable for non-systemically administering to the distal ileum, colon, and/or rectum.

In certain embodiments, provided herein is an ASBTI or a pharmaceutically acceptable salt thereof for use in the treatment of pruritis in a pediatric patient suffering from a pediatric cholestatic liver disease, wherein the ASBTI is non-systemically absorbed or is formulated to be non-systemically absorbed. In some embodiments, provided herein is a pharmaceutical composition for use in the treatment of pruritis, wherein the composition comprises a pediatric dosage form of an ASBTI and a pharmaceutically acceptable excipient, wherein the ASBTI is non-systemically absorbed or is formulated to be non-systemically absorbed. In some embodiments, a composition provided herein is suitable for non-systemically administering to the distal ileum, colon, and/or rectum.

In certain embodiments, provided herein is an ASBTI or a pharmaceutically acceptable salt thereof for use in lowering serum bile acid concentrations or hepatic bile acid concentrations in a pediatric patient suffering from a pediatric cholestatic liver disease, wherein the ASBTI is a non-systemically absorbed or is formulated to be non-systemically absorbed. In some embodiments, provided herein is a pharmaceutical composition for use in lowering serum bile acid concentrations or hepatic bile acid concentrations, wherein the composition comprises a pediatric dosage form of an ASBTI and a pharmaceutically acceptable excipient, wherein the ASBTI is non-systemically absorbed or is formulated to be non-systemically absorbed. In some embodiments, a composition provided herein is suitable for non-systemically administering to the distal ileum, colon, and/or rectum.

In some embodiments, an ASBTI provided herein is minimally absorbed or formulated to be minimally absorbed. In some embodiments, a pediatric dosage form of an ASBTI is non-systemically administered to the distal ileum, colon, and/or rectum of an individual in need thereof. In some embodiments, an ASBTI is non-systemically administered to the ileum, colon or rectum of an individual in need thereof. In some embodiments, less than 50%, less than 40%, less than 30%, less than 20%, less than 10%, less than 9%, less than 8%, less than 7%, less than 6%, less than 5%, less than 4%, less than 3%, less than 2%, or less than 1% of the ASBTI is systemically absorbed. In a preferred embodiment, less than 10% of the ASBTI is systemically absorbed. In another preferred embodiment, less than 5% of the ASBTI is systemically absorbed. In another preferred embodiment, less than 1% of the ASBTI is systemically absorbed.

In one aspect, provided herein is a method for treating a pediatric cholestatic liver disease in an individual in need thereof comprising non-systemically administering to the distal gastrointestinal tract of the individual in need thereof a therapeutically effective amount of a pediatric dosage form of an ASBTI or a pharmaceutically acceptable salt thereof. In one aspect, provided herein is a method for treating pruritis in an individual in need thereof comprising non-systemically administering to the distal gastrointestinal tract of the individual in need thereof a therapeutically effective amount of a pediatric dosage form of an ASBTI or a pharmaceutically acceptable salt thereof. In one aspect, provided herein is a method for lowering serum bile acid concentrations in an individual in need thereof comprising non-systemically administering to the distal gastrointestinal tract of the individual in need thereof a therapeutically effective amount of a pediatric dosage form of an ASBTI or a pharmaceutically acceptable salt thereof. In some embodiments, the distal gastrointestinal tract is jejunum, ileum, colon, or rectum. In some embodiments, the distal gastrointestinal tract is ileum, colon, or the rectum. In some embodiments, the distal gastrointestinal tract is jejunum. In some embodiments, the distal gastrointestinal tract is ileum.

In certain embodiments, the pediatric cholestatic liver disease is progressive familial intrahepatic cholestasis (PFIC), PFIC type 1, PFIC type 2, PFIC type 3, Alagille syndrome, Dubin-Johnson Syndrome, biliary atresia, post-Kasai biliary atresia, post-liver transplantation biliary atresia, post-liver transplantation cholestasis, post-liver transplantation associated liver disease, intestinal failure associated liver disease, bile acid mediated liver injury, pediatric primary sclerosing cholangitis, MRP2 deficiency syndrome, neonatal sclerosing cholangitis, a pediatric obstructive cholestasis, a pediatric non-obstructive cholestasis, a pediatric extrahepatic cholestasis, a pediatric intrahepatic cholestasis, a pediatric primary intrahepatic cholestasis, a pediatric secondary intrahepatic cholestasis, benign recurrent intrahepatic cholestasis (BRIC), BRIC type 1, BRIC type 2, BRIC type 3, total parenteral nutrition associated cholestasis, paraneoplastic cholestasis, Stauffer syndrome, drug-associated cholestasis, infection-associated cholestasis, or gallstone disease. In some embodiments, the pediatric cholestatic liver disease is a pediatric form of liver disease described herein.

In certain embodiments, a pediatric cholestatic liver disease is characterized by one or more symptoms selected from jaundice, pruritis, cirrhosis, hypercholemia, neonatal respiratory distress syndrome, lung pneumonia, increased serum concentration of bile acids, increased hepatic concentration of bile acids, increased serum concentration of bilirubin, hepatocellular injury, liver scarring, liver failure, hepatomegaly, xanthomas, malabsorption, splenomegaly, diarrhea, pancreatitis, hepatocellular necrosis, giant cell formation, hepatocellular carcinoma, gastrointestinal bleeding, portal hypertension, hearing loss, fatigue, loss of appetite, anorexia, peculiar smell, dark urine, light stools, steatorrhea, failure to thrive, and/or renal failure.

In certain embodiments, the pediatric patient is a new born, a pre-term new born, an infant, a toddler, a pre-schooler, a school-age child, a pre-pubescent child, post-pubescent child, an adolescent, or a teenager under the age of eighteen. In some embodiments, the pediatric patient is a new born, a pre-term new born, an infant, a toddler, a pre-schooler, or a school-age child. In some embodiments, the pediatric patient is a new born, a pre-term new born, an infant, a toddler, or a pre-schooler. In some embodiments, the pediatric patient is a new born, a pre-term new born, an infant, or a toddler. In some embodiments, the pediatric patient is a new born, a pre-term new born, or an infant. In some embodiments, the pediatric patient is a new born. In some embodiments, the pediatric patient is an infant. In some embodiments, the pediatric patient is a toddler.

In certain embodiments, the individual is an infant less than 2 years of age. In some cases, for any of the methods and/or compositions described herein, the individual is an infant between 0 to 18 months of age. In some cases, for any of the methods and/or compositions described herein, the individual is an infant between 1 to 18 months of age. In some cases, for any of the methods and/or compositions described herein, the individual is an infant between 2 to 18 months of age. In some cases, for any of the methods and/or compositions described herein, the individual is an infant between 3 to 18 months of age. In some cases, for any of the methods and/or compositions described herein, the individual is an infant between 4 to 18 months of age. In some cases, for any of the methods and/or compositions described herein, the individual is an infant between 6 to 18 months of age. In some cases, for any of the methods and/or compositions described herein, the individual is an infant between 18 to 24 months of age. In some cases, for any of the methods and/or compositions described herein, the individual is an infant between 6 to 12 months of age. In some instances, for any of the methods and/or compositions described herein, the individual is a child of between about 2 to about 10 years of age. In some instances, the individual is less than about 10 years old. In some instances, the individual is between about 10 to about 17 years old.

In some cases, for any of the methods and/or compositions described herein, the individual is a child between 6 months to 12 years of age.

Provided herein, in certain embodiments, are therapeutic methods and compositions using compounds that inhibit the Apical Sodium-dependent Bile Transporter (ASBT) or a pharmaceutically acceptable salt thereof, or any recuperative bile salt transporter for treatment of a pediatric cholestatic liver disease or pruritis or for lowering serum bile acid concentrations. In certain instances, use of the compounds provided herein reduces or inhibits recycling of bile acid salts in the gastrointestinal tract. In some embodiments, the methods provided herein reduce intraenterocyte bile acids/salts and/or damage to ileal or hepatocellular architecture caused by a pediatric cholestatic liver disease and/or allow for regeneration of the intestinal lining or liver. In some embodiments, the bile transport inhibitors are non-systemic compounds. In other embodiments, the bile acid transporter inhibitors are systemic compounds delivered non-systemically. In other embodiments, the bile acid transporter inhibitors are systemic compounds. In certain embodiments, the bile transport inhibitors described herein enhance enteroendocrine peptide secretion by intestinal L-cells.

In some embodiments of the methods described above, the ASBTI is a compound of Formula I or a pharmaceutically acceptable salt thereof, as described herein. In some embodiments of the methods described above, the ASBTI is a compound of Formula II or a pharmaceutically acceptable salt thereof, as described herein. In some embodiments of the methods described above, the ASBTI is a compound of Formula III or a pharmaceutically acceptable salt thereof, as described herein. In some embodiments of the methods described above, the ASBTI is a compound of Formula IV or a pharmaceutically acceptable salt thereof, as described herein. In some embodiments of the methods described above, the ASBTI is a compound of Formula V or a pharmaceutically acceptable salt thereof, as described herein. In some embodiments of the methods described above, the ASBTI is a compound of Formula VI or Formula VID or a pharmaceutically acceptable salt thereof, as described herein.

In some embodiments, provided herein is a method for treating or ameliorating a pediatric cholestatic liver disease comprising non-systemically administering to an individual in need thereof a therapeutically effective amount of a pediatric dosage form of an ASBTI of Formula I or a pharmaceutically acceptable salt thereof. In some embodiments, provided herein is a method for treating or ameliorating pruritis comprising non-systemically administering to an individual in need thereof a therapeutically effective amount of a pediatric dosage form of an ASBTI of Formula I or a pharmaceutically acceptable salt thereof. In some embodiments, provided herein is a method for increasing the levels of an enteroendocrine peptide or hormone in an individual suffering from a pediatric cholestatic liver disease comprising non-systemically administering to the individual in need thereof a therapeutically effective amount of a pediatric dosage form of an ASBTI of Formula I or a pharmaceutically acceptable salt thereof. In some embodiments, provided herein is a method for lowering serum bile acid concentrations or hepatic bile acid concentration comprising non-systemically administering to an individual in need thereof a therapeutically effective amount of a pediatric dosage form of an ASBTI of Formula I or a pharmaceutically acceptable salt thereof.

In some embodiments, provided herein is a method for treating or ameliorating a pediatric cholestatic liver disease comprising non-systemically administering to an individual in need thereof a therapeutically effective amount of a pediatric dosage form of an ASBTI of Formula II or a pharmaceutically acceptable salt thereof. In some embodiments, provided herein is a method for treating or ameliorating pruritis comprising non-systemically administering to an individual in need thereof a therapeutically effective amount of a pediatric dosage form of an ASBTI of Formula II or a pharmaceutically acceptable salt thereof. In some embodiments, provided herein is a method for increasing the levels of an enteroendocrine peptide or hormone in an individual suffering from a pediatric cholestatic liver disease comprising non-systemically administering to the individual in need thereof a therapeutically effective amount of a pediatric dosage form of an ASBTI of Formula II or a pharmaceutically acceptable salt thereof. In some embodiments, provided herein is a method for lowering serum bile acid concentrations or hepatic bile acid concentration comprising non-systemically administering to an individual in need thereof a therapeutically effective amount of a pediatric dosage form of an ASBTI of Formula II or a pharmaceutically acceptable salt thereof.

In some embodiments, provided herein is a method for treating or ameliorating a pediatric cholestatic liver disease comprising non-systemically administering to an individual in need thereof a therapeutically effective amount of a pediatric dosage form of an ASBTI of Formula III or a pharmaceutically acceptable salt thereof. In some embodiments, provided herein is a method for treating or ameliorating pruritis comprising non-systemically administering to an individual in need thereof a therapeutically effective amount of a pediatric dosage form of an ASBTI of Formula III or a pharmaceutically acceptable salt thereof. In some embodiments, provided herein is a method for increasing the levels of an enteroendocrine peptide or hormone in an individual suffering from a pediatric cholestatic liver disease comprising non-systemically administering to the individual in need thereof a therapeutically effective amount of a pediatric dosage form of an ASBTI of Formula III or a pharmaceutically acceptable salt thereof. In some embodiments, provided herein is a method for lowering serum bile acid concentrations or hepatic bile acid concentration comprising non-systemically administering to an individual in need thereof a therapeutically effective amount of a pediatric dosage form of an ASBTI of Formula III or a pharmaceutically acceptable salt thereof.

In some embodiments, provided herein is a method for treating or ameliorating a pediatric cholestatic liver disease comprising non-systemically administering to an individual in need thereof a therapeutically effective amount of a pediatric dosage form of an ASBTI of Formula IV or a pharmaceutically acceptable salt thereof. In some embodiments, provided herein is a method for treating or ameliorating pruritis comprising non-systemically administering to an individual in need thereof a therapeutically effective amount of a pediatric dosage form of an ASBTI of Formula IV or a pharmaceutically acceptable salt thereof. In some embodiments, provided herein is a method for increasing the levels of an enteroendocrine peptide or hormone in an individual suffering from a pediatric cholestatic liver disease comprising non-systemically administering to the individual in need thereof a therapeutically effective amount of a pediatric dosage form of an ASBTI of Formula IV or a pharmaceutically acceptable salt thereof. In some embodiments, provided herein is a method for lowering serum bile acid concentrations or hepatic bile acid concentration comprising non-systemically administering to an individual in need thereof a therapeutically effective amount of a pediatric dosage form of an ASBTI of Formula IV or a pharmaceutically acceptable salt thereof.

In some embodiments, provided herein is a method for treating or ameliorating a pediatric cholestatic liver disease comprising non-systemically administering to an individual in need thereof a therapeutically effective amount of a pediatric dosage form of an ASBTI of Formula V or a pharmaceutically acceptable salt thereof. In some embodiments, provided herein is a method for treating or ameliorating pruritis comprising non-systemically administering to an individual in need thereof a therapeutically effective amount of a pediatric dosage form of an ASBTI of Formula V or a pharmaceutically acceptable salt thereof. In some embodiments, provided herein is a method for increasing the levels of an enteroendocrine peptide or hormone in an individual suffering from a pediatric cholestatic liver disease comprising non-systemically administering to the individual in need thereof a therapeutically effective amount of a pediatric dosage form of an ASBTI of Formula V or a pharmaceutically acceptable salt thereof. In some embodiments, provided herein is a method for lowering serum bile acid concentrations or hepatic bile acid concentration comprising non-systemically administering to an individual in need thereof a therapeutically effective amount of a pediatric dosage form of an ASBTI of Formula V or a pharmaceutically acceptable salt thereof.

In some embodiments, provided herein is a method for treating or ameliorating a pediatric cholestatic liver disease comprising non-systemically administering to an individual in need thereof a therapeutically effective amount of a pediatric dosage form of an ASBTI of Formula VI or a pharmaceutically acceptable salt thereof. In some embodiments, provided herein is a method for treating or ameliorating pruritis comprising non-systemically administering to an individual in need thereof a therapeutically effective amount of a pediatric dosage form of an ASBTI of Formula VI or a pharmaceutically acceptable salt thereof. In some embodiments, provided herein is a method for increasing the levels of an enteroendocrine peptide or hormone in an individual suffering from a pediatric cholestatic liver disease comprising non-systemically administering to the individual in need thereof a therapeutically effective amount of a pediatric dosage form of an ASBTI of Formula VI or a pharmaceutically acceptable salt thereof. In some embodiments, provided herein is a method for lowering serum bile acid concentrations or hepatic bile acid concentration comprising non-systemically administering to an individual in need thereof a therapeutically effective amount of a pediatric dosage form of an ASBTI of Formula VI or a pharmaceutically acceptable salt thereof.

In certain embodiments, an ASBTI is any compound described herein that inhibits recycling of bile acids/salts in the gastrointestinal tract of an individual. In certain embodiments, an ASBTI is (–)-(3R,5R)-trans-3-butyl-3-ethyl-2,3,4,5-tetrahydro-7,8-dimethoxy-5-phenyl-1,4-benzothiazepine 1,1-dioxide; ("Compound 100A") or any other salt or analog thereof. In certain of any of the aforementioned embodiments, an ASBTI is 1-[4-[4-[(4R,5R)-3,3-dibutyl-7-(dimethylamino)-2,3,4,5-tetrahydro-4-hydroxy-1,1-di-oxido-1-benzothiepin-5-yl]phenoxy]butyl]4-aza-1-azoniabicyclo[2.2.2]octane methane sulfonate salt ("Compound 100B") or any other salt or analog thereof. In certain embodiments, an ASBTI is N, N-dimethylimido-dicarbonimidic diamide ("Compound 100C") or any salt or analog thereof. In certain embodiments, an ASBTI is any commercially available ASBTI including but not limited to SD-5613, A-3309, 264W94, S-8921, SAR-548304, BARI-1741, HMR-1453, TA-7552, R-146224, or SC-435. In some embodiments, an ASBTI is 1,1-dioxo-3,3-dibutyl-5-phenyl-7-methylthio-8-(N—{(R)-α-[N—((R)-1-carboxy-2-methyl-thio-ethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxybutyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxyethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]

benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—{(S)-1-[N—((S)-2-hydroxy-1-carboxyethyl)carbamoyl]propyl}carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-[N—{(R)-α-carboxy4-hydroxybenzyl}carbamoylmethoxy]-2,3,4,5-tetrahydro-1,2,5-benzothiadiazepine; or 1,1-dioxo-3,3-dibutyl-5-phenyl-7-methylthio-8-(N—{(R)-α-[N-(carboxymethyl)carbamoyl]benzyl} carbamoylmethoxy)-2,3,4,5-benzothiadiazepine; 1,1-dioxo-3,3-dibutyl-5-phenyl-7-methylthio-8-(N—{(R)-1'-phenyl-1'-[N'-(carboxymethyl)carbamoyl] methyl}carbamoylmethoxy)-2,3,4,5-tetrahydro-1,5-benzothiazepine; 1,1-dioxo-3,3-dibutyl-5-phenyl-7-methylthio-8-(N—{(R)-α-[N'—((S)-1-carboxypropyl)carbamoyl]-4-hydroxybenzyl} carbamoylmethoxy)-2,3,4,5-tetrahydro-1,5-benzothiazepine; 1,1-dioxo-3,3-dibutyl-5-phenyl-7-methylthio-8-(N—{(R)-1'-phenyl-1'-[N'-(carboxymethyl) carbamoyl] methyl} carbamoylmethoxy)-2,3,4,5-tetrahydro-1,5-benzothiazepine; 1,1-dioxo-3,3-dibutyl-5-phenyl-7-methylthio-8-(N—{(R)-α-[N'—((S)-1-carboxyethyl)carbamoyl]benzyl}carbamoylmethoxy)-2,3,4,5-tetrahydro-1,5-benzothiazepine; or a pharmaceutically acceptable salt thereof; 1-[[5-[[3-[(3S,4R,5R)-3-butyl-7-(dimethylamino)-3-ethyl-2,3,4,5-tetrahydro-4-hydroxy-1,1-dioxido-1-benzothiepin-5yl]phenyl]amino]-5-oxopentyl] amino]-1-deoxy-D-glucitol; or Potassium((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl)sulphate ethanolate, hydrate. In certain embodiments, an ASBTI is 264W94 (Glaxo), SC-435 (Pfizer), SD-5613 (Pfizer), or A3309 (Astra-Zeneca).

In certain embodiments, methods provided herein further comprise administration of a second agent selected from ursodiol, UDCA, cholestyramine/resins, antihistamine agents (e.g., hydroxyzine, diphenhydramine), rifampin, naloxone, Phenobarbital, dronabinol (CB1 agonist), methotrexate, corticosteroids, cyclosporine, colchicines, TPGS—vitamin A, D, E, or K optionally with polyethylene glycol, zinc, and a resin or sequestrant for absorbing bile acids or an analog thereof. In certain embodiments, methods provided herein further comprise administration of a second agent selected from a bile acid or salt with reduced toxicity or a hydrophilic bile acid such as ursodiol, norursodiol, ursodeoxycholic acid, chenodeoxycholic acid, cholic acid, taurocholic acid, ursocholic acid, glycocholic acid, glycodeoxycholic acid, taurodeoxycholic acid, taurocholate, glycochenodeoxycholic acid, or tauroursodeoxycholic acid.

In certain embodiments, provided herein are pediatric dosage forms such as a solution, syrup, suspension, elixir, powder for reconstitution as suspension or solution, dispersible/effervescent tablet, chewable tablet, gummy candy, lollipop, freezer pops, troches, oral thin strips, orally disintegrating tablet, sachet, soft gelatin capsule, and sprinkle oral powder or granules.

In some embodiments, the pediatric dosage of an ASBTI is between about 1 µg/kg/day and about 10 mg/kg/day. In some embodiments, the pediatric dosage of an ASBTI is between about 5 µg/kg/day and about 1 mg/kg/day. In some embodiments, the pediatric dosage of an ASBTI is between about 10 µg/kg/day and about 300 µg/kg/day. In some embodiments, the pediatric dosage of an ASBTI is any dosage from about 14 µg/kg/day and about 280 µg/kg/day. In some embodiments, the pediatric dosage of an ASBTI is any dosage from about 14 µg/kg/day and about 140 µg/kg/day. In some embodiments, the pediatric dosage of an ASBTI is between about 5 µg/kg/day and about 200 µg/kg/day. In some embodiments, the pediatric dosage of an ASBTI is between about 10 µg/kg/day and about 200 µg/kg/day. In some embodiments, the pediatric dosage of an ASBTI is between about 10 µg/kg/day and about 175 µg/kg/day. In some embodiments, the pediatric dosage of an ASBTI is between about 10 µg/kg/day and about 150 µg/kg/day. In some embodiments, the pediatric dosage of an ASBTI is between about 10 µg/kg/day and about 140 µg/kg/day. In some embodiments, the pediatric dosage of an ASBTI is between about 25 µg/kg/day and about 140 µg/kg/day. In some embodiments, the pediatric dosage of an ASBTI is between about 50 µg/kg/day and about 140 µg/kg/day. In some embodiments, the pediatric dosage of an ASBTI is between about 70 µg/kg/day and about 140 µg/kg/day. In some embodiments, the pediatric dosage of an ASBTI is between about 10 µg/kg/day and about 100 µg/kg/day. In some embodiments, the pediatric dosage of an ASBTI is 10 µg/kg/day. In some embodiments, the pediatric dosage of an ASBTI is 20 µg/kg/day. In some embodiments, the pediatric dosage of an ASBTI is 30 µg/kg/day. In some embodiments, the pediatric dosage of an ASBTI is 35 µg/kg/day. In some embodiments, the pediatric dosage of an ASBTI is 40 µg/kg/day. In some embodiments, the pediatric dosage of an ASBTI is 50 µg/kg/day. In some embodiments, the pediatric dosage of an ASBTI is 60 µg/kg/day. In some embodiments, the pediatric dosage of an ASBTI is 70 µg/kg/day. In some embodiments, the pediatric dosage of an ASBTI is 80 µg/kg/day. In some embodiments, the pediatric dosage of an ASBTI is 90 µg/kg/day. In some embodiments, the pediatric dosage of an ASBTI is 100 µg/kg/day. In some embodiments, the pediatric dosage of an ASBTI is 110 µg/kg/day. In some embodiments, the pediatric dosage of an ASBTI is 120 µg/kg/day. In some embodiments, the pediatric dosage of an ASBTI is 130 µg/kg/day. In some embodiments, the pediatric dosage of an ASBTI is 140 µg/kg/day. In some embodiments, the pediatric dosage of an ASBTI is 150 µg/kg/day. In some embodiments, the pediatric dosage of an ASBTI is 175 µg/kg/day.

In some embodiments, provided herein are pediatric dosages of an ASBTI between 14 µg/kg/day and 140 µg/kg/day, or between 14 µg/kg/day and 280 µg/kg/day.

In some embodiments, the pediatric dosage of an ASBTI is between about 0.5 mg/day and about 40 mg/day. In some embodiments, the pediatric dosage of an ASBTI is between about 0.5 mg/day and about 30 mg/day. In some embodiments, the pediatric dosage of an ASBTI is between about 1 mg/day and about 20 mg/day. In some embodiments, the pediatric dosage of an ASBTI is between about 1 mg/day and about 10 mg/day. In some embodiments, the pediatric dosage of an ASBTI is between about 1 mg/day and about 5 mg/day. In some embodiments, the pediatric dosage of an ASBTI is 1 mg/day. In some embodiments, the pediatric dosage of an ASBTI is 5 mg/day. In some embodiments, the pediatric dosage of an ASBTI is 10 mg/day. In some embodiments, the pediatric dosage of an ASBTI is 20 mg/day. In some embodiments, the pediatric dosage of an ASBTI is between 0.5 mg/day and 5 mg/day. In some embodiments, the pediatric dosage of an ASBTI is between 0.5 mg/day and 4.5 mg/day. In some embodiments, the pediatric dosage of an ASBTI is between 0.5 mg/day and 4 mg/day. In some embodiments, the pediatric dosage of an ASBTI is between 0.5 mg/day and 3.5 mg/day. In some embodiments, the pediatric dosage of an ASBTI is between 0.5 mg/day and 3 mg/day. In some embodiments, the pediatric dosage of an ASBTI is between 0.5 mg/day and 2.5 mg/day. In some embodiments, the pediatric dosage of an ASBTI is between 0.5 mg/day and 2 mg/day. In some embodiments, the pediatric dosage of an ASBTI is between 0.5 mg/day and 1.5 mg/day. In some embodiments, the pediatric dosage of an ASBTI is between 0.5 mg/day and 1 mg/day. In some embodiments, the pediatric dosage of an ASBTI is between 1 mg/day and 4.5 mg/day. In some embodiments, the pediatric dosage of an ASBTI is between 1 mg/day and 4 mg/day. In some embodiments, the pediatric dosage of an ASBTI is between 1 mg/day and 3.5 mg/day. In some embodiments, the pediatric dosage of an ASBTI is between 1 mg/day and 3 mg/day. In some embodiments, the pediatric dosage of an ASBTI is between 1 mg/day and 2.5 mg/day. In some embodiments, the pediatric dosage of an ASBTI is between 1 mg/day and 2 mg/day. In some embodiments, the pediatric dosage of an ASBTI is 0.5 mg/day. In some embodiments, the pediatric dosage of an ASBTI is 1 mg/day. In some embodiments, the pediatric dosage of an ASBTI is 1.5 mg/day. In some embodiments, the pediatric dosage of an ASBTI is 2 mg/day. In some embodiments, the pediatric dosage of an ASBTI is 2.5 mg/day. In some embodiments, the pediatric dosage of an ASBTI is 3 mg/day. In some embodiments, the pediatric dosage of an ASBTI is 3.5 mg/day. In some embodiments, the pediatric dosage of an ASBTI is 4 mg/day. In some embodiments, the pediatric dosage of an ASBTI is 4.5 mg/day. In some embodiments, the pediatric dosage of an ASBTI is 5 mg/day. In some embodiments, the pediatric dosage described herein is the dosage of the total composition administered.

In some embodiments, the pediatric dosage form comprises 0.5 mg of the ASBTI. In some embodiments, the pediatric dosage form comprises 1 mg of the ASBTI. In some embodiments, the pediatric dosage form comprises 2.5 mg of the ASBTI. In some embodiments, the pediatric dosage form comprises 5 mg of the ASBTI. In some embodiments, the pediatric dosage form comprises 10 mg of the ASBTI. In some embodiments, the pediatric dosage form comprises 20 mg of the ASBTI.

In certain embodiments, the pediatric dosage of an ASBTI is given once a day. In some embodiments, the pediatric dosage of an ASBTI is given q.d. In some embodiments, the pediatric dosage of an ASBTI is given once a day in the morning. In some embodiments, the pediatric dosage of an ASBTI is given once a day at noon. In some embodiments, the pediatric dosage of an ASBTI is given once a day in the evening or night. In some embodiments, the pediatric dosage of an ASBTI is given twice a day. In some embodiments, the pediatric dosage of an ASBTI is given b.i.d. In some embodiments, the pediatric dosage of an ASBTI is given twice a day, in the morning and noon. In some embodiments, the pediatric dosage of an ASBTI is given twice a day, in the morning and evening. In some embodiments, the pediatric dosage of an ASBTI is given twice a day, in the morning and night. In some embodiments, the pediatric dosage of an ASBTI is given twice a day, at noon and in the evening. In some embodiments, the pediatric dosage of an ASBTI is given twice a day, at noon and in the night. In some embodiments, the pediatric dosage of an ASBTI is given three times a day. In some embodiments, the pediatric dosage of an ASBTI is given t.i.d. In some embodiments, the pediatric dosage of an ASBTI is given four times a day. In some embodiments, the pediatric dosage of an ASBTI is given q.i.d. In some embodiments, the pediatric dosage of an ASBTI is given every four hours. In some embodiments, the pediatric dosage of an ASBTI is given q.q.h. In some embodiments, the pediatric dosage of an ASBTI is given every other day. In some embodiments, the pediatric dosage of an ASBTI is given q.o.d. In some embodiments, the pediatric dosage of an ASBTI is given three times a week. In some embodiments, the pediatric dosage of an ASBTI is given t.i.w.

Provided in certain embodiments herein are methods and dosage forms (e.g., oral or rectal dosage form) for use in the treatment of a pediatric cholestatic liver disease or pruritis, or lowering serum bile acid concentrations comprising a therapeutically effective amount of an ASBTI, or a pharmaceutically acceptable salt thereof, and a carrier. In some embodiments, provided herein is a method for treating cholestasis and/or a cholestatic liver disease comprising orally administering a therapeutically effective amount of a minimally absorbed ASBTI, or a pharmaceutically acceptable salt thereof, to an individual in need thereof. In some embodiments, provided herein is a method for treating cholestasis and/or a cholestatic liver disease comprising orally administering a therapeutically effective amount of a minimally absorbed ASBTI, or a pharmaceutically acceptable salt thereof, to an individual in need thereof. In some embodiments, the ASBTI, or salt thereof is a minimally absorbed ASBTI. In specific embodiments, the dosage form is an enteric formulation, an ileal-pH sensitive release formulation, or a suppository or other suitable form.

In some embodiments, a composition for use in the treatment of a pediatric cholestatic liver disease or pruritis, or lowering serum bile acid concentrations comprises at least one of a spreading agent or a wetting agent. In some embodiments, the composition comprises an absorption inhibitor. In some cases an absorption inhibitor is a mucoadhesive agent (e.g., a mucoadhesive polymer). In certain embodiments, the mucoadhesive agent is selected from methyl cellulose, polycarbophil, polyvinylpyrrolidone, sodium carboxymethyl cellulose, and combinations thereof. In some embodiments, the enteroendocrine peptide secretion enhancing agent is covalently linked to the absorption inhibitor. In certain embodiments, the pharmaceutical composition comprises an enteric coating. In some embodiments, a composition for use in treatment of cholestasis, a cholestatic liver disease or pruritis described above comprises a carrier. In certain embodiments, the carrier is a rectally suitable carrier. In certain embodiments, any pharmaceutical composition described herein is formulated as a suppository, an enema solution, a rectal foam, or a rectal gel. In some embodiments, any pharmaceutical composition described herein comprises an orally suitable carrier.

In some embodiments, a pediatric dosage form comprising an ASBTI is administered orally. In some embodiments, the ASBTI is administered as an ileal-pH sensitive release formulation that delivers the ASBTI to the distal ileum, colon and/or rectum of an individual. In some embodiments, the ASBTI is administered as an enterically coated formulation. In some embodiments, oral delivery of an ASBTI provided herein can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (the ileum) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

In some embodiments, the methods and compositions provided herein further comprise administration of a bile acid sequestrant or binder for reducing gastrointestinal side effects. In some embodiments, methods comprise administering a labile bile acid sequestrant, wherein the labile bile acid sequestrant has a low affinity in the colon or rectum of the individual for at least one bile acid. In some embodiments, a labile bile acid sequestrant provided herein releases a bile acid in the colon or the rectum of a human. In some embodiments, a labile bile acid sequestrant provided herein does not sequester a bile acid for excretion or elimination in feces. In some embodiments, a labile bile acid sequestrant provided herein is a non-systemic labile bile acid sequestrant. In some embodiments, non-systemic labile bile acid sequestrant is less than 1%, 2%, 3%, 4%, 5%, 6%, 7%, 8%, 9%, 10%, 15%, 20%, 25%, 30%, 35%, 40%, 45% absorbed systemically. In some embodiments, the labile bile acid sequestrant is lignin or a modified lignin. In some embodiments, the labile bile acid sequestrant is a polycationic polymer or copolymer. In certain embodiments, the labile bile acid sequestrant is a polymer or copolymer comprising one or more N-alkenyl-N-alkylamine residues; one or more N,N,N-trialkyl-N—(N'-alkenylamino)alkyl-azanium residues; one or more N,N,N-trialkyl-N-alkenyl-azanium residues; one or more alkenyl-amine residues; cholestyramine, cholestipol, or cholesevelamor a combination thereof.

In some embodiments of the methods described above, a pediatric dosage form comprising an ASBTI is administered before ingestion of food. In some embodiments of the methods described above, a pediatric dosage form comprising an ASBTI is administered with or after ingestion of food.

In some embodiments, the methods provided herein further comprise administration of vitamin supplements to compensate for reduced digestion of vitamins, in particular fat-soluble vitamins, in an individual with a pediatric cholestatic liver disease, pruritis, or elevated serum bile acid levels or concentrations. In some embodiments, the vitamin supplements comprise fat-soluble vitamins. In some embodiments, the fat-soluble vitamins are vitamin A, D, E, or K.

In some cases, for any of the methods described above, administration of an ASBTI reduces intraenterocyte bile acids/salts in an individual in need thereof. In some embodiments, the methods described herein reduce accumulation of bile acids/salts in ileal enterocytes of an individual in need thereof. In some cases, for any of the methods described above, administration of an ASBTI inhibits transport of bile acids/salts from ileal lumen into enterocytes of an individual in need thereof. In some cases, for any of the methods described above, administration of an ASBTI increases ileal luminal bile acids/salts in an individual in need thereof. In some cases, for any of the methods described above, administration of an ASBTI reduces damage to intestinal (e.g., ileal cells) or hepatocellular (e.g., liver cells) architecture associated with a pediatric cholestatic liver disease or elevated serum or hepatic bile acid concentrations in an individual in need thereof. In some cases, for any of the methods described above, administration of an ASBTI regenerates intestinal lining or liver cells that have been injured by cholestasis and/or by a cholestatic liver disease in an individual suffering from a cholestatic liver disease.

In some embodiments, provided herein are methods for the treatment of a pediatric cholestatic liver disease comprising administration of a therapeutically effective amount of a pediatric dosage form comprising a combination of an ASBTI and ursodiol to an individual in need thereof. In some embodiments, provided herein are methods for the treatment of a pediatric cholestatic liver disease comprising administration of a therapeutically effective amount of a combination of an ASBTI and a resin or sequestrant for absorbing bile acids to an individual in need thereof. In some embodiments, an ASBTI is administered in combination with one or more agent selected from the group consisting of ursodiol, norursodiol, UDCA, ursodeoxycholic acid, chenodeoxycholic acid, cholic acid, taurocholic acid, ursocholic acid, glycocholic acid, glycodeoxycholic acid, taurodeoxycholic acid, taurocholate, glycochenodeoxycholic acid, tauroursodeoxycholic acid, cholestyramine/resins, antihistamine agents (e.g., hydroxyzine, diphenhydramine), rifampin, naloxone, Phenobarbital, dronabinol (CB1 agonist), methotrexate, corticosteroids, cyclosporine, colchicines, TPGS—vitamin A, D, E, or K optionally with polyethylene glycol, zinc, a resin or sequestrant for absorbing bile acids.

In some embodiments, the methods provided herein further comprise partial external biliary diversion (PEBD) therapy.

Provided in some embodiments herein is a kit comprising any composition described herein (e.g., a pharmaceutical composition formulated for rectal administration) and a device for localized delivery within the rectum or colon. In certain embodiments, the device is a syringe, bag, or a pressurized container.

DETAILED DESCRIPTION OF THE INVENTION

Figure 1:
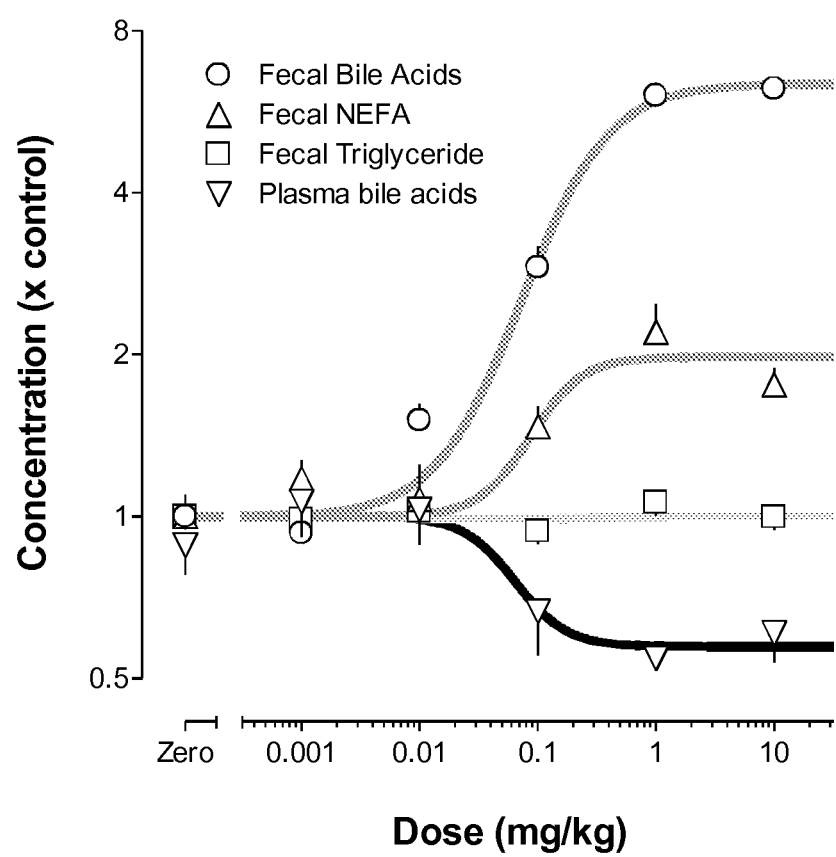
FIG. 1. Oral administration of 264W94 dose-dependently increased bile acids in the feces. Fecal bile acid concentrations were elevated up to 6.5 fold with an $ED_{50}$ of 0.17 mg/kg, when compared to vehicle treated rats. Fecal NEFA also slightly increased in 264W94 treated rats. Plasma bile acid concentrations were decreased dose-dependently in 264W94 treated rats.

Bile acids/salts play a critical role in activating digestive enzymes and solubilizing fats and fat-soluble vitamins and are involved in liver, biliary, and intestinal disease. Bile acids are synthesized in the liver by a multistep, multiorganelle pathway. Hydroxyl groups are added to specific sites on the steroid structure, the double bond of the cholesterol B ring is reduced and the hydrocarbon chain is shortened by three carbon atoms resulting in a carboxyl group at the end of the chain. The most common bile acids are cholic acid and chenodeoxycholic acid (the "primary bile acids"). Before exiting the hepatocytes and forming bile, the bile acids are conjugated to either glycine (to produce glycocholic acid or glycochenodeoxycholic acid) or taurine (to produce taurocholic acid or taurochenodeoxycholic acid). The conjugated bile acids are called bile salts and their amphipathic nature makes them more efficient detergents than bile acids. Bile salts, not bile acids, are found in bile.

Bile salts are excreted by the hepatocytes into the canaliculi to form bile. The canaliculi drain into the right and left hepatic ducts and the bile flows to the gallbladder. Bile is released from the gallbladder and travels to the duodenum, where it contributes to the metabolism and degradation of fat. The bile salts are reabsorbed in the terminal ileum and transported back to the liver via the portal vein. Bile salts often undergo multiple enterohepatic circulations before being excreted via feces. A small percentage of bile salts may be reabsorbed in the proximal intestine by either passive or carrier-mediated transport processes. Most bile salts are reclaimed in the distal ileum by a sodium-dependent apically located bile acid transporter referred to as apical sodium-dependent bile acid transporter (ASBT). At the basolateral surface of the enterocyte, a truncated version of ASBT is involved in vectorial transfer of bile acids/salts into the portal circulation. Completion of the enterohepatic circulation occurs at the basolateral surface of the hepatocyte by a transport process that is primarily mediated by a sodium-dependent bile acid transporter. Intestinal bile acid transport plays a key role in the enterohepatic circulation of bile salts. Molecular analysis of this process has recently led to important advances in our understanding of the biology, physiology and pathophysiology of intestinal bile acid transport.

Within the intestinal lumen, bile acid concentrations vary, with the bulk of the reuptake occurring in the distal intestine. Bile acids/salts alter the growth of bacterial flora in the gut. Described herein are certain compositions and methods that control bile acid concentrations in the intestinal lumen, thereby controlling the hepatocellular damage caused by bile acid accumulation in the liver.

In another aspect, the compositions and methods provided herein increase bile acid concentrations in the gut. The increased concentrations of bile acids/salts stimulate subsequent secretion of factors that protect and control integrity of the intestine when it is injured by pediatric cholestasis and/or a pediatric cholestatic liver disease (e.g., a pediatric cholestatic liver disease associated with pruritis, or a pediatric cholestatic liver disease associated with elevated serum bile acid concentrations or hepatic bile acid concentrations).

In yet another aspect, the compositions and methods described herein have an advantage over systemically absorbed agents. The compositions and methods described herein utilize ASBT inhibitors that are not systemically absorbed. Thus the compositions are effective without leaving the gut lumen, thereby reducing any toxicity and/or side effects associated with systemic absorption. The pediatric formulations described herein have an advantage over existing adult dosage forms and dosages to reduce harmful side effects and increase compliance.

In a further aspect, the compositions and methods described herein stimulate the release of enteroendocrine hormones GLP-2 and PYY. Increased secretion of GLP-2 or PYY allows for prevention or treatment of pediatric cholestasis and/or a pediatric cholestatic liver disease by controlling the adaptive process, attenuating intestinal injury, reducing bacterial translocation, inhibiting the release of free radical oxygen, inhibiting production of proinflammatory cytokines, or any combination thereof.

Described herein is the use of inhibitors of the ASBT or any recuperative bile salt transporter that are active in the gastrointestinal (GI) tract for treating or preventing pediatric cholestasis and/or a pediatric cholestatic liver disease in an individual in need thereof. In certain embodiments, described herein is the use of inhibitors of the ASBT or any recuperative bile salt transporter that are active in the gastrointestinal (GI) tract for treating or preventing pruritis in an individual in need thereof. In certain embodiments, described herein is the use of inhibitors of the ASBT or any recuperative bile salt transporter that are active in the gastrointestinal (GI) tract for lowering serum bile acid concentrations or hepatic bile acid concentrations in an individual in need thereof. In certain embodiments, the methods provided herein comprise administering a therapeutically effective amount of an ASBTI to an individual in need thereof. In some embodiments, such ASBT inhibitors are not systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some other embodiments, such ASBT inhibitors are systemically absorbed. In some embodiments, the ASBTI provided herein are formulated for non-systemic delivery to the distal ileum. In some embodiments, an ASBTI is minimally absorbed. In some embodiments, an ASBTI is non-systemically administered to the colon or the rectum of an individual in need thereof.

In some embodiments, such ASBT inhibitors are not systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some other embodiments, such ASBT inhibitors are systemically absorbed. In some embodiments, the ASBTI are formulated for non-systemic delivery to the distal ileum. In some embodiments, an ASBTI is minimally absorbed. In some embodiments, an ASBTI is non-systemically administered to the colon or the rectum of an individual in need thereof.

In some embodiments, less than 50%, less than 40%, less than 30%, less than 20%, less than 10%, less than 9%, less than 8%, less than 7%, less than 6%, less than 5%, less than 4%, less than 3%, less than 2%, or less than 1% of the ASBTI is systemically absorbed. In certain embodiments, ASBTIs described herein inhibit scavenging of bile salts by recuperative bile acid salt transporters in the distal gastrointestinal tract (e.g., the distal ileum, the colon and/or the rectum).

In some instances, the inhibition of bile salt recycling results in higher concentrations of bile salts in the lumen of the distal gastrointestinal tract or portions thereof (e.g., the distal small bowel and/or colon and/or rectum). As used herein, the distal gastrointestinal tract includes the region from the distal ileum to the anus. In some embodiments, the compounds described herein reduce intraenterocyte bile acids/salts or accumulation thereof. In some embodiments, the compounds described herein reduce damage to hepatocellular or intestinal architecture associated with cholestasis and/or a cholestatic liver disease.

Mammalian Microbiome, Bile Acid Pools and Metabolic Interactions

The integrated metabolism of the bile acid pools in the intestinal lumen lends itself to complex biochemical interactions between host and microbiome symbionts.

Bile acids/salts are synthesized from cholesterol in the liver by a multi-enzyme coordinated process and are crucial for the absorption of dietary fats and lipid-soluble vitamins in the intestine. Bile acids/salts play a role in maintaining the intestinal barrier function to prevent intestinal bacterial overgrowth and translocation, as well as invasion of underlying tissues by enteric bacteria.

Under normal conditions (i.e., when an individual is not suffering from pediatric cholestasis and/or a pediatric cholestatic liver disease), symbiotic gut microorganisms (microbiome) interact closely with the host's metabolism and are important determinants of health. Many bacterial species in the gut are capable of modifying and metabolizing bile acids/salts and the gut flora affects systemic processes such as metabolism and inflammation.

Bile acids/salts have strong antimicrobial and antiviral effects—deficiency leads to bacterial overgrowth and increased deconjugation, leading to less ileal resorption. In animals, conjugated bile acid feeding abolishes bacterial overgrowth, decreases bacterial translocation to lymph nodes and reduces endotoxemia.

Accordingly, the methods and compositions described herein allow for replacement, displacement, and/or redirection of bile acids/salts to different areas of the gastrointestinal tract thereby affecting (e.g., inhibiting or slowing) growth of microorganisms that may cause infection-associated cholestasis and/or a cholestatic liver disease.

Classes of Pediatric Cholestatic Liver Disease

As used herein, "cholestasis" means the disease or symptoms comprising impairment of bile formation and/or bile flow. As used herein, "cholestatic liver disease" means a liver disease associated with cholestasis. Cholestatic liver diseases are often associated with jaundice, fatigue, and pruritis. Biomarkers of cholestatic liver disease include elevated serum bile acid concentrations, elevated serum alkaline phosphatase (AP), elevated gamma-glutamyltranspeptidease, elevated conjugated hyperbilirubinemia, and elevated serum cholesterol.

Cholestatic liver disease can be sorted clinicopathologically between two principal categories of obstructive, often extrahepatic, cholestasis, and nonobstructive, or intrahepatic, cholestasis. In the former, cholestasis results when bile flow is mechanically blocked, as by gallstones or tumor, or as in extrahepatic biliary atresia.

The latter group who has nonobstructive intrahepatic cholestasis in turn fall into two principal subgroups. In the first subgroup, cholestasis results when processes of bile secretion and modification, or of synthesis of constituents of bile, are caught up secondarily in hepatocellular injury so severe that nonspecific impairment of many functions can be expected, including those subserving bile formation. In the second subgroup, no presumed cause of hepatocellular injury can be identified. Cholestasis in such patients appears to result when one of the steps in bile secretion or modification, or of synthesis of constituents of bile, is constitutively damages. Such cholestasis is considered primary.

Accordingly, provided herein are methods and compositions for stimulating epithelial proliferation and/or regeneration of intestinal lining and/or enhancement of the adaptive processes in the intestine in individuals with cholestasis and/or a cholestatic liver disease. In some of such embodiments, the methods comprise increasing bile acid concentrations and/or GLP-2 concentrations in the intestinal lumen.

Hypercholemia, and elevated levels of AP (alkaline phosphatase), LAP (leukocyte alkaline phosphatase), gamma GT (gamma-glutamyl transpeptidase), and 5'-nucleotidase are biochemical hallmarks of cholestasis and cholestatic liver disease. Accordingly, provided herein are methods and compositions for stimulating epithelial proliferation and/or regeneration of intestinal lining and/or enhancement of the adaptive processes in the intestine in individuals with hypercholemia, and elevated levels of AP (alkaline phosphatase), LAP (leukocyte alkaline phosphatase), gamma GT (gammaglutamyl transpeptidase or GGT), and/or 5'-nucleotidase. In some of such embodiments, the methods comprise increasing bile acid concentrations concentrations in the intestinal lumen. Further provided herein, are methods and compositions for reducing hypercholemia, and elevated levels of AP (alkaline phosphatase), LAP (leukocyte alkaline phosphatase), gamma GT (gamma-glutamyl transpeptidase), and 5'-nucleotidase comprising reducing overall bile acid load by excreting bile acid in the feces.

Pruritus is often associated with pediatric cholestasis and pediatric cholestatic liver diseases. It has been suggested that pruritus results from bile salts acting on peripheral pain afferent nerves. The degree of pruritus varies with the individual (i.e., some individuals are more sensitive to elevated levels of bile acids/salts). Administration of agents that reduce serum bile acid concentrations has been shown to reduce pruritus in certain individuals. Accordingly, provided herein are methods and compositions for stimulating epithelial proliferation and/or regeneration of intestinal lining and/or enhancement of the adaptive processes in the intestine in individuals with pruritus. In some of such embodiments, the methods comprise increasing bile acid concentrations in the intestinal lumen. Further provided herein, are methods and compositions for treating pruritus comprising reducing overall bile acid load by excreting bile acid in the feces.

Another symptom of pediatric cholestasis and pediatric cholestatic liver disease is the increase in serum concentration of conjugated bilirubin. Elevated serum concentrations of conjugated bilirubin result in jaundice and dark urine. The magnitude of elevation is not diagnostically important as no relationship has been established between serum levels of conjugated bilirubin and the severity of cholestasis and cholestatic liver disease. Conjugated bilirubin concentration rarely exceeds 30 mg/dL. Accordingly, provided herein are methods and compositions for stimulating epithelial proliferation and/or regeneration of intestinal lining and/or enhancement of the adaptive processes in the intestine in individuals with elevated serum concentrations of conjugated bilirubin. In some of such embodiments, the methods comprise increasing bile acid concentrations in the intestinal lumen. Further provided herein, are methods and compositions for treating elevated serum concentrations of conjugated bilirubin comprising reducing overall bile acid load by excreting bile acid in the feces.

Increased serum concentration of nonconjugated bilirubin is also considered diagnostic of cholestasis and cholestatic liver disease. Portions of serum bilirubin and covalently bound to albumin (delta bilirubin or biliprotein). This fraction may account for a large proportion of total bilirubin in patients with cholestatic jaundice. The presence of large quantities of delta bilirubin indicates long-standing cholestasis. Delta bilirubin in cord blood or the blood of a newborn is indicative of pediatric cholestasis/cholestatic liver disease that antedates birth. Accordingly, provided herein are methods and compositions for stimulating epithelial proliferation and/or regeneration of intestinal lining and/or enhancement of the adaptive processes in the intestine in individuals with elevated serum concentrations of nonconjugated bilirubin or delta bilirubin. In some of such embodiments, the methods comprise increasing bile acid concentrations in the intestinal lumen. Further provided herein, are methods and compositions for treating elevated serum concentrations of nonconjugated bilirubin and delta bilirubin comprising reducing overall bile acid load by excreting bile acid in the feces.

Pediatric cholestasis and cholestatic liver disease results in hypercholemia. During metabolic cholestasis, the hepatocytes retains bile salts. Bile salts are regurgitated from the hepatocyte into the serum, which results in an increase in the concentration of bile salts in the peripheral circulation. Furthermore, the uptake of bile salts entering the liver in portal vein blood is inefficient, which results in spillage of bile salts into the peripheral circulation. Accordingly, provided herein are methods and compositions for stimulating epithelial proliferation and/or regeneration of intestinal lining and/or enhancement of the adaptive processes in the intestine in individuals with hypercholemia. In some of such embodiments, the methods comprise increasing bile acid concentrations in the intestinal lumen. Further provided herein, are methods and compositions for treating hypercholemia comprising reducing overall bile acid load by excreting bile acid in the feces.

Hyperlipidemia is characteristic of some but not all cholestatic diseases. Serum cholesterol is elevated in cholestasis due to the decrease in circulating bile salts which contribute to the metabolism and degradation of cholesterol. Cholesterol retention is associated with an increase in membrane cholesterol content and a reduction in membrane fluidity and membrane function. Furthermore, as bile salts are the metabolic products of cholesterol, the reduction in cholesterol metabolism results in a decrease in bile acid/salt synthesis. Serum cholesterol observed in children with cholestasis ranges between about 1,000 mg/dL and about 4,000 mg/dL. Accordingly, provided herein are methods and compositions for stimulating epithelial proliferation and/or regeneration of intestinal lining and/or enhancement of the adaptive processes in the intestine in individuals with hyperlipidemia. In some of such embodiments, the methods comprise increasing bile acid concentrations concentrations in the intestinal lumen. Further provided herein, are methods and compositions for treating hyperlipidemia comprising reducing overall bile acid load by excreting bile acid in the feces.

In individuals with pediatric cholestasis and pediatric cholestatic liver diseases, xanthomas develop from the deposition of excess circulating cholesterol into the dermis. The development of xanthomas is more characteristic of obstructive cholestasis than of hepatocellular cholestasis. Planar xanthomas first occur around the eyes and then in the creases of the palms and soles, followed by the neck. Tuberous xanthomas are associated with chronic and long-term cholestasis. Accordingly, provided herein are methods and compositions for stimulating epithelial proliferation and/or regeneration of intestinal lining and/or enhancement of the adaptive processes in the intestine in individuals with xanthomas. In some of such embodiments, the methods comprise increasing bile acid concentrations in the intestinal lumen. Further provided herein, are methods and compositions for treating xanthomas comprising reducing overall bile acid load by excreting bile acid in the feces.

In children with chronic cholestasis, one of the major consequences of pediatric cholestasis and pediatric cholestatic liver disease is failure to thrive. Failure to thrive is a consequence of reduced delivery of bile salts to the intestine, which contributes to inefficient digestion and absorption of fats, and reduced uptake of vitamins (vitamins E, D, K, and A are all malabsorbed in cholestasis). Furthermore, the delivery of fat into the colon can result in colonic secretion and diarrhea. Treatment of failure to thrive involves dietary substitution and supplementation with long-chain triglycerides, medium-chain triglycerides, and vitamins. Ursodeoxycholic acid, which is used to treat some cholestatic conditions, does not form mixed micelles and has no effect on fat absorption. Accordingly, provided herein are methods and compositions for stimulating epithelial proliferation and/or regeneration of intestinal lining and/or enhancement of the adaptive processes in the intestine in individuals (e.g., children) with failure to thrive. In some of such embodiments, the methods comprise increasing bile acid concentrations in the intestinal lumen. Further provided herein, are methods and compositions for treating failure to thrive comprising reducing overall bile acid load by excreting bile acid in the feces.

Symptoms of pediatric cholestasis and pediatric cholestatic liver disease have been treated with choleretic agents (e.g., ursodiol), phenobarbitols, corticosteroids (e.g., prednisone and budesonide), immunosuppressive agents (e.g., azathioprine, cyclosporin A, methotrexate, chlorambucil and mycophenolate), sulindac, bezafibrate, tamoxifen, and lamivudine. Accordingly, in some embodiments, any of the methods disclosed herein further comprise administration of an additional active agent selected from: choleretic agents (e.g., ursodiol), phenobarbitols, corticosteroids (e.g., prednisone and budesonide), immunosuppressive agents (e.g., azathioprine, cyclosporin A, methotrexate, chlorambucil and mycophenolate), sulindac, bezafibrate, tamoxifen, lamivudine, and combinations thereof. In some embodiments, the methods are used to treat individuals that are non-responsive to treatment with choleretic agents (e.g., ursodiol), phenobarbitols, corticosteroids (e.g., prednisone and budesonide), immunosuppressive agents (e.g., azathioprine, cyclosporin A, methotrexate, chlorambucil and mycophenolate), sulindac, bezafibrate, tamoxifen, lamivudine, and combinations thereof. In some embodiments, the methods are used to treat individuals that are non-responsive to treatment with choleretic agents. In some embodiments, the methods are used to treat individuals that are non-responsive to treatment with ursodiol.

Progressive Familial Intrahepatic Cholestasis (PFIC)

PFIC 1

PFIC 1 (also known as, Byler disease or FIC1 deficiency) is associated with mutations in the ATP8B1 gene (also designated as FIC1). This gene, which encodes a P-type ATPase, is located on human chromosome 18 and is also mutated in the milder phenotype, benign recurrent intrahepatic cholestasis type 1 (BRIC1) and in Greenland familial cholestasis. FIC1 protein is located on the canalicular membrane of the hepatocyte but within the liver it is mainly expressed in cholangiocytes. P-type ATPase appears to be an aminophospholipid transporter responsible for maintaining the enrichment of phosphatidylserine and phophatidylethanolamine on the inner leaflet of the plasma membrane in comparison of the outer leaflet. The asymmetric distribution of lipids in the membrane bilayer plays a protective role against high bile salt concentrations in the canalicular lumen. The abnormal protein function may indirectly disturb the biliary secretion of bile acids. The anomalous secretion of bile acids/salts leads to hepatocyte bile acid overload.

PFIC-1 typically presents in infants (e.g., age 6-18 months). The infants may show signs of pruritus, jaundice, abdominal distension, diarrhea, malnutrition, and shortened stature. Biochemically, individuals with PFIC-1 have elevated serum transaminases, elevated bilirubin, elevated serum bile acid levels, and low levels of gammaGT. The individual may also have liver fibrosis. Individuals with PFIC-1 typically do not have bile duct proliferation. Most individuals with PFIC-1 will develop end-stage liver disease by 10 years of age. No medical treatments have proven beneficial for the long term treatment of PFIC-1. In order to reduce extrahepatic symptoms (e.g., malnutrition and failure to thrive), children are often administered medium chain triglycerides and fat-soluble vitamins. Ursodiol has not been demonstrated as effective in individuals with PFIC-1.

Disclosed herein, in certain embodiments, are methods of treating PFIC-1 in an individual in need thereof comprising non-systemically administering a therapeutically effective amount of an Apical Sodium-dependent Bile Acid Transporter Inhibitor (ASBTI) or a pharmaceutically acceptable salt thereof. In some embodiments, such ASBT inhibitors are not systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some other embodiments, such ASBT inhibitors are systemically absorbed. In some embodiments, the ASBTI are formulated for non-systemic delivery to the distal ileum. In some embodiments, an ASBTI is minimally absorbed. In some embodiments, an ASBTI is non-systemically administered to the colon or the rectum of an individual in need thereof. In some embodiments, the methods further comprise administering a therapeutically-effective amount of a secondary bile acid (e.g., ursodiol), a corticosteroid (e.g., prednisone and budesonide), an immunosuppressive agent (e.g., azathioprine, cyclosporin A, methotrexate, chlorambucil and mycophenolate), sulindac, bezafibrate, tamoxifen, lamivudine or any combination thereof.

PFIC 2

PFIC 2 (also known as, Byler Syndrome or BSEP deficiency) is associated with mutations in the ABCB11 gene (also designated BSEP). The ABCB11 gene encodes the ATP-dependent canalicular bile salt export pump (BSEP) of human liver and is located on human chromosome 2. BSEP protein, expressed at the hepatocyte canalicular membrane, is the major exporter of primary bile acids/salts against extreme concentration gradients. Mutations in this protein are responsible for the decreased biliary bile salt secretion described in affected patients, leading to decreased bile flow and accumulation of bile salts inside the hepatocyte with ongoing severe hepatocellular damage.

PFIC-2 typically presents in infants (e.g., age 6-18 months). The infants may show signs of pruritus. Biochemically, individuals with PFIC-2 have elevated serum transaminases, elevated bilirubin, elevated serum bile acid levels, and low levels of gammaGT. The individual may also have portal inflammation and giant cell hepatitis. Further, individuals often develop hepatocellular carcinoma. No medical treatments have proven beneficial for the long term treatment of PFIC-1. In order to reduce extrahepatic symptoms (e.g., malnutrition and failure to thrive), children are often administered medium chain triglycerides and fat-soluble vitamins. Ursodiol has not been demonstrated as effective in individuals with PFIC-2.

Disclosed herein, in certain embodiments, are methods of treating PFIC-2 in an individual in need thereof comprising non-systemically administering a therapeutically effective amount of an Apical Sodium-dependent Bile Acid Transporter Inhibitor (ASBTI) or a pharmaceutically acceptable salt thereof. In some embodiments, such ASBT inhibitors are not systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some other embodiments, such ASBT inhibitors are systemically absorbed. In some embodiments, the ASBTI are formulated for non-systemic delivery to the distal ileum. In some embodiments, an ASBTI is minimally absorbed. In some embodiments, an ASBTI is non-systemically administered to the colon or the rectum of an individual in need thereof. In some embodiments, the methods further comprise administering a therapeutically-effective amount of a secondary bile acid (e.g., ursodiol), a corticosteroid (e.g., prednisone and budesonide), an immunosuppressive agent (e.g., azathioprine, cyclosporin A, methotrexate, chlorambucil and mycophenolate), sulindac, bezafibrate, tamoxifen, lamivudine or any combination thereof.

PFIC 3

PFIC3 (also known as MDR3 deficiency) is caused by a genetic defect in the ABCB4 gene (also designated MDR3) located on chromosome 7. Class III Multidrug Resistance (MDR3) P-glycoprotein (P-gp), is a phospholipid translocator involved in biliary phospholipid (phosphatidylcholine) excretion in the canalicular membrane of the hepatocyte.

PFIC3 results from the toxicity of bile in which detergent bile salts are not inactivated by phospholipids, leading to bile canaliculi and biliary epithelium injuries.

PFIC-3 also presents in early childhood. As opposed to PFIC-1 and PFIC-2, individuals have elevated gammaGT levels. Individuals also have portal inflammation, fibrosis, cirrhosis, and massive bile duct proliferation. Individuals may also develop intrahepatic gallstone disease. Ursodiol has been effective in treating or ameliorating PFIC-3.

Disclosed herein, in certain embodiments, are methods of treating PFIC-3 in an individual in need thereof comprising non-systemically administering a therapeutically effective amount of an Apical Sodium-dependent Bile Acid Transporter Inhibitor (ASBTI) or a pharmaceutically acceptable salt thereof. In some embodiments, such ASBT inhibitors are not systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some other embodiments, such ASBT inhibitors are systemically absorbed. In some embodiments, the ASBTI are formulated for non-systemic delivery to the distal ileum. In some embodiments, an ASBTI is minimally absorbed. In some embodiments, an ASBTI is non-systemically administered to the colon or the rectum of an individual in need thereof. In some embodiments, the methods further comprise administering a therapeutically-effective amount of a secondary bile acid (e.g., ursodiol), a corticosteroid (e.g., prednisone and budesonide), an immunosuppressive agent (e.g., azathioprine, cyclosporin A, methotrexate, chlorambucil and mycophenolate), sulindac, bezafibrate, tamoxifen, lamivudine or any combination thereof.

Benign Recurrent Intrahepatic Cholestasis (BRIC)
BRIC 1

BRIC1 is caused by a genetic defect of the FIC1 protein in the canalicular membrane of hepatocytes. BRIC1 is typically associated with normal serum cholesterol and γ-glutamyltranspeptidase levels, but elevated serum bile salts. Residual FIC1 expression and function is associated with BRIC1. Despite recurrent attacks of cholestasis or cholestatic liver disease, there is no progression to chronic liver disease in a majority of patients. During the attacks, the patients are severely jaundiced and have pruritis, steatorrhea, and weight loss. Some patients also have renal stones, pancreatitis, and diabetes.

BRIC 2

BRIC2 is caused by mutations in ABCB11, leading to defective BSEP expression and/or function in the canalicular membrane of hepatocytes.

BRIC 3

BRIC3 is related to the defective expression and/or function of MDR3 in the canalicular membrane of hepatocytes. Patients with MDR3 deficiency usually display elevated serum γ-glutamyltranspeptidase levels in the presence of normal or slightly elevated bile acid levels.

Dubin-Johnson Syndrome (DJS)

DJS is characterized by conjugated hyperbilirubinemia due to inherited dysfunction of MRP2. Hepatic function is preserved in affected patients. Several different mutations have been associated with this condition, resulting either in the complete absence of immunohistochemically detectable MRP2 in affected patients or impaired protein maturation and sorting.

Acquired Cholestatic Disease
Pediatric Primary Sclerosing Cholangitis (PSC)

Pediatric PSC is a chronic inflammatory hepatic disorder slowly progressing to end stage liver failure in most of the affected patients. In pediatric PSC inflammation, fibrosis and obstruction of large and medium sized intra- and extrahepatic ductuli is predominant.

Gallstone Disease

Gallstone disease is one of the most common and costly of all digestive diseases with a prevalence of up to 17% in Caucasian women. Cholesterol containing gallstones are the major form of gallstones and supersaturation of bile with cholesterol is therefore a prerequisite for gallstone formation. ABCB4 mutations may be involved in the pathogenesis of cholesterol gallstone disease.

Drug Induced Cholestasis

Inhibition of BSEP function by drugs is an important mechanism of drug-induced cholestasis, leading to the hepatic accumulation of bile salts and subsequent liver cell damage. Several drugs have been implicated in BSEP inhibition. Most of these drugs, such as rifampicin, cyclosporine, glibenclamide, or troglitazone directly cis-inhibit ATP-dependent taurocholate transport in a competitive manner, while estrogen and progesterone metabolites indirectly trans-inhibits Bsep after secretion into the bile canaliculus by Mrp2. Alternatively, drug-mediated stimulation of MRP2 can promote cholestasis or cholestatic liver disease by changing bile composition.

Total Parenteral Nutrition Associated Cholestasis

TPNAC is one of the most serious clinical scenarios where cholestasis or cholestatic liver disease occurs rapidly and is highly linked with early death. Infants, who are usually premature and who have had gut resections are dependent upon TPN for growth and frequently develop cholestasis or cholestatic liver disease that rapidly progresses to fibrosis, cirrhosis, and portal hypertension, usually before 6 months of life. The degree of cholestasis or cholestatic liver disease and chance of survival in these infants have been linked to the number of septic episodes, likely initiated by recurrent bacterial translocation across their gut mucosa. Although there are also cholestatic effects from the intravenous formulation in these infants, septic mediators likely contribute the most to altered hepatic function.

Alagille Syndrome

Alagille syndrome is a genetic disorder that affects the liver and other organs. It often presents during infancy (e.g., age 6-18 months) through early childhood (e.g., age 3-5 years) and may stabilize after the age of 10. Symptoms may include chronic progressive cholestasis, ductopenia, jaundice, pruritus, xanthomas, congenital heart problems, paucity of intrahepatic bile ducts, poor linear growth, hormone resistance, posterior embryotoxon, Axenfeld anomaly, retinitis pigmentosa, pupillary abnormalities, cardiac murmur, atrial septal defect, ventricular septal defect, patent ductus arteriosus, and Tetralogy of Fallot. Individuals diagnosed with Alagille syndrome have been treated with ursodiol, hydroxyzine, cholestyramine, rifampicin, and phenobarbital. Due to a reduced ability to absorb fat-soluble vitamins, individuals with Alagille Syndrome are further administered high dose multivitamins.

Disclosed herein, in certain embodiments, are methods of treating Alagille syndrome in an individual in need thereof comprising non-systemically administering a therapeutically effective amount of an ASBTI or a pharmaceutically acceptable salt thereof. In some embodiments, such ASBT inhibitors are not systemically absorbed. In some of such embodiments, such bile salt transport inhibitors include a moiety or group that prevents, reduces or inhibits the systemic absorption of the compound in vivo. In some embodiments, a charged moiety or group on the compounds prevents, reduces or inhibits the compounds from leaving the gastrointestinal tract and reduces the risk of side effects due to systemic absorption. In some other embodiments, such ASBT inhibitors are systemically absorbed. In some embodiments, the ASBTI are formulated for non-systemic delivery to the distal ileum. In some embodiments, an ASBTI is minimally absorbed. In some embodiments, an ASBTI is non-systemically administered to the colon or the rectum of an individual in need thereof. In some embodiments, the methods further comprise administering a therapeutically-effective amount of a secondary bile acid (e.g., ursodiol), a corticosteroid (e.g., prednisone and budesonide), an immunosuppressive agent (e.g., azathioprine, cyclosporin A, methotrexate, chlorambucil and mycophenolate), sulindac, bezafibrate, tamoxifen, lamivudine or any combination thereof.

Biliary Atresia

Biliary atresia is a life-threatening condition in infants in which the bile ducts inside or outside the liver do not have normal openings. With biliary atresia, bile becomes trapped, builds up, and damages the liver. The damage leads to scarring, loss of liver tissue, and cirrhosis. Without treatment, the liver eventually fails and the infant needs a liver transplant to stay alive. The two types of biliary atresia are fetal and perinatal. Fetal biliary atresia appears while the baby is in the womb. Perinatal biliary atresia is much more common and does not become evident until 2 to 4 weeks after birth.

Post-Kasai Biliary Atresia

Biliary atresia is treated with surgery called the Kasai procedure or a liver transplant. The Kasai procedure is usually the first treatment for biliary atresia. During a Kasai procedure, the pediatric surgeon removes the infant's damaged bile ducts and brings up a loop of intestine to replace them. While the Kasai procedure can restore bile flow and correct many problems caused by biliary atresia, the surgery doesn't cure biliary atresia. If the Kasai procedure is not successful, infants usually need a liver transplant within 1 to 2 years. Even after a successful surgery, most infants with biliary atresia slowly develop cirrhosis over the years and require a liver transplant by adulthood. Possible complications after the Kasai procedure include ascites, bacterial cholangitis, portal hypertension, and pruritis.

Post Liver Transplantation Biliary Atresia

If the atresia is complete, liver transplantation is the only option. Although liver transplantation is generally successful at treating biliary atresia, liver transplantation may have complications such as organ rejection. Also, a donor liver may not become available. Further, in some patients, liver transplantation may not be successful at curing biliary atresia.

Xanthoma

Xanthoma is a skin condition associated cholestatic liver diseases, in which certain fats build up under the surface of the skin. Cholestasis results in several disturbances of lipid metabolism resulting in formation of an abnormal lipid particle in the blood called lipoprotein X. Lipoprotein X is formed by regurgitation of bile lipids into the blood from the liver and does not bind to the LDL receptor to deliver cholesterol to cells throughout the body as does normal LDL. Lipoprotein X increases liver cholesterol production by five fold and blocks normal removal of lipoprotein particles from the blood by the liver.

Compounds

In some embodiments, provided herein are ASBT inhibitors that reduce or inhibit bile acid recycling in the distal gastrointestinal (GI) tract, including the distal ileum, the colon and/or the rectum. In certain embodiments, the ASBTIs are systemically absorbed. In certain embodiments, the ASBTIs are not systemically absorbed. In some embodiments, ASBTIs described herein are modified or substituted (e.g., with a -L-K group) to be non-systemic. In certain embodiments, any ASBT inhibitor is modified or substituted with one or more charged groups (e.g., K) and optionally, one or more linker (e.g., L), wherein L and K are as defined herein.

In some embodiments, an ASBTI suitable for the methods described herein is a compound of Formula I:

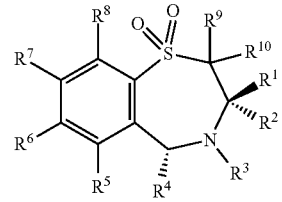

Formula I wherein:

$R^1$ is a straight chained $C_{1-6}$ alkyl group;

$R^2$ is a straight chained $C_{1-6}$ alkyl group;

$R^3$ is hydrogen or a group $OR^{11}$ in which $R^{11}$ is hydrogen, optionally substituted $C_{1-6}$ alkyl or a $C_{1-6}$ alkylcarbonyl group;

$R^4$ is pyridyl or optionally substituted phenyl or $-L_z-K_z$; wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

$R^5$, $R^6$, $R^7$ and $R^8$ are the same or different and each is selected from hydrogen, halogen, cyano, $R^5$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, OCF3, OCN, SCN, NHCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, NHCOCF$_3$, NHSO$_2R^{15}$, $OCH_2OR^{15}$, OCH=CHRIS, $O(CH_2CH_2O)_nR^{15}$, $O(CH_2)_pSO_3R^{15}$, $O(CH_2)_pNR^{12}R^{13}$, $O(CH_2)_pN^+R^{12}R^{13}R^{14}$ and $-W-R^{31}$, wherein W is O or NH and $R^{31}$ is selected from

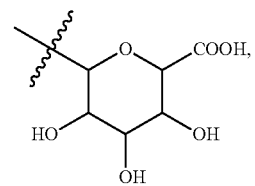 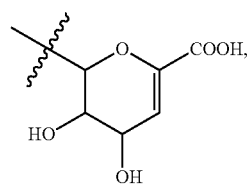

-continued

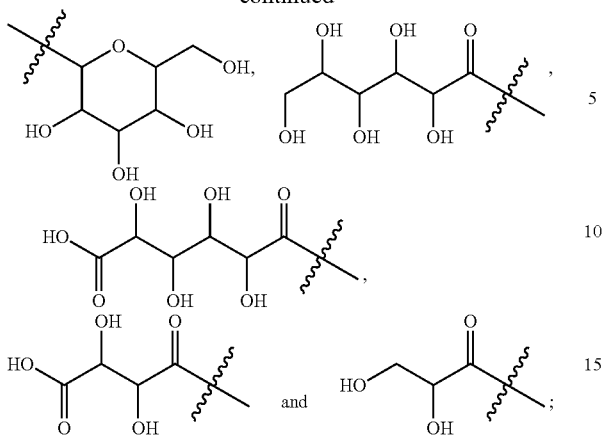

and wherein p is an integer from 1-4, n is an integer from 0-3 and, $R^{12}$, $R^{13}$, $R^{14}$ and $R^{15}$ are independently selected from hydrogen and optionally substituted $C_{1-6}$ alkyl; or $R^6$ and $R^7$ are linked to form a group

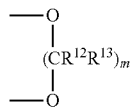

wherein $R^{12}$ and $R^{13}$ are as hereinbefore defined and m is 1 or 2; and $R^9$ and $R^{10}$ are the same or different and each is selected from hydrogen or $C_{1-6}$ alkyl; and salts, solvates and physiologically functional derivatives thereof.

In some embodiments of the methods, the compound of Formula I is a compound
wherein
$R^1$ is a straight chained $C_{1-6}$ alkyl group;
$R^2$ is a straight chained $C_{1-6}$ alkyl group;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is optionally substituted phenyl;
$R^5$, $R^6$ and $R^8$ are independently selected from hydrogen, $C_{1-4}$ alkyl optionally substituted by fluorine, $C_{1-4}$ alkoxy, halogen, or hydroxy;
$R^7$ is selected from halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, OCN, SCN, HNCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_pR^{15}$, $O(CH_2)_pSO_3R^{15}$, $O(CH_2)_pNR^{12}R^{13}$ and $O(CH_2)_pN^+R^{12}R^{13}R^{14}$;
wherein n, p and $R^{12}$ to $R^{15}$ are as hereinbefore defined;
with the proviso that at least two of $R^5$ to $R^8$ are not hydrogen; and
salts solvates and physiologically functional derivatives thereof.

In some embodiments of the methods described herein, the compound of Formula I is a compound
wherein
$R^1$ is a straight chained $C_{1-6}$ alkyl group;
$R^2$ is a straight chained $C_{1-6}$ alkyl group;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is un-substituted phenyl;
$R^5$ is hydrogen or halogen;
$R^6$ and $R^8$ are independently selected from hydrogen, $C_{1-4}$ alkyl optionally substituted by fluorine, $C_{1-4}$ alkoxy, halogen, or hydroxy;
$R^7$ is selected from $OR^{15}$, $S(O)_nR^{15}$, $OCOR^{15}$, $OCF_3$, OCN, SCN, CHO, $OCH_2OR^{15}$, $OCH=CHR^{15}$, $O(CH_2CH_2O)nR^{15}$, $O(CH_2)_pSO_3R^{15}$, $O(CH_2)_pNR^{12}R^{13}$ and $O(CH_2)_pN^+R^{12}R^{13}R^{14}$ wherein p is an integer from 1-4, n is an integer from 0-3, and $R^{12}$, $R^{13}$, $R^{14}$, and $R^{15}$ are independently selected from hydrogen and optionally substituted $C_{1-6}$ alkyl;
$R^9$ and $R^{10}$ are the same or different and each is selected from hydrogen or $C_{1-6}$ alkyl; and
salts, solvates and physiologically functional derivatives thereof.

In some embodiments of the methods, wherein the compound of Formula I is a compound
wherein
$R^1$ is methyl, ethyl or n-propyl;
$R^2$ is methyl, ethyl, n-propyl, n-butyl or n-pentyl;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is un-substituted phenyl;
$R^5$ is hydrogen;
$R^6$ and $R^8$ are independently selected from hydrogen, $C_{1-4}$ alkyl optionally substituted by fluorine, $C_{1-4}$ alkoxy, halogen, or hydroxy;
$R^7$ is selected from $OR^{15}$, $S(O)_nR^{15}$, $OCOR^{15}$, $OCF_3$, OCN, SCN, CHO, $OCH_2OR^{15}$, $OCH=CHR^{15}$, $O(CH_2CH_2O)nR^{15}$, $O(CH_2)_pSO_3R^{15}$, $O(CH_2)_pNR^{12}R^{13}$ and $O(CH_2)_pN^+R^{12}R^{13}R^{14}$ wherein p is an integer from 1-4, n is an integer from 0-3, and $R^{12}$, $R^{13}$, $R^{14}$, and $R^{15}$ are independently selected from hydrogen and optionally substituted $C_{1-6}$ alkyl;
$R^9$ and $R^{10}$ are the same or different and each is selected from hydrogen or $C_{1-6}$ alkyl; and
salts, solvates and physiologically functional derivatives thereof.

In some embodiments of the methods, the compound of Formula I is a compound
wherein
$R^1$ is methyl, ethyl or n-propyl;
$R^2$ is methyl, ethyl, n-propyl, n-butyl or n-pentyl;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is un-substituted phenyl;
$R^5$ is hydrogen;
$R^6$ is $C_{1-4}$ alkoxy, halogen, or hydroxy;
$R^7$ is $OR^{15}$, wherein $R^{15}$ is hydrogen or optionally substituted $C_{1-6}$ alkyl;
$R^8$ is hydrogen or halogen;
$R^9$ and $R^{10}$ are the same or different and each is selected from hydrogen or $C_{1-6}$ alkyl; and
salts, solvates and physiologically functional derivatives thereof.

In some embodiments of the methods, the compound of Formula I is
(3R,5R)-3-Butyl-3-ethyl-2,3,4,5-tetrahydro-7,8-dimethoxy-5-phenyl-1,4-benzothiazepine 1,1-dioxide;
(3R,5R)-3-Butyl-3-ethyl-2,3,4,5-tetrahydro-7,8-dimethoxy-5-phenyl-1,4-benzothiazepin-4-ol 1,1-dioxide;
(±)-Trans-3-butyl-3-ethyl-2,3,4,5-tetrahydro-7,8-dimethoxy-5-phenyl-1,4-benzothiazepine 1,1-dioxide;
(±)-Trans-3-butyl-3-ethyl-2,3,4,5-tetrahydro-7,8-dimethoxy-5-phenyl-1,4,-benzothiazepin-4-ol 1,1-dioxide;
(3R,5R)-7-Bromo-3-butyl-3-ethyl-2,3,4,5-tetrahydro-8-methoxy-5-phenyl-1,4-benzothiazepine 1,1-dioxide;
(3R,5R)-7-Bromo-3-butyl-3-ethyl-2,3,4,5-tetrahydro-8-methoxy-5-phenyl-1,4-benxothiaxepin-4-ol 1,1-dioxide;
(3R,5R)-3-Butyl-3-ethyl-2,3,4,5-tetrahydro-5-phenyl-1,4-benzothiazepine-7,8-diol 1,1-dioxide;
(3R,5R)-3-Butyl-3-ethyl-2,3,4,5-tetrahydro-8-methoxy-5-phenyl-1,4-benzothiazepin-7-ol 1,1-dioxide;
(3R,5R)-3-Butyl-3-ethyl-2,3,4,5-tetrahydro-7-methoxy-5-phenyl-1,4-benzothiazepin-8-ol 1,1-dioxide;
(±)-Trans-3-butyl-3-ethyl-2,3,4,5-tetrahydro-8-methoxy-5-phenyl-1,4-benzothiazepine 1,1-dioxide;
(±)-Trans-3-butyl-3-ethyl-2,3,4,5-tetrahydro-5-phenyl-1,4-benzothiazepin-8-ol 1,1-dioxide;
(±)-Trans-3-butyl-3-ethyl-2,3,4,5-tetrahydro-5-phenyl-1,4-benzothiazepine-4,8-diol;
(±)-Trans-3-butyl-3-ethyl-2,3,4,5-tetrahydro-5-phenyl-1,4-benzothiazepin-8-thiol 1,1-dioxide;
(±)-Trans-3-butyl-3-ethyl-2,3,4,5-tetrahydro-5-phenyl-1,4-benzothiazepin-8-sulfonic acid 1,1-dioxide;
(±)-Trans-3-butyl-3-ethyl-2,3,4,5-tetrahydro-8,9-dimethoxy-5-phenyl-1,4-benzothiazepine 1,1-dioxide;
(3R,5R)-3-butyl-7,8-diethoxy-2,3,4,5-tetrahydro-5-phenyl-1,4-benzothiazepine 1,1-dioxide;
(±)-Trans-3-butyl-8-ethoxy-3-ethyl-2,3,4,5-tetrahydro-5-phenyl-1,4-benzothiazepine 1,1-dioxide;
(±)-Trans-3-butyl-3-ethyl-2,3,4,5-tetrahydro-8-isopropoxy-5-phenyl-1,4-benzothiazepine 1,1-dioxide hydrochloride;
(±)-Trans-3-butyl-3-ethyl-2,3,4,5-tetrahydro-5-phenyl-1,4-benzothiazepin-8-carbaldehyde-1,1-dioxide;
3,3-Diethyl-2,3,4,5-tetrahydro-7,8-dimethoxy-5-phenyl-1,4-benzothiazepine 1,1-dioxide;
3,3-Diethyl-2,3,4,5-tetrahydro-8-methoxy-5-phenyl-1,4-benzothiazepine 1,1-dioxide;
3,3-Diethyl-2,3,4,5-tetrahydro-5-phenyl-1,4-benzothiazpin-4,8-diol 1,1-dioxide;
(RS)-3,3-Diethyl-2,3,4,5-tetrahydro-4-hydroxy-7,8-dimethoxy-5-phenyl-1,4-benzothiazepine 1,1-dioxide;
(±)-Trans-3-butyl-8-ethoxy-3-ethyl-2,3,4,5-tetrahydro-5-phenyl-1,4-benzothiazepin-4-ol-1-dioxide;
(±)-Trans-3-butyl-3-ethyl-2,3,4,5-tetrahydro-8-isopropoxy-5-phenyl-1,4-benzothiazepin-4-ol 1,1-dioxide;
(±)-Trans-3-butyl-3-ethyl-2,3,4,5-tetrahydro-7,8,9-trimethoxy-5-phenyl-1,4-benzothiazepin-4-ol 1,1-dioxide;
(3R,5R)-3-butyl-3-ethyl-2,3,4,5-tetrahydro-5-phenyl-1,4-benzothiazepin-4,7,8-triol 1,1-dioxide;
(±)-Trans-3-butyl-3-ethyl-2,3,4,5-tetrahydro-4,7,8-trimethoxy-5-phenyl-1,4-benzothiazepine 1,1-dioxide;
3,3-Diethyl-2,3,4,5-tetrahydro-5-phenyl-1,4-benzothiazepin-8-ol 1,1-dioxide;
3,3-Diethyl-2,3,4,5-tetrahydro-7-methoxy-5-phenyl-1,4-benzothiazepin-8-ol 1,1-dioxide;
3,3Dibutyl-2,3,4,5-tetrahydro-5-phenyl-1,4-benzothiazepin-8-ol 1,1-dioxide;
(±)-Trans-3-Butyl-3-ethyl-2,3,4,5-tetrahydro-1,1-dioxo-5-phenyl-1,4-benzothiazepin-8-yl hydrogen sulfate; or 3,3-Diethyl-2,3,4,5-tetrahydro-1,1-dioxo-5-phenyl-1,4-benzothiazepin-8-yl hydrogen sulfate.
In some embodiments, the compound of Formula I is

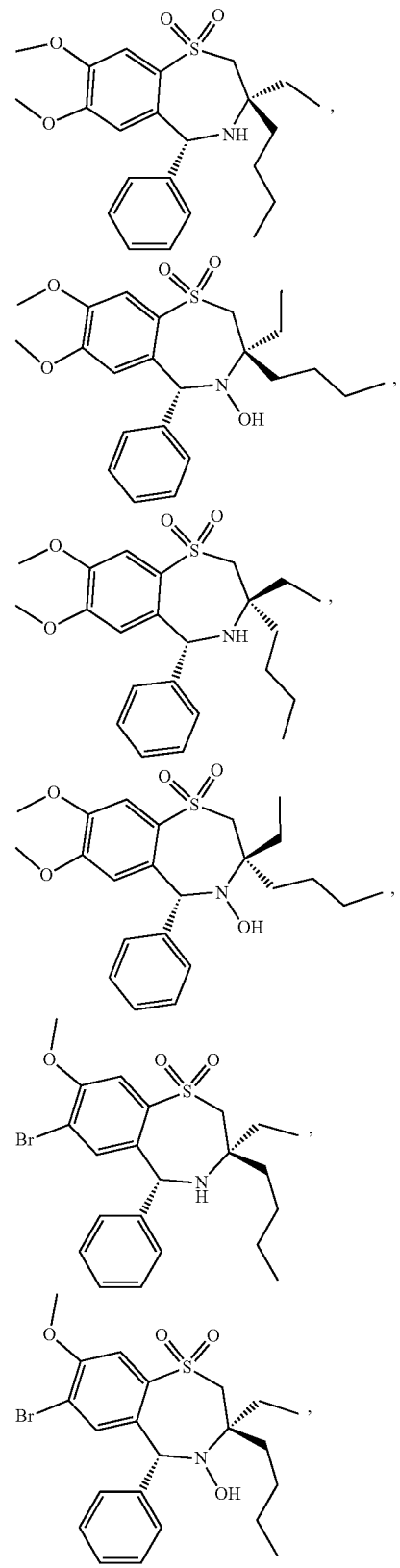

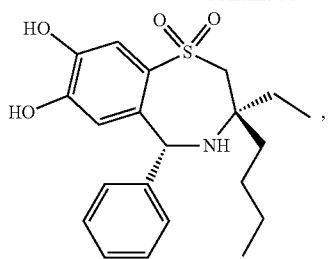,
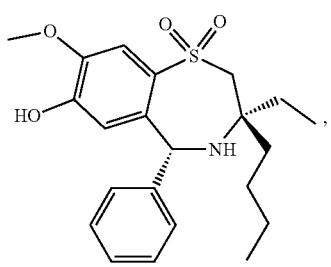,
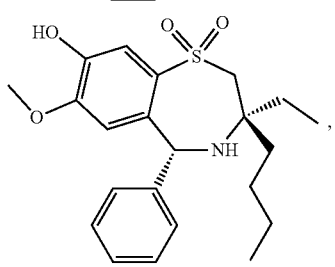,
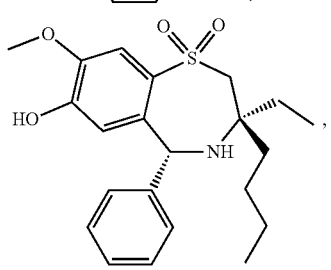,
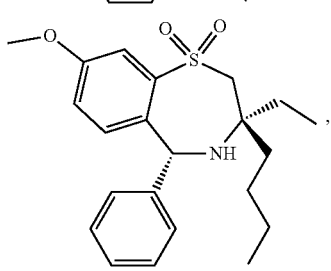,
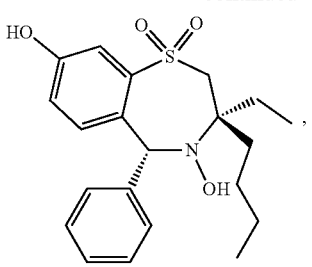,
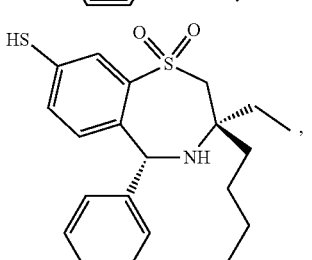,
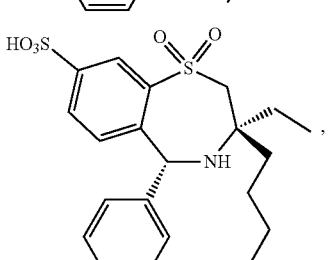,
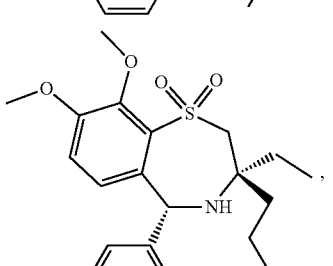,
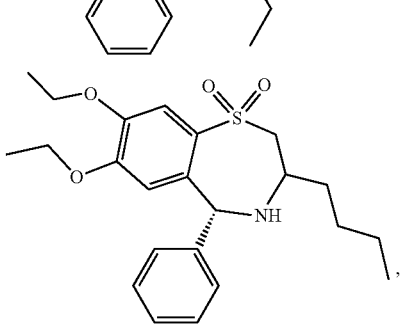,
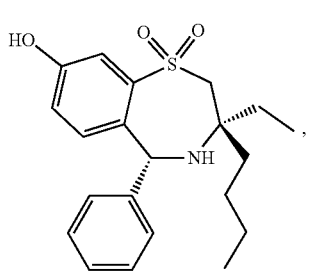,
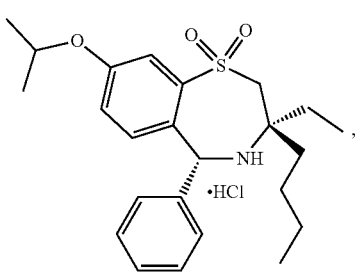

35
-continued
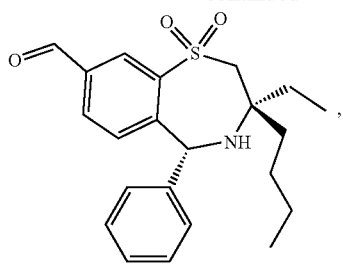
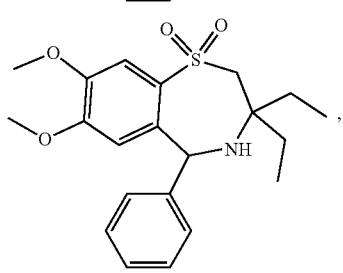
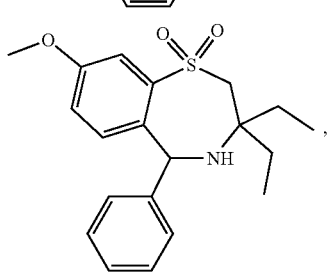
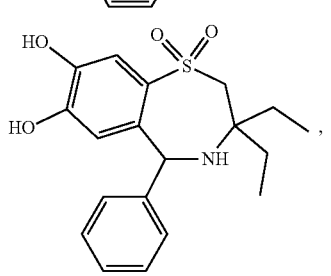
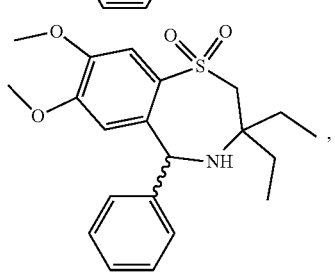
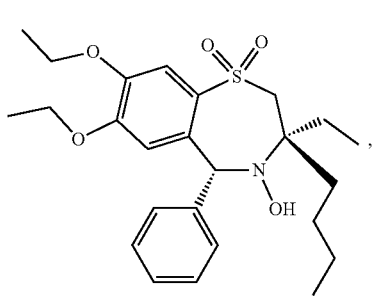
36
-continued
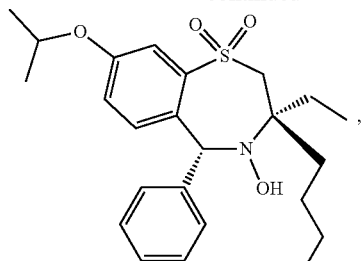
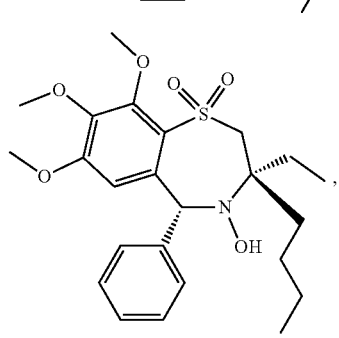
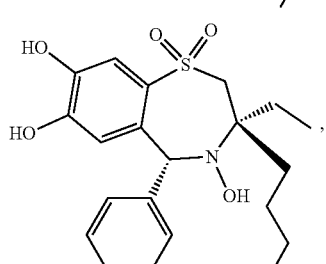
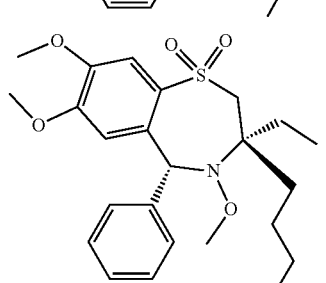
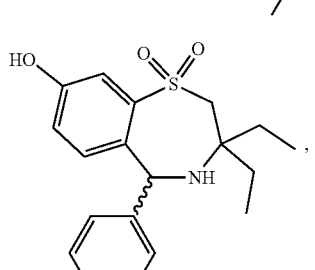
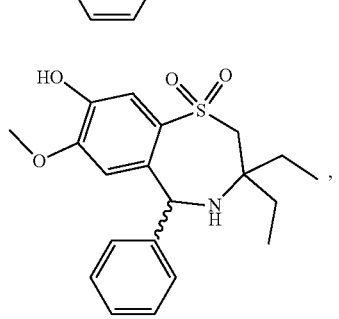

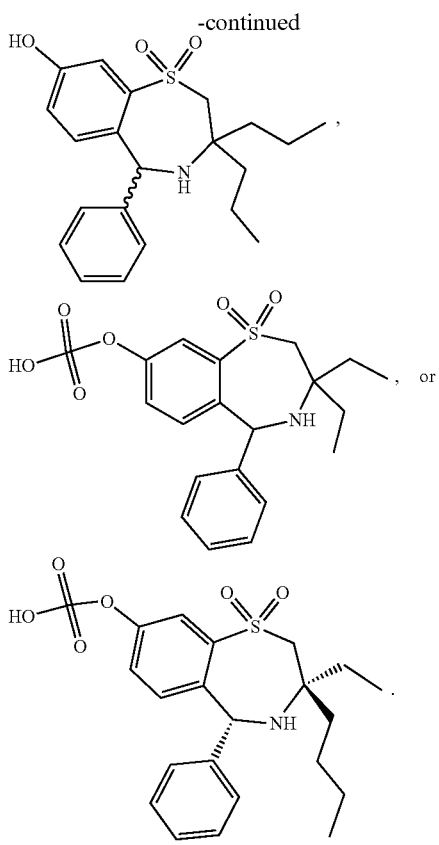

In some embodiments of the methods, the compound of Formula I is

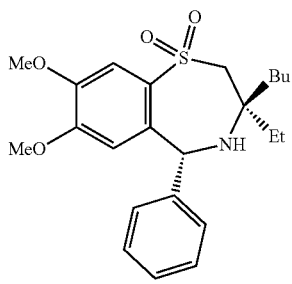

In some embodiments, the compound of Formula I is not a structure shown as:

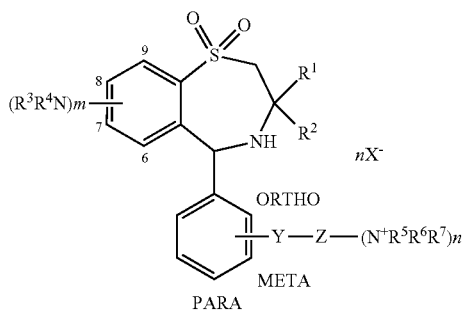

wherein m represents an integer of 1 or 2, and $R^3$ and $R^4$, which may be mutually different, each represents an alkyl group having 1 to 5 carbon atoms.

In some embodiments, an ASBTI suitable for the methods described herein is a compound of Formula II Formula II

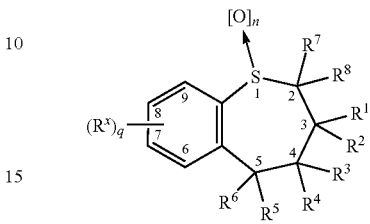

wherein:
q is an integer from 1 to 4;
n is an integer from 0 to 2;
$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene,
wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or
$R^1$ and $R^2$ taken together with the carbon to which they are attached form $C_3$-$C_{10}$ cycloalkyl;
$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or
$R^3$ and $R^4$ together =O, =$NOR^{11}$, =S, =$NNR^{11}R^{12}$, =$NR^9$, or =$CR^{11}R^{12}$
wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;
$R^5$ and $R^6$ are independently selected from the group consisting of H, alkyl, alkenyl, alkynyl, aryl, cycloalkyl, heterocycle, quaternary heterocycle, quaternary heteroaryl, $OR^9$, $SR^9$, $S(O)R^9$, $SO_2R^9$, $SO_3R^9$, and -$L_z$-$K_z$;
wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $R^{15}$, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$.

wherein:
$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, quaternary heteroarylalkyl, and -G-T-V-W, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, $C_2$-$C_7$ polyol, amino acid, peptide, or polypeptide, and G, T and V are each independently a bond, —O—, —S—, —N(H)—, substituted or unsubstituted alkyl, —O-alkyl, —N(H)-alkyl, —C(O)N(H)—, —N(H)C(O)—, —N(H)C(O)N(H)—, substituted or unsubstituted alkenyl, substituted or unsubstituted alkynyl, substituted or unsubstituted aryl, substituted or unsubstituted arylalkyl, substituted or unsubstituted alkenylalkyl, alkynylalkyl, substituted or unsubstituted heteroalkyl, substituted or unsubstituted heterocycle, substituted or unsubstituted carboxyalkyl, substituted or unsubstituted carboalkoxyalkyl, or substituted or unsubstituted cycloalkyl, and W is quaternary heterocycle, quaternary heteroaryl, quaternary heteroarylalkyl, $N^+R^9R^{11}R^{12}A^-$, $P^+R^9R^{10}R^{11}A^-$, $OS(O)_2OM$, or $S^+R^9R^{10}A^-$, and $R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl; and $R^7$ and $R^8$ are independently selected from the group consisting of hydrogen and alkyl; and one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $SR^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}R^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)M, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_3R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen or SH;
provided that when $R^5$ or $R^6$ is phenyl, only one of $R^1$ or $R^2$ is H;
provided that when q=1 and $R^x$ is styryl, anilido, or anilinocarbonyl, only one of $R^5$ or $R^6$ is alkyl; or a pharmaceutically acceptable salt, solvate, or prodrug thereof.

In some embodiments of the methods, the compound of Formula II is a compound wherein
q is an integer from 1 to 4;
n is 2;

$R^1$ and $R^2$ are independently selected from the group consisting of H, alkyl, alkoxy, dialkylamino, and alkylthio,
wherein alkyl, alkoxy, dialkylamino, and alkylthio are optionally substituted with one or more substituents selected from the group consisting of $OR^9$, $NR^9R^{10}$, $SR^9$, $SO_2R^9$, $CO_2R^9$, CN, halogen, oxo, and $CONR^9R^{10}$;
each $R^9$ and $R^{10}$ are each independently selected from the group consisting of H, alkyl, cycloalkyl, aryl, acyl, heterocycle, and arylalkyl;
$R^3$ and $R^4$ are independently selected from the group consisting of H, alkyl, acyloxy, $OR^9$, $NR^9R^{10}$, $SR^9$, and $SO_2R^9$, wherein $R^9$ and $R^{10}$ are as defined above;
$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or
$R^{11}$ and $R^{12}$ together with the nitrogen or carbon atom to which they are attached form a cyclic ring;
$R^5$ and $R^6$ are independently selected from the group consisting of H, alkyl, aryl, cycloalkyl, heterocycle, and $-L_z-K_z$;
wherein z is 1 or 2; each L is independently a substituted or unsubstituted alkyl, a substituted or unsubstituted heteroalkyl, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;
wherein alkyl, aryl, cycloalkyl, and heterocycle can be substituted with one or more substituent groups independently selected from the group consisting of alkyl, aryl, haloalkyl, cycloalkyl, heterocycle, arylalkyl, quaternary heterocycle, quaternary heteroaryl, halogen, oxo, $OR^{13}$, $OR^{13}R^{14}$, $NR^{13}R^{14}$, $SR^{13}$, $SO_2R^{13}$, $NR^{13}NR^{14}R^{15}$, $NO_2$, $CO_2R^{13}$, CN, OM, and $CR^{13}$,
wherein:
$A^-$ is a pharmaceutically acceptable anion and M is a pharmaceutically acceptable cation;
$R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein $R^{13}$, $R^{14}$ and $R^{15}$ are optionally substituted with one or more groups selected from the group consisting of quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, and $CONR^9R^{10}$; or
$R^{14}$ and $R^{15}$, together with the nitrogen atom to which they are attached, form a cyclic ring; and
is selected from the group consisting of alkyl, alkenyl, alkynyl, cycloalkyl, aryl, acyl, heterocycle, ammoniumalkyl, alkylammoniumalkyl, and arylalkyl; and
$R^7$ and $R^8$ are independently selected from the group consisting of hydrogen and alkyl; and
one or more $R^x$ are independently selected from the group consisting of H, alkyl, acyloxy, aryl, arylalkyl, halogen, haloalkyl, cycloalkyl, heterocycle, heteroaryl, $OR^{13}$, $NR^{13}R^{14}$, $SR^{13}$, $S(O)_2R^{13}$, $NR^{13}NR^{14}R^{15}$, $NO_2$, $CO_2R^{13}$, CN, $SO_2NR^{13}R^{14}$, $NR^{14}C(O)R^{13}$, $C(O)NR^{13}R^{14}$, $NR^{14}C(O)R^{13}$, and $COR^{13}$;
provided that both $R^5$ and $R^6$ cannot be hydrogen;
provided that when $R^5$ or $R^6$ is phenyl, only one of $R^1$ or $R^2$ is H;
provided that when q=1 and $R^x$ is styryl, anilido, or anilinocarbonyl, only one of $R^5$ or $R^6$ is alkyl; or a pharmaceutically acceptable salt, solvate, or prodrug thereof.

In some embodiments, the compound of Formula II is a compound wherein
q is 1;
n is 2;
$R^x$ is $N(CH_3)_2$;
$R^7$ and $R^8$ are independently H;
$R^1$ and $R^2$ is alkyl;
$R^3$ is H, and $R^4$ is OH;
$R^5$ is H, and $R^6$ is selected from the group consisting of alkyl, alkenyl, alkynyl, aryl, cycloalkyl, heterocycle, quaternary heterocycle, quaternary heteroaryl, $OR^9$, $SR^9$, $S(O)R^9$, $SO_2R^9$, $SO_3R^9$, and $-L_z-K_z$;
wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;
wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $R^{15}$, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$,
wherein $A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7) OR^8$ and
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, quaternary heteroarylalkyl, and -G-T-V-W,
wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$,

43

$S^+R^9A^-$, PR, $P^+R^9R^{10}A^-$, $P(O)R^9$, phenylene, carbohydrate, $C_2$-$C_7$ polyol, amino acid, peptide, or polypeptide, and G, T and V are each independently a bond, —O—, —S—, —N(H)—, substituted or unsubstituted alkyl, —O-alkyl, —N(H)-alkyl, —C(O)N(H)—, —N(H)C(O)—, —N(H)C(O)N(H)—, substituted or unsubstituted alkenyl, substituted or unsubstituted alkynyl, substituted or unsubstituted aryl, substituted or unsubstituted arylalkyl, substituted or unsubstituted alkenylalkyl, alkynylalkyl, substituted or unsubstituted heteroalkyl, substituted or unsubstituted heterocycle, substituted or unsubstituted carboxyalkyl, substituted or unsubstituted carboalkoxyalkyl, or substituted or unsubstituted cycloalkyl, and W is quaternary heterocycle, quaternary heteroaryl, quaternary heteroarylalkyl, $N^+R^9R^{11}R^{12}A^-$, $P^+R^9R^{10}R^{11}A^-$, $OS(O)_2OM$, or $S^+R^9R^{10}A^-$, and $R^9$ and $R^{10}$ are independently selected from the group consisting of H, alkyl, alkenyl, alkynyl, cycloalkyl, aryl, acyl, heterocycle, ammoniumalkyl, arylalkyl, and alkylammoniumalkyl;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O) R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl;

or a pharmaceutically acceptable salt, solvate, or prodrug thereof.

In some embodiments, the compound of Formula II is a compound wherein q is 1;
n is 2;
$R^x$ is $N(CH_3)_2$;
$R^7$ and $R^8$ are independently H;
$R^1$ and $R^2$ is independently $C_1$-$C_4$ alkyl;
$R^3$ is H, and $R^4$ is OH;
$R^5$ is H, and $R^6$ is aryl substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $R^{15}$, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$,

44 wherein $A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7) OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, quaternary heteroarylalkyl, and -G-T-V-W, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, $C_2$-$C_7$ polyol, amino acid, peptide, or polypeptide, and G, T and V are each independently a bond, —O—, —S—, —N(H)—, substituted or unsubstituted alkyl, —O-alkyl, —N(H)-alkyl, —C(O)N(H)—, —N(H)C(O)—, —N(H)C(O)N(H)—, substituted or unsubstituted alkenyl, substituted or unsubstituted alkynyl, substituted or unsubstituted aryl, substituted or unsubstituted arylalkyl, substituted or unsubstituted alkenylalkyl, alkynylalkyl, substituted or unsubstituted heteroalkyl, substituted or unsubstituted heterocycle, substituted or unsubstituted carboxyalkyl, substituted or unsubstituted carboalkoxyalkyl, or substituted or unsubstituted cycloalkyl, and W is quaternary heterocycle, quaternary heteroaryl, quaternary heteroarylalkyl, $N^+R^9R^{10}R^{11}R^{12}A^-$, $P^+R^9R^{10}R^{11}A^-$, $OS(O)_2OM$, or $S^+R^9R^{10}A^-$, and $R^9$ and $R^{10}$ are independently selected from the group consisting of H, alkyl, alkenyl, alkynyl, cycloalkyl, aryl, acyl, heterocycle, ammoniumalkyl, arylalkyl, and alkylammoniumalkyl;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O) R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl;

or a pharmaceutically acceptable salt, solvate, or prodrug thereof.

In some embodiments of the methods, the compound of Formula II is a compound wherein $R^5$ and $R^6$ are independently selected from the group consisting of H, aryl, heterocycle, quaternary heterocycle, and quaternary heteroaryl wherein the aryl, heteroaryl, quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $OR^{13}R^{14}$, $NR^{13}R^{14}$, S $R^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $PR^{13}R^{14}R^{15}A^-$, $P(OR^{13})OR^{14}$, $S^+R^{13}R^{14}A^-$, $N^+R^9R^{11}R^{12}A^-$ and $-L_z-K_z$.

In some embodiments of the methods, the compound of Formula II is a compound wherein $R^5$ or $R^6$ is —Ar—$(R^y)_t$ t is an integer from 0 to 5;

Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and one or more $R^y$ are independently selected from the group consisting of alkyl, alkenyl, alkynyl, polyalkyl, polyether, aryl, halo alkyl, cycloalkyl, heterocycle, arylalkyl, halogen, oxo, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, $N^+R^9R^{11}R^{12}A^-$ and $-L_z-K_z$;

wherein said alkyl, alkenyl, alkynyl, polyalkyl, polyether, aryl, haloalkyl, cycloalkyl, and heterocycle can be further substituted with one or more substituent groups selected from the group consisting of $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$, and or phenylene;

wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene.

In some embodiments of the methods, the compound of Formula II is a compound wherein $R^5$ or $R^6$ is

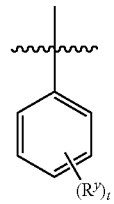

In some embodiments of the methods, the compound of Formula II is a compound wherein n is 1 or 2. In some embodiments of the methods, the compound of Formula II is a compound wherein $R^1$ and $R^2$ are independently H or $C_{1-7}$ alkyl. In some embodiments of the methods, the compound of Formula II is a compound wherein each $C_{1-7}$ alkyl is independently ethyl, n-propyl, n-butyl, or isobutyl. In some embodiments of the methods, the compound of Formula II is a compound wherein $R^3$ and $R^4$ are independently H or $OR^9$. In some embodiments of the methods, compound of Formula II is a compound wherein $R^9$ is H In some embodiments of the methods, the compound of Formula II is a compound wherein one or more $R^x$ are in the 7-, 8- or 9-position of the benzo ring of Formula II. In some embodiments of the methods, the compound of Formula II is a compound wherein $R^x$ is in the 7-position of the benzo ring of Formula II. In some embodiments of the methods, the compound of Formula II is a compound wherein one or more $R^x$ are independently selected from $OR^{13}$ and $NR^{13}R^{14}$.

In some embodiments of the methods, the compound of Formula II is a compound wherein:

q is 1 or 2;

n is 2;

$R^1$ and $R^2$ are each alkyl;

$R^3$ is hydroxy;

$R^4$ and $R^6$ are hydrogen;

$R^5$ has the formula

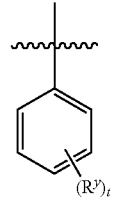

wherein t is an integer from 0 to 5;

one or more $R^Y$ are $OR^3$ or $OR^{13}R^{14}$;

$R^{13}$ and $R^{14}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl;

wherein said alkyl, alkenyl, alkynyl, arylalkyl, heterocycle, and polyalkyl groups optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide;

$R^{13}$ and $R^{14}$ are optionally substituted with one or more groups independently selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein A is a pharmaceutically acceptable anion, and M is a pharmaceutically acceptable cation, $R^9$ and $R^{10}$ are independently selected from the group consisting of H, alkyl, alkenyl, alkynyl, cycloalkyl, aryl, acyl, heterocycle, ammoniumalkyl, arylalkyl, and alkylammoniumalkyl;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH; or $R^{11}$ and $R^{12}$ together with the nitrogen or carbon atom to which they are attached form a cyclic ring; and $R^{16}$ and $R^{17}$ are independently selected from the substituents constituting $R^9$ and M;

$R^7$ and $R^8$ are hydrogen; and one or more $R^x$ are independently selected from the group consisting of alkoxy, alkylamino and dialkylamino and —W—$R^{31}$, wherein W is O or NH and $R^{31}$ is selected from

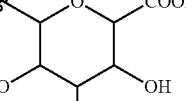
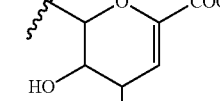
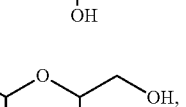
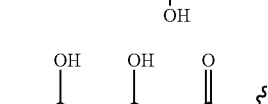
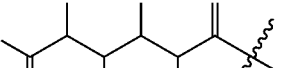

or a pharmaceutically acceptable salt, solvate, or prodrug thereof.

In some embodiments, a compound of Formula II is

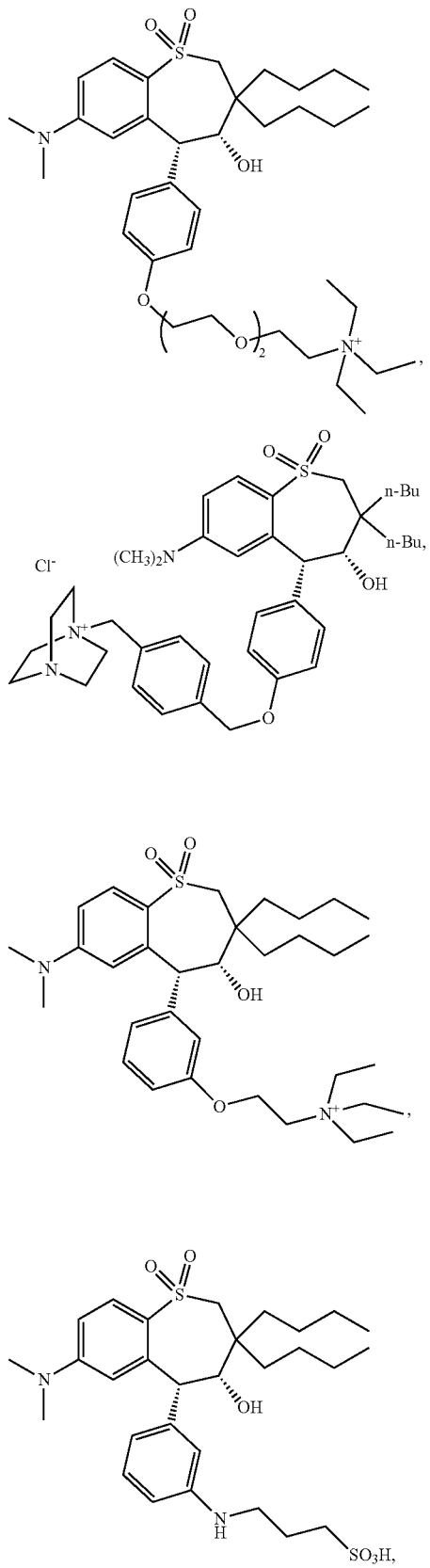

-continued

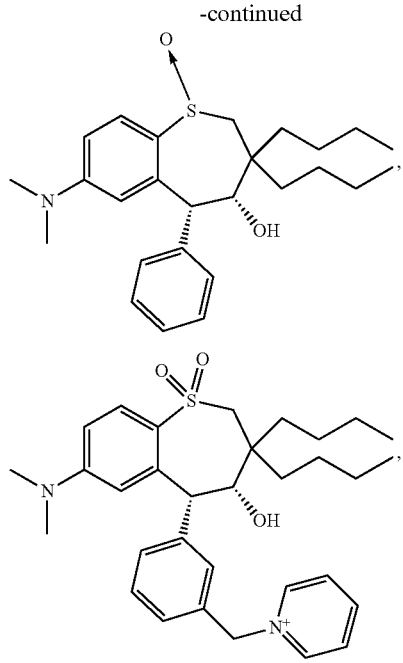

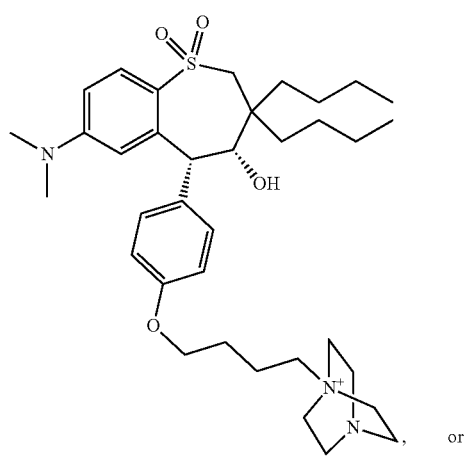

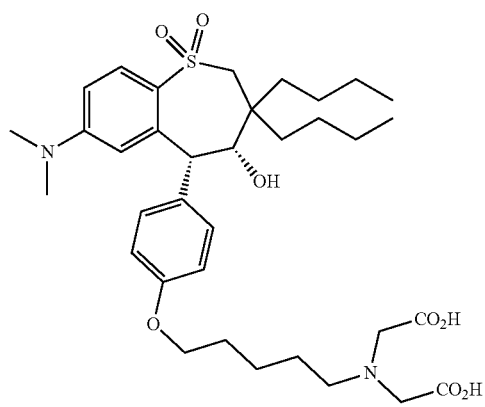

or the like.

In some embodiments of the methods, the compound of Formula II is

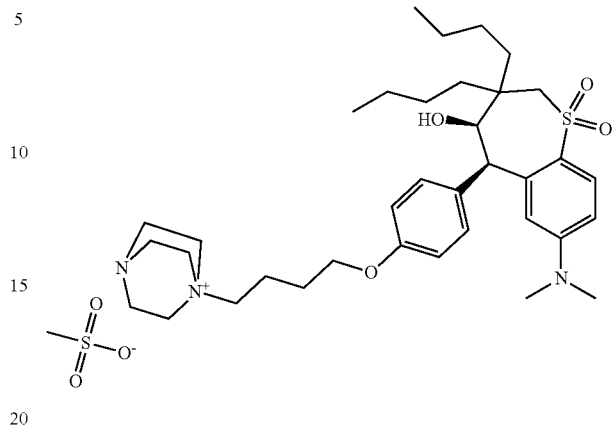

In certain embodiments, ASBTIs suitable for the methods described herein are non-systemic analogs of Compound 100C. Certain compounds provided herein are Compound 100C analogues modified or substituted to comprise a charged group. In specific embodiments, the Compound 100C analogues are modified or substituted with a charged group that is an ammonium group (e.g., a cyclic or acyclic ammonium group). In certain embodiments, the ammonium group is a non-protic ammonium group that contains a quaternary nitrogen.

In some embodiments, a compound of Formula II is

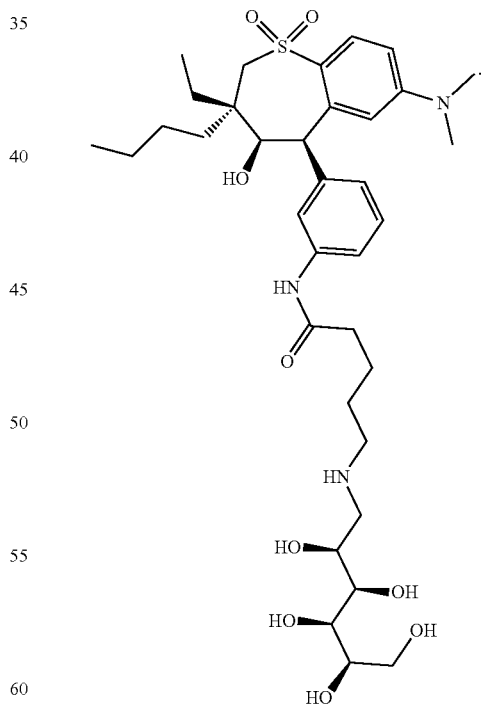

In some embodiments, a compound of Formula II is 1-[[5-[[3-[(3S,4R,5R)-3-butyl-7-(dimethylamino)-3-ethyl-2,3,4,5-tetrahydro-4-hydroxy-1,1-dioxido-1-benzothiepin-5yl]phenyl]amino]-5-oxopentyl]amino]-1-deoxy-D-glucitol or SA HMR1741 (a.k.a. BARI-1741).

In some embodiments, a compound of Formula II is

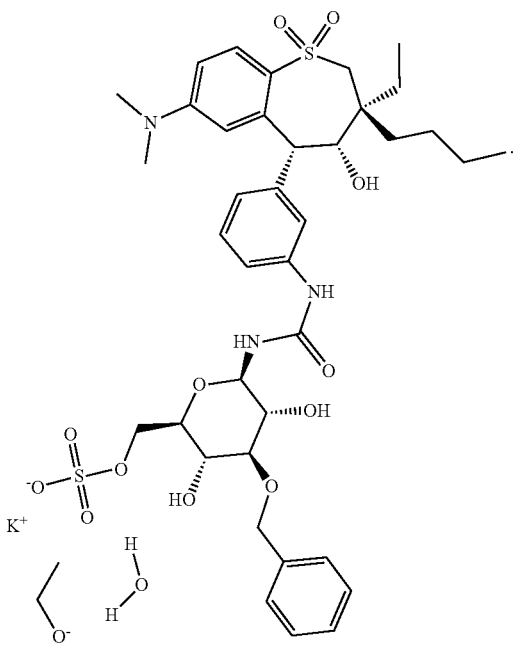

In some embodiments, a compound of Formula II is potassium((2R,3R,4S,5R,6R)-4-benzyloxy-6-{3-[3-((3S, 4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl) sulphate ethanolate, hydrate or SAR548304B (a.k.a. SAR-548304).

In some embodiments, an ASBTI suitable for the methods described herein is a compound of Formula III:

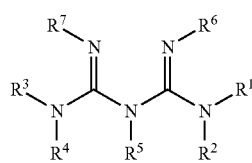

Formula III wherein:

each $R^1$, $R^2$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;

each $R^3$, $R^4$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

$R^5$ is H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, each $R^6$, $R^7$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;

each X is independently NH, S, or O;
each Y is independently NH, S, or O;

$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein
each A is independently NR$^1$, S(O)$_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;
n is 0-7;

K is a moiety that prevents systemic absorption;
provided that at least one of $R^1$, $R^2$, $R^3$ or $R^4$ is -L-K;
or a pharmaceutically acceptable prodrug thereof.

In some embodiments of a compound of Formula III, $R^1$ and $R^3$ are -L-K. In some embodiments, $R^1$, $R^2$ and $R^3$ are -L-K.

In some embodiments, at least one of $R^1$, $R^2$, $R^3$, $R^4$, $R^5$, $R^6$ and $R^7$ is H. In certain embodiments, $R^5$, $R^6$, $R^7$ are H and $R^1$, $R^2$, $R^3$ and $R^4$ are alkyl, aryl, alkyl-aryl, or heteroalkyl. In some embodiments, $R^1$ and $R^2$ are H. In some embodiments, $R^1$, $R^2$, $R^5$, $R^6$ and $R^7$ are H. In some embodiments, $R^6$ and $R^7$ together form a bond. In certain embodiments, $R^5$, $R^6$ and $R^7$ are H, alkyl or O-alkyl.

In some embodiments, $R^1$ and $R^3$ are -L-K. In some embodiments, $R^1$, $R^2$ and $R^3$ are -L-K. In some embodiments, $R^3$ and $R^4$ are -L-K. In some embodiments, $R^1$ and $R^2$ together with the nitrogen to which they are attached form a 3-8 membered ring and the ring is substituted with -L-K. In some embodiments, $R^1$ or $R^2$ or $R^3$ or $R^4$ are aryl optionally substituted with -L-K. In some embodiments, $R^1$ or $R^2$ or $R^3$ or $R^4$ are alkyl optionally substituted with -L-K. In some embodiments, $R^1$ or $R^2$ or $R^3$ or $R^4$ are alky-aryl optionally substituted with -L-K. In some embodiments, $R^1$ or $R^2$ or $R^3$ or $R^4$ are heteroalkyl optionally substituted with -L-K.

In some embodiments, L is a $C_1$-$C_7$alkyl. In some embodiments, L is heteroalkyl. In certain embodiments, L is $C_1$-$C_7$alkyl-aryl. In some embodiments, L is $C_1$-$C_7$alkyl-aryl-$C_1$-$C_7$alkyl.

In certain embodiments, K is a non-protic charged group. In some specific embodiments, each K is a ammonium group. In some embodiments, each K is a cyclic non-protic ammonium group. In some embodiments, each K is an acyclic non-protic ammonium group.

In certain embodiments, each K is a cyclic non-protic ammonium group of structure:

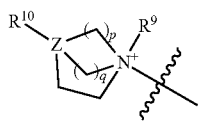

In certain embodiments, K is an acyclic non-protic ammonium group of structure:

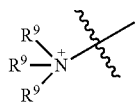

wherein p, q, $R^9$, $R^{10}$ and Z are as defined above. In certain embodiments, p is 1. In other embodiments, p is 2. In further embodiments, p is 3. In some embodiments, q is 0. In other embodiments, q is 1. In some other embodiments, q is 2.

The compounds further comprise 1, 2, 3 or 4 anionic counterions selected from $Cl^-$, $Br^-$, $I^-$, $R^{11}O_3^-$, ($SO_3^-$—$R^{11}$—$SO_3^-$), $R^{11}CO_2^-$, ($CO_2^-$—$R^{11}$—$CO_2^-$), $(R^{11})_2(P=O)O^-$ and $(R^{11})(P=O)O_2^{2-}$ wherein $R^{11}$ is as defined above. In some embodiments, the counterion is $Cl^-$, $Br^-$, $I^-$, $CH_2CO_2^-$, $CH_3SO_3^-$, or $C_6H_5SO_3^-$, or $CO_2^-$—$(CH_2)_2$—$CO_2^-$. In some embodiments, the compound of Formula III has one K group and one counterion. In other embodiments, the compound of Formula III has one K group, and two molecules of the compound of Formula III have one counterion. In yet other embodiments, the compound of Formula III has two K groups and two counterions. In some other embodiments, the compound of Formula III has one K group comprising two ammonium groups and two counterions.

Also described herein are compounds having the Formula IIIA:

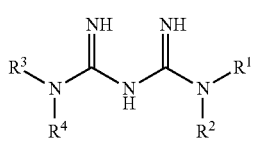

Formula IIIA wherein:
each $R^1$, $R^2$ is independently H, substituted or unsubstituted alkyl, or -L-K; or $R^1$ and $R^2$ together with the nitrogen to which they are attached form a 3-8-membered ring that is optionally substituted with $R^8$;

and $R^3$, $R^4$, $R^8$, L and K are as defined above.

In some embodiments of compounds of Formula IIIA, L is $A_n$, wherein each A is substituted or unsubstituted alkyl, or substituted or unsubstituted heteroalkyl, and n is 0-7. In certain specific embodiments of the compound of Formula IIIA, $R^1$ is H. In some embodiments of Formula IIIA, $R^1$ and $R^2$ together with the nitrogen to which they are attached form a 3-8-membered ring that is optionally substituted with -L-K.

Also described herein are compounds having the Formula IIIB:

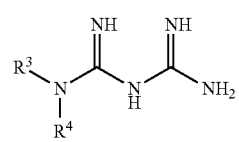

Formula IIIB wherein:
each $R^3$, $R^4$ is independently H, substituted or unsubstituted alkyl, substituted or unsubstituted heteroalkyl, substituted or unsubstituted aryl, substituted or unsubstituted alkyl-aryl, or -L-K;
and $R^1$, $R^2$, L and K are as defined above.

In certain embodiments of Formula IIIB, $R^3$ is H. In certain embodiments, $R^3$ and $R^4$ are each -L-K. In some embodiments, $R^3$ is H and $R^4$ is substituted or unsubstituted alkyl, substituted or unsubstituted heteroalkyl, substituted or unsubstituted aryl, substituted or unsubstituted alkyl-aryl containing one or two -L-K groups.

In some embodiments, an ASBTI suitable for the methods described herein is a compound of Formula IIIC

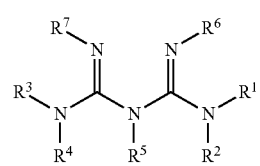

Formula IIIC wherein:
each $R^1$, $R^2$ is independently H, hydroxy, alkyl, alkoxy, —C(=X)$YR^8$, —YC(=X)$R^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;
each $R^3$, $R^4$ is independently H, hydroxy, alkyl, alkoxy, —C(=X)$YR^8$, —YC(=X)$R^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

$R^5$ is H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, each $R^6$, $R^7$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;

each X is independently NH, S, or O;

each Y is independently NH, S, or O;

$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein
each A is independently NR$^1$, S(O)$_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;
n is 0-7;

K is a moiety that prevents systemic absorption;
or a pharmaceutically acceptable salt thereof.

In some specific embodiments of Formula I, II or III, K is selected from

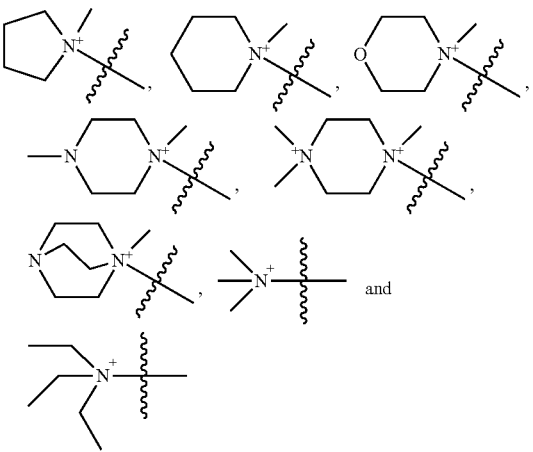

In some embodiments, an ASBTI suitable for the methods described herein is a compound of Formula IV:

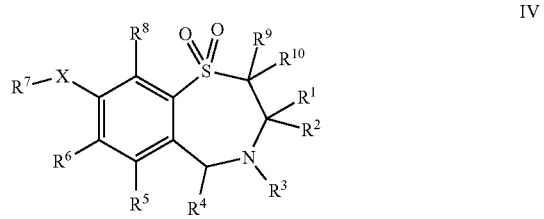

wherein
$R^1$ is a straight chain $C_{1-6}$ alkyl group;
$R^2$ is a straight chain $C_{1-6}$ alkyl group;
$R^3$ is hydrogen or a group OR$^{11}$ in which R$^{11}$ is hydrogen, optionally substituted $C_{1-6}$ alkyl or a $C_{1-6}$ alkylcarbonyl group;
$R^4$ is pyridyl or an optionally substituted phenyl;
$R^5$, $R^6$ and $R^8$ are the same or different and each is selected from:
hydrogen, halogen, cyano, R$^{15}$-acetylide, OR$^{15}$, optionally substituted $C_{1-6}$ alkyl, COR$^{15}$, CH(OH)R$^{15}$, S(O)$_n$R$^{15}$, P(O)(OR$^{15}$)$_2$, OCOR$^{15}$, OCF$_3$, OCN, SCN, NHCN, CH$_2$OR$^{15}$, CHO, (CH$_2$)$_p$CN, CONR$^{12}$R$^{13}$, (CH$_2$)$_p$CO$_2$R$^{15}$, (CH$_2$)$_p$NR$^{12}$R$^{13}$, CO$_2$R$^{15}$, NHCOCF$_3$, NHSO$_2$R$^{15}$, OCH$_2$OR$^{15}$, OCH=CHR$^{15}$, O(CH$_2$CH$_2$O)$_n$R$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$ wherein
p is an integer from 1-4,
n is an integer from 0-3 and
$R^{12}$, $R^{13}$, $R^{14}$ and $R^{15}$ are independently selected from hydrogen and optionally substituted $C^{1-6}$ alkyl;
$R^7$ is a group of the formula

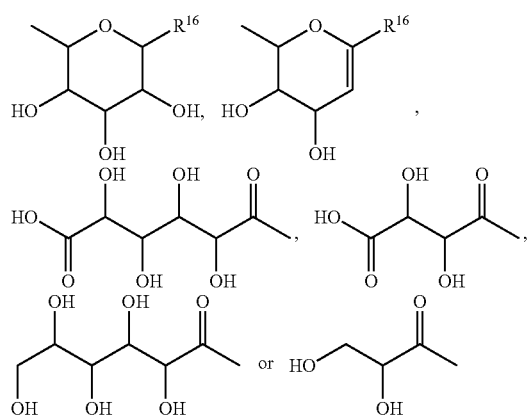

wherein the hydroxyl groups may be substituted by acetyl, benzyl,
or —(C$_1$-C$_6$)-alkyl-R$^{17}$,
wherein the alkyl group may be substituted with one or more hydroxyl groups;
$R^{16}$ is —COOH, —CH$_2$—OH, —CH$_2$—O-Acetyl, —COOMe or —COOEt;
$R^{17}$ is H, —OH, —NH$_2$, —COOH or COOR$^{18}$;
$R^{18}$ is (C$_1$-C$_4$)-alkyl or —NH—(C$_1$-C$_4$)-alkyl;
X is —NH— or —O—; and $R^9$ and $R^{10}$ are the same or different and each is hydrogen or $C_1$-$C_6$ alkyl; and salts thereof.

In some embodiments, a compound of Formula IV has the structure of Formula IVA or Formula IVB:

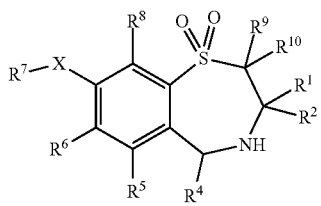

Formula IVA

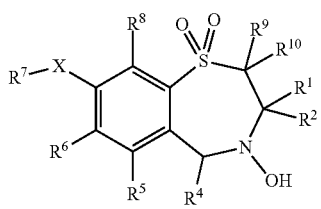

Formula IVB

In some embodiments, a compound of Formula IV has the structure of Formula IVC:

IVC

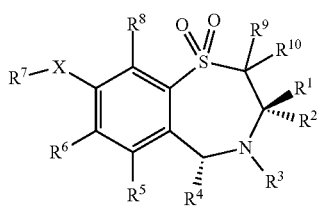

In some embodiments of Formula IV, X is O and $R^7$ is selected from

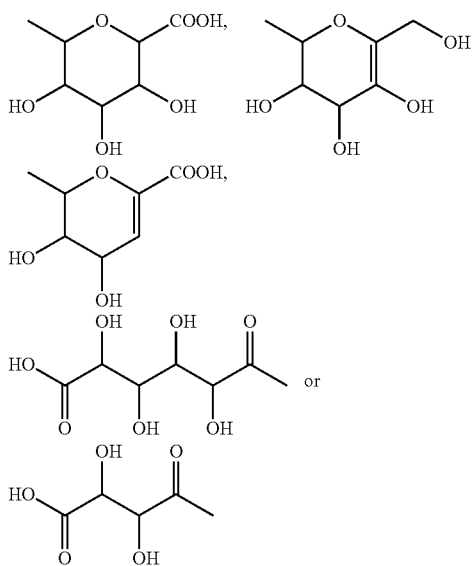

In some embodiments, a compound of Formula IV is:

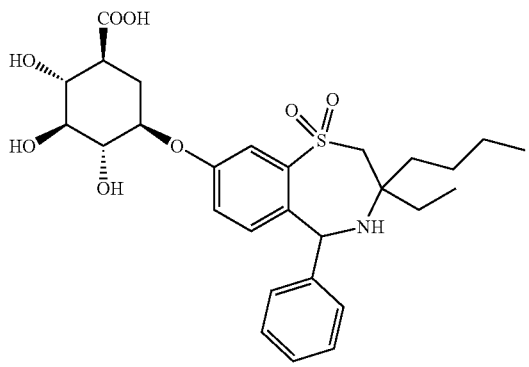 [SMILES: CCCCC1(CC)CS(=O)(=O)c2cc(O[C@@H]3C[C@H](C(=O)O)[C@@H](O)[C@H](O)[C@H]3O)ccc2C(c2ccccc2)N1]

In some embodiments, an ASBTI suitable for the methods described herein is a compound of Formula V:

V

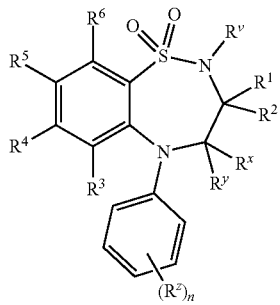

wherein:
$R^v$ is selected from hydrogen or $C_{1-6}$alkyl;
One of $R^1$ and $R^2$ are selected from hydrogen or $C_{1-6}$alkyl and the other is selected from $C_{1-6}$alkyl;
$R^x$ and $R^y$ are independently selected from hydrogen, hydroxy, amino, mercapto, $C_{1-6}$alkyl, $C_{1-6}$alkoxy, N—($C_{1-6}$alkyl)amino, N,N—($C_{1-6}$alkyl)$_2$amino, $C_{1-6}$alkylS(O)$_a$ wherein a is 0 to 2;
$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
n is 0-5;
one of $R^4$ and $R^5$ is a group of formula (VA):

VA

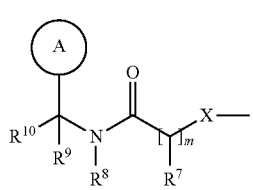

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—;
wherein $R^a$ is hydrogen or $C_{1-6}$alkyl and b is 0-2;
Ring A is aryl or heteroaryl;
wherein Ring A is optionally substituted on carbon by one or more substituents selected from $R^{18}$;
$R^7$ is hydrogen, $C_{1-6}$alkyl, carbocyclyl or heterocyclyl;
wherein $R^7$ is optionally substituted on carbon by one or more substituents selected from $R^{19}$; and wherein if said heterocyclyl contains an —NH— group, that nitrogen may be optionally substituted by a group selected from $R^{20}$;
$R^8$ is hydrogen or $C_{1-6}$-alkyl;
$R^9$ is hydrogen or $C_{1-6}$alkyl;
$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkynyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$; or $R^{10}$ is a group of formula (VB):

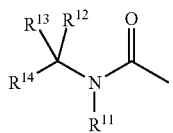

VB wherein:
$R^{11}$ is hydrogen or $C_{1-6}$-alkyl;
$R^{12}$ and $R^{13}$ are independently selected from hydrogen, halo, carbamoyl, sulphamoyl, $C_{1-10}$alkyl, $C_{2-10}$alkynyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;

$R^{14}$ is selected from hydrogen, halo, carbamoyl, sulphamoyl, hydroxyaminocarbonyl, $C_{1-10}$alkyl, $C_{2-10}$alkenyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (VC):

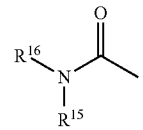

VC $R^{15}$ is hydrogen or $C_{1-6}$alkyl; and $R^{16}$ is hydrogen or $C_{1-6}$alkyl; wherein $R^{16}$ may be optionally substituted on carbon by one or more groups selected from $R^{31}$;
or $R^{15}$ and $R^{16}$ together with the nitrogen to which they are attached form a heterocyclyl; wherein said heterocyclyl may be optionally substituted on carbon by one or more $R^{37}$; and wherein if said heterocyclyl contains an —NH— group, that nitrogen may be optionally substituted by a group selected from $R^{38}$;
m is 1-3; wherein the values of $R^7$ may be the same or different;
$R^{17}$, $R^{18}$, $R^{19}$, $R^{23}$, $R^{25}$, $R^{29}$, $R^{31}$ and $R^{37}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$, $R^{31}$ and $R^{37}$ may be independently optionally substituted on carbon by one or more $R^{34}$; and wherein if said heterocyclyl contains an —NH— group, that nitrogen may be optionally substituted by a group selected from $R^{35}$;
$R^{21}$, $R^{22}$, $R^{27}$, $R^{28}$, $R^{32}$ or $R^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein R$^{36}$ is selected from hydrogen or $C_{1-6}$alkyl, and x is 0-2;
p, q, r and s are independently selected from 0-2;
$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}$, $R^{24}$, $R^{26}$, $R^{30}$, $R^{35}$ and $R^{38}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; and wherein a "heteroaryl" is a totally unsaturated, mono or bicyclic ring containing 3-12 atoms of which at least one atom is chosen from nitrogen, sulphur and oxygen, which heteroaryl may, unless otherwise specified, be carbon or nitrogen linked;

wherein a "heterocyclyl" is a saturated, partially saturated or unsaturated, mono or bicyclic ring containing 3-12 atoms of which at least one atom is chosen from nitrogen, sulphur and oxygen, which heterocyclyl may, unless otherwise specified, be carbon or nitrogen linked, wherein a —$CH_2$— group can optionally be replaced by a —C(O)— group, and a ring sulphur atom may be optionally oxidised to form an S-oxide; and wherein a "carbocyclyl" is a saturated, partially saturated or unsaturated, mono or bicyclic carbon ring that contains 3-12 atoms; wherein a —$CH_2$— group can optionally be replaced by a —C(O) group; or a pharmaceutically acceptable salt or in vivo hydrolysable ester or amide formed on an available carboxy or hydroxy group thereof.

In some embodiments, compound of Formula V is 1,1-dioxo-3,3-dibutyl-5-phenyl-7-methylthio-8-(N—{(R)-α-[N—((R)-1-carboxy-2-methylthio-ethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxybutyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxyethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—{(S)-1-[N—((S)-2-hydroxy-1-carboxyethyl)carbamoyl]propyl}carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-[N—{(R)-α-carboxy-4-hydroxybenzyl}carbamoylmethoxy]-2,3,4,5-tetrahydro-1,2,5-benzothiadiazepine; or 1,1-dioxo-3,3-dibutyl-5-phenyl-7-methylthio-8-(N—{(R)-α-[N-(carboxymethyl)carbamoyl]benzyl} carbamoylmethoxy)-2,3,4,5-tetrahydro-1,2,5-benzothiadiazepine, or a salt thereof.

In some embodiments, compound of Formula V is

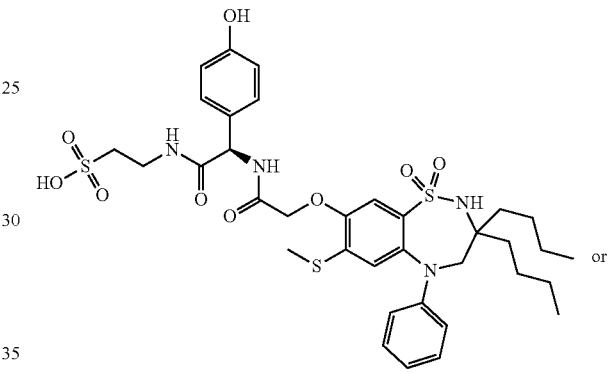

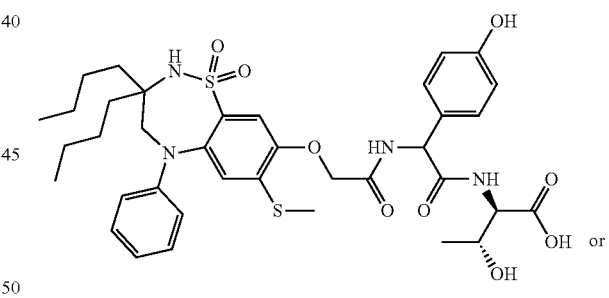

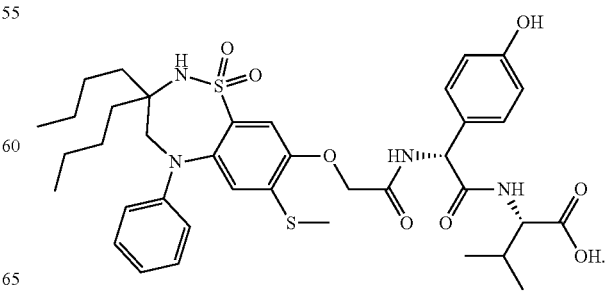

In some embodiments, an ASBTI suitable for the methods described herein is a compound of Formula VI:

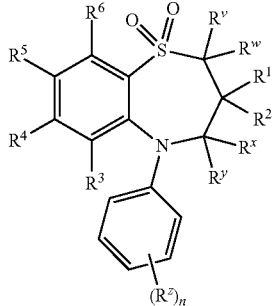

VI wherein:
R$^v$ and R$^w$ are independently selected from hydrogen or C$_{1-6}$alkyl;
one of R$^1$ and R$^2$ is selected from hydrogen or C$_{1-6}$alkyl and the other is selected from C$_{1-6}$alkyl;
R$^x$ and R$^y$ are independently selected from hydrogen or C$_{1-6}$alkyl, or one of R$^x$ and R$^y$ is hydrogen or C$_{1-6}$alkyl and the other is hydroxy or C$_{1-6}$alkoxy;
R$^z$ is selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulphamoyl and N,N—(C$_{1-6}$alkyl)$_2$sulphamoyl;
n is 0-5;
one of R$^4$ and R$^5$ is a group of formula (VIA):

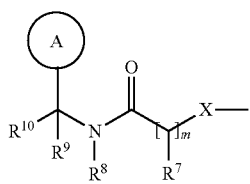

VIA

R$^3$ and R$^6$ and the other of R$^4$ and R$^5$ are independently selected from hydrogen, halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, N—(C$_{1-6}$alkyl)sulphamoyl and N,N—(C$_{1-6}$alkyl)$_2$sulphamoyl; wherein R$^3$ and R$^6$ and the other of R$^4$ and R$^5$ may be optionally substituted on carbon by one or more R$^7$;
X is —O—, —N(R$^a$)—, —S(O)$_b$— or —CH(R$^a$)—; wherein R$^a$ is hydrogen or C$_{1-6}$alkyl and b is 0-2;
Ring A is aryl or heteroaryl; wherein Ring A is optionally substituted on carbon by one or more substituents selected from R$^{18}$;
R$^7$ is hydrogen, C$_{1-6}$alkyl, carbocyclyl or heterocyclyl; wherein R$^7$ is optionally substituted on carbon by one or more substituents selected from R$^{19}$; and wherein if said heterocyclyl contains an —NH— group, that nitrogen may be optionally substituted by a group selected from R$^{20}$;
R$^8$ is hydrogen or C$_{1-6}$alkyl;
R$^9$ is hydrogen or C$_{1-6}$alkyl;
R$^{10}$ is hydrogen, halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, N,N,N—(C$_{1-10}$alkyl)$_3$ammonio, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{21}$—(C$_{1-10}$alkylene)$_q$- or heterocyclyl-(C$_{1-10}$alkylene)$_r$-R$^{22}$—(C$_{1-10}$alkylene)$_s$-; wherein R$^{10}$ is optionally substituted on carbon by one or more substituents selected from R$^{23}$; and wherein if said heterocyclyl contains an —NH— group, that nitrogen may be optionally substituted by a group selected from R$^{24}$; or R$^{10}$ is a group of formula (VIB):

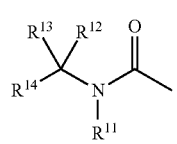

VIB wherein:
R$^{11}$ is hydrogen or C$_{1-6}$alkyl;
R$^{12}$ and R$^{13}$ are independently selected from hydrogen, halo, nitro, cyano, hydroxy, amino, carbamoyl, mercapto, sulphamoyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, carbocyclyl or heterocyclyl; wherein R$^{12}$ and R$^{13}$ may be independently optionally substituted on carbon by one or more substituents selected from R$^{25}$; and wherein if said heterocyclyl contains an —NH— group, that nitrogen may be optionally substituted by a group selected from R$^{26}$;
R$^{14}$ is selected from hydrogen, halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, N,N,N—(C$_{1-10}$alkyl)$_3$ammonio, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{27}$—(C$_{1-10}$alkylene)$_q$- or heterocyclyl-(C$_{1-10}$alkylene)$_r$-R$^{28}$—(C$_{1-10}$alkylene)$_s$-; wherein R$^{14}$ may be optionally substituted on carbon by one or more substituents selected from R$^{29}$; and wherein if said heterocyclyl contains an —NH— group, that nitrogen may be optionally substituted by a group selected from R$^{30}$; or R$^{14}$ is a group of formula (VIC):

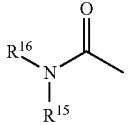

VIC

R$^{15}$ is hydrogen or C$_{1-6}$alkyl;
R$^{16}$ is hydrogen or C$_{1-6}$alkyl; wherein R$^{16}$ may be optionally substituted on carbon by one or more groups selected from R$^{31}$;
n is 1-3; wherein the values of R$^7$ may be the same or different;
R$^{17}$, R$^{18}$, R$^{19}$, R$^{23}$, R$^{25}$, R$^{29}$ or R$^{31}$ are independently selected from halo, nitro, cyano, hydroxy, amino, carbamoyl, mercapto, sulphamoyl, hydroxyaminocarbonyl, amidino, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, (C$_{1-10}$alkyl)$_3$silyl, N—(C$_{1-10}$alkyl)amino, N,N—(C$_{1-10}$alkyl)$_2$amino, N,N,N—(C$_{1-10}$alkyl)$_3$ammonio, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{32}$—(C$_{1-10}$alkylene)$_q$- or heterocyclyl-(C$_{1-10}$alkylene)$_r$-R$^{33}$—(C$_{1-10}$alkylene)$_s$-; wherein R$^7$, R$^{18}$, R$^{19}$, R$^{23}$, R$^{25}$, R$^{29}$ or R$^{31}$ may be independently optionally substituted on carbon by one or more R$^{34}$; and wherein if said heterocyclyl contains an —NH— group, that nitrogen may be optionally substituted by a group selected from R$^{35}$;
R$^{21}$, R$^{22}$, R$^{27}$, R$^{28}$, R$^{32}$ or R$^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein R$^{36}$ is selected from hydrogen or C$_{1-6}$alkyl, and x is 0-2;
p, q, r and s are independently selected from 0-2;
R$^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;
R$^{20}$, R$^{24}$, R$^{26}$, R$^{30}$ or R$^{35}$ are independently selected from C$_{1-6}$alkyl, C$_{1-6}$alkanoyl, C$_{1-6}$alkylsulphonyl, C$_{1-6}$alkoxycarbonyl, carbamoyl, N—(C$_{1-6}$alkyl)carbamoyl, N,N—(C$_{1-6}$alkyl)carbamoyl, benzyl, benzyloxycarbonyl, benzoyl and phenylsulphonyl;
or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

In some embodiments, a compound of Formula VI has the structure of Formula VID:

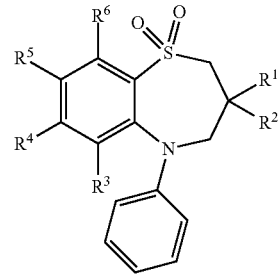

VID wherein:
R$^1$ and R$^2$ are independently selected from C$_{1-6}$alkyl; one of R$^4$ and R$^5$ is a group of formula (VIE):

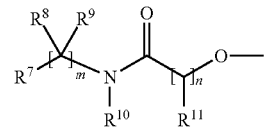

VIE

R$^3$ and R$^6$ and the other of R$^4$ and R$^5$ are independently selected from hydrogen, halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N—(C$_{1-4}$alkyl)amino, N,N—(C$_{1-4}$alkyl)$_2$amino, C$_{1-4}$alkanoylamino, N—(C$_{1-4}$alkyl)carbamoyl, N,N—(C$_{1-4}$alkyl)$_2$carbamoyl, C$_{1-4}$alkylS(O)$_a$ wherein a is 0 to 2, C$_{1-4}$alkoxycarbonyl, N—(C$_{1-4}$alkyl)sulphamoyl and N,N—(C$_{1-4}$alkyl)$_2$sulphamoyl; wherein R$^3$ and R$^6$ and the other of R$^4$ and R$^5$ may be optionally substituted on carbon by one or more R$^{14}$;
R$^7$ is carboxy, sulpho, sulphino, phosphono, —P(O)(OR$^a$)(OR$^b$), P(O)(OH)(OR$_a$), —P(O)(OH)(R$^a$) or P(O)(OR$^a$)(R$^b$), wherein R$^a$ and R$^b$ are independently selected from C$_{1-6}$alkyl; or R$^7$ is a group of formula (VIF):

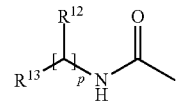

VIF

R$^8$ and R$^9$ are independently hydrogen, C$_{1-4}$alkyl or a saturated cyclic group, or R$^8$ and R$^9$ together form C$_{2-6}$alkylene; wherein R$^8$ and R$^9$ or R$^8$ and R$^9$ together may be independently optionally substituted on carbon by one or more substituents selected from R$^{15}$; and wherein if said saturated cyclic group contains an —NH— moiety, that nitrogen may be optionally substituted by one or more R$^{20}$.
R$^{10}$ is hydrogen or C$_{1-4}$alkyl; wherein R$^{10}$ is optionally substituted on carbon by one or more substituents selected from R$^{24}$;

$R^{11}$ is hydrogen, $C^{1-4}$alkyl, carbocyclyl or heterocyclyl; wherein $R^{11}$ is optionally substituted on carbon by one or more substituents selected from $R^{16}$; and wherein if said heterocyclyl contains an —NH— moiety, that nitrogen may be optionally substituted by one or more $R^{21}$.

$R^{12}$ is hydrogen or $C_{1-4}$alkyl, carbocyclyl or heterocyclyl; wherein $R^{12}$ optionally substituted on carbon by one or more substituents selected from $R^{17}$; and wherein if said heterocyclyl contains an —NH— moiety, that nitrogen may be optionally substituted by one or more $R^{22}$.

$R^{13}$ is carboxy, sulpho, sulphino, phosphono, —P(O)(OR$^c$)(OR$^d$), —P(O)(OH)(OR$^c$), —P(O)(OH)(R$^c$) or —P(O)(OR$^c$)(R$^d$) wherein R$^c$ and R$^d$ are independently selected from $C_{1-6}$alkyl;

m is 1-3; wherein the values of $R^8$ and $R^9$ may be the same or different;

n is 1-3; wherein the values of $R^{11}$ may be the same or different;

p is 1-3; wherein the values of $R^{12}$ may be the same or different;

$R^{14}$ and $R^{16}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{14}$ and $R^{16}$ may be independently optionally substituted on carbon by one or more $R^{18}$;

$R^{15}$ and $R^{17}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl, carbocyclyl, heterocyclyl, sulpho, sulphino, amidino, phosphono, —P(O)(OR$^e$)(OR$^f$), —P(O)(OH)(OR$^e$), —P(O)(OH)(R$^e$) or —P(O)(OR$^e$)(R$^f$), wherein R$^e$ and R$^f$ are independently selected from $C_{1-6}$alkyl; wherein $R^{15}$ and $R^{17}$ may be independently optionally substituted on carbon by one or more $R^{19}$; and wherein if said heterocyclyl contains an —NH— moiety, that nitrogen may be optionally substituted by one or more $R^{23}$;

$R^{18}$, $R^{19}$ and $R^{25}$ are independently selected from halo, hydroxy, cyano, carbamoyl, ureido amino nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{20}$, $R^{21}$, $R^{22}$, $R^{23}$ and $R^{26}$ are independently $C_{1-4}$alkyl, $C_{1-4}$alkanoyl, $C_{1-4}$alkylsulphonyl, sulphamoyl, N—($C_{1-4}$alkyl)sulphamoyl, N,N—($C_{1-4}$alkyl)$_2$sulphamoyl, $C_{1-4}$alkoxycarbonyl, carbamoyl, N—($C_{1-4}$alkyl)carbamoyl, N,N—($C_{1-4}$alkyl)$_2$carbamoyl, benzyl, phenethyl, benzoyl, phenylsulphonyl and phenyl;

$R^{24}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl, carbocyclyl, heterocyclyl; wherein $R^{24}$ may be independently optionally substituted on carbon by one or more $R^{25}$; and wherein if said heterocyclyl contains an —NH— moiety, that nitrogen may be optionally substituted by one or more $R^{26}$;

wherein any saturated cyclic group is a totally or partially saturated, mono or bicyclic ring containing 3-12 atoms of which 0-4 atoms are chosen from nitrogen, sulphur or oxygen, which may be carbon or nitrogen linked;

wherein any heterocyclyl is a saturated, partially saturated or unsaturated, mono or bicyclic ring containing 3-12 atoms of which at least one atom is chosen from nitrogen, sulphur or oxygen, which may be carbon or nitrogen linked, wherein a —CH$_2$— group can optionally be replaced by a —C(O)— or a ring sulphur atom may be optionally oxidised to form the S-oxides; and wherein any carbocyclyl is a saturated, partially saturated or unsaturated, mono or bicyclic carbon ring that contains 3-12 atoms, wherein a —CH$_2$— group can optionally be replaced by a —C(O)—;

or a pharmaceutically acceptable salt thereof.

In some embodiments, a compound of Formula IV is 1,1-dioxo-3,3-dibutyl-5-phenyl-7-methylthio-8-(N—{(R)-1'-phenyl-1'-[N'-(carboxymethyl) carbamoyl] methyl} carbamoylmethoxy)-2,3,4,5-tetrahydro-1,5-benzothiazepine; 1,1-dioxo-3,3-dibutyl-5-phenyl-7-methylthio-8-(N—{(R)-α-[N'—((S)-1-carboxypropyl)carbamoyl]-4-hydroxybenzyl} carbamoylmethoxy)-2,3,4,5-tetrahydro-1,5-benzothiazepine; 1,1-dioxo-3,3-dibutyl-5-phenyl-7-methylthio-8-(N—{(R)-1'-phenyl-1'-[N'-(carboxymethyl) carbamoyl] methyl} carbamoylmethoxy)-2,3,4,5-tetrahydro-1,5-benzothiazepine; 1,1-dioxo-3,3-dibutyl-5-phenyl-7-methylthio-8-(N—{(R)-α-[N'—((S)-1-carboxyethyl) carbamoyl]benzyl} carbamoylmethoxy)-2,3,4,5-tetrahydro-1,5-benzothiazepine; or a salt thereof.

In some embodiments, any compound described herein is covalently conjugated to a bile acid using any suitable method. In some embodiments, compounds described herein are covalently bonded to a cyclodextrin or a biodegradable polymer (e.g., a polysaccharide).

In certain embodiments compounds described herein are not systemically absorbed. Moreover, provided herein are compounds that inhibit bile salt recycling in the gastrointestinal tract of an individual. In some embodiments, compounds described herein, may not be transported from the gut lumen and/or do not interact with ASBT. In some embodiments, compounds described herein, do not affect, or minimally affect, fat digestion and/or absorption. In certain embodiments, the administration of a therapeutically effective amount of any compound described herein does not result in gastrointestinal disturbance or lactic acidosis in an individual. In certain embodiments, compounds described herein are administered orally. In some embodiments, an ASBTI is released in the distal ileum. An ASBTI compatible with the methods described herein may be a direct inhibitor, an allosteric inhibitor, or a partial inhibitor of the Apical Sodium-dependent Bile acid Transporter.

In certain embodiments, compounds that inhibit ASBT or any recuperative bile acid transporters are compounds that are described in EP1810689, U.S. Pat. Nos. 6,458,851, 7,413,536, 7,514,421, US Appl. Publication Nos. 2002/

0147184, 2003/0119809, 2003/0149010, 2004/0014806, 2004/0092500, 2004/0180861, 2004/0180860, 2005/0031651, 2006/0069080, 2006/0199797, 2006/0241121, 2007/0065428, 2007/0066644, 2007/0161578, 2007/0197628, 2007/0203183, 2007/0254952, 2008/0070888, 2008/0070892, 2008/0070889, 2008/0070984, 2008/0089858, 2008/0096921, 2008/0161400, 2008/0167356, 2008/0194598, 2008/0255202, 2008/0261990, WO 2002/50027, WO2005/046797, WO2006/017257, WO2006/105913, WO2006/105912, WO2006/116499, WO2006/117076, WO2006/121861, WO2006/122186, WO2006/124713, WO2007/050628, WO2007/101531, WO2007/134862, WO2007/140934, WO2007/140894, WO2008/028590, WO2008/033431, WO2008/033464, WO2008/031501, WO2008/031500, WO2008/033465, WO2008/034534, WO2008/039829, WO2008/064788, WO2008/064789, WO2008/088836, WO2008/104306, WO2008/124505, and WO2008/130616; the compounds described therein that inhibit recuperative bile acid transport are hereby incorporated herein by reference.

In certain embodiments, compounds that inhibit ASBT or any recuperative bile acid transporters are compounds described in WO93/16055, WO94/18183, WO94/18184, WO96/05188, WO96/08484, WO96/16051, WO97/33882, WO98/38182, WO99/35135, WO98/40375, WO99/64409, WO99/64410, WO00/01687, WO00/47568, WO00/61568, DE 19825804, WO00/38725, WO00/38726, WO00/38727 (including those compounds with a 2,3,4,5-tetrahydro-1-benzothiepine 1,1-dioxide structure), WO00/38728, WO01/66533, WO02/50051, EP0864582 (e.g. (3R,5R)-3-butyl-3-ethyl-1,1-dioxido-5-Phenyl-2,3,4,5-tetrahydro-1,4-benzothiazepin-8-yl (β-D-glucopyranosiduronic acid, WO94/24087, WO98/07749, WO98/56757, WO99/32478, WO99/35135, WO00/20392, WO00/20393, WO00/20410, WO00/20437, WO01/34570, WO00/35889, WO01/68637, WO01/68096, WO02/08211, WO03/020710, WO03/022825, WO03/022830, WO03/0222861, JP10072371, U.S. Pat. Nos. 5,910,494; 5,723,458; 5,817,652; 5,663,165; 5,998,400; 6,465,451, 5,994,391; 6,107,494; 6,387,924; 6,784,201; 6,875,877; 6,740,663; 6,852,753; 5,070,103, 6,114,322, 6,020,330, 7,179,792, EP251315, EP417725, EP489-423, EP549967, EP573848, EP624593, EP624594, EP624595, EP869121, EP1070703, WO04/005247, compounds disclosed as having IBAT activity in Drugs of the Future, 24, 425-430 (1999), Journal of Medicinal Chemistry, 48, 5837-5852, (2005) and Current Medicinal Chemistry, 13, 997-1016, (2006); the compounds described therein that inhibit recuperative bile acid transport are hereby incorporated herein by reference.

In some embodiments, compounds that inhibit ASBT or any recuperative bile acid transporter are benzothiepines, benzothiazepines (including 1,2-benzothiazepines; 1,4-benzothiazepines; 1,5-benzothiazepines; and/or 1,2,5-benzothiadiazepines). In some embodiments, compounds that inhibit ASBT or any recuperative bile acid transporter include and are not limited to S-8921 (disclosed in EP597107, WO 93/08155), 264W94 (GSK) disclosed in WO 96/05188; SC-435 (1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt), SC-635 (Searle); 2164U90 (3-butyl-3-ethyl-2,3,4,5-tetrahydro-5-phenyl-1,4-benzothiazepine 1,1-dioxide); BARI-1741 (Aventis SA), AZD 7508 (Astra Zeneca); barixibat (11-(D-gluconamido)-N-{2-[(1S,2R,3S)-3-hydroxy-3-phenyl-2-(2-pyridyl)-1-(2-pyridylamino)propyl]phenyl}undecanamide) or the like, or combinations thereof. In some embodiments, an ASBTI is:

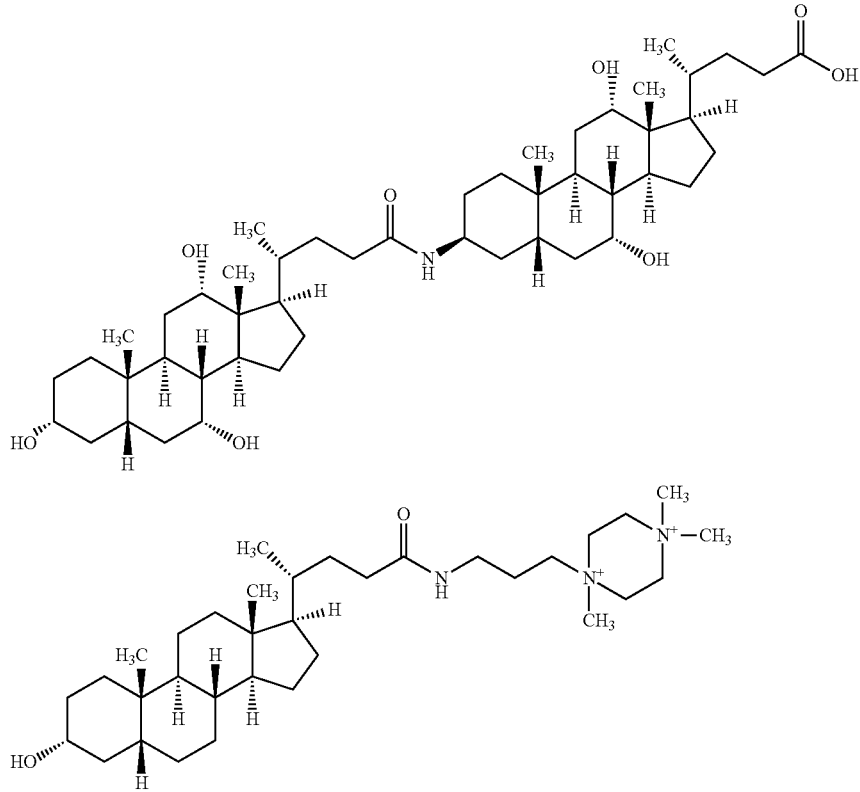

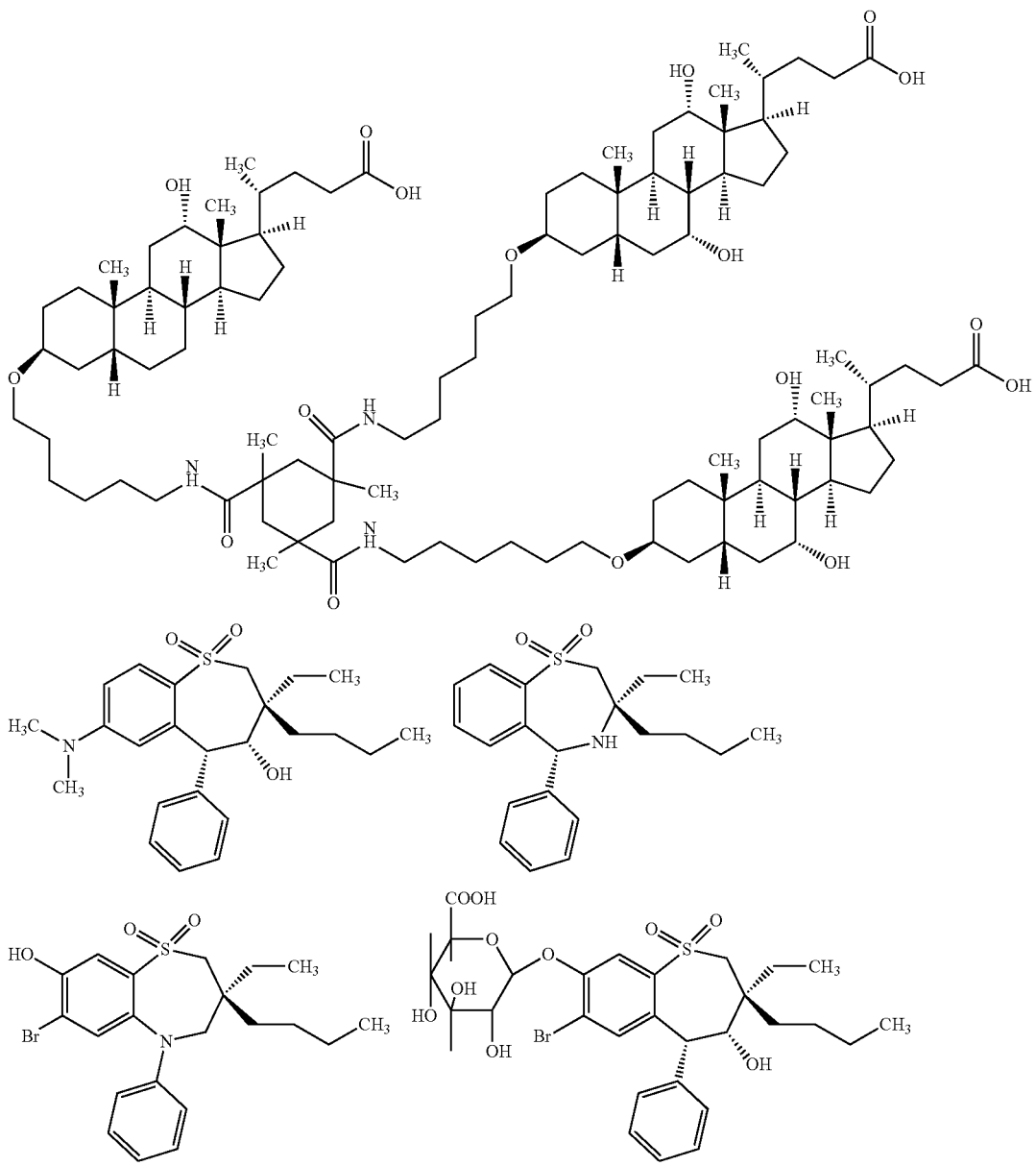
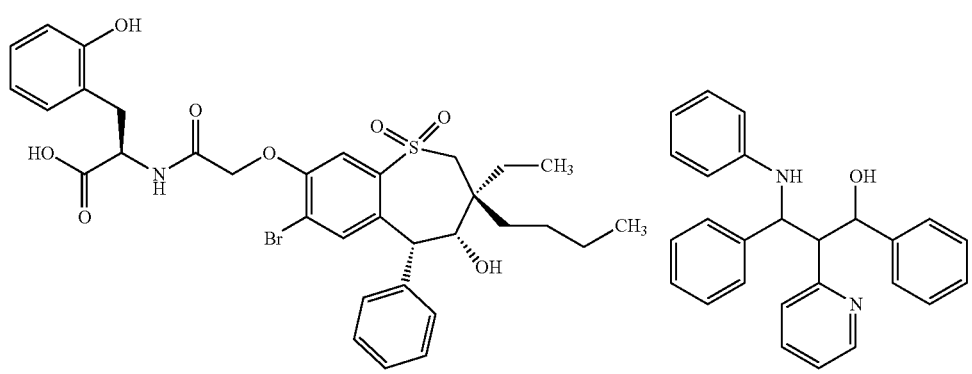

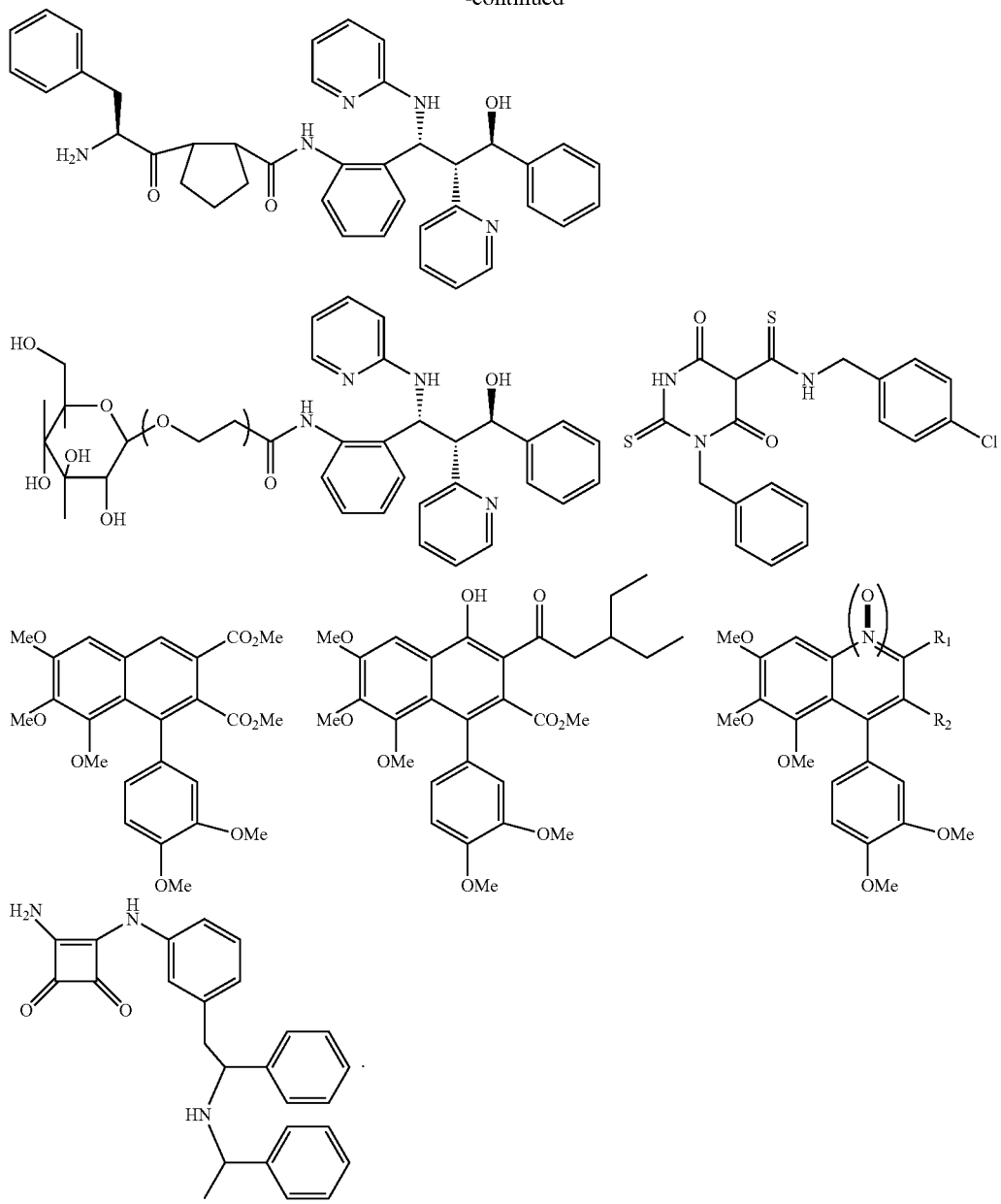

In certain embodiments, compounds described herein have one or more chiral centers. As such, all stereoisomers are envisioned herein. In various embodiments, compounds described herein are present in optically active or racemic forms. It is to be understood that the compounds of the present invention encompasses racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer is utilized as the therapeutic compound described herein. In certain embodiments, compounds described herein contains one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference for such disclosure). General methods for the preparation of compound as described herein are modified by the use of appropriate reagents and conditions, for the introduction of the various moieties found in the formulae as provided herein. As a guide the following synthetic methods are utilized.

Formation of Covalent Linkages by Reaction of an Electrophile with a Nucleophile The compounds described herein are modified using various electrophiles and/or nucleophiles to form new functional groups or substituents. Table A entitled "Examples of Covalent Linkages and Precursors Thereof" lists selected non-limiting examples of covalent linkages and precursor functional groups which yield the covalent linkages. Table A is used as guidance toward the variety of electrophiles and nucleophiles combinations available that provide covalent linkages. Precursor functional groups are shown as electrophilic groups and nucleophilic groups.

TABLE A

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it is necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. In some embodiments it is contemplated that each protective group be removable by a different means. Protective groups that are cleaved under totally disparate reaction conditions fulfill the requirement of differential removal.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a Pd⁰-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups are selected from:

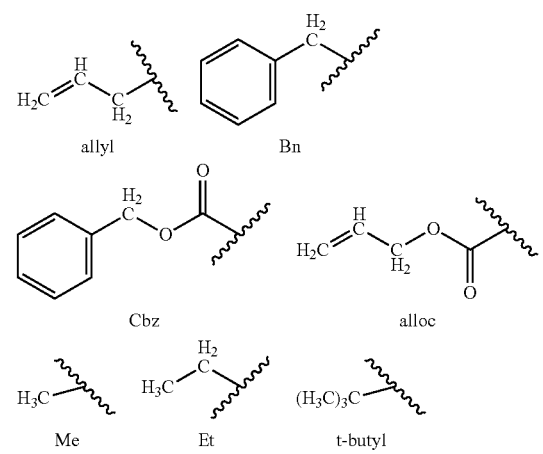

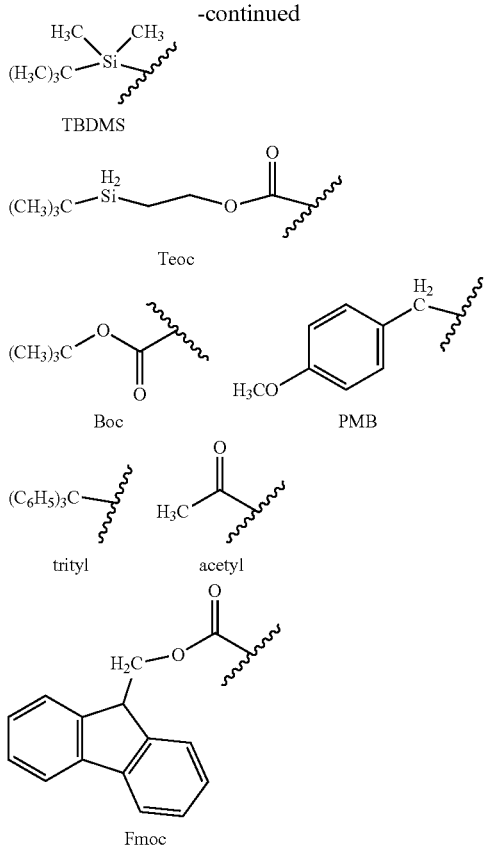

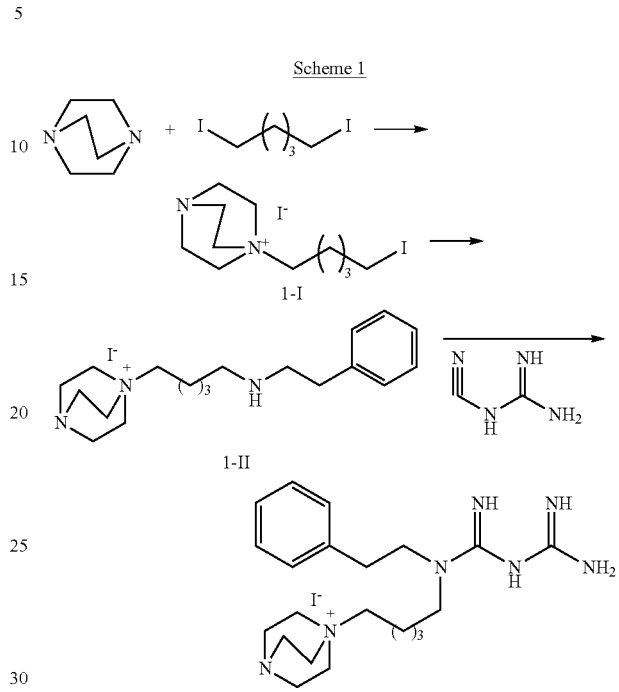

Other protecting groups, plus a detailed description of techniques applicable to the creation of protecting groups and their removal are described in Greene and Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

In some embodiments, ASBTIs described herein are synthesized as described in, for example, WO 96/05188, U.S. Pat. Nos. 5,994,391; 7,238,684; 6,906,058; 6,020,330; and 6,114,322. In some embodiments, ASBTIs described herein are synthesized starting from compounds that are available from commercial sources or that are prepared using procedures outlined herein. In some embodiments, compounds described herein are prepared according to the process set forth in Scheme 1:

In certain embodiments, the synthesis begins with a reaction of 1,4-diazabicyclo[2.2.2]octane with 4-iodo-1-chloro butane to provide a compound of structure 1-I. Such compounds are prepared in any suitable manner, e.g., as set forth in Tremont, S. J. et. al., *J. Med. Chem.* 2005, 48, 5837-5852. The compound of structure 1-I is then subjected to a reaction with phenethylamine to provide a compound of structure 1-II. The compound of structure 1-II is then allowed to react with dicyanodiamide to provide a compound of Formula I.

In some embodiments, a first compound of Formula III is subjected to a further reaction to provide a second compound of Formula III as shown in Scheme 2 below.

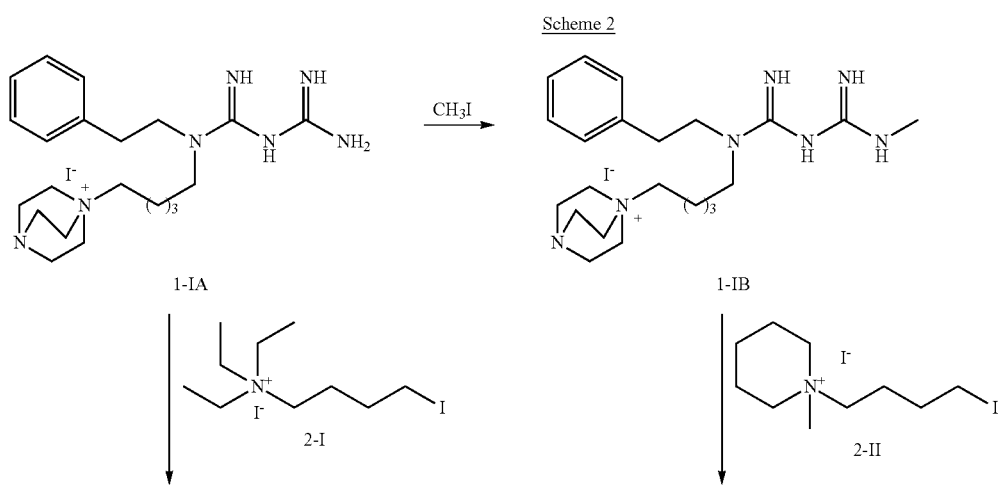

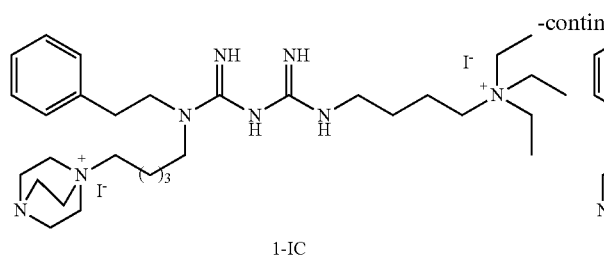

1-IC

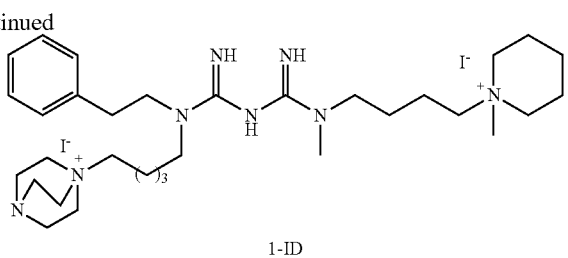

1-ID

A first compound of Formula III, 1-IA, is alkylated with iodomethane to provide a second compound of Formula III, 1-IB. Alkylation of 1-IB with a compound of structure 2-II provides a further compound of Formula III, IC. In an alternative embodiment, a first compound of Formula III, 1-IA, is alkylated with a compound of structure 2-I to provide a second compound of Formula III, 1-IC In some embodiments, compounds described herein are prepared according to the process set forth in Scheme 3:

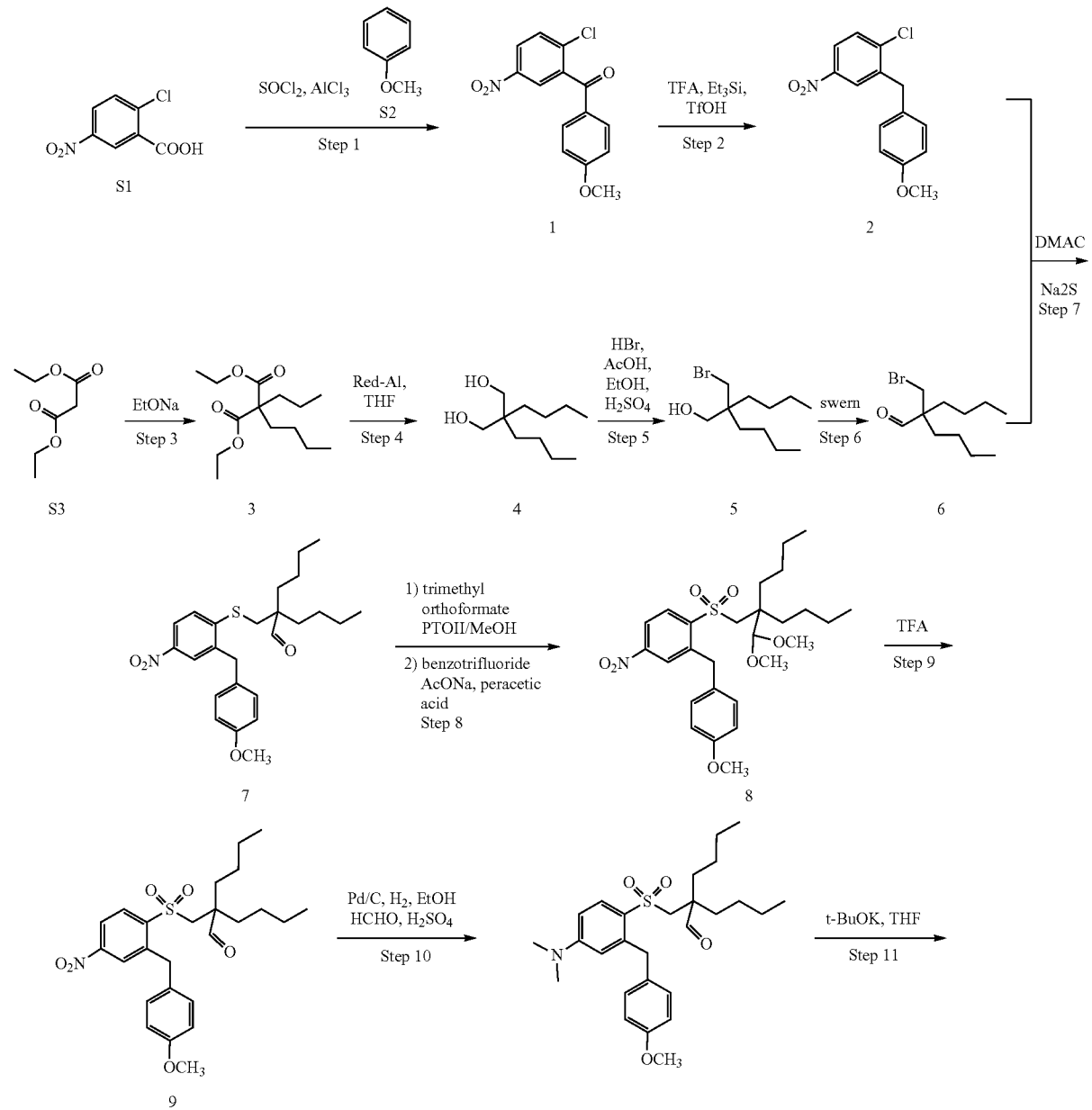

-continued
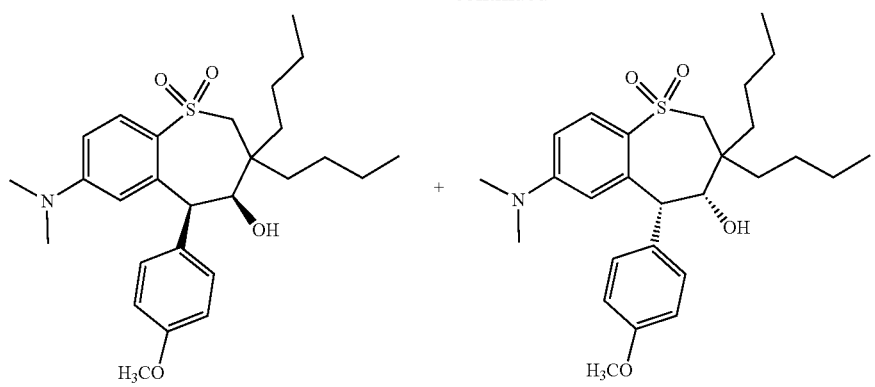
11 (LP002, racemic mixture)
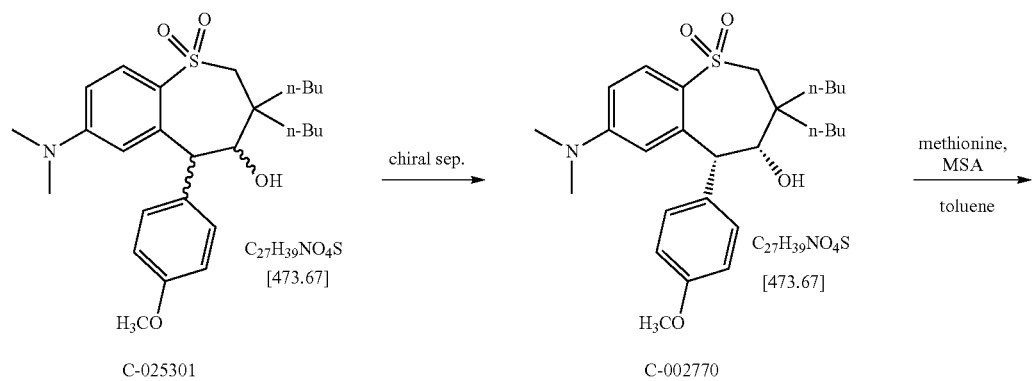
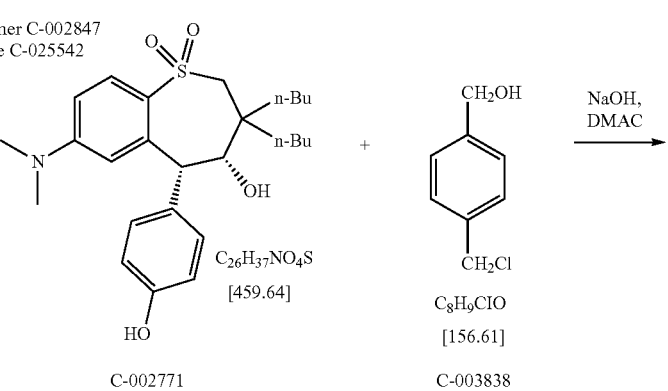
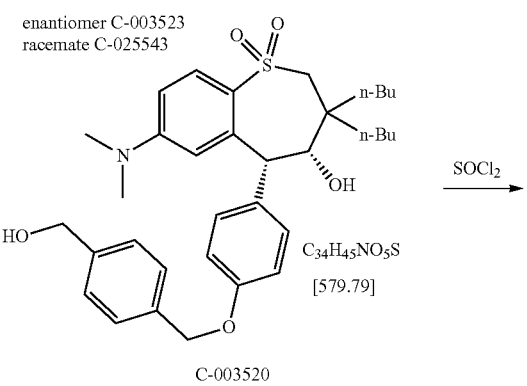

-continued

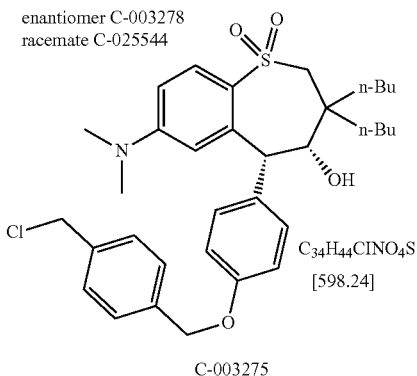

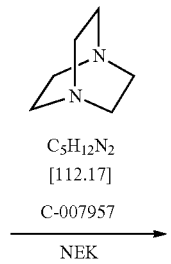

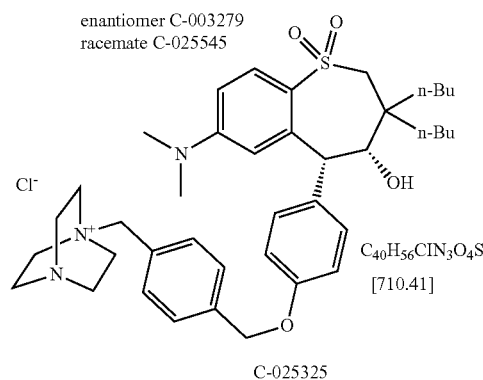

General Definitions

The term "bile acid," as used herein, includes steroid acids (and/or the carboxylate anion thereof), and salts thereof, found in the bile of an animal (e.g., a human), including, by way of non-limiting example, cholic acid, cholate, deoxycholic acid, deoxycholate, hyodeoxycholic acid, hyodeoxycholate, glycocholic acid, glycocholate, taurocholic acid, taurocholate, chenodeoxycholic acid, ursodeoxycholic acid, ursodiol, a tauroursodeoxycholic acid, a glycoursodeoxycholic acid, a 7-B-methyl cholic acid, a methyl lithocholic acid, chenodeoxycholate, lithocholic acid, lithocolate, and the like. Taurocholic acid and/or taurocholate are referred to herein as TCA. Any reference to a bile acid used herein includes reference to a bile acid, one and only one bile acid, one or more bile acids, or to at least one bile acid. Therefore, the terms "bile acid," "bile salt," "bile acid/salt," "bile acids," "bile salts," and "bile acids/salts" are, unless otherwise indicated, utilized interchangeably herein. Any reference to a bile acid used herein includes reference to a bile acid or a salt thereof. Furthermore, pharmaceutically acceptable bile acid esters are optionally utilized as the "bile acids" described herein, e.g., bile acids/salts conjugated to an amino acid (e.g., glycine or taurine). Other bile acid esters include, e.g., substituted or unsubstituted alkyl ester, substituted or unsubstituted heteroalkyl esters, substituted or unsubstituted aryl esters, substituted or unsubstituted heteroaryl esters, or the like. For example, the term "bile acid" includes cholic acid conjugated with either glycine or taurine: glycocholate and taurocholate, respectively (and salts thereof). Any reference to a bile acid used herein includes reference to an identical compound naturally or synthetically prepared. Furthermore, it is to be understood that any singular reference to a component (bile acid or otherwise) used herein includes reference to one and only one, one or more, or at least one of such components. Similarly, any plural reference to a component used herein includes reference to one and only one, one or more, or at least one of such components, unless otherwise noted. Moreover, as used herein, bile acid/salt mimics or mimetics described herein are compounds that mimic the agonist signaling properties of the bile acid/salt, especially at TGR5 (GPBAR1, BG37, Axor109) receptors. Examples include those described in WO 2010/014836, which is incorporated herein for such disclosure. In some embodiments, bile acid mimetics include triterpenoid, such as oleanolic acid, ursolic acid, or the like.

The term "subject", "patient" or "individual" are used interchangeably herein and refer to mammals and non-mammals, e.g., suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

Unless otherwise stated, the following terms used in this application, including the specification and claims, have the definitions given below with regard to "pediatric" or "pediatric patients" includes Neonatal (children ages 0 to 4 weeks), Infant Children (ages 4 weeks to 2 years), Children (ages 2 to 5 years), Children (ages 6 to 11 years) and Adolescents (12 to 18 years).

The term "about," as used herein, includes any value that is within 10% of the described value.

The term "between," as used herein, is inclusive of the lower and upper number of the range.

The term "colon," as used herein, includes the cecum, ascending colon, hepatic flexure, splenic flexure, descending colon, and sigmoid.

The term "composition," as used herein includes the disclosure of both a composition and a composition administered in a method as described herein. Furthermore, in some embodiments, the composition of the present invention is or comprises a "formulation," an oral dosage form or a rectal dosage form as described herein.

The terms "treat," "treating" or "treatment," and other grammatical equivalents as used herein, include alleviating, inhibiting or reducing symptoms, reducing or inhibiting severity of, reducing incidence of, reducing or inhibiting recurrence of, delaying onset of, delaying recurrence of, abating or ameliorating a disease or condition symptoms, ameliorating the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "prevent," "preventing" or "prevention," and other grammatical equivalents as used herein, include preventing additional symptoms, preventing the underlying causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

Where combination treatments or prevention methods are contemplated, it is not intended that the agents described herein be limited by the particular nature of the combination. For example, the agents described herein are optionally administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent. Furthermore, combination treatments are optionally administered separately or concomitantly.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the agents described herein, and at least one co-agent, are both administered to a patient simultaneously in the form of a single entity or dosage. The term "non-fixed combination" means that at least one of the agents described herein, and at least one co-agent, are administered to a patient as separate entities either simultaneously, concurrently or sequentially with variable intervening time limits, wherein such administration provides effective levels of the two or more agents in the body of the patient. In some instances, the co-agent is administered once or for a period of time, after which the agent is administered once or over a period of time. In other instances, the co-agent is administered for a period of time, after which, a therapy involving the administration of both the co-agent and the agent are administered. In still other embodiments, the agent is administered once or over a period of time, after which, the co-agent is administered once or over a period of time. These also apply to cocktail therapies, e.g. the administration of three or more active ingredients.

As used herein, the terms "co-administration", "administered in combination with" and their grammatical equivalents are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that may be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that are optionally employed with the agents and methods described herein are found in sources e.g., Goodman and Gilman, The Pharmacological Basis of Therapeutics, current ed.; Pergamon; and Remington's, Pharmaceutical *Sciences* (current edition), Mack Publishing Co., Easton, Pa. In certain embodiments, the agents and compositions described herein are administered orally.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "carrier" as used herein, refers to relatively nontoxic chemical agents that, in certain instances, facilitate the incorporation of an agent into cells or tissues.

The term "non-systemic" or "minimally absorbed" as used herein refers to low systemic bioavailability and/or absorption of an administered compound. In some instances a non-systemic compound is a compound that is substantially not absorbed systemically. In some embodiments, ASBTI compositions described herein deliver the ASBTI to the distal ileum, colon, and/or rectum and not systemically (e.g., a substantial portion of the ASBTI is not systemically absorbed. In some embodiments, the systemic absorption of a non-systemic compound is <0.1%, <0.3%, <0.5%, <0.6%, <0.7%, <0.8%, <0.9%, <1%, <1.5%, <2%, <3%, or <5% of the administered dose (wt. % or mol %). In some embodiments, the systemic absorption of a non-systemic compound is <10% of the administered dose. In some embodiments, the systemic absorption of a non-systemic compound is <15% of the administered dose. In some embodiments, the systemic absorption of a non-systemic compound is <25% of the administered dose. In an alternative approach, a non-systemic ASBTI is a compound that has lower systemic bioavailability relative to the systemic bioavailability of a systemic ASBTI (e.g., compound 100A, 100C). In some embodiments, the bioavailability of a non-systemic ASBTI described herein is <30%, <40%, <50%, <60%, or <70% of the bioavailability of a systemic ASBTI (e.g., compound 100A, 100C).

In another alternative approach, the compositions described herein are formulated to deliver <10% of the administered dose of the ASBTI systemically. In some embodiments, the compositions described herein are formulated to deliver <20% of the administered dose of the ASBTI systemically. In some embodiments, the compositions described herein are formulated to deliver <30% of the administered dose of the ASBTI systemically. In some embodiments, the compositions described herein are formulated to deliver <40% of the administered dose of the ASBTI systemically. In some embodiments, the compositions described herein are formulated to deliver <50% of the administered dose of the ASBTI systemically. In some embodiments, the compositions described herein are formulated to deliver <60% of the administered dose of the ASBTI systemically. In some embodiments, the compositions described herein are formulated to deliver <70% of the administered dose of the ASBTI systemically. In some embodiments, systemic absorption is determined in any suitable manner, including the total circulating amount, the amount cleared after administration, or the like.

The term "ASBT inhibitor" refers to a compound that inhibits apical sodium-dependent bile transport or any recuperative bile salt transport. The term Apical Sodium-dependent Bile Transporter (ASBT) is used interchangeably with the term Ileal Bile Acid Transporter (IBAT).

The term "enhancing enteroendocrine peptide secretion" refers to a sufficient increase in the level of the enteroendocrine peptide agent, for example, to treat any disease or disorder described herein. In some embodiments, enhanced enteroendocrine peptide secretion reverses or alleviates symptoms of cholestasis or a cholestatic liver disease.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, sulfosalicylate, maleate, laurate, malate, fumarate, succinate, tartrate, amsonate, pamoate, p-toluenesulfonate, mesylate and the like. Furthermore, pharmaceutically acceptable salts include, by way of non-limiting example, alkaline earth metal salts (e.g., calcium or magnesium), alkali metal salts (e.g., sodium-dependent or potassium), ammonium salts and the like.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halo, alkoyl, alkoyloxo, isocyanato, thiocyanato, isothiocyanato, nitro, haloalkyl, haloalkoxy, fluoroalkyl, amino, alkyl-amino, dialkyl-amino, amido.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, isopropyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl. A "heteroalkyl" group substitutes any one of the carbons of the alkyl group with a heteroatom having the appropriate number of hydrogen atoms attached (e.g., a $CH_2$ group to an NH group or an O group).

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{10}$alkylene. In another aspect, an alkylene is a $C_1$-$C_6$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and the like.

An "alkoxy" group refers to a (alkyl)O— group, where alkyl is as defined herein.

The term "alkylamine" refers to the —$N(alkyl)_xH_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula —C(O)NHR or —NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following moieties:

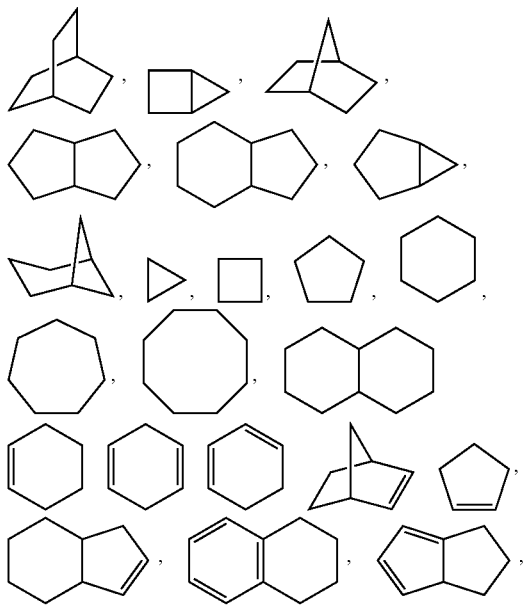

and the like. Monocyclic cycloalkyls include, but are not limited to, cyclopropyl, cyclobutyl, cyclopentyl, cyclohexyl, cycloheptyl, and cyclooctyl.

The term "heterocyclo" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Illustrative examples of heteroaryl groups include the following moieties:

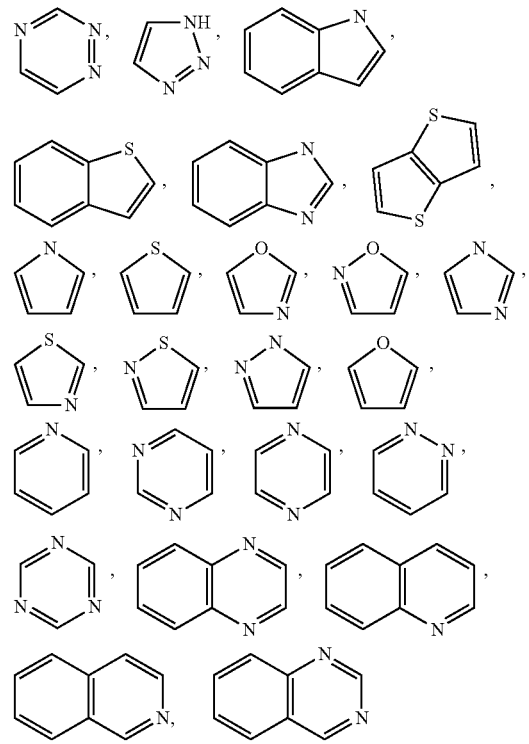

and the like.

A "heteroalicyclic" group or "heterocyclo" group refers to a cycloalkyl group, wherein at least one skeletal ring atom is a heteroatom selected from nitrogen, oxygen and sulfur. In various embodiments, the radicals are with an aryl or heteroaryl. Illustrative examples of heterocyclo groups, also referred to as non-aromatic heterocycles, include:

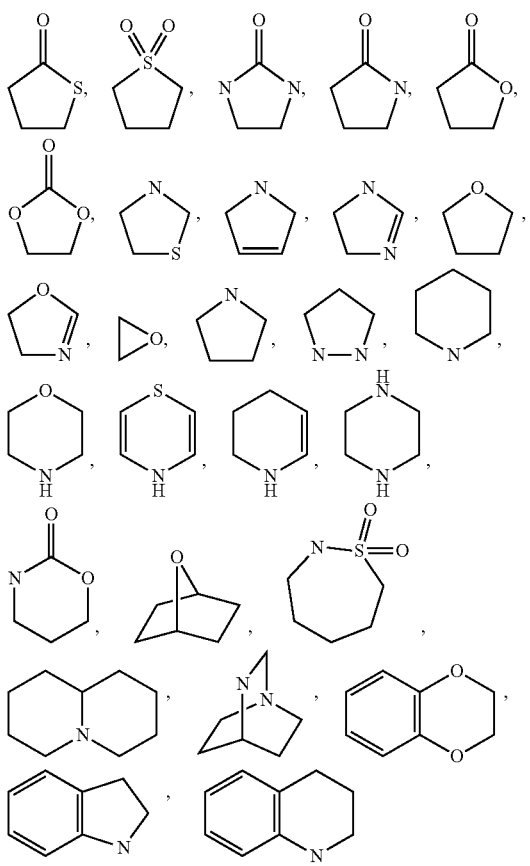

and the like. The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In some embodiments, up to two heteroatoms are consecutive, such as, by way of example, —$CH_2$—NH—$OCH_3$ and —$CH_2$—O—Si($CH_3$)$_3$.

A "cyano" group refers to a —CN group.
An "isocyanato" group refers to a —NCO group.
A "thiocyanato" group refers to a —CNS group.
An "isothiocyanato" group refers to a —NCS group.
"Alkoyloxy" refers to a RC(=O)O— group.
"Alkoyl" refers to a RC(=O)— group.

The term "modulate," as used herein refers to having some affect on (e.g., increasing, enhancing or maintaining a certain level).

The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, arylalkoxy, aralkyloxy, arylalkyloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art and may be found in references such as Greene and Wuts, above. In some embodiments, alkyl groups described herein are optionally substituted with an O that is connected to two adjacent carbon atoms (i.e., forming an epoxide).

The term "therapeutically effective amount" or an "effective amount" as used herein, refers to a sufficient amount of a therapeutically active agent to provide a desired effect in a subject or individual. In some embodiments, a "therapeutically effective amount" or an "effective amount" of an ASBTI refers to a sufficient amount of an ASBTI to treat cholestasis or a cholestatic liver disease in a subject or individual.

L-Cells

Inventors have discovered that enteroendocrine L-cells play a role in repair. The epithelial barrier is also a key component in host defence. A further pre-proglucagon splice product, GLP-2, is secreted by enteroendocrine L-cells in the distal small intestine and has been shown to improve intestinal wound healing in a TGF-B (anti-inflammatory cytokine TGF-B), mediated process, small bowel responding better than large bowel. GLP-2 has also been shown to ameliorate the barrier dysfunction induced by experimental stress and food allergy. Again, L-cells are activated by luminal nutrients, and the barrier compromise observed in TPN may partly reflect its hyposecretion in the absence of enteral stimuli. Moreover, GLP-2 is also responsible, at least in part for growth and adaptation observed in short-bowel models. Therefore, abnormal enteroendocrine cells (EEC) function may predispose to GI inflammatory disorders, and the underlying nutrient-EEC-vagal pathways are targets in the injured gut as contemplated in the present embodiments.

L-cells are scattered throughout the epithelial layer of the gut from the duodenum to the rectum, with the highest numbers occurring in the ileum, colon, and rectum. They are characterized by an open-cell morphology, with apical microvilli facing into the gut lumen and secretory vesicles located adjacent to the basolateral membrane, and are therefore in direct contact with nutrients in the intestinal lumen. Furthermore, L-cells are located in close proximity to both neurons and the microvasculature of the intestine, thereby allowing the L-cell to be affected by both neural and hormonal signals. As well as Glucagon-Like Peptide 1 (GLP-1) and Glucagon-Like Peptide 2 (GLP-2), L-cells also secrete peptide YY (PYY), and glutamate. The cells are just one member of a much larger family of enteroendocrine cells that secrete a range of hormones, including ghrelin, GIP, cholecystokinin, somatostatin, and secretin, which are involved in the local coordination of gut physiology, as well as in playing wider roles in the control of cytokine release and/or controlling the adaptive process, attenuating intestinal injury, reducing bacterial translocation, inhibiting the release of free radical oxygen, or any combination thereof. L-cells are unevenly distributed in the gastrointestinal tract, within higher concentrations in the distal portion of the gastrointestinal tract (e.g., in the distal ileum, colon and rectum).

Bile Acid

Bile contains water, electrolytes and a numerous organic molecules including bile acids, cholesterol, phospholipids and bilirubin. Bile is secreted from the liver and stored in the gall bladder, and upon gall bladder contraction, due to ingestion of a fatty meal, bile passes through the bile duct into the intestine. Bile acids/salts are critical for digestion and absorption of fats and fat-soluble vitamins in the small intestine. Adult humans produce 400 to 800 mL of bile daily. The secretion of bile can be considered to occur in two stages. Initially, hepatocytes secrete bile into canaliculi, from which it flows into bile ducts and this hepatic bile contains large quantities of bile acids, cholesterol and other organic molecules. Then, as bile flows through the bile ducts, it is modified by addition of a watery, bicarbonate-rich secretion from ductal epithelial cells. Bile is concentrated, typically five-fold, during storage in the gall bladder.

The flow of bile is lowest during fasting, and a majority of that is diverted into the gallbladder for concentration. When chyme from an ingested meal enters the small intestine, acid and partially digested fats and proteins stimulate secretion of cholecystokinin and secretin, both of which are important for secretion and flow of bile. Cholecystokinin (cholecysto=gallbladder and kinin=movement) is a hormone which stimulates contractions of the gallbladder and common bile duct, resulting in delivery of bile into the gut. The most potent stimulus for release of cholecystokinin is the presence of fat in the duodenum. Secretin is a hormone secreted in response to acid in the duodenum, and it simulates biliary duct cells to secrete bicarbonate and water, which expands the volume of bile and increases its flow out into the intestine.

Bile acids/salts are derivatives of cholesterol. Cholesterol, ingested as part of the diet or derived from hepatic synthesis, are converted into bile acids/salts in the hepatocyte. Examples of such bile acids/salts include cholic and chenodeoxycholic acids, which are then conjugated to an amino acid (such as glycine or taurine) to yield the conjugated form that is actively secreted into canaliculi. The most abundant of the bile salts in humans are cholate and deoxycholate, and they are normally conjugated with either glycine or taurine to give glycocholate or taurocholate respectively.

Free cholesterol is virtually insoluble in aqueous solutions, however in bile it is made soluble by the presence of bile acids/salts and lipids. Hepatic synthesis of bile acids/salts accounts for the majority of cholesterol breakdown in the body. In humans, roughly 500 mg of cholesterol are converted to bile acids/salts and eliminated in bile every day. Therefore, secretion into bile is a major route for elimination of cholesterol. Large amounts of bile acids/salts are secreted into the intestine every day, but only relatively small quantities are lost from the body. This is because approximately 95% of the bile acids/salts delivered to the duodenum are absorbed back into blood within the ileum, by a process is known as "Enterohepatic Recirculation".

Venous blood from the ileum goes straight into the portal vein, and hence through the sinusoids of the liver. Hepatocytes extract bile acids/salts very efficiently from sinusoidal blood, and little escapes the healthy liver into systemic circulation. Bile acids/salts are then transported across the hepatocytes to be resecreted into canaliculi. The net effect of this enterohepatic recirculation is that each bile salt molecule is reused about 20 times, often two or three times during a single digestive phase. Bile biosynthesis represents the major metabolic fate of cholesterol, accounting for more than half of the approximate 800 mg/day of cholesterol that an average adult uses up in metabolic processes. In comparison, steroid hormone biosynthesis consumes only about 50 mg of cholesterol per day. Much more that 400 mg of bile salts is required and secreted into the intestine per day, and this is achieved by re-cycling the bile salts. Most of the bile salts secreted into the upper region of the small intestine are absorbed along with the dietary lipids that they emulsified at the lower end of the small intestine. They are separated from the dietary lipid and returned to the liver for re-use. Re-cycling thus enables 20-30 g of bile salts to be secreted into the small intestine each day.

Bile acids/salts are amphipathic, with the cholesterol-derived portion containing both hydrophobic (lipid soluble) and polar (hydrophilic) moieties while the amino acid conjugate is generally polar and hydrophilic. This amphipathic nature enables bile acids/salts to carry out two important functions: emulsification of lipid aggregates and solubilization and transport of lipids in an aqueous environment. Bile acids/salts have detergent action on particles of dietary fat which causes fat globules to break down or to be emulsified. Emulsification is important since it greatly increases the surface area of fat available for digestion by lipases which cannot access the inside of lipid droplets. Furthermore, bile acids/salts are lipid carriers and are able to solubilize many lipids by forming micelles and are critical for transport and absorption of the fat-soluble vitamins.

Pharmaceutical Compositions and Methods of Use

In some embodiments, compositions described herein are administered for delivery of enteroendocrine peptide secretion enhancing agents to a subject or individual. In certain embodiments, any compositions described herein are formulated for ileal, rectal and/or colonic delivery. In more specific embodiments, the composition is formulated for non-systemic or local delivery to the rectum and/or colon. It is to be understood that as used herein, delivery to the colon includes delivery to sigmoid colon, transverse colon, and/or ascending colon. In still more specific embodiments, the composition is formulated for non-systemic or local delivery to the rectum and/or colon is administered rectally. In other specific embodiments, the composition is formulated for non-systemic or local delivery to the rectum and/or colon is administered orally.

In some embodiments, provided herein is a composition comprising an enteroendocrine peptide secretion enhancing agent and, optionally, a pharmaceutically acceptable carrier for alleviating symptoms of pediatric cholestasis or a pediatric cholestatic liver disease in an individual.

In certain embodiments, the composition comprises an enteroendocrine peptide secretion enhancing agent and an absorption inhibitor. In specific embodiments, the absorption inhibitor is an inhibitor that inhibits the absorption of the (or at least one of the) specific enteroendocrine peptide secretion enhancing agent with which it is combined. In some embodiments, the composition comprises an enteroendocrine peptide secretion enhancing agent, an absorption inhibitor and a carrier (e.g., an orally suitable carrier or a rectally suitable carrier, depending on the mode of intended administration). In certain embodiments, the composition comprises an enteroendocrine peptide secretion enhancing agent, an absorption inhibitor, a carrier, and one or more of a cholesterol absorption inhibitor, an enteroendocrine peptide, a peptidase inhibitor, a spreading agent, and a wetting agent.

In other embodiments, the compositions described herein are administered orally for non-systemic delivery of the bile salt active component to the rectum and/or colon, including the sigmoid colon, transverse colon, and/or ascending colon. In specific embodiments, compositions formulated for oral administration are, by way of non-limiting example, enterically coated or formulated oral dosage forms, such as, tablets and/or capsules. It is to be understood that the terms "subject" and "individual" are utilized interchangeably herein and include, e.g., humans and human patients in need of treatment.

Absorption Inhibitors

In certain embodiments, the composition described herein as being formulated for the non-systemic delivery of ASBTI further includes an absorption inhibitor. As used herein, an absorption inhibitor includes an agent or group of agents that inhibit absorption of a bile acid/salt.

Suitable bile acid absorption inhibitors (also described herein as absorption inhibiting agents) include, by way of non-limiting example, anionic exchange matrices, polyamines, quaternary amine containing polymers, quaternary ammonium salts, polyallylamine polymers and copolymers, colesevelam, colesevelam hydrochloride, Cholesta-Gel (N,N,N-trimethyl-6-(2-propenylamino)-1-hexanaminium chloride polymer with (chloromethyl) oxirane, 2-propen-1-amine and N-2-propenyl-1-decanamine hydrochloride), cyclodextrins, chitosan, chitosan derivatives, carbohydrates which bind bile acids, lipids which bind bile acids, proteins and proteinaceous materials which bind bile acids, and antibodies and albumins which bind bile acids. Suitable cyclodextrins include those that bind bile acids/salts such as, by way of non-limiting example, β-cyclodextrin and hydroxypropyl-β-cyclodextrin. Suitable proteins, include those that bind bile acids/salts such as, by way of non-limiting example, bovine serum albumin, egg albumin, casein, α-acid glycoprotein, gelatin, soy proteins, peanut proteins, almond proteins, and wheat vegetable proteins.

In certain embodiments the absorption inhibitor is cholestyramine. In specific embodiments, cholestyramine is combined with a bile acid. Cholestyramine, an ion exchange resin, is a styrene polymer containing quaternary ammonium groups crosslinked by divinylbenzene. In other embodiments, the absorption inhibitor is colestipol. In specific embodiments, colestipol is combined with a bile acid. Colestipol, an ion exchange resin, is a copolymer of diethylenetriamine and 1-chloro-2,3-epoxypropane.

In certain embodiments of the compositions and methods described herein the ASBTI is linked to an absorption inhibitor, while in other embodiments the ASBTI and the absorption inhibitor are separate molecular entities. In specific embodiments the bile acid, bile acid mimic or the modified bile acid is linked to a bile acid adsorption inhibitor described herein.

Cholesterol Absorption Inhibitors

In certain embodiments, a composition described herein optionally includes at least one cholesterol absorption inhibitor. Suitable cholesterol absorption inhibitors include, by way of non-limiting example, ezetimibe (SCH 58235), ezetimibe analogs, ACT inhibitors, stigmastanyl phosphorylcholine, stigmastanyl phosphorylcholine analogues, β-lactam cholesterol absorption inhibitors, sulfate polysaccharides, neomycin, plant saponins, plant sterols, phytostanol preparation FM-VP4, Sitostanol, β-sitosterol, acyl-CoA: cholesterol-O-acyltransferase (ACAT) inhibitors, Avasimibe, Implitapide, steroidal glycosides and the like. Suitable ezetimibe analogs include, by way of non-limiting example, SCH 48461, SCH 58053 and the like. Suitable ACT inhibitors include, by way of non-limiting example, trimethoxy fatty acid anilides such as Cl-976, 3-[decyldimethylsilyl]-N-[2-(4-methylphenyl)-1-phenylethyl]-propanamide, melinamide and the like. β-lactam cholesterol absorption inhibitors include, by way of non-limiting example, (3R-4S)-1,4-bis-(4-methoxyphenyl)-3-(3-phenylpropyl)-2-azetidinone and the like.

Peptidase Inhibitors

In some embodiments, the compositions described herein optionally include at least one peptidase inhibitor. Such peptidase inhibitors include, but are not limited to, dipeptidyl peptidase-4 inhibitors (DPP-4), neutral endopeptidase inhibitors, and converting enzyme inhibitors. Suitable dipeptidyl peptidase-4 inhibitors (DPP-4) include, by way of non-limiting example, Vildaglipti, 2S)-1-{2-[(3-hydroxy-1-adamantyl)amino]acetyl}pyrrolidine-2-carbonitrile, Sitagliptin, (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one, Saxagliptin, and (1S,3S,5S)-2-[(2S)-2-amino-2-(3-hydroxy-1-adamantyl)acetyl]-2-azabicyclo[3.1.0]hexane-3-carbonitrile. Such neutral endopeptidase inhibitors include, but are not limited to, Candoxatrilat and Ecadotril.

Spreading Agents/Wetting Agents

In certain embodiments, the composition described herein optionally comprises a spreading agent. In some embodiments, a spreading agent is utilized to improve spreading of the composition in the colon and/or rectum. Suitable spreading agents include, by way of non-limiting example, hydroxyethylcellulose, hydroxypropylmethyl cellulose, polyethylene glycol, colloidal silicon dioxide, propylene glycol, cyclodextrins, microcrystalline cellulose, polyvinylpyrrolidone, polyoxyethylated glycerides, polycarbophil, di-n-octyl ethers, Cetiol™ OE, fatty alcohol polyalkylene glycol ethers, Aethoxal™ B), 2-ethylhexyl palmitate, Cegesoft™ C 24), and isopropyl fatty acid esters.

In some embodiments, the compositions described herein optionally comprise a wetting agent. In some embodiments, a wetting agent is utilized to improve wettability of the composition in the colon and rectum. Suitable wetting agents include, by way of non-limiting example, ionic or non-ionic surfactants. In some embodiments, surfactants are selected from, by way of non-limiting example, SLS, poloxamers (e.g., poloxamer 188), polysorbate (e.g., 20 or 80), stearyl heptanoate, caprylic/capric fatty acid esters of saturated fatty alcohols of chain length $C_{12}$-$C_{18}$, isostearyl digylcerol isostearic acid, sodium dodecyl sulphate, isopropyl myristate, isopropyl palmitate, and isopropyl myristate/isopropyl stearate/isopropyl palmitate mixture.

Vitamins

In some embodiments, the methods provided herein further comprise administering one or more vitamins.

In some embodiments, the vitamin is vitamin A, B1, B2, B3, B5, B6, B7, B9, B12, C, D, E, K, folic acid, pantothenic acid, niacin, riboflavin, thiamine, retinol, beta carotene, pyridoxine, ascorbic acid, cholecalciferol, cyanocobalamin, tocopherols, phylloquinone, menaquinone.

In some embodiments, the vitamin is a fat soluble vitamin such as vitamin A, D, E, K, retinol, beta carotene, cholecalciferol, tocopherols, phylloquinone. In a preferred embodiment, the fat soluble vitamin is tocopherol polyethylene glycol succinate (TPGS).

Bile Acid Sequestrants/Binders

In some embodiments, a labile bile acid sequestrant is an enzyme dependent bile acid sequestrant. In certain embodiments, the enzyme is a bacterial enzyme. In some embodiments, the enzyme is a bacterial enzyme found in high concentration in human colon or rectum relative to the concentration found in the small intestine. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

In certain embodiments, a labile bile acid sequestrant is a time dependent bile acid sequestrant. In some embodiments, a labile bile acid sequestrant releases a bile acid or is degraded after 1, 2, 3, 4, 5, 6, 7, 8, 9, or 10 seconds of sequestration. In some embodiments, a labile bile acid sequestrant releases a bile acid or is degraded after 15, 20, 25, 30, 35, 40, 45, 50, or 55 seconds of sequestration. In some embodiments, a labile bile acid sequestrant releases a bile acid or is degraded after 1, 2, 3, 4, 5, 6, 7, 8, 9, or 10 minutes of sequestration. In some embodiments, a labile bile acid sequestrant releases a bile acid or is degraded after about 15, 20, 25, 30, 35, 45, 50, or 55 minutes of sequestration. In some embodiments, a labile bile acid sequestrant releases a bile acid or is degraded after about 1, 2, 3, 4, 5, 6, 7, 8, 9, 10, 11, 12, 13, 14, 15, 16, 17, 18, 19, 20, 21, 22, 23, or 24 hours of sequestration. In some embodiments, a labile bile acid sequestrant releases a bile acid or is degraded after 1, 2, or 3 days of sequestration.

In some embodiments, the labile bile acid sequestrant has a low affinity for bile acid. In certain embodiments, the labile bile acid sequestrant has a high affinity for a primary bile acid and a low affinity for a secondary bile acid.

In some embodiments, the labile bile acid sequestrant is a pH dependent bile acid sequestrant. In certain embodiments, the pH dependent bile acid sequestrant has a high affinity for bile acid at a pH of 6 or below and a low affinity for bile acid at a pH above 6. In certain embodiments, the pH dependent bile acid sequestrant has a high affinity for bile acid at a pH of 6.5 or below and a low affinity for bile acid at a pH above 6.5. In certain embodiments, the pH dependent bile acid sequestrant has a high affinity for bile acid at a pH of 7 or below and a low affinity for bile acid at a pH above 7. In certain embodiments, the pH dependent bile acid sequestrant has a high affinity for bile acid at a pH of 7.1 or below and a low affinity for bile acid at a pH above 7.1. In certain embodiments, the pH dependent bile acid sequestrant has a high affinity for bile acid at a pH of 7.2 or below and a low affinity for bile acid at a pH above 7.2. In certain embodiments, the pH dependent bile acid sequestrant has a high affinity for bile acid at a pH of 7.3 or below and a low affinity for bile acid at a pH above 7.3. In certain embodiments, the pH dependent bile acid sequestrant has a high affinity for bile acid at a pH of 7.4 or below and a low affinity for bile acid at a pH above 7.4. In certain embodiments, the pH dependent bile acid sequestrant has a high affinity for bile acid at a pH of 7.5 or below and a low affinity for bile acid at a pH above 7.5. In certain embodiments, the pH dependent bile acid sequestrant has a high affinity for bile acid at a pH of 7.6 or below and a low affinity for bile acid at a pH above 7.6. In certain embodiments, the pH dependent bile acid sequestrant has a high affinity for bile acid at a pH of 7.7 or below and a low affinity for bile acid at a pH above 7.7. In certain embodiments, the pH dependent bile acid sequestrant has a high affinity for bile acid at a pH of 7.8 or below and a low affinity for bile acid at a pH above 7.8. In some embodiments, the pH dependent bile acid sequestrant degrades at a pH above 6. In some embodiments, the pH dependent bile acid sequestrant degrades at a pH above 6.5. In some embodiments, the pH dependent bile acid sequestrant degrades at a pH above 7. In some embodiments, the pH dependent bile acid sequestrant degrades at a pH above 7.1. In some embodiments, the pH dependent bile acid sequestrant degrades at a pH above 7.2. In some embodiments, the pH dependent bile acid sequestrant degrades at a pH above 7.3. In some embodiments, the pH dependent bile acid sequestrant degrades at a pH above 7.4. In some embodiments, the pH dependent bile acid sequestrant degrades at a pH above 7.5. In some embodiments, the pH dependent bile acid sequestrant degrades at a pH above 7.6. In some embodiments, the pH dependent bile acid sequestrant degrades at a pH above 7.7. In some embodiments, the pH dependent bile acid sequestrant degrades at a pH above 7.8. In some embodiments, the pH dependent bile acid sequestrant degrades at a pH above 7.9.

In certain embodiments, the labile bile acid sequestrant is lignin or a modified lignin. In some embodiments, the labile bile acid sequestrant is a polycationic polymer or copolymer. In certain embodiments, the labile bile acid sequestrant is a polymer or copolymer comprising one or more N-alkenyl-N-alkylamine residues; one or more N,N,N-trialkyl-N—(N'-alkenylamino)alkyl-azanium residues; one or more N,N,N-trialkyl-N-alkenyl-azanium residues; one or more alkenyl-amine residues; or a combination thereof.

In some embodiments, the bile acid binder is cholestyramine, and various compositions including cholestyramine, which are described, for example, in U.S. Pat. Nos. 3,383,281; 3,308,020; 3,769,399; 3,846,541; 3,974,272; 4,172,120; 4,252,790; 4,340,585; 4,814,354; 4,874,744; 4,895,723; 5,695,749; and 6,066,336. In some embodiments, the bile acid binder is cholestipol or colesevelam.

Methods

Provided herein, in certain embodiments, are methods for treating pediatric cholestasis or a pediatric cholestatic liver disease comprising non-systemic administration of a therapeutically effective amount of an ASBTI. Provided herein, in certain embodiments, are methods for treating pediatric cholestasis or a pediatric cholestatic liver disease comprising contacting the gastrointestinal tract, including the distal ileum and/or the colon and/or the rectum, of an individual in need thereof with an ASBTI. Also provided herein are methods for reducing intraenterocyte bile acids, reducing damage to hepatocellular or intestinal architecture caused by cholestasis or a cholestatic liver disease, of an individual comprising administration of a therapeutically effective amount of an ASBTI to an individual in need thereof.

In some embodiments, provided herein is a method of treating pediatric cholestasis or a pediatric cholestatic liver disease in an individual comprising delivering to ileum or colon of the individual a therapeutically effective amount of any ASBTI described herein. In some embodiments, provided herein are methods for reducing damage to hepatocellular or intestinal architecture or cells from cholestasis or a cholestatic liver disease comprising administration of a therapeutically effective amount of an ASBTI. In certain embodiments, provided herein are methods for reducing intraenterocyte bile acids/salts comprising administration of a therapeutically effective amount of an ASBTI to an individual in need thereof.

In some embodiments, the methods provide for inhibition of bile salt recycling upon administration of any of the compounds described herein to an individual. In some embodiments, an ASBTI described herein is systemically absorbed upon administration. In some embodiments, an ASBTI described herein is not absorbed systemically. In some embodiments, an ASBTI herein is administered to the individual orally. In some embodiments, an ASBTI described herein is delivered and/or released in the distal ileum of an individual.

In certain instances, contacting the distal ileum of a pediatric individual with an ASBTI (e.g., any ASBTI described herein) inhibits bile acid reuptake and increases the concentration of bile acids/salts in the vicinity of L-cells in the distal ileum and/or colon and/or rectum, thereby reducing intraenterocyte bile acids, reducing serum and/or hepatic bile acid levels, reducing overall bile acid load, and/or reducing damage to ileal architecture caused by cholestasis or a cholestatic liver disease. Without being limited to any particular theory, reducing serum and/or hepatic bile acid levels ameliorates cholestasis and/or cholestatic disease.

Administration of a compound described herein is achieved in any suitable manner including, by way of non-limiting example, by oral, enteric, parenteral (e.g., intravenous, subcutaneous, intramuscular), intranasal, buccal, topical, rectal, or transdermal administration routes. Any compound or composition described herein is administered in a method or formulation appropriate to treat a new born or an infant. Any compound or composition described herein is administered in an oral formulation (e.g., solid or liquid) to treat a new born or an infant. In some embodiments, the pediatric dosage form is selected from a solution, syrup, suspension, elixir, powder for reconstitution as suspension or solution, dispersible/effervescent tablet, chewable tablet, lollipop, freezer pops, troches, oral thin strips, orally disintegrating tablet, orally disintegrating strip, and sprinkle oral powder or granules. In some embodiments, a compound or composition described herein is administered in a method or pediatric dosage form formulation appropriate to treat children. In some embodiments, a compound or composition described herein is administered in a method or pediatric dosage form formulation appropriate to treat adolescents. In some embodiments, a compound or composition described herein is administered in a method or pediatric dosage form formulation appropriate to treat a newborn or an infant. In some embodiments, a compound or composition described herein is administered in an oral formulation (e.g., solid or liquid) to treat a newborn or an infant. In some embodiments, the pediatric dosage form described herein is administered prior to ingestion of food, with food or after ingestion of food.

In certain embodiments, a compound or a composition comprising a compound described herein is administered for prophylactic and/or therapeutic treatments. In therapeutic applications, the compositions are administered to an individual already suffering from a disease or condition, in an amount sufficient to cure or at least partially arrest the symptoms of the disease or condition. In various instances, amounts effective for this use depend on the severity and course of the disease or condition, previous therapy, the individual's health status, weight, and response to the drugs, and the judgment of the treating physician.

In prophylactic applications, compounds or compositions containing compounds described herein are administered to an individual susceptible to or otherwise at risk of a particular disease, disorder or condition. In certain embodiments of this use, the precise amounts of compound administered depend on the individual's state of health, weight, and the like. Furthermore, in some instances, when a compound or composition described herein is administered to an individual, effective amounts for this use depend on the severity and course of the disease, disorder or condition, previous therapy, the individual's health status and response to the drugs, and the judgment of the treating physician.

In certain instances, wherein following administration of a selected dose of a compound or composition described herein, an individual's condition does not improve, upon the doctor's discretion the administration of a compound or composition described herein is optionally administered chronically, that is, for an extended period of time, including throughout the duration of the individual's life in order to ameliorate or otherwise control or limit the symptoms of the individual's disorder, disease or condition.

In certain embodiments, an effective amount of a given agent varies depending upon one or more of a number of factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In some embodiments, doses administered include those up to the maximum tolerable dose. In some embodiments, doses administered include those up to the maximum tolerable dose by a newborn or an infant.

In certain embodiments, about 0.001-5000 mg per day, from about 0.001-1500 mg per day, about 0.001 to about 100 mg/day, about 0.001 to about 50 mg/day, or about 0.001 to about 30 mg/day, or about 0.001 to about 10 mg/day of a compound described herein is administered to an individual in need thereof. In various embodiments, the desired dose is conveniently presented in a single dose or in divided doses administered simultaneously (or over a short period of time) or at appropriate intervals, for example as two, three, four or more sub-doses per day. In various embodiments, a single dose is from about 0.001 mg/kg to about 500 mg/kg. In various embodiments, a single dose is from about 0.001, 0.01, 0.1, 1, or 10 mg/kg to about 10, 50, 100, or 250 mg/kg. In various embodiments, a single dose of an ASBTI is from about 0.001 mg/kg to about 100 mg/kg. In various embodiments, a single dose of an ASBTI is from about 0.001 mg/kg to about 50 mg/kg. In various embodiments, a single dose of an ASBTI is from about 0.001 mg/kg to about 10 mg/kg. In various embodiments, a single dose of an ASBTI is administered every 6 hours, every 12 hours, every 24 hours, every 48 hours, every 72 hours, every 96 hours, every 5 days, every 6 days, or once a week.

In the case wherein the patient's status does improve, upon the doctor's discretion an ASBTI is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%. In some embodiments the total single dose of an ASBTI is in the range described above.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In certain instances, there are a large number of variables in regard to an individual treatment regime, and considerable excursions from these recommended values are considered within the scope described herein. Dosages described herein are optionally altered depending on a number of variables such as, by way of non-limiting example, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are optionally determined by pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. In certain embodiments, data obtained from cell culture assays and animal studies are used in formulating a range of dosage for use in human. In specific embodiments, the dosage of compounds described herein lies within a range of circulating concentrations that include the $ED_{50}$ with minimal toxicity. The dosage optionally varies within this range depending upon the dosage form employed and the route of administration utilized.

In some embodiments, the systemic exposure of a therapeutically effective amount of any non-systemic ASBTI described herein (e.g., an ASBTI that comprises a non-systemic moiety such as L-K or other groups described herein) is reduced when compared to the systemic exposure of a therapeutically effective amount of any systemically absorbed ASBTI (e.g. Compounds 100A, 100C). In some embodiments, the AUC of a therapeutically effective amount of any non-systemic ASBTI described herein (e.g., an ASBTI that comprises a non-systemic moiety such as L-K or other groups described herein) is at least 10%, at least 20%, at least 30%, at least 40%, at least 50%, at least 60%, at least 70%, at least 80% or at least 90% reduced when compared to the AUC of any systemically absorbed ASBTI (e.g. Compounds 100A, 100C).

In some embodiments, the systemic exposure of a therapeutically effective amount of a compound of Formula I that is not systemically absorbed (e.g., a compound of Formula I that comprises a non-systemic moiety such as L-K or other groups described herein) is reduced when compared to the systemic exposure of a therapeutically effective amount of Compound 100A. In some embodiments, the AUC of a therapeutically effective amount of a compound of Formula I that is not systemically absorbed (e.g., a compound of Formula I that comprises a non-systemic moiety such as L-K or other groups described herein) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula I that is not systemically absorbed (e.g., a compound of Formula I that comprises a non-systemic moiety such as L-K or other groups described herein) is about 50% reduced when compared to the AUC of a therapeutically effective amount of Compound 100A. In other embodiments, the AUC of a therapeutically effective amount of a compound of Formula I that is not systemically absorbed (e.g., a compound of Formula I that comprises a non-systemic moiety such as L-K or other groups described herein) is about 75% reduced when compared to the AUC of a therapeutically effective amount of Compound 100A.

In some embodiments, the systemic exposure of a therapeutically effective amount of a compound of Formula II that is not systemically absorbed (e.g., a compound of Formula II that comprises a non-systemic moiety such as L-K or other groups described herein) is reduced when compared to the systemic exposure of a therapeutically effective amount of Compound 100A. In some embodiments, the AUC of a therapeutically effective amount of a compound of Formula II that is not systemically absorbed (e.g., a compound of Formula II that comprises a non-systemic moiety such as L-K or other groups described herein) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula II that is not systemically absorbed (e.g., a compound of Formula II that comprises a non-systemic moiety such as L-K or other groups described herein) is about 50% reduced when compared to the AUC of a therapeutically effective amount of Compound 100A. In other embodiments, the AUC of a therapeutically effective amount of a compound of Formula II that is not systemically absorbed (e.g., a compound of Formula II that comprises a non-systemic moiety such as L-K or other groups described herein) is about 75% reduced when compared to the AUC of a therapeutically effective amount of Compound 100A.

In some embodiments, the systemic exposure of a therapeutically effective amount of a compound of Formula III, IIIA, IIIB or IIIC is reduced when compared to the systemic exposure of a therapeutically effective amount of Compound 100C. In some embodiments, the AUC of a therapeutically effective amount of a compound of Formula III, IIIA, IIIB or IIIC is about 10%, about 20%, about 30%, about 40%, about 50%, about 60%, about 70%, about 80% or about 90% reduced when compared to the AUC of a therapeutically effective amount of Compound 100C. In some embodiments, the AUC of a therapeutically effective amount of a compound of Formula III, IIIA, IIIB or IIIC is about 50% reduced when compared to the AUC of a therapeutically effective amount of Compound 100C. In other embodiments, the AUC of a therapeutically effective amount of a compound of Formula III, IIIA, IIIB or IIIC is about 75% reduced when compared to the AUC of a therapeutically effective amount of Compound 100C.

In some embodiments, the systemic exposure of a therapeutically effective amount of a compound of Formula IV that is not systemically absorbed (e.g., a compound of Formula IV that comprises a non-systemic moiety such as L-K or other groups described herein) is reduced when compared to the systemic exposure of a therapeutically effective amount of Compound 100A. In some embodiments, the AUC of a therapeutically effective amount of a compound of Formula IV that is not systemically absorbed (e.g., a compound of Formula I that comprises a non-systemic moiety such as L-K or other groups described herein) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula IV that is not systemically absorbed (e.g., a compound of Formula IV that comprises a non-systemic moiety such as L-K or other groups described herein) is about 50% reduced when compared to the AUC of a therapeutically effective amount of Compound 100A. In other embodiments, the AUC of a therapeutically effective amount of a compound of Formula IV that is not systemically absorbed (e.g., a compound of Formula IV that comprises a non-systemic moiety such as L-K or other groups described herein) is about 75% reduced when compared to the AUC of a therapeutically effective amount of Compound 100A.

In some embodiments, the systemic exposure of a therapeutically effective amount of a compound of Formula V that is not systemically absorbed (e.g., a compound of Formula V that comprises a non-systemic moiety such as L-K or other groups described herein) is reduced when compared to the systemic exposure of a therapeutically effective amount of Compound 100A. In some embodiments, the AUC of a therapeutically effective amount of a compound of Formula V that is not systemically absorbed (e.g., a compound of Formula V that comprises a non-systemic moiety such as L-K or other groups described herein) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula I that is not systemically absorbed (e.g., a compound of Formula V that comprises a non-systemic moiety such as L-K or other groups described herein) is about 50% reduced when compared to the AUC of a therapeutically effective amount of Compound 100A. In other embodiments, the AUC of a therapeutically effective amount of a compound of Formula I that is not systemically absorbed (e.g., a compound of Formula V that comprises a non-systemic moiety such as L-K or other groups described herein) is about 75% reduced when compared to the AUC of a therapeutically effective amount of Compound 100A.

In some embodiments, the systemic exposure of a therapeutically effective amount of a compound of Formula VI or VID that is not systemically absorbed (e.g., a compound of Formula VI or VID that comprises a non-systemic moiety such as L-K or other groups described herein) is reduced when compared to the systemic exposure of a therapeutically effective amount of Compound 100A. In some embodiments, the AUC of a therapeutically effective amount of a compound of Formula VI or VID that is not systemically absorbed (e.g., a compound of Formula VI or VID that comprises a non-systemic moiety such as L-K or other groups described herein) is about 10%, about 20%, about 30%, about 40%, about 50%, about 60%, about 70%, about 80% or about 90% reduced when compared to the AUC of a therapeutically effective amount of Compound 100A. In some embodiments, the AUC of a therapeutically effective amount of a compound of Formula VI or VID that is not systemically absorbed (e.g., a compound of Formula VI or VID that comprises a non-systemic moiety such as L-K or other groups described herein) is about 50% reduced when compared to the AUC of a therapeutically effective amount of Compound 100A. In other embodiments, the AUC of a therapeutically effective amount of a compound of Formula I that is not systemically absorbed (e.g., a compound of Formula VI or VID that comprises a non-systemic moiety such as L-K or other groups described herein) is about 75% reduced when compared to the AUC of a therapeutically effective amount of Compound 100A.

In certain embodiments, the Cmax of a therapeutically effective amount of any non-systemic ASBTI described herein (e.g., an ASBTI that comprises a non-systemic moiety such as L-K or other groups described herein) is at least 10%, at least 20%, at least 30%, at least 40%, at least 50%, at least 60%, at least 70%, at least 80% or at least 90% reduced when compared to the Cmax of any systemically absorbed ASBTI (e.g. Compound 100A).

By way of example, the Cmax of a therapeutically effective amount of a compound of Formula III, IIIA, IIIB or IIIC is about 10%, about 20%, about 30%, about 40%, about 50%, about 60%, about 70%, about 80% or about 90% reduced when compared to the Cmax of a therapeutically effective amount of Compound 100C. In some embodiments, the Cmax of a therapeutically effective amount of a compound of Formula III, IIIA, IIIB or IIIC is about 25% reduced when compared to the Cmax of a therapeutically effective amount of Compound 100C. In certain embodiments, the Cmax of a therapeutically effective amount of a compound of III, IIIA or IIIB is about 50% reduced when compared to the Cmax of a therapeutically effective amount of Compound 100C. In other embodiments, the Cmax of a therapeutically effective amount of a compound of Formula III, IIIA, IIIB or IIIC is about 75% reduced when compared to the Cmax of a therapeutically effective amount of Compound 100C.

In certain embodiments, the pharmaceutical composition administered includes a therapeutically effective amount of a bile salt, a bile acid mimic, or a bile salt mimic, an absorption inhibitor and a carrier (e.g., an orally suitable carrier or a rectally suitable carrier, depending on the mode of intended administration). In certain embodiments, the pharmaceutical composition used or administered comprises a bile salt, a bile acid mimic, or a bile salt mimic, an absorption inhibitor, a carrier, and one or more of a cholesterol absorption inhibitor, an enteroendocrine peptide, a peptidase inhibitor, a spreading agent, and a wetting agent.

In a specific embodiment, the pharmaceutical composition used to prepare a rectal dosage form or administered rectally comprises a bile salt, a bile acid mimic, or a bile salt mimic, an absorption inhibitor, a rectally suitable carrier, an optional cholesterol absorption inhibitor, an optional enteroendocrine peptide, an optional peptidase inhibitor, an optional spreading agent, and an optional wetting agent. In certain embodiments, rectally administered compositions evokes an anorectal response. In specific embodiments, the anorectal response is an increase in secretion of one or more enteroendocrine by cells (e.g., L-cells) in the colon and/or rectum (e.g., in the epithelial layer of the colon and/or rectum). In some embodiments, the anorectal response persists for at least 1, 2, 3, 4, 5, 6, 7, 8, 9, 10, 11, 12, 13, 14, 15, 16, 17, 18, 19, 20, 21, 22, 23 or 24 hours. In other embodiments the anorectal response persists for a period between 24 hours and 48 hours, while in other embodiments the anorectal response persists for persists for a period greater than 48 hours.

In another specific embodiment, the pharmaceutical composition used to prepare an oral dosage form or administered orally comprises a bile salt, a bile acid mimic, or a bile salt mimic, an absorption inhibitor, an orally suitable carrier, an optional cholesterol absorption inhibitor, an optional enteroendocrine peptide, an optional peptidase inhibitor, an optional spreading agent, and an optional wetting agent. In certain embodiments, the orally administered compositions evokes an anorectal response. In specific embodiments, the anorectal response is an increase in secretion of one or more enteroendocrine by cells in the colon and/or rectum (e.g., in L-cells the epithelial layer of the colon and/or rectum). In some embodiments, the anorectal response persists for at least 1, 2, 3, 4, 5, 6, 7, 8, 9, 10, 11, 12, 13, 14, 15, 16, 17, 18, 19, 20, 21, 22, 23 or 24 hours. In other embodiments the anorectal response persists for a period between 24 hours and 48 hours, while in other embodiments the anorectal response persists for persists for a period greater than 48 hours.

Routes of Administration and Dosage

In some embodiments, the compositions described herein and the compositions administered in the methods described herein are formulated to inhibit bile acid reuptake, or reduce serum or hepatic bile acid levels. In certain embodiments, the compositions described herein are formulated for rectal or oral administration. In some embodiments, such formulations are administered rectally or orally, respectively. In some embodiments, the compositions described herein are combined with a device for local delivery of the compositions to the rectum and/or colon (sigmoid colon, transverse colon, or ascending colon). In certain embodiments, for rectal administration the composition described herein are formulated as enemas, rectal gels, rectal foams, rectal aerosols, suppositories, jelly suppositories, or retention enemas. In some embodiments, for oral administration the compositions described herein are formulated for oral administration and enteric delivery to the colon.

In certain embodiments, the compositions or methods described herein are non-systemic. In some embodiments, compositions described herein deliver the ASBTI to the distal ileum, colon, and/or rectum and not systemically (e.g., a substantial portion of the enteroendocrine peptide secretion enhancing agent is not systemically absorbed). In some embodiments, oral compositions described herein deliver the ASBTI to the distal ileum, colon, and/or rectum and not systemically (e.g., a substantial portion of the enteroendocrine peptide secretion enhancing agent is not systemically absorbed). In some embodiments, rectal compositions described herein deliver the ASBTI to the distal ileum, colon, and/or rectum and not systemically (e.g., a substantial portion of the enteroendocrine peptide secretion enhancing agent is not systemically absorbed). In certain embodiments, non-systemic compositions described herein deliver less than 90% w/w of the ASBTI systemically. In certain embodiments, non-systemic compositions described herein deliver less than 80% w/w of the ASBTI systemically. In certain embodiments, non-systemic compositions described herein deliver less than 70% w/w of the ASBTI systemically. In certain embodiments, non-systemic compositions described herein deliver less than 60% w/w of the ASBTI systemically. In certain embodiments, non-systemic compositions described herein deliver less than 50% w/w of the ASBTI systemically. In certain embodiments, non-systemic compositions described herein deliver less than 40% w/w of the ASBTI systemically. In certain embodiments, non-systemic compositions described herein deliver less than 30% w/w of the ASBTI systemically. In certain embodiments, non-systemic compositions described herein deliver less than 25% w/w of the ASBTI systemically. In certain embodiments, non-systemic compositions described herein deliver less than 20% w/w of the ASBTI systemically. In certain embodiments, non-systemic compositions described herein deliver less than 15% w/w of the ASBTI systemically. In certain embodiments, non-systemic compositions described herein deliver less than 10% w/w of the ASBTI systemically. In certain embodiments, non-systemic compositions described herein deliver less than 5% w/w of the ASBTI systemically. In some embodiments, systemic absorption is determined in any suitable manner, including the total circulating amount, the amount cleared after administration, or the like.

In certain embodiments, the compositions and/or formulations described herein are administered at least once a day. In certain embodiments, the formulations containing the ASBTI are administered at least twice a day, while in other embodiments the formulations containing the ASBTI are administered at least three times a day. In certain embodiments, the formulations containing the ASBTI are administered up to five times a day. It is to be understood that in certain embodiments, the dosage regimen of composition containing the ASBTI described herein to is determined by considering various factors such as the patient's age, sex, and diet.

The concentration of the ASBTI administered in the formulations described herein ranges from about 1 mM to about 1 M. In certain embodiments the concentration of the ASBTI administered in the formulations described herein ranges from about 1 mM to about 750 mM. In certain embodiments the concentration of the ASBTI administered in the formulations described herein ranges from about 1 mM to about 500 mM. In certain embodiments the concentration of the ASBTI administered in the formulations described herein ranges from about 5 mM to about 500 mM. In certain embodiments the concentration of the ASBTI administered in the formulations described herein ranges from about 10 mM to about 500 mM. In certain embodiments the concentration of the administered in the formulations described herein ranges from about 25 mM to about 500 mM. In certain embodiments the concentration of the ASBTI administered in the formulations described herein ranges from about 50 mM to about 500 mM. In certain embodiments the concentration of the ASBTI administered in the formulations described herein ranges from about 100 mM to about 500 mM. In certain embodiments the concentration of the ASBTI administered in the formulations described herein ranges from about 200 mM to about 500 mM.

In certain embodiments, any composition described herein comprises a therapeutically effective amount (e.g., to treat cholestasis or a cholestatic liver disease) of ursodiol. In some embodiments, ursodiol may be substituted for any other therapeutic bile acid or salt. In some embodiments, compositions described herein comprise or methods described herein comprise administering about 0.01 mg to about 10 g of ursodiol. In certain embodiments, a composition described herein comprises or a method described herein comprises administering about 0.1 mg to about 500 mg of ursodiol. In certain embodiments, a composition described herein comprises or a method described herein comprises administering about 0.1 mg to about 100 mg of ursodiol. In certain embodiments, a composition described herein comprises or a method described herein comprises administering about 0.1 mg to about 50 mg of ursodiol. In certain embodiments, a composition described herein comprises or a method described herein comprises administering about 0.1 mg to about 10 mg of ursodiol. In certain embodiments, a composition described herein comprises or a method described herein comprises administering about 0.5 mg to about 10 mg of ursodiol. In some embodiments, compositions described herein comprise or methods described herein comprise administering about 0.1 mmol to about 1 mol of ursodiol. In certain embodiments, a composition described herein comprises or a method described herein comprises administering about 0.01 mmol to about 500 mmol of ursodiol. In certain embodiments, a composition described herein comprises or a method described herein comprises administering about 0.1 mmol to about 100 mmol of ursodiol. In certain embodiments, a composition described herein comprises or a method described herein comprises administering about 0.5 mmol to about 30 mmol of ursodiol. In certain embodiments, a composition described herein comprises or a method described herein comprises administering about 0.5 mmol to about 20 mmol of ursodiol. In certain embodiments, a composition described herein comprises or a method described herein comprises administering about 1 mmol to about 10 mmol of ursodiol. In certain embodiments, a composition described herein comprises or a method described herein comprises administering about 0.01 mmol to about 5 mmol of ursodiol. In certain embodiments, a composition described herein comprises or a method described herein comprises administering about 0.1 mmol to about 1 mmol of ursodiol. In various embodiments, certain bile acids/salts have different potencies and dosing is optionally adjusted accordingly. For example, the investigation in TGR5-transfected CHO cells of TGR5 agonist potency of natural bile acids/salts indicates the following rank of potency: Lithocholic acid (LCA) >deoxycholic acid (DCA)>murocholic acid (Muro-CA)>lagodeoxycholic acid (lago-DCA)>chenodeoxycholic (CDCA)>cholic acid (CA)>hyodeoxycholic acid (HDCA>ursodeoxycholic acid (UDCA); and assays on TGR5-transfected CHO cells demonstrate that $EC_{50}$ (in µM) for UDCA was 36.4, TauroCA (TCA) 4.95 and LCA 0.58.

In certain embodiments, by targeting the distal gastrointestinal tract (e.g., distal ileum, colon, and/or rectum), compositions and methods described herein provide efficacy (e.g., in reducing microbial growth and/or alleviating symptoms of cholestasis or a cholestatic liver disease) with a reduced dose of enteroendocrine peptide secretion enhancing agent (e.g., as compared to an oral dose that does not target the distal gastrointestinal tract).

Rectal Administration Formulations

The pharmaceutical compositions described herein for the non-systemic delivery of a compound described herein to the rectum and/or colon are formulated for rectal administration as rectal enemas, rectal foams, rectal gels, and rectal suppositories. The components of such formulations are described herein. It is to be understood that as used herein, pharmaceutical compositions and compositions are or comprise the formulations as described herein. In some embodiments, rectal formulations comprise rectal enemas, foams, gels, or suppositories.

In certain embodiments, liquid carrier vehicles or co-solvents in the compositions and/or formulations described herein include, by way of non-limiting example, purified water, propylene glycol, PEG200, PEG300, PEG400, PEG600, polyethyleneglycol, ethanol, 1-propanol, 2-propanol, 1-propen-3-ol (allyl alcohol), propylene glycol, glycerol, 2-methyl-2-propanol, formamide, methyl formamide, dimethyl formamide, ethyl formamide, diethyl formamide, acetamide, methyl acetamide, dimethyl acetamide, ethyl acetamide, diethyl acetamide, 2-pyrrolidone, N-methyl-2-pyrrolidone, N-ethyl-2-pyrrolidone, tetramethyl urea, 1,3-dimethyl-2-imidazolidinone, propylene carbonate, 1,2-butylene carbonate, 2,3-butylene carbonate, dimethyl sulfoxide, diethyl sulfoxide, hexamethyl phosphoramide, pyruvic aldehyde dimethylacetal, dimethylisosorbide and combinations thereof.

In some embodiments, stabilizers used in compositions and/or formulations described herein include, but are not limited to, partial glycerides of polyoxyethylenic saturated fatty acids.

In certain embodiments, surfactants/emulsifiers used in the compositions and/or formulations described herein include, by way of non-limiting example, mixtures of cetostearylic alcohol with sorbitan esterified with polyoxyethylenic fatty acids, polyoxyethylene fatty ethers, polyoxyethylene fatty esters, fatty acids, sulfated fatty acids, phosphated fatty acids, sulfosuccinates, amphoteric surfactants, non-ionic poloxamers, non-ionic meroxapols, petroleum derivatives, aliphatic amines, polysiloxane derivatives, sorbitan fatty acid esters, laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and combinations thereof.

In some embodiments, non-ionic surfactants used in compositions and/or formulations described herein include, by way of non-limiting example, phospholipids, alkyl poly (ethylene oxide), poloxamers (e.g., poloxamer 188), polysorbates, sodium dioctyl sulfosuccinate, Brij™-30 (Laureth-4), Brij™-58 (Ceteth-20) and Brij™-78 (Steareth-20), Brij™-721 (Steareth-21), Crillet-1 (Polysorbate 20), Crillet-2 (Polysorbate 40), Crillet-3 (Polysorbate 60), Crillet 45 (Polysorbate 80), Myrj-52 (PEG-40 Stearate), Myrj-53 (PEG-50 Stearate), Pluronic™ F77 (Poloxamer 217), Pluronic™ F87 (Poloxamer 237), Pluronic™ F98 (Poloxamer 288), Pluronic™ L62 (Poloxamer 182), Pluronic™ L64 (Poloxamer 184), Pluronic™ F68 (Poloxamer 188), Pluronic™ L81 (Poloxamer 231), Pluronic™ L92 (Poloxamer 282), Pluronic™ L101 (Poloxamer 331), Pluronic™ P103 (Poloxamer 333), Pluracare™ F 108 NF (Poloxamer 338), and Pluracare™ F 127 NF (Poloxamer 407) and combinations thereof. Pluronic™ polymers are commercially purchasable from BASF, USA and Germany.

In certain embodiments, anionic surfactants used in compositions and/or formulations described herein include, by way of non-limiting example, sodium laurylsulphate, sodium dodecyl sulfate (SDS), ammonium lauryl sulfate, alkyl sulfate salts, alkyl benzene sulfonate, and combinations thereof.

In some embodiments, the cationic surfactants used in compositions and/or formulations described herein include, by way of non-limiting example, benzalkonium chloride, benzethonium chloride, cetyl trimethylammonium bromide, hexadecyl trimethyl ammonium bromide, other alkyltrimethylammonium salts, cetylpyridinium chloride, polyethoxylated tallow and combinations thereof.

In certain embodiments, the thickeners used in compositions and/or formulations described herein include, by way of non-limiting example, natural polysaccharides, semi-synthetic polymers, synthetic polymers, and combinations thereof. Natural polysaccharides include, by way of non-limiting example, acacia, agar, alginates, carrageenan, guar, arabic, tragacanth gum, pectins, dextran, gellan and xanthan gums. Semi-synthetic polymers include, by way of non-limiting example, cellulose esters, modified starches, modified celluloses, carboxymethylcellulose, methyl cellulose, ethyl cellulose, hydroxyethyl cellulose, hydroxypropyl cellulose and hydroxypropyl methylcellulose. Synthetic polymers include, by way of non-limiting example, polyoxyalkylenes, polyvinyl alcohol, polyacrylamide, polyacrylates, carboxypolymethylene (carbomer), polyvinylpyrrolidone (povidones), polyvinylacetate, polyethylene glycols and poloxamer. Other thickeners include, by way of nonlimiting example, polyoxyethyleneglycol isostearate, cetyl alcohol, Polyglycol 300 isostearate, propyleneglycol, collagen, gelatin, and fatty acids (e.g., lauric acid, myristic acid, palmitic acid, stearic acid, palmitoleic acid, linoleic acid, linolenic acid, oleic acid and the like).

In some embodiments, chelating agents used in the compositions and/or formulations described herein include, by way of non-limiting example, ethylenediaminetetraacetic acid (EDTA) or salts thereof, phosphates and combinations thereof.

In some embodiments, the concentration of the chelating agent or agents used in the rectal formulations described herein is a suitable concentration, e.g., about 0.1%, 0.15%, 0.2%, 0.25%, 0.3%, 0.4%, or 0.5% (w/v).

In some embodiments, preservatives used in compositions and/or formulations described herein include, by way of non-limiting example, parabens, ascorbyl palmitate, benzoic acid, butylated hydroxyanisole, butylated hydroxytoluene, chlorobutanol, ethylenediamine, ethylparaben, methylparaben, butyl paraben, propylparaben, monothioglycerol, phenol, phenylethyl alcohol, propylparaben, sodium benzoate, sodium propionate, sodium formaldehyde sulfoxylate, sodium metabisulfite, sorbic acid, sulfur dioxide, maleic acid, propyl gallate, benzalkonium chloride, benzethonium chloride, benzyl alcohol, chlorhexidine acetate, chlorhexidine gluconate, sorbic acid, potassium sorbitol, chlorbutanol, phenoxyethanol, cetylpyridinium chloride, phenylmercuric nitrate, thimerosal, and combinations thereof.

In certain embodiments, antioxidants used in compositions and/or formulations described herein include, by way of non-limiting example, ascorbic acid, ascorbyl palmitate, butylated hydroxyanisole, butylated hydroxytoluene, hypophosphorous acid, monothioglycerol, propyl gallate, sodium ascorbate, sodium sulfite, sodium bisulfite, sodium formaldehyde sulfoxylate, potassium metabisulphite, sodium metabisulfite, oxygen, quinones, t-butyl hydroquinone, erythorbic acid, olive (*Olea europaea*) oil, pentasodium pentetate, pentetic acid, tocopheryl, tocopheryl acetate and combinations thereof.

Pharmaceutically acceptable preservatives include quaternary ammonium salts such as benzalkonium chloride, alcohols such as benzyl alcohol, organic acids or salts and derivatives thereof such as benzoic acid, sodium benzoate, sorbic acid, potassium sorbate, propionic acid, sodium propionate, parabens such as methyl parahydroxybenzoate, propyl parahydroxybenzoate, ethyl parahydroxybenzoate or butyl parahydroxybenzoate, aqua conservans; chlorhexidine diacetate,-digluconate. Given the intended use of the present composition, the preservatives are preferably suitable for pediatric use. Preferred preservatives are parabens such as methyl parahydroxybenzoate, propyl parahydroxybenzoate, ethyl parahydroxybenzoate or butyl parahydroxybenzoate, in particular methyl parahydroxybenzoate or propyl parahydroxybenzoate. The preservatives are present in a composition in a concentration in order to provide sufficient antimicrobial activity in the preconcentrate composition or in the liquid composition upon reconstitution. Preferably, the concentration of the preservatives in a resulting reconstituted liquid composition ranges up to about 3% (w/w), more preferably up to about 2.5% (w/w), more preferably up to about 2% (w/w), depending on the actual preservative being used.

The composition of the present invention may also contain one or more anti-oxidants, such as, for example, sodium metabisulfite, sodium bisulfite, sodium sulfite, sodium thiosulfate, ascorbic acid, BHA (butylhydroxyanisol), BHT (butylhydroxytoluene), vitamin E, propylgallate, ascorbyl palmitate, or complex forming agents such as EDTA (ethylenediaminetetraacetic acid), citric acid, tartaric acid, sodium-hexametaphosphate and the like. Given the intended use of the present composition, the antioxidants or the complex forming agents are preferably suitable for pediatric use. Preferred antioxidants are BHA, BHT, vitamin E or propylgallate. In some embodiments, concentration of the antioxidant or antioxidants used in the rectal formulations described herein is sufficient to achieve a desired result, e.g., about 0.1%, 0.15%, 0.2%, 0.25%, 0.3%, 0.4%, or 0.5% (w/v).

The lubricating agents used in compositions and/or formulations described herein include, by way of non-limiting example, natural or synthetic fat or oil (e.g., a tris-fatty acid glycerate and the like). In some embodiments, lubricating agents include, by way of non-limiting example, glycerin (also called glycerine, glycerol, 1,2,3-propanetriol, and trihydroxypropane), polyethylene glycols (PEGs), polypropylene glycol, polyisobutene, polyethylene oxide, behenic acid, behenyl alcohol, sorbitol, mannitol, lactose, polydimethylsiloxane and combinations thereof.

In certain embodiments, mucoadhesive and/or bioadhesive polymers are used in the compositions and/or formulations described herein as agents for inhibiting absorption of the enteroendocrine peptide secretion enhancing agent across the rectal or colonic mucosa. Bioadhesive or mucoadhesive polymers include, by way of non-limiting example, hydroxypropyl cellulose, polyethylene oxide homopolymers, polyvinyl ether-maleic acid copolymers, methyl cellulose, ethyl cellulose, propyl cellulose, hydroxyethyl cellulose, hydroxypropyl cellulose, hydroxypropylmethyl cellulose, carboxymethylcellulose, polycarbophil, polyvinylpyrrolidone, carbopol, polyurethanes, polyethylene oxide-polypropyline oxide copolymers, sodium carboxymethyl cellulose, polyethylene, polypropylene, lectins, xanthan gum, alginates, sodium alginate, polyacrylic acid, chitosan, hyaluronic acid and ester derivatives thereof, vinyl acetate homopolymer, calcium polycarbophil, gelatin, natural gums, karaya, tragacanth, algin, chitosan, starches, pectins, and combinations thereof.

In some embodiments, buffers/pH adjusting agents used in compositions and/or formulations described herein include, by way of non-limiting example, phosphoric acid, monobasic sodium or potassium phosphate, triethanolamine (TRIS), BICINE, HEPES, Trizma, glycine, histidine, arginine, lysine, asparagine, aspartic acid, glutamine, glutamic acid, carbonate, bicarbonate, potassium metaphosphate, potassium phosphate, monobasic sodium acetate, acetic acid, acetate, citric acid, sodium citrate anhydrous, sodium citrate dihydrate and combinations thereof. In certain embodiments, an acid or a base is added to adjust the pH. Suitable acids or bases include, by way of non-limiting example, HCL, NaOH and KOH.

In certain embodiments, concentration of the buffering agent or agents used in the rectal formulations described herein is sufficient to achieve or maintain a physiologically desirable pH, e.g., about 0.1%, 0.2%, 0.3%, 0.4%, 0.5%, 0.6%, 0.8%, 0.9%, or 1.0% (w/w).

The tonicity modifiers used in compositions and/or formulations described herein include, by way of non-limiting example, sodium chloride, potassium chloride, sodium phosphate, mannitol, sorbitol or glucose.

Pediatric Dosage Formulations and Compositions

Provided herein, in certain embodiments, is a pediatric dosage formulation or composition comprising a therapeutically effective amount of any compound described herein. In certain instances, the pharmaceutical composition comprises an ASBT inhibitor (e.g., any ASBTI described herein).

In certain embodiments, suitable dosage forms include, by way of non-limiting example, aqueous or non-aqueous oral dispersions, liquids, gels, syrups, elixirs, slurries, suspensions, solutions, controlled release formulations, fast melt formulations, effervescent formulations, lyophilized formulations, chewable tablets, gummy candy, orally disintegrating tablets, powders for reconstitution as suspension or solution, sprinkle oral powder or granules, dragees, delayed release formulations, extended release formulations, pulsatile release formulations, multiparticulate formulations, and mixed immediate release and controlled release formulations. In some embodiments, provided herein is a pharmaceutical composition wherein the pediatric dosage form is selected from a solution, syrup, suspension, elixir, powder for reconstitution as suspension or solution, dispersible/effervescent tablet, chewable tablet, gummy candy, lollipop, freezer pops, troches, oral thin strips, orally disintegrating tablet, orally disintegrating strip, sachet, and sprinkle oral powder or granules.

In another aspect, provide herein is a pharmaceutical composition wherein at least one excipient is a flavoring agent or a sweetener. In some embodiments, provided herein is a coating. In some embodiments, provided herein is a taste-masking technology selected from coating of drug particles with a taste-neutral polymer by spray-drying, wet granulation, fluidized bed, and microencapsulation; coating with molten waxes of a mixture of molten waxes and other pharmaceutical adjuvants; entrapment of drug particles by complexation, flocculation or coagulation of an aqueous polymeric dispersion; adsorption of drug particles on resin and inorganic supports; and solid dispersion wherein a drug and one or more taste neutral compounds are melted and cooled, or co-precipitated by a solvent evaporation. In some embodiments, provided herein is a delayed or sustained release formulation comprising drug particles or granules in a rate controlling polymer or matrix.

Suitable sweeteners include sucrose, glucose, fructose or intense sweeteners, i.e. agents with a high sweetening power when compared to sucrose (e.g. at least 10 times sweeter than sucrose). Suitable intense sweeteners comprise aspartame, saccharin, sodium or potassium or calcium saccharin, acesulfame potassium, sucralose, alitame, xylitol, cyclamate, neomate, neohesperidin dihydrochalcone or mixtures thereof, thaumatin, palatinate, stevioside, rebaudioside, Magnasweet®. The total concentration of the sweeteners may range from effectively zero to about 300 mg/ml based on the liquid composition upon reconstitution.

In order to increase the palatability of the liquid composition upon reconstitution with an aqueous medium, one or more taste-making agents may be added to the composition in order to mask the taste of the ASBT inhibitor. A taste-masking agent can be a sweetener, a flavoring agent or a combination thereof. The taste-masking agents typically provide up to about 0.1% or 5% by weight of the total pharmaceutical composition. In a preferred embodiment of the present invention, the composition contains both sweetener(s) and flavor(s).

A flavoring agent herein is a substance capable of enhancing taste or aroma of a composition. Suitable natural or synthetic flavoring agents can be selected from standard reference books, for example Fenaroli's Handbook of Flavor Ingredients, 3rd edition (1995). Non-limiting examples of flavoring agents and/or sweeteners useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidin DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. Flavoring agents can be used singly or in combinations of two or more. In some embodiments, the aqueous liquid dispersion comprises a sweetening agent or flavoring agent in a concentration ranging from about 0.0010% to about 5.0% the volume of the aqueous dispersion. In one embodiment, the aqueous liquid dispersion comprises a sweetening agent or flavoring agent in a concentration ranging from about 0.001% to about 1.0% the volume of the aqueous dispersion. In another embodiment, the aqueous liquid dispersion comprises a sweetening agent or flavoring agent in a concentration ranging from about 0.005% to about 0.5% the volume of the aqueous dispersion. In yet another embodiment, the aqueous liquid dispersion comprises a sweetening agent or flavoring agent in a concentration ranging from about 0.01% to about 1.0% the volume of the aqueous dispersion. In yet another embodiment, the aqueous liquid dispersion comprises a sweetening agent or flavoring agent in a concentration ranging from about 0.01% to about 0.5% the volume of the aqueous dispersion.

In certain embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition, as used herein, refers to a mixture of a compound described herein, such as, for example, a compound of Formula I-VI, with other chemical components, such as carriers, stabilizers, diluents, dispersing agents, suspending agents, thickening agents, and/or excipients. In certain instances, the pharmaceutical composition facilitates administration of the compound to an individual or cell. In certain embodiments of practicing the methods of treatment or use provided herein, therapeutically effective amounts of compounds described herein are administered in a pharmaceutical composition to an individual having a disease, disorder, or condition to be treated. In specific embodiments, the individual is a human. As discussed herein, the compounds described herein are either utilized singly or in combination with one or more additional therapeutic agents.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes.

In certain embodiments, a pharmaceutical compositions described herein includes one or more compound described herein as an active ingredient in free-acid or free-base form, or in a pharmaceutically acceptable salt form. In some embodiments, the compounds described herein are utilized as an N-oxide or in a crystalline or amorphous form (i.e., a polymorph). In some situations, a compound described herein exists as tautomers. All tautomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the compounds presented herein are also considered to be described herein.

A "carrier" includes, in some embodiments, a pharmaceutically acceptable excipient and is selected on the basis of compatibility with compounds described herein, such as, compounds of any of Formula I-VI, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Moreover, in certain embodiments, the pharmaceutical compositions described herein are formulated as a dosage form. As such, in some embodiments, provided herein is a dosage form comprising a compound described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In certain aspects, the composition or formulation containing one or more compounds described herein is orally administered for local delivery of an ASBTI, or a compound described herein to the colon and/or rectum. Unit dosage forms of such compositions include a pill, tablet or capsules formulated for enteric delivery to colon. In certain embodiments, such pills, tablets or capsule contain the compositions described herein entrapped or embedded in microspheres. In some embodiments, microspheres include, by way of non-limiting example, chitosan microcores HPMC capsules and cellulose acetate butyrate (CAB) microspheres. In certain embodiments, oral dosage forms are prepared using conventional methods known to those in the field of pharmaceutical formulation. For example, in certain embodiments, tablets are manufactured using standard tablet processing procedures and equipment. An exemplary method for forming tablets is by direct compression of a powdered, crystalline or granular composition containing the active agent(s), alone or in combination with one or more carriers, additives, or the like. In alternative embodiments, tablets are prepared using wet-granulation or dry-granulation processes. In some embodiments, tablets are molded rather than compressed, starting with a moist or otherwise tractable material.

In certain embodiments, tablets prepared for oral administration contain various excipients, including, by way of non-limiting example, binders, diluents, lubricants, disintegrants, fillers, stabilizers, surfactants, preservatives, coloring agents, flavoring agents and the like. In some embodiments, binders are used to impart cohesive qualities to a tablet, ensuring that the tablet remains intact after compression. Suitable binder materials include, by way of non-limiting example, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), Veegum, and combinations thereof. In certain embodiments, diluents are utilized to increase the bulk of the tablet so that a practical size tablet is provided. Suitable diluents include, by way of non-limiting example, dicalcium phosphate, calcium sulfate, lactose, cellulose, kaolin, mannitol, sodium chloride, dry starch, powdered sugar and combinations thereof. In certain embodiments, lubricants are used to facilitate tablet manufacture; examples of suitable lubricants include, by way of non-limiting example, vegetable oils such as peanut oil, cottonseed oil, sesame oil, olive oil, corn oil, and oil of theobroma, glycerin, magnesium stearate, calcium stearate, stearic acid and combinations thereof. In some embodiments, disintegrants are used to facilitate disintegration of the tablet, and include, by way of non-limiting example, starches, clays, celluloses, algins, gums, crosslinked polymers and combinations thereof. Fillers include, by way of non-limiting example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. In certain embodiments, stabilizers are used to inhibit or retard drug decomposition reactions that include, by way of example, oxidative reactions. In certain embodiments, surfactants are anionic, cationic, amphoteric or nonionic surface active agents.

In some embodiments, ASBTIs, or other compounds described herein are orally administered in association with a carrier suitable for delivery to the distal gastrointestinal tract (e.g., distal ileum, colon, and/or rectum).

In certain embodiments, a composition described herein comprises an ASBTI, or other compounds described herein in association with a matrix (e.g., a matrix comprising hypromellose) that allows for controlled release of an active agent in the distal part of the ileum and/or the colon. In some embodiments, a composition comprises a polymer that is pH sensitive (e.g., a MMX™ matrix from Cosmo Pharmaceuticals) and allows for controlled release of an active agent in the distal part of the ileum. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of about 7 to about 8). In some embodiments, a composition suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an enteroendocrine peptide secretion enhancing agent (e.g., bile acid) to the distal ileum. In some embodiments, a dosage form comprising an enteroendocrine peptide secretion enhancing agent (e.g., bile acid) is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the distal ileum and/or the colon. In some embodiments, bacterially activated systems are suitable for targeted delivery to the distal part of the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pharmaceutical composition described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences,* 20th Edition (2000), a film coating is provided around the formulation of the compound of Formula I. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

In further embodiments, a tablet or capsule comprising an ASBTI or other compounds described herein is film-coated for delivery to targeted sites within the gastrointestinal tract. Examples of enteric film coats include and are not limited to hydroxypropylmethylcellulose, polyvinyl pyrrolidone, hydroxypropyl cellulose, polyethylene glycol 3350, 4500, 8000, methyl cellulose, pseudo ethylcellulose, amylopectin and the like.

Solid Dosage Forms for Pediatric Administration

Solid dosage forms for pediatric administration of the present invention can be manufactured by standard manufacturing techniques. Non-limiting examples of oral solid dosage forms for pediatric administration are described below.

Effervescent Compositions

The effervescent compositions of the invention may be prepared according to techniques well-known in the art of pharmacy.

Effervescent formulations contain and effervescent couple of a base component and an acid component, which components reach in the presence of water to generate a gas. In some embodiments, the base component may comprise, for example, an alkali metal or alkaline earth metal carbonate, or bicarbonate. The acid component may comprise, for example, an aliphatic carboxylic acid or a salt thereof, such as citric acid. The base and acid components may each independently constitute, for example, 25% to 55% (w/w) of the effervescent composition. The ratio of acid component to base component may be within the range of 1:2 to 2:1.

The effervescent compositions of the invention may be formulated using additional pharmaceutically acceptable carriers or excipients as appropriate. For example, one or more taste masking agents may be used. Dyes may also be used, as pediatric patients often prefer colorful pharmaceutical combinations. The compositions may take the form of, for example, tablets, granules or powders, granules or powders presented in a sachet.

Chewable Tablets

The chewable tablets of the invention may be prepared according to techniques well-known in the art of pharmacy.

Chewable tablets are tablets that are intended to disintegrate in the mouth under the action of chewing or sucking and where, in consequence, the active ingredient has greater opportunity to come into contact with the bitter-taste receptors on the tongue.

One method of overcoming this issue is to absorb the active ingredient onto a suitable substrate. This approach is described in U.S. Pat. No. 4,647,459.

Another approach involves forming the active ingredient into an aggregate along with a pre-swelled substantially anhydrous hydrocolloid. The hydrocolloid absorbs saliva and acquires a slippery texture which enables it to lubricate the particles of aggregate and mask the taste of the active ingredient. This approach is described in European patent application 0190826.

Another approach involves employing a water-insoluble hygroscopic excipient such as microcrystalline cellulose. This approach is described in U.S. Pat. No. 5,275,823.

In addition to the above approaches, the chewable tablets of the present invention can also contain other stand tabletting excipients such as a disintegrant and a taste-masking agent.

Orodispersible Tablets

The orodispersible tablets of the invention may be prepared according to techniques well-known in the art of pharmacy.

In orodispersible tablets of the invention, the excipient mixtures is such as to provide it with a disintegration rate so that its disintegration in the buccal cavity occurs in an extremely short time and especially shorter than sixty seconds. In some embodiments, the excipient mixture is characterized by the fact that the active substance is in the form of coated or non-coated microcrystals of microgranules. In some embodiments, the orodispersible tablet comprises one or several disintegrating agents of the carboxymethylcellulose type or insoluble reticulated PVP type, one or several swelling agents which may comprise a carboxymethylcellulose, a starch, a modified starch, or a microcrystalline cellulose or optionally a direct compression sugar.

Powders for Reconstitution

The powder for reconstitution pharmaceutical compositions of the invention may be prepared according to techniques well-known in the art of pharmacy.

In some embodiments, the powder for reconstitution compositions of the invention comprise an effective amount of at least one internal dehydrating agent. The internal dehydrating agent can enhance the stability of the powder. In some embodiments, the internal dehydrating agent is magnesium citrate or disodium carbonate. In some embodiments, the powder composition comprises a pharmaceutically acceptable diluents, such as sucrose, dextrose, mannitol, xylitol, or lactose.

Powder compositions of the inventions may be placed in sachets or bottles for contemporaneous dissolution or for short term storage in liquid form (e.g. 7 days).

Gummy Candies

The gummy candies of the invention may be prepared according to techniques well-known in the art of pharmacy.

Traditional gummy candy is made from a gelatin base. Gelatin gives the candy its elasticity, the desired chewy consistency, and a longer shelf life. In some embodiments, the gummy candy pharmaceutical composition of the invention includes a binding agent, a sweetener, and an active ingredient.

In some embodiments, the binding agent is a pectin gel, gelatin, food starch, or any combination thereof.

In some embodiments, the gummy candy comprises sweeteners, a binding agent, natural and/or artificial flavors and colors and preservatives. In some embodiments, the gummy candy comprises glucose syrup, natural cane juice, gelatin, citric acid, lactic acid, natural colors, natural flavors, fractionated coconut oil, and carnauba wax.

Liquid Dosage Forms

The pharmaceutical liquid dosage forms of the invention may be prepared according to techniques well-known in the art of pharmacy.

A solution refers to a liquid pharmaceutical formulation wherein the active ingredient is dissolved in the liquid. Pharmaceutical solutions of the invention include syrups and elixers. A suspension refers to a liquid pharmaceutical formulation wherein the active ingredient is in a precipitate in the liquid.

In a liquid dosage form, it is desirable to have a particular pH and/or to be maintained within a specific pH range. In order to control the pH, a suitable buffer system can be used. In addition, the buffer system should have sufficient capacity to maintain the desired pH range. Examples of the buffer system useful in the present invention include but are not limited to, citrate buffers, phosphate buffers, or any other suitable buffer known in the art. Preferably the buffer system include sodium citrate, potassium citrate, sodium bicarbonate, potassium bicarbonate, sodium dihydrogen phosphate and potassium dihydrogen phosphate, etc. The concentration of the buffer system in the final suspension varies according to factors such as the strength of the buffer system and the pH/pH ranges required for the liquid dosage form. In one embodiment, the concentration is within the range of 0.005 to 0.5 w/v % in the final liquid dosage form.

The pharmaceutical composition comprising the liquid dosage form of the present invention can also include a suspending/stabilizing agent to prevent settling of the active material. Over time the settling could lead to caking of the active to the inside walls of the product pack, leading to difficulties with redispersion and accurate dispensing. Suitable stabilising agents include but are not limited to, the polysaccharide stabilizers such as xanthan, guar and tragacanth gums as well as the cellulose derivatives HPMC (hydroxypropyl methylcellulose), methyl cellulose and Avicel RC-591 (microcrystalline cellulose/sodium carboxymethyl cellulose). In another embodiment, polyvinylpyrrolidone (PVP) can also be used as a stabilizing agent.

In addition to the aforementioned components, the ASBTI oral suspension form can also optionally contain other excipients commonly found in pharmaceutical compositions such as alternative solvents, taste-masking agents, antioxidants, fillers, acidifiers, enzyme inhibitors and other components as described in Handbook of Pharmaceutical Excipients, Rowe et al., Eds., $4^{th}$ Edition, Pharmaceutical Press (2003), which is hereby incorporated by reference.

Addition of an alternative solvent may help increase solubility of an active ingredient in the liquid dosage form, and consequently the absorption and bioavailability inside the body of a subject. Preferably the alternative solvents include methanol, ethanol or propylene glycol and the like.

In another aspect, the present invention provides a process for preparing the liquid dosage form. The process comprises steps of bringing ASBTI or its pharmaceutically acceptable salts thereof into mixture with the components including glycerol or syrup or the mixture thereof, a preservative, a buffer system and a suspending/stabilizing agent, etc., in a liquid medium. In general, the liquid dosage form is prepared by uniformly and intimately mixing these various components in the liquid medium. For example, the components such as glycerol or syrup or the mixture thereof, a preservative, a buffer system and a suspending/stabilizing agent, etc., can be dissolved in water to form the aqueous solution, then the active ingredient can be then dispersed in the aqueous solution to form a suspension.

In some embodiments, the liquid dosage form provided herein can be in a volume of between 5 ml to 50 ml. In some embodiments, the liquid dosage form provided herein can be in a volume of between 5 ml to 40 ml. In some embodiments, the liquid dosage form provided herein can be in a volume of between 5 ml to 30 ml. In some embodiments, the liquid dosage form provided herein can be in a volume of between 5 ml to 20 ml. In some embodiments, the liquid dosage form provided herein can be in a volume of between 10 ml to 30 ml. In some embodiments, the ASBTI can be in an amount ranging from about 0.001% to 90% of the total volume. In some embodiments, the ASBTI can be in an amount ranging from about 0.01% to 80% of the total volume. In some embodiments, the ASBTI can be in an amount ranging from about 0.10% to 70% of the total volume. In some embodiments, the ASBTI can be in an amount ranging from about 1% to 60% of the total volume. In some embodiments, the ASBTI can be in an amount ranging from about 1% to 50% of the total volume. In some embodiments, the ASBTI can be in an amount ranging from about 1% to 40% of the total volume. In some embodiments, the ASBTI can be in an amount ranging from about 1% to 30% of the total volume. In some embodiments, the ASBTI can be in an amount ranging from about 1% to 20% of the total volume. In some embodiments, the ASBTI can be in an amount ranging from about 1% to 10% of the total volume. In some embodiments, the ASBTI can be in an amount ranging from about 5% to 70% of the total volume. In some embodiments, the ASBTI can be in an amount ranging from about 5% to 60% of the total volume. In some embodiments, the ASBTI can be in an amount ranging from about 5% to 50% of the total volume. In some embodiments, the ASBTI can be in an amount ranging from about 5% to 40% of the total volume. In some embodiments, the ASBTI can be in an amount ranging from about 5% to 30% of the total volume. In some embodiments, the ASBTI can be in an amount ranging from about 5% to 20% of the total volume. In some embodiments, the ASBTI can be in an amount ranging from about 5% to 10% of the total volume. In some embodiments, the ASBTI can be in an amount ranging from about 10% to 50% of the total volume. In some embodiments, the ASBTI can be in an amount ranging from about 10% to 40% of the total volume. In some embodiments, the ASBTI can be in an amount ranging from about 10% to 30% of the total volume. In some embodiments, the ASBTI can be in an amount ranging from about 10% to 20% of the total volume. In one embodiment, the resulted liquid dosage form can be in a liquid volume of 10 ml to 30 ml, preferably 20 ml, and the active ingredient can be in an amount ranging from about 0.001 mg/ml to about 16 mg/ml, or from about 0.025 mg/ml to about 8 mg/ml, or from about 0.1 mg/ml to about 4 mg/ml, or about 0.25 mg/ml, or about 0.5 mg/ml, or about 1 mg/ml, or about 2 mg/ml, or about 4 mg/ml, or about 5 mg/ml, or about 8 mg/ml, or about 10 mg/ml, or about 12 mg/ml, or about 14 mg/ml or about 16 mg/ml.

Bile Acid Sequestrant

In certain embodiments, an oral formulation for use in any method described herein is, e.g., an ASBTI in association with a labile bile acid sequestrant. A labile bile acid sequestrant is a bile acid sequestrant with a labile affinity for bile acids. In certain embodiments, a bile acid sequestrant described herein is an agent that sequesters (e.g., absorbs or is charged with) bile acid, and/or the salts thereof.

In specific embodiments, the labile bile acid sequestrant is an agent that sequesters (e.g., absorbs or is charged with) bile acid, and/or the salts thereof, and releases at least a portion of the absorbed or charged bile acid, and/or salts thereof in the distal gastrointestinal tract (e.g., the colon, ascending colon, sigmoid colon, distal colon, rectum, or any combination thereof). In certain embodiments, the labile bile acid sequestrant is an enzyme dependent bile acid sequestrant. In specific embodiments, the enzyme is a bacterial enzyme. In some embodiments, the enzyme is a bacterial enzyme found in high concentration in human colon or rectum relative to the concentration found in the small intestine. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like. In some embodiments, the labile bile acid sequestrant is a time dependent bile acid sequestrant (i.e., the bile acid sequesters the bile acid and/or salts thereof and after a time releases at least a portion of the bile acid and/or salts thereof). In some embodiments, a time dependent bile acid sequestrant is an agent that degrades in an aqueous environment over time. In certain embodiments, a labile bile acid sequestrant described herein is a bile acid sequestrant that has a low affinity for bile acid and/or salts thereof, thereby allowing the bile acid sequestrant to continue to sequester bile acid and/or salts thereof in an environ where the bile acids/salts and/or salts thereof are present in high concentration and release them in an environ wherein bile acids/salts and/or salts thereof are present in a lower relative concentration. In some embodiments, the labile bile acid sequestrant has a high affinity for a primary bile acid and a low affinity for a secondary bile acid, allowing the bile acid sequestrant to sequester a primary bile acid or salt thereof and subsequently release a secondary bile acid or salt thereof as the primary bile acid or salt thereof is converted (e.g., metabolized) to the secondary bile acid or salt thereof. In some embodiments, the labile bile acid sequestrant is a pH dependent bile acid sequestrant. In some embodiments, the pH dependent bile acid sequestrant has a high affinity for bile acid at a pH of 6 or below and a low affinity for bile acid at a pH above 6. In certain embodiments, the pH dependent bile acid sequestrant degrades at a pH above 6.

In some embodiments, labile bile acid sequestrants described herein include any compound, e.g., a macrostructured compound, that can sequester bile acids/salts and/or salts thereof through any suitable mechanism. For example, in certain embodiments, bile acid sequestrants sequester bile acids/salts and/or salts thereof through ionic interactions, polar interactions, static interactions, hydrophobic interactions, lipophilic interactions, hydrophilic interactions, steric interactions, or the like. In certain embodiments, macrostructured compounds sequester bile acids/salts and/or sequestrants by trapping the bile acids/salts and/or salts thereof in pockets of the macrostructured compounds and, optionally, other interactions, such as those described above. In some embodiments, bile acid sequestrants (e.g., labile bile acid sequestrants) include, by way of non-limiting example, lignin, modified lignin, polymers, polycationic polymers and copolymers, polymers and/or copolymers comprising anyone one or more of N-alkenyl-N-alkylamine residues; one or more N,N,N-trialkyl-N—(N'-alkenylamino)alkyl-azanium residues; one or more N,N,N-trialkyl-N-alkenyl-azanium residues; one or more alkenyl-amine residues; or a combination thereof, or any combination thereof.

Covalent Linkage of the Drug with a Carrier

In some embodiments, strategies used for colon targeted delivery include, by way of non-limiting example, covalent linkage of the ASBTI or other compounds described herein to a carrier, coating the dosage form with a pH-sensitive polymer for delivery upon reaching the pH environment of the colon, using redox sensitive polymers, using a time released formulation, utilizing coatings that are specifically degraded by colonic bacteria, using bioadhesive system and using osmotically controlled drug delivery systems.

In certain embodiments of such oral administration of a composition containing an ASBTI or other compounds described herein involves covalent linking to a carrier wherein upon oral administration the linked moiety remains intact in the stomach and small intestine. Upon entering the colon the covalent linkage is broken by the change in pH, enzymes, and/or degradation by intestinal microflora. In certain embodiments, the covalent linkage between the ASBTI and the carrier includes, by way of non-limiting example, azo linkage, glycoside conjugates, glucuronide conjugates, cyclodextrin conjugates, dextran conjugates, and amino-acid conjugates (high hydrophilicity and long chain length of the carrier amino acid).

Coating with Polymers: pH-Sensitive Polymers

In some embodiments, the oral dosage forms described herein are coated with an enteric coating to facilitate the delivery of an ASBTI or other compounds described herein to the colon and/or rectum. In certain embodiments, an enteric coating is one that remains intact in the low pH environment of the stomach, but readily dissolved when the optimum dissolution pH of the particular coating is reached which depends upon the chemical composition of the enteric coating. The thickness of the coating will depend upon the solubility characteristics of the coating material. In certain embodiments, the coating thicknesses used in such formulations described herein range from about 25 µm to about 200 µm.

In certain embodiments, the compositions or formulations described herein are coated such that an ASBTI or other compounds described herein of the composition or formulation is delivered to the colon and/or rectum without absorbing at the upper part of the intestine. In a specific embodiment, specific delivery to the colon and/or rectum is achieved by coating of the dosage form with polymers that degrade only in the pH environment of the colon. In alternative embodiments, the composition is coated with an enteric coat that dissolves in the pH of the intestines and an outer layer matrix that slowly erodes in the intestine. In some of such embodiments, the matrix slowly erodes until only a core composition comprising an enteroendocrine peptide secretion enhancing agent (and, in some embodiments, an absorption inhibitor of the agent) is left and the core is delivered to the colon and/or rectum.

In certain embodiments, pH-dependent systems exploit the progressively increasing pH along the human gastrointestinal tract (GIT) from the stomach (pH 1-2 which increases to 4 during digestion), small intestine (pH 6-7) at the site of digestion and it to 7-8 in the distal ileum. In certain embodiments, dosage forms for oral administration of the compositions described herein are coated with pH-sensitive polymer(s) to provide delayed release and protect the enteroendocrine peptide secretion enhancing agents from gastric fluid. In certain embodiments, such polymers are be able to withstand the lower pH values of the stomach and of the proximal part of the small intestine, but disintegrate at the neutral or slightly alkaline pH of the terminal ileum and/or ileocecal junction. Thus, in certain embodiments, provided herein is an oral dosage form comprising a coating, the coating comprising a pH-sensitive polymer. In some embodiments, the polymers used for colon and/or rectum targeting include, by way of non-limiting example, methacrylic acid copolymers, methacrylic acid and methyl methacrylate copolymers, Eudragit L100, Eudragit S100, Eudragit L-30D, Eudragit FS-30D, Eudragit L100-55, polyvinylacetate phthalate, hydroxypropyl ethyl cellulose phthalate, hydroxypropyl methyl cellulose phthalate 50, hydroxypropyl methyl cellulose phthalate 55, cellulose acetate trimellitate, cellulose acetate phthalate and combinations thereof.

In certain embodiments, oral dosage forms suitable for delivery to the colon and/or rectum comprise a coating that has a biodegradable and/or bacteria degradable polymer or polymers that are degraded by the microflora (bacteria) in the colon. In such biodegradable systems suitable polymers include, by way of non-limiting example, azo polymers, linear-type-segmented polyurethanes containing azo groups, polygalactomannans, pectin, glutaraldehyde crosslinked dextran, polysaccharides, amylose, guar gum, pectin, chitosan, inulin, cyclodextrins, chondroitin sulphate, dextrans, locust bean gum, chondroitin sulphate, chitosan, poly(-caprolactone), polylactic acid and poly(lactic-co-glycolic acid).

In certain embodiments of such oral administration of compositions containing one or more ASBTIs or other compounds described herein, the compositions are delivered to the colon without absorbing at the upper part of the intestine by coating of the dosage forms with redox sensitive polymers that are degraded by the microflora (bacteria) in the colon. In such biodegradable systems such polymers include, by way of non-limiting example, redox-sensitive polymers containing an azo and/or a disulfide linkage in the backbone.

In some embodiments, compositions formulated for delivery to the colon and/or rectum are formulated for time-release. In some embodiments, time release formulations resist the acidic environment of the stomach, thereby delaying the release of the enteroendocrine peptide secretion enhancing agents until the dosage form enters the colon and/or rectum.

In certain embodiments the time released formulations described herein comprise a capsule (comprising an enteroendocrine peptide secretion enhancing agent and an optional absorption inhibitor) with hydrogel plug. In certain embodiments, the capsule and hydrogel plug are covered by a water-soluble cap and the whole unit is coated with an enteric polymer. When the capsule enters the small intestine the enteric coating dissolves and the hydrogels plug swells and dislodges from the capsule after a period of time and the composition is released from the capsule. The amount of hydrogel is used to adjust the period of time to the release the contents.

In some embodiments, provided herein is an oral dosage form comprising a multi-layered coat, wherein the coat comprises different layers of polymers having different pH-sensitivities. As the coated dosage form moves along GIT the different layers dissolve depending on the pH encountered. Polymers used in such formulations include, by way of non-limiting example, polymethacrylates with appropriate pH dissolution characteristics, Eudragit® RL and Eudragit® RS (inner layer), and Eudragit® FS (outer layer). In other embodiments the dosage form is an enteric coated tablets having an outer shell of hydroxypropylcellulose or hydroxypropylmethylcellulose acetate succinate (HPMCAS).

In some embodiments, provided herein is an oral dosage form that comprises coat with cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxopropyl methylcellulose succinate, carboxymethyl ethylcellulose, hydroxypropyl methylcellulose acetate succinate, polymers and copolymers formed from acrylic acid, methacrylic acid, and combinations thereof.

Combination Therapy

In certain instances, provided herein are combination compositions and/or therapies comprising any compound described herein and an additional therapeutic agent. In some embodiments, the additional therapeutic agent is a L-cell endocrine peptide enhancer. In some instances, the L-cell endocrine peptide enhancer is a GLP-2 enhancer. In some embodiments, the GLP-2 enhancer is GLP-2, a GLP-2 secretion enhancer, a GLP-2 degradation inhibitor, the like, or a combination thereof. In certain instances, enhanced GLP-2 concentration provides regeneration of intestinal lining and/or heals injury to the gastrointestinal structures and/or reduces induction of cytokines and/or enhances the adaptive process, attenuates intestinal injury, reduces bacterial translocation, inhibits the release of free radical oxygen, or any combination thereof. In some instances, the L-cell endocrine peptide enhancer is a PYY enhancer. In some instances, the L-cell endocrine peptide enhancer is an oxyntomodulin enhancer. In some instances, enhanced PYY or oxyntomodulin secretion heals injury to intestine caused by an cholestasis or a cholestatic liver disease.

TGR5 Receptor Modulators

In some instances, the additional therapeutic agent modulates bile acid receptors in the gastrointestinal lumen. In some embodiments, the additional therapeutic agent agonizes or partially agonizes bile acid receptors (e.g., TGR5 receptors or Farnesoid-X receptors) in the gastrointestinal tract. In some embodiments, the additional therapeutic agent is a bile acid analog. In certain instances the additional therapeutic agent is a TGR5 agonist. In certain instances, administration of a TGR5 agonist in combination with any of the compounds described herein enhances the secretion of enteroendocrine peptides from L-cells. TGR5 modulators (e.g., agonists) include, and are not limited to, the compounds described in, WO 2008/091540, WO 2008/067219 and U.S. Appl. No. 2008/0221161.

Enteroendocrine Peptides

In some embodiments, the additional therapeutic agent is an enteroendocrine peptide. In some embodiments, enteroendocrine peptides heals injury to intestine or liver due to a cholestatic liver disease. Examples of enteroendocrine peptides that are administered as additional therapeutic agents include and are not limited to GLP-1 or GLP-1 analogs such as Taspoglutide® (Ipsen), or the like.

Combination Therapy with Fat Soluble Vitamins

In some embodiments, the methods provided herein further comprise administering one or more vitamins. In some embodiments, the vitamin is vitamin A, B1, B2, B3, B5, B6, B7, B9, B12, C, D, E, K, folic acid, pantothenic acid, niacin, riboflavin, thiamine, retinol, beta carotene, pyridoxine, ascorbic acid, cholecalciferol, cyanocobalamin, tocopherols, phylloquinone, menaquinone.

In some embodiments, the vitamin is a fat soluble vitamin such as vitamin A, D, E, K, retinol, beta carotene, cholecalciferol, tocopherols, phylloquinone. In a preferred embodiment, the fat soluble vitamin is tocopherol polyethylene glycol succinate (TPGS).

Combination Therapy with Partial External Biliary Diversion (PEBD)

In some embodiments, the methods provided herein further comprise using partial external biliary diversion as a treatment for patients who have not yet developed cirrhosis. This treatment helps reduce the circulation of bile acids/salts in the liver in order to reduce complications and prevent the need for early transplantation in many patients.

This surgical technique involves isolating a segment of intestine 10 cm long for use as a biliary conduit (a channel for the passage of bile) from the rest of the intestine. One end of the conduit is attached to the gallbladder and the other end is brought out to the skin to form a stoma (a surgically constructed opening to permit the passage of waste). Partial external biliary diversion may be used for patients who are unresponsive to all medical therapy, especially older, larger patients. This procedure may not be of help to young patients such as infants. Partial external biliary diversion may decrease the intensity of the itching and abnormally low levels of cholesterol in the blood.

Combination Therapy with ASBTI and Ursodiol

In some embodiments, an ASBTI is administered in combination with ursodiol or ursodeoxycholic acid, chenodeoxycholic acid, cholic acid, taurocholic acid, ursocholic acid, glycocholic acid, glycodeoxycholic acid, taurodeoxycholic acid, taurocholate, glycochenodeoxycholic acid, tauroursodeoxycholic acid. In some instances an increase in the concentration of bile acids/salts in the distal intestine induces intestinal regeneration, attenuating intestinal injury, reducing bacterial translocation, inhibiting the release of free radical oxygen, inhibiting production of proinflammatory cytokines, or any combination thereof or any combination thereof.

An ASBTI and a second active ingredient are used such that the combination is present in a therapeutically effective amount. That therapeutically effective amount arises from the use of a combination of an ASBTI and the other active ingredient (e.g., ursodiol) wherein each is used in a therapeutically effective amount, or by virtue of additive or synergistic effects arising from the combined use, each can also be used in a subclinical therapeutically effective amount, i.e., an amount that, if used alone, provides for reduced effectiveness for the therapeutic purposes noted herein, provided that the combined use is therapeutically effective. In some embodiments, the use of a combination of an ASBTI and any other active ingredient as described herein encompasses combinations where the ASBTI or the other active ingredient is present in a therapeutically effective amount, and the other is present in a subclinical therapeutically effective amount, provided that the combined use is therapeutically effective owing to their additive or synergistic effects. As used herein, the term "additive effect" describes the combined effect of two (or more) pharmaceutically active agents that is equal to the sum of the effect of each agent given alone. A synergistic effect is one in which the combined effect of two (or more) pharmaceutically active agents is greater than the sum of the effect of each agent given alone. Any suitable combination of an ASBIT with one or more of the aforementioned other active ingredients and optionally with one or more other pharmacologically active substances is contemplated as being within the scope of the methods described herein.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g, from more than zero weeks to less than four weeks. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In certain embodiments, provided herein are combination therapies. In certain embodiments, the compositions described herein comprise an additional therapeutic agent. In some embodiments, the methods described herein comprise administration of a second dosage form comprising an additional therapeutic agent. In certain embodiments, combination therapies the compositions described herein are administered as part of a regimen. Therefore, additional therapeutic agents and/or additional pharmaceutical dosage form can be applied to a patient either directly or indirectly, and concomitantly or sequentially, with the compositions and formulations described herein.

Kits

In another aspect, provided herein are kits containing a device for rectal administration pre-filled a pharmaceutical composition described herein. In certain embodiments, kits contain a device for oral administration and a pharmaceutical composition as described herein. In certain embodiments the kits includes prefilled sachet or bottle for oral administration, while in other embodiments the kits include prefilled bags for administration of rectal gels. In certain embodiments the kits includes prefilled syringes for administration of oral enemas, while in other embodiments the kits include prefilled syringes for administration of rectal gels. In certain embodiments the kits includes prefilled pressurized cans for administration of rectal foams.

Release in Distal Ileum and/or Colon

In certain embodiments, a dosage form comprises a matrix (e.g., a matrix comprising hypromellose) that allows for controlled release of an active agent in the distal jejunum, proximal ileum, distal ileum and/or the colon. In some embodiments, a dosage form comprises a polymer that is pH sensitive (e.g., a MMX™ matrix from Cosmo Pharmaceuticals) and allows for controlled release of an active agent in the ileum and/or the colon. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of about 7 to about 8). In some embodiments, a dosage form suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an ASBTI to the distal ileum. In some embodiments, a dosage form comprising an ASBTI is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the ileum and/or the colon. In some embodiments, bacterially activated systems are suitable for targeted delivery to the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences,* 20th Edition (2000), a film coating is provided around the formulation of the compound of Formula I-VI. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

An ASBT inhibitor (e.g., a compound of Formula I-VI) is used in the preparation of medicaments for the prophylactic and/or therapeutic treatment of cholestasis or a cholestatic liver disease. A method for treating any of the diseases or conditions described herein in an individual in need of such treatment, involves administration of pharmaceutical compositions containing at least one ASBT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

Screening Process

Provided in certain embodiments herein are processes and kits for identifying compounds suitable for treating cholestasis or a cholestatic liver disease. In certain embodiments, provided herein are assays for identifying compounds that selectively inhibits the ASBT by:
  a. providing cells that are a model of intestinal cells;
  b. contacting the cells with a compound (e.g., a compound as described herein);
  c. detecting or measuring the effect of the compound on the inhibition of ASBT activity.

In certain embodiments, provided herein are assays for identifying compounds that are non-systemic compounds by
  a. providing cells that are a model of intestinal permeability (e.g., Caco-2 cells);
  b. culturing the cells as a monolayer on semi-permeable plastic supports that are fitted into the wells of multi-well culture plates;
  c. contacting the apical or basolateral surface of the cells with a compound (e.g., a compound as described herein) and incubating for a suitable length of time;
  d. detecting or measuring the concentration of the compound on both sides of the monolayer by liquid-chromatography-mass spectrometry (LC-MS) and computing intestinal permeability of the compound.

In certain embodiments, non-systemic compounds are identified by suitable parallel artificial membrane permeability assays (PAMPA).

In certain embodiments, non-systemic compounds are identified by use of isolated vascular-perfused gut preparations.

In certain embodiments, provided herein are assays for identifying compounds that inhibit recycling of bile acid salts by
  a. providing cells that are a model of intestinal cells with apical bile acid transporters (e.g., BHK cells, CHO cells);
  b. incubating the cells with a compound (e.g., a compound as described herein) and/or a radiolabeled bile acid (e.g., $^{14}C$ taurocholate) for a suitable length of time;
  c. washing the cells with a suitable buffer (e.g. phosphate buffered saline);
  d. detecting or measuring the residual concentration of the radiolabeled bile acid in the cells.

EXAMPLES

Example 1: Synthesis of 1-phenethyl-1-((1,4-diazabicyclo[2.2.2]octenyl)pentyl)imidodicarbonimidic Diamide, Iodide Salt

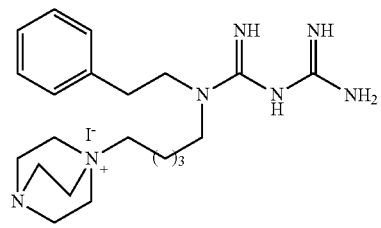

Step 1: Synthesis of 5-(1,4-diazabicyclo[2.2.2]octenyl)-1-iodo Pentane, Iodide Salt

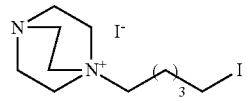

1,4-diazabicyclo[2.2.2]octane is suspended in THF. Diiodopentane is added dropwise and the mixture is refluxed overnight. The reaction mixture is filtered.

Step 2: Synthesis of N-phenethyl-5-(1,4-diazabicyclo[2.2.2]octenyl)-1-iodo Pentane, Iodide salt

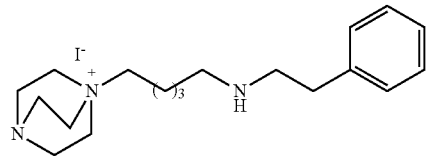

5-(1,4-diazabicyclo[2.2.2]octenyl)-1-iodo pentane, iodide salt is suspended in acetonitrile. Phenethylamine is added dropwise and the mixture is refluxed overnight. The reaction mixture is filtered.

Step 3: Synthesis of 1-phenethyl-1-((1,4-diazabicyclo[2.2.2]octenyl)pentyl)imidodicarbonimidic Diamide, Iodide Salt N-phenethyl-5-(1,4-diazabicyclo[2.2.2]octenyl)-1-iodo pentane, iodide salt is heated with dicyanodiamide in n-butanol for 4 h. The reaction mixture is concentrated under reduced pressure.

The compounds in Table 1 are prepared using methods as described herein, and using appropriate starting materials.

TABLE 1
| Compound No. | Structure |
|---|---|
| 1 | 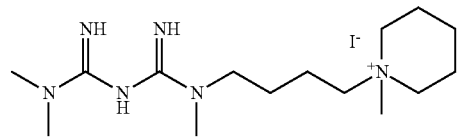 [SMILES: CN(C)C(=N)NC(=N)N(C)CCCC[N+]1(C)CCCCC1 ; [I-]] |
| 2 | 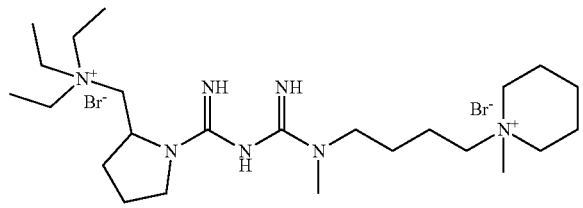 [SMILES: CC[N+](CC)(CC)CC1CCCN1C(=N)NC(=N)N(C)CCCC[N+]1(C)CCCCC1 ; [Br-] ; [Br-]] |
| 3 | 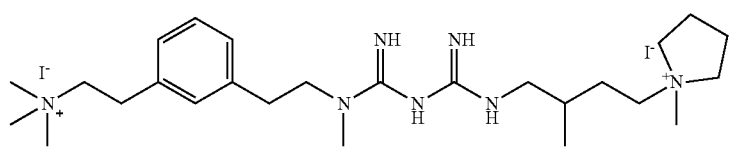 [SMILES: CC(CC[N+]1(C)CCCC1)CNC(=N)NC(=N)N(C)CCc1cccc(CC[N+](C)(C)C)c1 ; [I-] ; [I-]] |
| 4 | 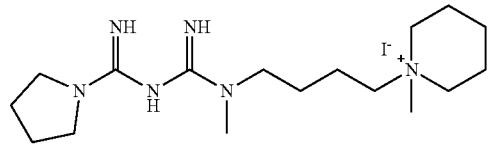 [SMILES: CN(CCCC[N+]1(C)CCCCC1)C(=N)NC(=N)N1CCCC1 ; [I-]] |
| 5 | 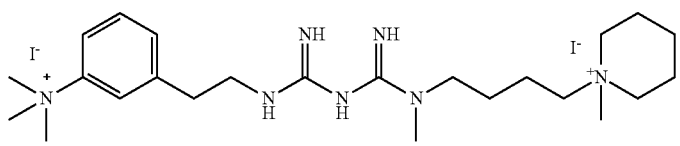 [SMILES: CN(CCCC[N+]1(C)CCCCC1)C(=N)NC(=N)NCCc1cccc([N+](C)(C)C)c1 ; [I-] ; [I-]] |
| 6 | 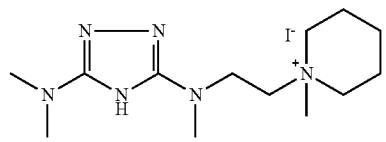 [SMILES: CN(C)c1nnc(N(C)CC[N+]2(C)CCCCC2)[nH]1 ; [I-]] |
| 7 | 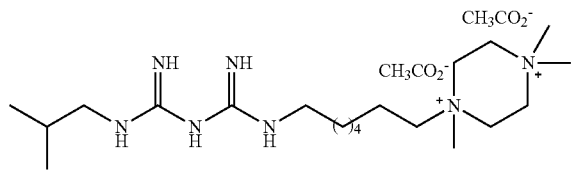 [SMILES: CC(C)CNC(=N)NC(=N)NCCCC[N+]1(C)CC[N+](C)(C)CC1 ; "CH3CO2-" ; "CH3CO2-"] |
| 8 | 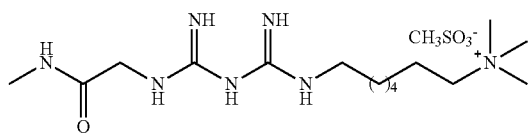 |
| 9 | 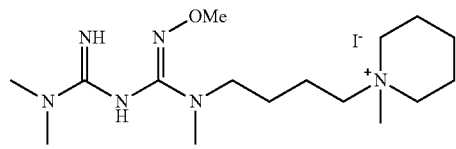 [SMILES: CO/N=C(/NC(=N)N(C)C)N(C)CCCC[N+]1(C)CCCCC1 ; [I-]] |

TABLE 1-continued

| Compound No. | Structure |
|---|---|
| 10 | [structure: triethylammonium bromide group attached to pyrrolidine with bis-guanidine linker to morpholinium methyl bromide] |
| 11 | [structure: methylguanidine-guanidine-ethyl-N-methyl-N-(1-phenylethyl) ammonium iodide] |

Example 2: In Vitro Assay for Inhibition of ASBT-Mediated Bile Acid Uptake

Baby hamster kidney (BHK) cells are transfected with cDNA of human ASBT. The cells are seeded in 96-well tissue culture plates at 60,000 cells/well. Assays are run within 24 hours of seeding.

On the day of the assay the cell monolayer is washed with 100 mL of assay buffer. The test compound is added to each well along with 6 mM [$^{14}$C] taurocholate in assay buffer (final concentration of 3 mM [$^{14}$C] taurocholate in each well). The cell cultures are incubated for 2 h at 37 TC. The wells are washed with PBS. Scintillation counting fluid is added to each well, the cells are shaken for 30 minutes prior to measuring amount of radioactivity in each well. A test compound that has significant ASBT inhibitory activity provides an assay wherein low levels of radioactivity are observed in the cells.

Example 3: In Vitro Assay for Secretion of GLP-2

Human NCI-H716 cells are used as a model for L-cells. Two days before each assay experiment, cells are seeded in 12-well culture plates coated with Matrigel® to induce cell adhesion. On the day of the assay, cells are washed with buffer. The cells are incubated for 2 hours with medium alone, or with test compound. The extracellular medium is assayed for the presence of GLP-2. Peptides in the medium are collected by reverse phase adsorption and the extracts are stored until assay. The presence of GLP-2 is assayed using ELISA. The detection of increased levels of GLP-2 in a well containing a test compound identifies the test compound as a compound that can enhance GLP-2 secretions from L-cells.

Example 4: In Vivo Bioavailability Assay

The test compounds are solubilized in saline solutions. Sprague Dawley rats are dosed at 2-10 mg/kg body weight by iv and oral dosing. Peripheral blood samples are taken from the femoral artery at selected time periods up to 8 hours. Plasma concentrations of the compounds are determined by quantitative HPLC and/or mass spectrometry. Clearance and AUC values are determined for the compounds.

For oral dosing, bioavailability is calculated by also drawing plasma samples from the portal vein. Cannulae are inserted in the femoral artery and the hepatic portal vein to obtain estimates of total absorption of drug without first-pass clearance in the liver. The fraction absorbed (F) is calculated by $$F = AUC_{po}/AUC_{iv}$$

Example 5: Assay to Determine Ileal Intraenterocyte and Luminal Bile Acid Levels Ileal luminal bile acid levels in SD rats are determined by flushing a 3-cm section of distal ileum with sterile, cold PBS. After flushing with additional PBS, the same section of ileum is weighed and then homogenized in fresh PBS for determination of interenterocyte bile acid levels. A LC/MS/MS system is used to evaluate cholic acid, DCA, LCA, chenodeoxycholic acid, and ursodeoxycholic acid levels.

Example 6: Animal to Determine Effect of Therapy on Cholestasis or a Cholestatic Liver Disease Mdr2 knock out mouse model of cholestasis or a cholestatic liver disease induced rats (by carbon tetrachloride/phenobarbital) is used to test compositions described herein. The animals are orally administered a composition comprising an ASBTI such as 100B, 264W94; SD5613; SAR548304B; SA HMR1741; 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl] carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-methylpropyl)carbamoyl]-4-hydroxybenzyl] carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl) carbamoyl]-4-hydroxybenzyl}carbamoylmethoxy)-2,3,4,5-tetrahydro-1,2,5-benzothiadiazepine; or 1,1-dioxo-3,3-dibutyl-5-phenyl-7-methylthio-8-[N—((R)-α-carboxy-4-hydroxybenzyl)carbamoylmethoxy]-2,3,4,5-tetrahydro-1,2,5-benzothiadiazepine.

Cholestasis or cholestatic liver disease is quantitated by total bile acid and bilirubin in serum versus that in control mice/rats administered with placebo. Serum bile acids/salts are determined by ELISA with specific antibodies for cholic and CCDCA. Serum bilirubin levels are determined by automated routine assays. Alternatively, livers of the mice can be harvested and pathology of the hepatocellular damage can be measured.

Example 7 Investigation of Orally Delivered LUM001 and 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane Methane Sulfonate (Compound 100B) on Plasma GLP-2 Levels in Normal Rats 12-week-old male HSD rats are fasted for 16 h and given oral dose of 0, 3, 30, 100 mg/kg of the ASBTIs LUM001 or 1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methane sulfonate (Synthesized by Nanosyn Inc., CA, USA) in a mixture of valine-pyrrolidine in water (n=5 per group). Blood samples in volume of 0.6 ml for each time point are taken from the caudal vein with a heparinized capillary tube 0, 1, 3 and 5 h after the administration of compounds and plasma GLP-2 level are determined. Aprotinin and 10 µl of DPP-IV inhibitor per ml of blood are used for blood sample preservation during 10 min centrifugation and for storage at −70° C. or below. GLP-2 (Active pM) is tested by any commercially available ELISA kits.

Example 8: Tablet Formulation 10 kg of a compound of Formula I-VI is first screened through a suitable screen (e.g. 500 micron). 25 kg Lactose monohydrate, 8 kg hydroxypropylmethyl cellulose, the screened compound of Formula I-VI and 5 kg calcium hydrogen phosphate (anhydrous) are then added to a suitable blender (e.g. a tumble mixer) and blended. The blend is screened through a suitable screen (e.g. 500 micron) and reblended. About 50% of the lubricant (2.5 kg, magnesium stearate) is screened, added to the blend and blended briefly. The remaining lubricant (2 kg, magnesium stearate) is screened, added to the blend and blended briefly. The granules are screened (e.g. 200 micron) to obtain granulation particles of the desired size. In some embodiments, the granules are optionally coated with a drug release controlling polymer such as polyvinylpyrrolidine, hydroxypropylcellulose, hydroxypropylmethyl cellulose, methyl cellulose, or a methacrylic acid copolymer, to provide an extended release formulation. The granules are filled in gelatin capsules.

Example 9: Pediatric Formulation

Disintegrating Tablet Formulation

The following example describes a large scale preparation (100 kg) of an ASBTI compound of Formula I-VI (e.g., LUM-001 or LUM-002).

| Active ingredient (LUM-001) | 2.5 kg |
|---|---|
| Lactose monohydrate NF | 47.5 kg |
| Pregelatinized starch NF | 18 kg |
| microcrystalline cellulose NF | 17 kg |
| croscarmellose sodium NF | 6.5 kg |
| povidone K29/32 USP | 8.5 kg |
| | 100 kg |

Pass ASBTI (2.5 kg), lactose monohydrate NF (47.5 kg), pregelatinized starch NF (18 kg), microcrystalline cellulose NF (17 kg), croscarmellose sodium NF (6.5 kg) and povidone K29/32 USP (8.5 kg) through a #10 mesh screen. Add the screened material to a 600 Collette mixer. Mix for 6 minutes at low speed, without chopper. Add the direct blend mixture from the previous step to a 20-cubic foot V-shell PK blender (Model C266200). Pass magnesium stearate NF (0.5 to 1 kg) through a 10 mesh screen into a properly prepared container. Add approximately half of the magnesium stearate to each side of the PK blender and blend for 5 minutes. Add the blended mixture from the previous step to Kikusui tablet press for compression into tablets. The compression equipment can be outfitted to make tooling for 50 mg tablet, 75 mg tablet and 100 mg tablet.

Example 10: Effervescent Tablet

The active ingredient, anhydrous monosodium citrate, sodium bicarbonate and aspartame are mixed together and granulated by the addition of a solution of the polyvinylpyrrolidone in the alcohol. The granules obtained after mixing are dried and passed through a calibrator, and the resulting granules are then mixed with the sodium benzoate and flavorings. The granulated material is compressed into tablets using an alternative machine fitted with 20 mm punches.

A rotative machine fitted with 20 mm punches may also be used for tabletting.

| Active ingredient | 4.4 mg |
|---|---|
| Sodium bicarbonate | 20.5 mg |
| Monosodium citrate anhydrous | 20.6 mg |
| Aspartame | 1.25 mg |
| Polyvinylpyrrolidone | 1.0 mg |
| Sodium benzoate | 1.5 mg |
| Orange flavor IFF 29G44 | 0.5 mg |
| Lemon flavor IFF 29M194 | 0.25 mg |
| Absolute alcohol for granulation | |

Example 11: Chewable Tablet

A 40% (w/w) solution of the Eudragit E100 in ethanol was added with mixing to the active ingredient and blended until granules were formed. The resulting granules were dried and then sieved through a 16 mesh screen.

| Active ingredient | 4.0 mg |
|---|---|
| Eudragit E100 | 0.6 mg |
| Sorbitol: Direct Compression Grade | 18.8 mg |
| Lactose: Direct Compression Grade | 15.6 mg |
| Croscaimellose Sodium Type A | 1.2 mg |
| Aspartame | 0.3 mg |
| Aniseed flavoring | 0.6 mg |
| Butterscotch flavoring | 0.6 mg |
| Magnesium Stearate | 0.6 mg |
| Microcrystalline Cellulose (Avicel PH102) | 4.7 mg |
| | 47 mg |

The active ingredient granules and extragranular excipients were put into a cone blender and mixed thoroughly. The resulting mix was discharged from the blender and compressed on a suitable rotary tablet press fitted with the appropriate punches.

Example 12: Orodispersible Tablet

The active ingredient is introduced in a fluidized air bed installation and a solution of ethylcellulose in ethanol is sprayed thereon.

The excipients are sieved and the coated active ingredient is homogenized with the excipients in a mixing apparatus under dry conditions.

Distribution and tabletting are carried out on a compressing machine equipped with punches having a diameter equal to 16 mm and a radius of curvature equal to 20 mm.

The pressure is 15 kNewtons±1. The hardness of the thus obtained tablets is 50 Newtons±5. The time of disintegration in the mouth is from 15 to 20 seconds.

| | |
|---|---|
| Active ingredient (with ethylcellulose) | 4.0 mg |
| Reticulated polyvinylpyrrolidone | 20.0 mg |
| Starch | 40 mg |
| Sweetener | 1.0 mg |
| Flavor | 1.0 mg |
| Magnesium stearate | 1.0 mg |
| | 67.0 mg |

Example 13: Powder Formulation

A pulverulent mixture of active ingredient and polyvidone (5 parts by weight) is granulated with 7% of purified water (weight/weight).

A premix is prepared with the following constituents: carbasalate calcium (amount corresponding to parts by weight of acetylsalicylic acid); anhydrous citric acid (168 parts by weight); sodium bicarbonate (232 parts by weight); lactose (1500 parts by weight); magnesium citrate (180 parts by weight); potassium benzoate (250 parts by weight). The premix is then dry compacted.

The pulverulent active ingredient mixture and the dry compacted premix, and the following compounds: aspartame and artificial vanilla flavoring, which are in powder form, are mixed.

The mixture of powders can be packaged directly in sachets.

| | |
|---|---|
| Active ingredient | 4.0 mg |
| Polividone | 0.2 mg |
| Carbasalate calcium | 2.6 mg |
| Citic acid | 6.7 mg |
| Sodium bicarbonate | 9.3 mg |
| Lactose | 60 mg |
| Magnesium citrate | 7.2 mg |
| Potassium benzoate | 10 mg |
| | 100 mg |

Example 14: Gummy Candy

About 50 lbs of warm water is mixed with about 50 lbs of gelatin in the mixing tank, to form 100 lbs of gelling compound having a homogeneous 50/50 blend of water and gelatin. About 0.1% to 10% of sodium bisulfate by weight is added to the gelling compound to reduce the pH of the gelling compound to about 3.5.

In the mixing weigh vessel, the gelling compound is mixed with about 6 lbs of water, 38.3 lbs of sucrose, and 50 lbs of corn syrup to form the candy slurry. If the active ingredient is not a heat sensitive drug, the active ingredient is added to the candy slurry prior to cooking. About 0.1% sodium citrate by weight is be added to the candy slurry to maintain the pH of the slurry at about 3.0 to 3.5.

Next, the candy slurry is heated to a temperature of about 180° F. prior to being passed through the storage buffer tank, to the static cooker. In the static cooker, the candy slurry is heated to a temperature of about 240° F. to 245° F., dehydrating the slurry to a brix of about 78.

After the candy is cooked, the cooked candy is sent to the vacuum chamber, where the candy is further dehydrated to a brix of about 80. After leaving the vacuum, the cooked candy is placed in the dossier where about 1.5% of strawberry flavoring by weight and about 1% of red cabbage coloring by weight is added to the cooked candy. To balance the flavoring, about 0.1% citric acid by weight and about 0.1% lactic acid by weight is added to the cooked candy.

After adding the flavoring and coloring, the cooked candy is deposited into the mogul machine and then cured. After the candies are cured, they are added to a tumbling drum to break off any starch that is remaining on the candies. As the candies are being tumbled, about 1% fractionated coconut oil by weight and about 1% carnauba wax by weight is poured into the drum to coat the candies to prevent them from sticking together.

| | |
|---|---|
| Active ingredient (5 mg) | 5% |
| Lactic acid | 1% |
| Citric Acid | 1% |
| Sucrose | 23.5% |
| Corn Syrup | 50.0% |
| Gelatin | 7% |
| Sodium bisufate | 0.1%-10% |
| Flavoring (natural/artificial) | 1.5% |
| Colorant (natural/artificial) | 1.0% |

Example 15: Taste-Masked Liquid Formulations

An aqueous pharmaceutical composition of the present invention is formulated by preparing a mixture of hydroxyethylcellulose dissolved in 50 milliliters of purified water with 0.5 mL of—orange flavoring agent, with potassium phosphate dibasic and potassium phosphate monobasic added (from a hot water mixture). 4.0 mg of active ingredient is then added and mixed until dissolved. Sodium hydroxide is added to adjust the pH to from about 6.7 to about 6.9.

| | |
|---|---|
| Active ingredient | 4.0 mg |
| Hydroxyethylcellulose | 10 mg |
| Potassium phosphate dibasic | 4.5 mg |
| Potassium phosphate monobasic | 4.5 mg |
| Sodium hydroxide | 0.1 mL |
| Orange flavoring | 0.5 mL |
| Purified water | 50 mL |

Alternative liquid oral formulations are provided below. For each of the formulations below, a sweetener from 0.500 to 2% such as sucralose, mannitol, sucrose and/or a flavoring agent from 0.5% to 2% such as grape, cherry, bubble gum, orange, lemon, strawberry can be added. Polypropylene glycol can be replaced with one of the PEGs.

| Ingredients | Concentration |
|---|---|
| LUM001 | 0.02 to 4 mg/mL |
| Propylene glycol | 10 to 300 mg/mL |
| Water, q.s. to | 1 mL |

| Ingredients | Concentration |
| --- | --- |
| LUM001 | 0.02 to 4 mg/mL |
| PEG 200 (or 300, 400, 600) | 10 to 300 mg/mL |
| Water, q.s. to | 1 mL |

| Ingredients | Concentration |
| --- | --- |
| LUM001 | 0.02 to 4 mg/mL |
| Propylene glycol | 10 to 300 mg/mL |
| Sodium lauryl sulfate | 1 to 10 mg/mL |
| Water, q.s. to | 1 mL |

| Ingredients | Concentration |
| --- | --- |
| LUM001 | 0.02 to 4 mg/mL |
| Propylene glycol | 10 to 300 mg/mL |
| Poloxamer 188 | 1 to 10 mg/mL |
| Water, q.s. to | 1 mL |

Example 16: Sachet Formulation

The following formulation is used to produce a sachet for pediatric use. A sweetener from 0.50% to 2% such as sucralose, mannitol, sucrose and/or a flavoring agent from 0.50% to 2% such as grape, cherry, bubble gum, orange, lemon, strawberry can be added. Sugar and sodium lauryl sulfate can be exchanged with other surfactants.

| Ingredients | Concentration |
| --- | --- |
| LUM001 | 0.05 to 10 mg |
| Soluble Diluent | 10 to 500 mg |
| Sugar | 10 to 250 mg |
| Sodium lauryl sulfate | 5 to 50 mg |
| Flavoring agent | 10 to 100 mg |

Example 17: Animal Study

Animal preparation. Male Zucker diabetic fatty rats (ZDF/GmiCrl-fa/fa) were purchased from Charles River (Raleigh, NC) and housed under controlled conditions (12:12 light-dark cycle, 24° C. and 50% relative humidity) with free access to rodent food (Purina 5008, Harlan Teklad, Indianapolis, IN). All rats arrived at seven weeks of age (±3 days). After a one-week acclimation period, rats were anesthetized with isoflurane (Abbott Laboratories, IL) and tail-vein blood samples were collected at 9 am without fasting. Blood glucose levels were measured using a glucometer (Bayer, Leverkusen, Germany). In order to ensure balanced treatment groups, ZDF rats were assigned to six treatment groups based upon baseline glucose: vehicle (0.5% HPMC, 0.1% Tween80) and five doses of 264W94 (0.001, 0.01, 0.1, 1, 10 mg/kg). All treatments were given via oral gavage twice a day and animals were followed for two weeks with blood samples collected from tail vein at the end of each week at 9 am without fasting. Fecal samples were collected for 24 hours during the second week of treatment.

Measurement of clinical chemistry parameters. Non-esterified fatty acids (NEFA), bile acids, and bile acids in fecal extraction were measured using the Olympus AU640 clinical chemistry analyzer (Beckman Coulter, Irving, TX).

Changes in fecal bile acid excretion and plasma bile acid concentrations Oral administration of 264W94 dose-dependently increased bile acids in the feces. Fecal bile acid concentrations were elevated up to 6.5 fold with an $ED_{50}$ of 0.17 mg/kg, when compared to vehicle treated rats. Fecal NEFA also slightly increased in 264W94 treated rats. In contrast, plasma bile acid concentrations were decreased dose-dependently in 264W94 treated rats. See FIG. 1.

Figure 2:
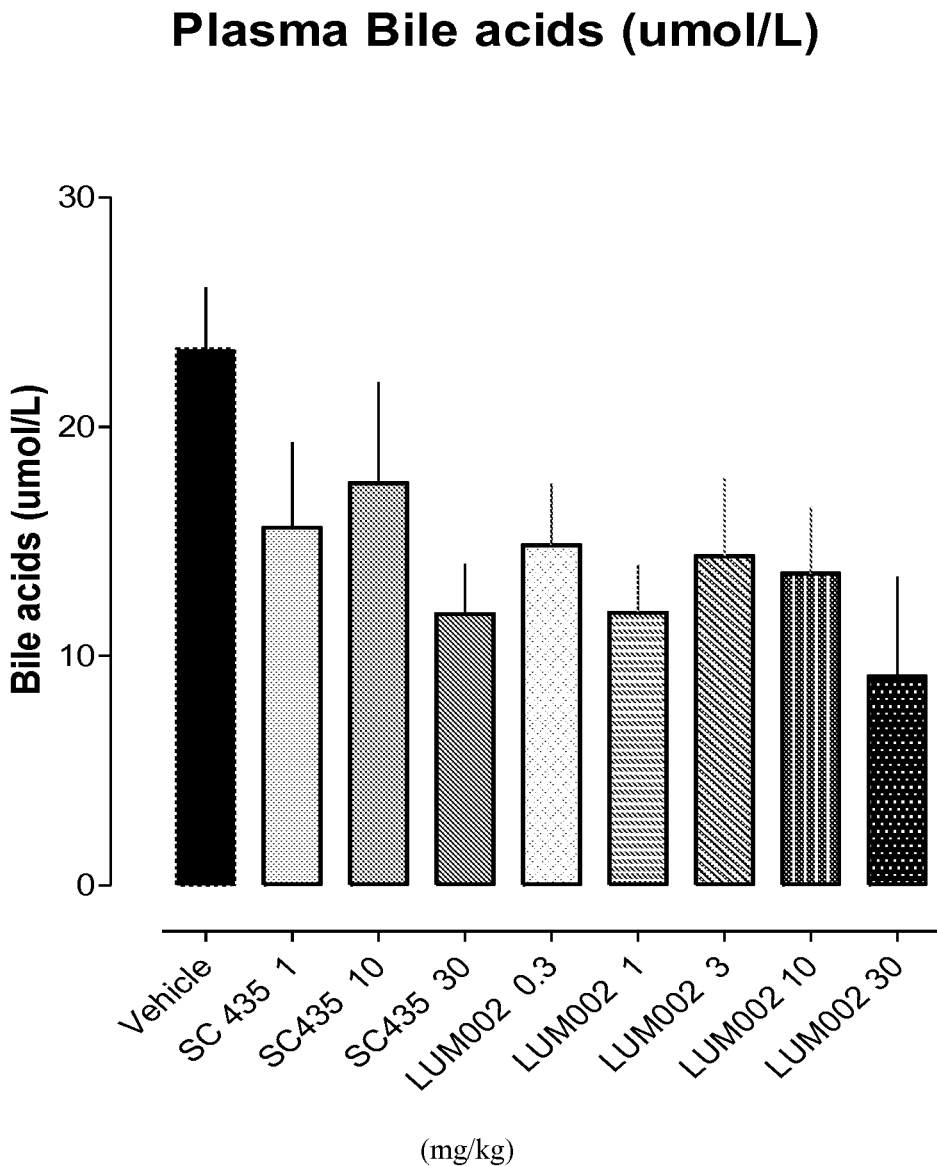
FIG. 2. Plasma bile acid levels of ZDF rats after administration of ascending doses of SC-435 and LUM002. Male ZDF rats (n=4) were administered vehicle, SC-435 (1, 10 or 30 mg/kg) or LUM002 (0.3, 1, 3, 10 or 30 mg/kg) by oral gavage twice a day for 2 weeks. Plasma bile acid levels were determined at the end of the second week. Data are expressed as mean values±SEM.

Plasma bile acid levels of ZDF rats after administration of ascending doses of SC-435 and LUM002. Male ZDF rats (n=4) were administered vehicle, SC-435 (1, 10 or 30 mg/kg) or LUM002 (0.3, 1, 3, 10 or 30 mg/kg) by oral gavage twice a day for 2 weeks. Plasma bile acid levels were determined at the end of the second week. Plasma bile acid levels were decreased for all doses of SC-435 and LUM002. Data are expressed as mean values±SEM. See FIG. 2.

Example 18

Animal Study on the Duration of Action and Time to Onset of ASBTI Activity of a Single Oral Dose of LUM001 on Postprandial Total Serum Bile Acids in Beagle Dogs
Test Compound: LUM001—Form I Dosage preparation and administration: LUM001 was dissolved in water at concentrations that required the administration of 0.2 ml/kg of solution. Solutions were placed into gelatin capsules, Torpac Inc., size 13 Batch 594, East Hanover NJ, and administered orally.

Dogs: Male beagle dogs were obtained from Covance Research Products, Cumberland VA or Marshall Farms USA, Inc., North Rose NY. A total of 20 dogs, 1 to 5 years old, 6.8 to 15.6 kg body weight, were used in these experiments. The dogs were conditioned to a 12 hour light/dark cycle and maintained on a feeding restriction of 1 hour per day access to food (Richman Standard Certified Canine Diet #5007, PMI Nutrition, Inc., St Louis MO) from 7 to 8 AM. They were trained to eat a special meal promptly within 20 minutes when presented (1 can. 397 g, Evanger's 100% Beef for Dogs, Evanger's Dog and Cat Food Co., Inc., Wheeling IL, mixed with 50 g of sharp cheddar cheese).

Serum Total Bile Acid (SBA) Measurement: SBA was measured by an enzymatic assay. SBA values are expressed as µg of total bile acids/ml of serum.

Control Experiments to Estimate the Rise and Duration of Elevation in Systemic Serum Bile Acid: Previous work demonstrated that SBA of beagle dogs rises to a peak level one hour after feeding the meal described above, and remains at a plateau for 4 hours and then declines. To estimate the details of this plateau, 6 dogs were given a test meal and blood samples for SBA measurement were collected at −30, 0, 30, 60, 65, 70, 80, 90, 120, 180, 240, 360, 480, 720, 1410 and 1440 minutes from the time of feeding. Any remaining food was removed 20 min after it was first presented to the dogs. To establish a method for extending the elevated plateau of SBA, 6 dogs were given the meal at 0 hr and an additional ½ size meal again 4 hr after their first meal. Blood samples were taken at 0, 1, 2, 3, 4, 4.5, 6, 7 and 8 hr. The curves for SBA level vs time obtained in these experiments were used as references for determining blood sampling times in experiments with LUM001. Wherever possible, experimental design permitting, in experiments with test compound, each dog served as its own simultaneous control, and the mean 1 hr SBA value served as the reference to which all other mean values were compared.

Experiments to Measure Time to Onset of Activity of LUM001: LUM001 was administered at 0, 0.01, 0.05, 0.2 and 1 mg/kg, p.o. to dogs, n=6, 1 hr after feeding the standard experimental meal. Blood samples for SBA measurement were taken at −30, 0, 30, 60, 65, 70, 80, 90, 120 and 180 minutes from the time of feeding. Each dog served as its own control, and mean SBA levels were compared to the mean SBA level at 60 minutes.

TABLE 1

Onset of Activity of LUM001 on Dog Serum Bile Acids
Serum Bile Acid (μg/ml)

| SD-5613 Time (min) | Water, n = 6 | | 0.01 mg/kg, n = 6 | | 0.05 mg/kg, n = 6 | | 0.2 mg/kg, n = 6 | | 1 mg/kg, n = 6 | |
|---|---|---|---|---|---|---|---|---|---|---|
| | Mean | SEM | Mean | SEM | Mean | SEM | Mean | SEM | Mean | SEM |
| −30 | 2.2 | 0.3 | 1.5 | 0.1 | 1.4 | 0.1 | 2.4 | 0.5 | 2.1 | 0.2 |
| 0 | 2.0 | 0.3 | 1.4 | 0.1 | 2.1 | 0.6 | 1.9 | 0.2 | 2.8 | 0.4 |
| 30 | 6.9 | 2.1 | 5.8 | 2.5 | 6.8 | 2.3 | 9.1 | 2.1 | 7.6 | 1.8 |
| 60 | 17.8 | 3.2 | 14.6 | 2.8 | 10.4 | 1.2 | 19.1 | 2.7 | 13.8 | 1.4 |
| 65 | 16.6 | 3.6 | 13.9 | 2.4 | 12.2 | 1.7 | 14.9 | 1.7 | 13.5 | 1.4 |
| 70 | 16.2 | 1.9 | 14.1 | 2.2 | 12.0 | 1.6 | 16.7 | 2.3 | 15.4 | 1.8 |
| 80 | 16.1 | 2.3 | 12.8 | 1.8 | 10.0 | 1.3 | 14.3 | 2.2 | 12.1 | 1.4 |
| 90 | 15.2 | 2.8 | 11.0 | 2.0 | 8.8 | 1.6 | 9.8* | 0.6 | 7.4* | 1.2 |
| 120 | 15.5 | 3.6 | 10.8 | 1.7 | 6.5* | 1.2 | 4.8* | 0.3 | 3.0* | 0.1 |
| 180 | 14.7 | 3.1 | 11.0 | 1.6 | 6.5* | 1.2 | 4.0 | 0.6 | 2.6* | 0.2 |

All animals were fed at 0 minutes dosed at 60 minutes.

*= p < 0.05 compared to 60 minute value in the same curve by two-tailed paired two-sample t-test.

Experiments to Measure the Duration of Action of LUM001: In dogs a single experimental meal produces a postprandial rise in SBA that is elevated to a peak at 1 hour after feeding and constant for an additional 3 hours. Previous experiments (2) indicate that LUM001 remains active for more than 4.5 hours. To measure the duration of action of an ASBT inhibitor using postprandial SBA levels requires that in the control situation the SBA levels remain elevated and constant for the entire period of compound action, or that the compound be administered long before the postprandial rise occurs, and remain active in the empty digestive system for long periods before feeding. Accordingly, two alternative methods were used to provide a window of constant SBA elevation that could be used to measure the duration of action of ASBT inhibitors.

Method 1: Two Meals for Extended SBA Elevation: LUM001 was administered at 0.05 and 0.2 mg/kg, p.o. to 6 dogs 1 hr after feeding them a meal. At 4 hours after the meal was offered, a second meal of ½ the size of the first meal was offered. It too was consumed as promptly and thoroughly as the first meal, and provided an extended, constant SBA plateau. Blood samples for SBA measurement were taken at 0, 1, 1.5, 2, 4, 4.5, 5, 5.5, 6, 6.5, 7, 7.5 and 8 hours from the time of offering the first meal. Mean SBA levels were compared to the mean SBA level at 1 hour, each dog serving as its own control. The end of activity is considered to occur at time point at which the mean SBA value is not significantly lower than the 1 hr mean value.

TABLE 2

Duration of Action of LUM001 on Dog Serum Bile Acids I
Serum Bile Acid (μg/ml)

| SD-5613 Time (hr) | Water, n = 6 | | 0.05 mg/kg, n = 6 | | 0.2 mg/kg, n = 6 | |
|---|---|---|---|---|---|---|
| | Mean | SEM | Mean | SEM | Mean | SEM |
| 0 | 2.5 | 0.5 | 1.4 | 0.1 | 1.3 | 0.1 |
| 1 | 13.1 | 1.3 | 9.2 | 1.8 | 11.1 | 1.5 |
| 1.5 | | | 9.6 | 2.0 | 9.1 | 0.6 |
| 2 | 14.6 | 1.2 | 6.7 | 0.6 | 3.8* | 0.4 |
| 3 | 14.4 | 1.7 | | | | |
| 4 | 14.8 | 1.2 | 5.1* | 0.7 | 2.5* | 0.4 |

TABLE 2-continued

Duration of Action of LUM001 on Dog Serum Bile Acids I
Serum Bile Acid (μg/ml)

| SD-5613 Time (hr) | Water, n = 6 | | 0.05 mg/kg, n = 6 | | 0.2 mg/kg, n = 6 | |
|---|---|---|---|---|---|---|
| | Mean | SEM | Mean | SEM | Mean | SEM |
| 4.5 | 16.6 | 1.5 | 6.4 | 0.7 | 3.3* | 0.6 |
| 5 | 15.8 | 2.0 | 7.0 | 0.7 | 3.1* | 0.4 |
| 6 | 15.5 | 2.1 | 7.0 | 0.9 | 3.6* | 0.7 |
| 7 | 14.4 | 2.5 | 7.4 | 0.8 | 3.9* | 0.5 |
| 8 | 13.3 | 1.5 | 6.5 | 1.1 | 5.8* | 0.8 |

All animals were fed a full meal at 0 hour, dosed orally with the compound at 1 hour and then fed an additional one-half meal at 4 hours. *=p<0.05 compared to the mean value in the same curve at 1 hour by two-tailed paired two-sample t-test.

Method 2: One Meal and Extended Interval Between Dosing and Feeding: Alternatively, 6 dogs were dosed with water or LUM001, at 0.05 mg/kg, p.o. at 1.5 hours prior to being fed, or 0.05, or 0.2 mg/kg, at 2 hours prior to feeding. This moved the elevated SBA plateau out in time from the dose point. Blood samples for SBA measurement were taken immediately before dosing (0 or 0.5 hr), at feeding (2 hr), 2.5, 3, 4 and 5 hours after feeding. This allowed detection of activity out to 5.5 and 6 hours after dosing without feeding the dogs a second time. Mean SBA levels were compared to the corresponding mean SBA levels in water treated controls. The end of activity is considered to occur at the first time point at which the mean SBA value is not significantly lower than the corresponding control mean value.

Serum Bile Acid (SBA) Analysis: On Day −1, blood was drawn for baseline SBA at approximately 30 minutes before and after breakfast and 30 minutes after lunch and dinner. During the treatment period, samples were obtained on days

TABLE 3

Duration of Action of LUM001 on Dog Serum Bile Acids II
Serum Bile Acid (µg/ml)

| Dosing Time | | | 0.5 hr | | 0 hr | | 0 hr | |
|---|---|---|---|---|---|---|---|---|
| Feeding time | 2 hr | | 2 hr | | 2 hr | | 2 hr | |
| SD-5613 | Water, n = 6 | | 0.05 mg/kg, n = 9 | | 0.05 mg/kg, n = 9 | | 0.05 mg/kg, n = 9 | |
| Time (hr) | Mean | SEM | Mean | SEM | Mean | SEM | Mean | SEM |
| 0 | | | | | 1.7 | 0.1 | 1.3 | 0.1 |
| 0.5 | | | 1.8 | 0.3 | | | | |
| 2 | 2.0 | 0.3 | 1.7 | 0.1 | 2.0 | 0.5 | 1.7 | 0.3 |
| 2.5 | 6.9 | 2.1 | 2.5 | 0.6 | | | | |
| 3 | 17.8 | 3.2 | 9.7 | 2.6 | 9.0* | 1.4 | 4.1* | 0.6 |
| 4 | 15.5 | 3.6 | 12.4 | 2.0 | 10.8 | 1.2 | 6.5* | 0.8 |
| 5 | 14.7 | 3.1 | 11.6 | 2.4 | 10.6 | 0.9 | 7.9* | 1.1 |

*= p < 0.05 vs water treatment by two-tailed two-sample t-test without assuming equal variances.

Conclusion: In the dog SBA model, the $ED_{50}$ dose (0.2 mg/kg) of LUM001 administered orally 1 hour after feeding significantly lowered serum bile acid levels within 30 minutes of dosing and these levels remained significantly lowered for at least 6 hours. By comparison, a threshold dose of 0.05 mg/kg significantly lowered SBA levels within approximately 1 to 2 hours after dosing but the significant decrease was not sustained beyond 3 hours after dosing. Increasing the dose above the $ED_{50}$ level to 1 mg/kg did not shorten the onset time to significant SBA lowering and still sustained a maximal suppression for 2 hours after dosing. When LUM001 was administered 2 hours prior to feeding, a dose of 0.2 mg/kg was required produce a significant effect that was sustained for at least 2-3 hours after feeding. The results from these studies indicate that the presence of food in the GI tract has a significant impact on the pharmacodynamic activity of the ASBT inhibitor, most likely by altering the residence time of the drug in the small intestine.

Example 19

A Randomized, Double-Blind, Placebo Controlled, Safety, Tolerability, Pharmacokinetic, and Pharmacodynamic Study of Ascending Multiple Oral Doses of LUM001 in Healthy Subjects This Phase 1 study was a randomized, double-blind, placebo-controlled study of ascending multiple oral doses of LUM001 in healthy, adult subjects. This study was conducted at a single center. There were 13 LUM001 dosing panels: 10, 20, 60, 100, and 20 mg every morning (qAM) (2) (i.e., the regimen was tested a second time in the study), 5 mg every evening (qPM), 0.5, 1, 2.5, 5, 2.5 (2), 5 (2), and 0.5 to 5 mg qAM dose titration. Most of the dosing panels included subjects treated with matching placebo. Shown in the graphs are data from the 0.5 (n=16), 1.0 (n=8), 2.5 (n=8), 5.0 (n=8) and 10 (n=8) mg dosing groups.

For the qAM dosing panels, LUM001 or placebo was administered each day of the treatment period (28 days) immediately prior to the morning meal at approximately 08:00 and after any necessary blood work was drawn.

Figure 3:
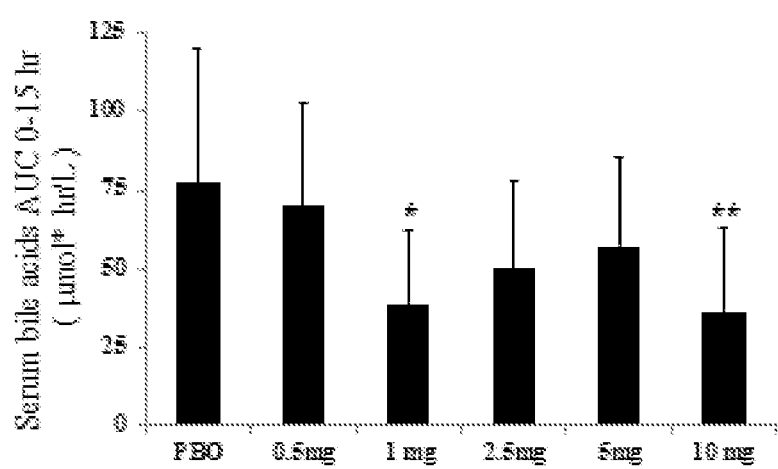
FIG. 3. Serum bile acid (SBA) analysis of healthy subjects after administration of ascending multiple oral doses of LUM001 a randomized, double-blind, placebo-controlled study. Shown in the graphs are data from the 0.5 (n=16), 1.0 (n=8), 2.5 (n=8), 5.0 (n=8) and 10 (n=8) mg dosing groups. On Day 1, blood was drawn for baseline SBA at approximately 30 minutes before and after breakfast and 30 minutes after lunch and dinner. Samples were obtained on day 14.

2, 14 and 28 (14 day results are presented in FIG. 3) at −30, 30, 60 120, and 240 minutes after each of the 3 daily meals for analysis. For each sample, approximately 3 mL of venous blood were collected by venipuncture or saline lock.

SBA were analyzed as part of the routine clinical analysis of the serum samples collected at each time point.

Figure 4:
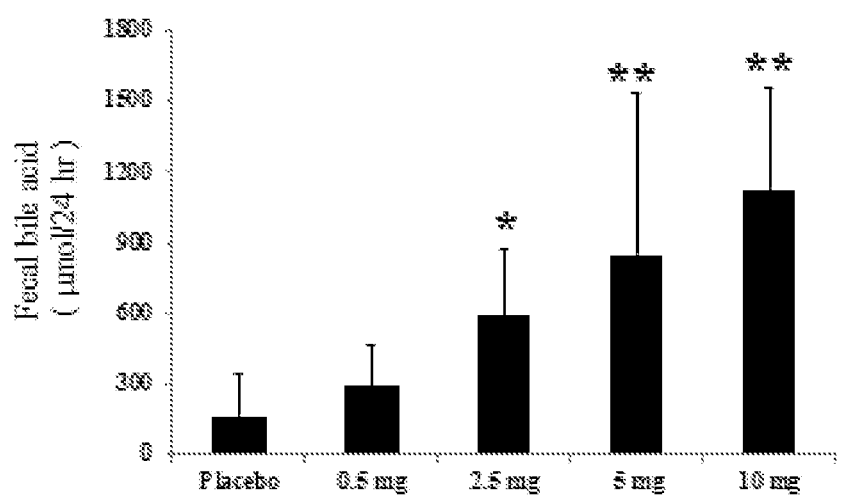
FIG. 4. Fecal bile acid analysis of healthy subjects after administration of ascending multiple oral doses of LUM001 a randomized, double-blind, placebo-controlled study. Fecal samples were collected for all panels except the dose-titration panel, 2.5 (2) and 5 mg (2), on Days 9 through 14 and 23 through 28.

Fecal Bile Acid Analysis: Fecal samples were collected for all panels except the dose-titration panel, 2.5 (2) and 5 mg (2), on Days 9 through 14 and 23 through 28 (data shown in FIG. 4). Twenty-four hour FBA excretions were quantified by Pharmacia for Days 9 through 14 and 23 through 28. Feces were collected in a 24-hour collection container beginning at 08:00 and ending 24 hours later. This procedure was followed on Days 9 through 14 and 23 through 28, with new collection containers issued for each 24-hour period. The weight of each 24-hour fecal collection was recorded on the CRFs. Specimens were stored in 24-hour containers, frozen at approximately −80° C. prior to analysis.

An aliquot for each 24-hour fecal sample collected on Days 23 through 28 was combined, homogenized, and analyzed for bile acid species concentrations by ANAPHARM. The fecal bile acid species evaluated include chenodeoxycholic acid, cholic acid, deoxycholic acid, and lithocholic acid.

Conclusion: The results showed a significant reduction in serum bile acids and significant increase in fecal bile acids.

Example 20

Pediatric Study to Test Efficacy of ASBTI in Lowering Serum Bile Acids in Pediatric Patients LUM001 has been administered to forty patients under the age of 18 years old. Table below shows the exemplary characteristics of five children who received LUM001. The drug was administered once-a-day (QD) in the morning for fourteen days. The levels of systemic exposure of LUM001 were measured on day eight and the drug was confirmed to be minimally absorbed by the children. These doses are similar to those using to treat children with cholestatic diseases.

TABLE 4

Pharmacokinetics of LUM001 in pediatric
subjects (study NB-00-02-014)

| Subject Number | LUM001 treatment (mg) | Sex | Dose μg/kg | Average serum drug exposure (ng/ml) |
|---|---|---|---|---|
| 0309 | 1.0 | MALE | 35.0 | 0.0 |
| 0304 | 1.0 | MALE | 24.3 | 0.0 |
| 0308 | 1.0 | MALE | 28.9 | 0.0 |
| 0410 | 2.5 | FEMALE | 42.0 | 0.0 |
| 0510 | 5.0 | MALE | 168.4 | 0,0 |

Figure 5:
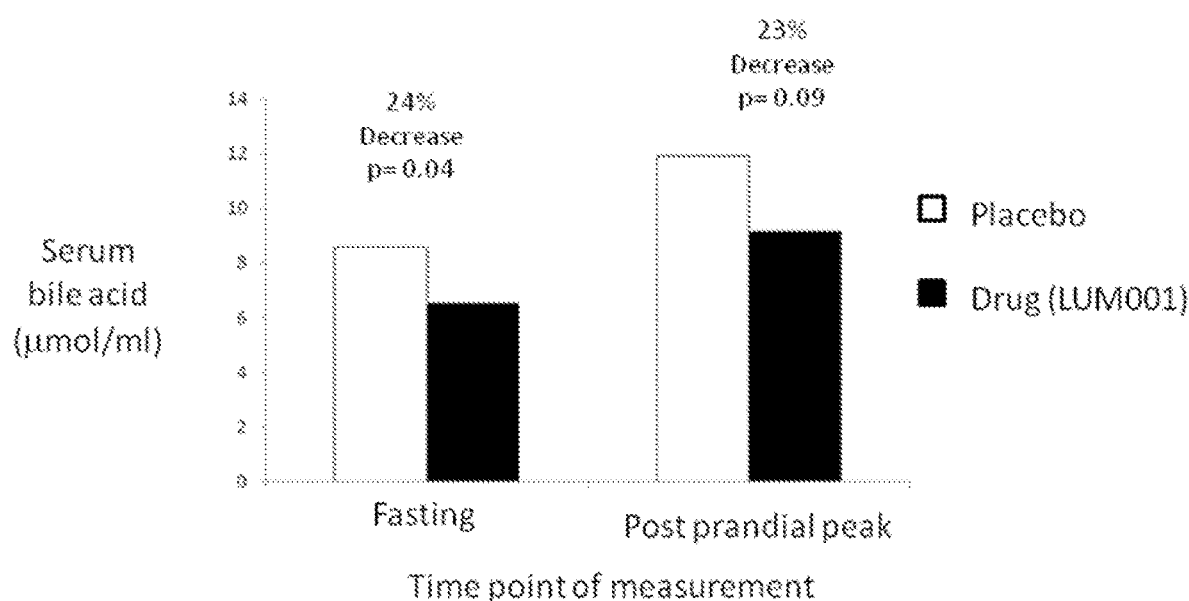
FIG. 5. Fasting serum bile acid levels and morning post-prandial peak in children under the age of 12. LUM001 was administered once-a-day (QD) in the morning for fourteen days. The placebo patients had an average fasting serum bile acid level of 8.6 µmol/L and a post-prandial peak serum bile acid level of 11.9 µmol/L. For the LUM001 treated patients the values were 6.5 µmol/L and 9.2, respectively, representing a 24% and 23% decrease.

The efficacy of LUM001 was determined by measuring total serum bile acids after eight days of dosing in children and adolescents under the age of eighteen. Thirty minutes before the next drug administration, at approximately 8 am in the morning, serum bile acid levels were measured. The child had refrained from food for 12 hours prior to this sample thus providing a fasted level of serum bile acid. After breakfast, serum bile acids were measured for up to the next 4 hours (8 am to noon) and the peak serum bile acid concentration noted. LUM001 was shown to generally decrease both the fasting and post-prandial peak levels of serum bile acids (see table). In the table below the placebo patients had an average fasting serum bile acid level of 8.6 μmol/L and a post-prandial peak serum bile acid level of 11.9 μmol/L. For the LUM001 treated patients the values were 6.5 μmol/L and 9.2, respectively, representing a 24% and 23% decrease (see FIG. 5).

TABLE 5

Fasting SBA and morning post-prandial peak in pediatric subjects

| | Patients | | | | | | | | | |
|---|---|---|---|---|---|---|---|---|---|---|
| | 301 | 307 | 405 | 408 | 508 | 304 | 308 | 309 | 401 | 510 |
| Drug dose (mg) | Placebo | Placebo | Placebo | Placebo | Placebo | 1 | 1 | 1 | 2.5 | 5 |
| Fasting serum bile acid (μmol/l) | 9.1 | 7.4 | 10.5 | 8.3 | 7.7 | 5.6 | 6.8 | 6.9 | 6.0 | 7.4 |
| Morning Post-prandial peak (μmol/l) | 11.9 | 10.7 | 13.1 | 13.4 | 10.4 | 8.4 | 9.3 | 10.0 | 6.8 | 11.3 |

Example 21

Clinical Trial to Test Efficacy of ASBTI in Treatment and or Alleviation of Symptoms of Pediatric Cholestasis or a Pediatric Cholestatic Liver Disease This study will determine efficacy of ASBTI treatment in patients afflicted with pediatric cholestasis or a pediatric cholestatic liver disease.

Subjects under the age of 12, clinically diagnosed with cholestasis or a cholestatic liver disease will be enrolled. Subjects may be diagnosed by symptoms such as jaundice, chronic pruritus, total serum bile acid/bilirubin elevation.

Subjects who have life threatening renal disease, cardiovascular disease, or congenital anomalies will be excluded.

Subjects will be administered a daily oral dose of compound LUM001 formulated for release in the distal ileum. Alternatively, any of the following compounds can be the subject of the clinical trial: 264W94; SAR548304B; SA HMR1741; 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; or 1,1-dioxo-3,3-dibutyl-5-phenyl-7-methylthio-8-[N—((R)-α-carboxy-4-hydroxybenzyl)carbamoylmethoxy]-2,3,4,5-tetrahydro-1,2,5-benzothiadiazepine.

The primary endpoint is the proportion of subjects showing resolution or improvement of baseline signs and symptoms, e.g., jaundice, serum levels of bile acids/salts and/or bilirubin, pruritus.

Example 22

Clinical Trial to Test Efficacy of ASBTI in Treatment and or Alleviation of Symptoms of Progressive Familial Intrahepatic Cholestasis 1 (PFIC-1)

This study will determine efficacy of an ASBTI for treatment in pediatric patients afflicted with PFIC1.

Patients genetically diagnosed with anomalies in ATP8B1, ABCB11, or ABCB4 gene and who present with PFIC-1 are eligible for enrollment.

Inclusion criteria include severe pruritus (greater than grade II); non-responsive to ursodiol; native liver; genetic or immunohistochemical findings consistent with PFIC1 or Alagille syndrome; informed consent; age 12 months or older.

Exclusion criteria include chronic diarrhea requiring IV fluid or nutritional interventions; surgical interruption of the enterohepatic circulation; or decompensated cirrhosis (PT>16 s, alb<3.0 gr/dl, ascites, diuretic therapy, variceal hemorrhage, encephalopathy).

Subjects will be administered a daily oral dose of LUM001 formulated for release in the distal ileum. Alternatively, any of the following compounds can be the subject of the clinical trial: 264W94; SAR548304B; SA HMR1741; 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl]carbamoylmethoxy)-2,3,4,5-tetrahydro-1,2, 5-benzothiadiazepine; 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5- benzothiadiazepine; 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; or 1,1-dioxo-3,3-dibutyl-5-phenyl-7-methylthio-8-[N—((R)-α-carboxy-4-hydroxybenzyl)carbamoylmethoxy]-2,3,4,5-tetrahydro-1,2,5-benzothiadiazepine.

Stage 1 will be a 4 week dose escalation study to determine patient minimum tolerated dose. Dose 1: 14 ug/kg/day for 7 days; dose 2: 35 ug/kg/day for 7 days; dose 3; 70 ug/kg/day for 7 days; dose 4: 140 ug/kg/day for 7 days.

Stage 2 will be a double-blind placebo controlled cross-over study. Subjects will be randomized to maximum tolerated dose or placebo for 8 weeks, followed by a 2 week drug holiday, and cross-over to receive the alternative regimen for 8 week.

The primary endpoint is the proportion of subjects showing resolution or improvement of baseline signs and symptoms, e.g., jaundice, serum levels of bile acids/salts and/or bilirubin, pruritis.

Example 23

Clinical Trial to Test Efficacy of ASBTI in Treatment and or Alleviation of Symptoms of Benign Recurrent Intrahepatic Cholestasis or a Cholestatic Liver Disease (BRIC)

The purpose of this study is to determine the effect of a non-systemic ASBTI suspension in treating BRIC. An enteric ileal pH-release suspension of an ASBTI may also be administered to a subject once a day.

Pediatric patients genetically diagnosed with anomalies in ATP8B1, ABCB11, or ABCB4 gene and present non-chronic but recurrent cholestasis or a cholestatic liver disease symptoms will be enrolled.

Subjects will be administered a daily oral dose of compound LUM001 formulated for release in the distal ileum. Alternatively, any of the following compounds can be the subject of the clinical trial: 264W94; SD5613; SAR548304B; SA HMR1741; 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; or 1,1-dioxo-3,3-dibutyl-5-phenyl-7-methylthio-8-[N—((R)-α-carboxy-4-hydroxybenzyl)carbamoylmethoxy]-2,3,4,5-tetrahydro-1,2,5-benzothiadiazepine. The primary endpoint is the proportion of subjects showing resolution or improvement of baseline signs and symptoms, e.g., jaundice, serum levels of bile acids/salts and/or bilirubin, pruritis.

Example 24

Clinical Trial to Test Efficacy of ASBTI in Treatment and or Alleviation of Symptoms of Total Parenteral Nutrition Associated Cholestasis or a Cholestatic Liver Disease (TPN-AC)

The purpose of this study is to determine the effect of a non-systemic ASBTI suspension in treating TPN-AC. An enteric ileal pH-release suspension of an ASBTI may also be administered to a subject once a day.

Pediatric patients clinically diagnosed with TPN-AC and associated symptoms will be enrolled.

Subjects will be administered a daily oral dose of compound LUM001 formulated for release in the distal ileum. Alternatively, any of the following compounds can be the subject of the clinical trial: 264W94; SAR548304B; SA HMR1741; 1,1-Dioxo-3,3-dibutyl-5-phenyl-7-methylthio-8-(N—[(R)-α-[N-(2-sulphoethyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-(R)-hydroxypropyl)carbamoyl]-4-hydroxybenzyl]carbamoylmethoxy)-2,3,4,5-tetrahydro-1,2,5-benzothiadiazepine; 1,1-Dioxo-3,3-dibutyl-5-phenyl-7-methylthio-8-(N—[(R)-α-[N—((S)-1-carboxy-2-methylpropyl)carbamoyl]-4-hydroxybenzyl]carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; or 1,1-dioxo-3,3-dibutyl-5-phenyl-7-methylthio-8-[N—((R)-α-carboxy-4-hydroxybenzyl)carbamoylmethoxy]-2,3,4,5-tetrahydro-1,2,5-benzothiadiazepine. The primary endpoint is the proportion of subjects showing resolution or improvement of baseline signs and symptoms, e.g., jaundice, serum levels of bile acids/salts and/or bilirubin, pruritis.

Example 25

Clinical Trial to Test Efficacy of LUM-001 in Treatment and or Alleviation of Symptoms of FIC1 Disease and Alagille Syndrome Pediatric patients who suffer from FIC1 disease (n=15) and Alagille syndrome (n=20) aged 12 months and older will be tested.

Inclusion criteria will include (1) severe pruritus (≥grade II) unresponsive to routine pharmacologic therapy, (2) native liver, (3) genetic or clinical findings consistent with FIC1 disease or genetic findings of Alagille syndrome, and (4) informed consent and assent as appropriate.

Exclusion criteria will include (1) chronic diarrhea requiring specific intravenous fluid or nutritional intervention for the diarrhea and/or its sequelae or (2) surgical interruption of the enterohepatic circulation, (3) decompensated cirrhosis (PT>16 s, alb<3.0 gr/dl, ascites, diuretic therapy, variceal hemorrhage, encephalopathy).

Stage 1: 4 week dose escalation of LUM-001 (doses based on adolescent/adult doses) to determine patient maximum tolerated dose. Dose 1-14 μg/kg/day for seven days; Dose 2-35 μg/kg/day for seven days; Dose 3-70 μg/kg/day for seven days; Dose 4-140 μg/kg/day for seven days.

Stage 2: double-blinded placebo controlled cross-over study. Randomized to maximum tolerated dose or placebo for 8 weeks, followed by 2 weeks wash out, and crossed-over to receive the alternative regimen for 8 weeks.

Possible Stage 3 with open label therapy.

Primary endpoint: safety and tolerability of LUM-001.

Secondary endpoints: changes in pruritus scores, clinical laboratories, fecal bile acid secretion, serum bile acids and serum 7α-hydroxy-4-cholesten-3-one (7αC4).

Baseline assessment will include: FIC1 or Jagged 1 genotyping, complete history and physical, comprehensive clinical laboratory profile, 72 hour fecal bile acid collection, serum levels of bile acids, bile acid synthesis marker (7αC4).

Stage 1-Baseline assessments (except genotyping, history and physical) will be repeated at the end of each 7-day treatment period. Pruritus scoring will be assessed by the parents, child (if possible) and by clinician(s) at the beginning and end of each dose.

Stage 2-Baseline assessments (except genotyping, history and physical) will be repeated at the end of each 8 week treatment period.

LUM-001 was shown to be well-tolerated in a pediatric multiple-dose study: 2 weeks daily up to 5 mg q.d. (39 treated subjects aged 10-17).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating or ameliorating progressive familial intrahepatic cholestasis (PFIC) in a pediatric subject comprising administering to the pediatric subject an Apical Sodium-dependent Bile Acid Transporter Inhibitor (ASBTI), wherein the ASBTI is

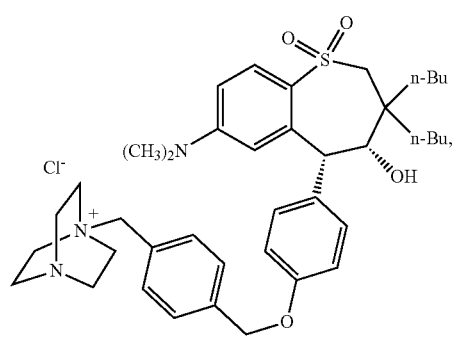

or a pharmaceutically acceptable salt, solvate, or prodrug thereof.

2. A method for treating or ameliorating pruritus in a pediatric subject having progressive familial intrahepatic cholestasis (PFIC) comprising administering to the pediatric subject an Apical Sodium-dependent Bile Acid Transporter Inhibitor (ASBTI), wherein the ASBTI is

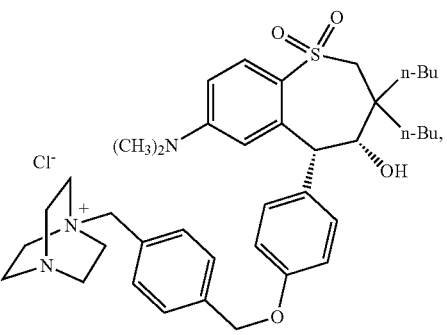

or a pharmaceutically acceptable salt thereof.

3. The method of claim 1, wherein the method comprises reducing serum lipoprotein X, liver enzymes, bilirubin, intraenterocyte bile acids/salts, or necrosis and/or damage to hepatocellular architecture.

4. The method of claim 1 comprising administering to the pediatric subject a pharmaceutical composition comprising the ASBTI, or the pharmaceutically acceptable salt thereof.

5. The method of claim 4, wherein the composition is a pediatric dosage form.

6. The method of claim 5, wherein the pediatric dosage form is selected from a solution, syrup, suspension, elixir, powder for reconstitution as suspension or solution, dispersible/effervescent tablet, chewable tablet, gummy candy, lollipop, freezer pops, troches, oral thin strips, orally disintegrating tablet, sachet, soft gelatin capsule, and sprinkle oral powder or granules.

7. The method of claim 6, wherein the pediatric dosage form comprises between about 0.1 mg to about 100 mg of the ASBTI.

8. The method of claim 6, wherein the pediatric dosage form comprises between about 0.001 mg/kg and about 50 mg/kg of the ASBTI.

9. The method of claim 8, wherein the pediatric dosage form comprises between about 0.01 mg/kg and about 10 mg/kg of the ASBTI.

10. The method of claim 6, wherein the pediatric dosage form of the ASBTI comprises between about 1 µg/kg/day to about 10 mg/kg/day.

11. The method of claim 1, wherein the pediatric cholestatic liver disease is PFIC type 1, PFIC type 2, or PFIC type 3.

12. The method of claim 1, wherein the PFIC is characterized by one or more symptoms selected from jaundice, pruritus, cirrhosis, hypercholemia, neonatal respiratory distress syndrome, lung pneumonia, increased serum concentration of bile acids, increased hepatic concentration of bile acids, increased serum concentration of bilirubin, hepatocellular injury, liver scarring, liver failure, hepatomegaly, malabsorption, splenomegaly, diarrhea, pancreatitis, hepatocellular necrosis, giant cell formation, hepatocellular carcinoma, gastrointestinal bleeding, portal hypertension, hearing loss, fatigue, loss of appetite, anorexia, peculiar smell, dark urine, light stools, steatorrhea, failure to thrive, and renal failure.

13. The method of claim 1, wherein the pediatric subject is between 2 months to 12 years old.

14. The method of claim 1, wherein less than 10% of the ASBTI is systemically absorbed.

15. The method of claim 1, wherein the ASBTI is effective for decreasing at least 20% of serum and/or hepatic bile acid levels in the pediatric subject as compared to bile acid levels prior to administration of the ASBTI.

16. The method of claim 1, wherein the ASBTI is effective for decreasing at least 30% of serum and/or hepatic bile acid levels in the pediatric subject as compared to bile acid levels prior to administration of the ASBTI.

17. The method of claim 1, wherein the ASBTI is effective for decreasing at least 40% of serum and/or hepatic bile acid levels in the pediatric subject as compared to bile acid levels prior to administration of the ASBTI.

18. The method of claim 1, wherein the ASBTI is effective for decreasing at least 50% of serum and/or hepatic bile acid levels in the pediatric subject as compared to bile acid levels prior to administration of the ASBTI.

19. The method of claim 4, wherein the composition further comprises a bile acid sequestrant or binder.

20. A method for treating or ameliorating progressive familial intrahepatic cholestasis (PFIC) comprising administering to a pediatric subject a pharmaceutical composition comprising an Apical Sodium-dependent Bile Acid Transporter Inhibitor (ASBTI), wherein the ASBTI is

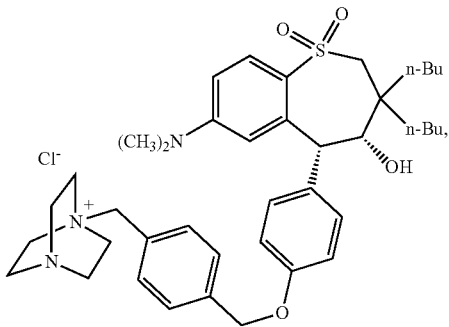

or a pharmaceutically acceptable salt, solvate, or prodrug thereof.

* * * * *